US008637294B2

(12) United States Patent
Day et al.

(10) Patent No.: US 8,637,294 B2
(45) Date of Patent: Jan. 28, 2014

(54) **VARIANT *HYPOCREA JERCORINA* CBH1 CELLULASES**

(75) Inventors: Anthony Day, San Francisco, CA (US); Frits Goedegebuur, Vlaardingen (NL); Peter Gualfetti, San Francisco, CA (US); Colin Mitchinson, Half Moon Bay, CA (US); Paulien Neefe, Zoetermeer (NL); Mats Sandgren, Uppsala (SE); Andrew Shaw, San Francisco, CA (US); Jerry Stahlberg, Uppsala (SE)

(73) Assignee: Danisco US Inc., Palo Alto, CA (US)

( * ) Notice: Subject to any disclaimer, the term of this patent is extended or adjusted under 35 U.S.C. 154(b) by 639 days.

(21) Appl. No.: 11/728,219

(22) Filed: Mar. 22, 2007

(65) Prior Publication Data

US 2007/0173431 A1    Jul. 26, 2007

Related U.S. Application Data

(62) Division of application No. 10/641,678, filed on Aug. 15, 2003.

(60) Provisional application No. 60/404,063, filed on Aug. 16, 2002, provisional application No. 60/458,853, filed on Mar. 27, 2003, provisional application No. 60/456,368, filed on Mar. 21, 2003, provisional application No. 60/458,696, filed on Mar. 27, 2003.

(51) Int. Cl.
*C12N 9/42* (2006.01)
*C12P 19/02* (2006.01)
*C12P 19/00* (2006.01)
*G01N 33/53* (2006.01)

(52) U.S. Cl.
USPC .............. 435/209; 435/7.6; 435/72; 435/105; 536/23.2

(58) Field of Classification Search
USPC ........... 435/69.1, 209, 252.3, 320.1; 536/23.2
See application file for complete search history.

(56) References Cited

U.S. PATENT DOCUMENTS

| 4,435,307 | A | 3/1984 | Barbesgaard et al. ... 252/174.12 |
| 4,816,567 | A | 3/1989 | Cabilly et al. ................ 530/387 |
| 4,822,516 | A | 4/1989 | Suzuki et al. ............ 252/174.12 |
| 5,246,853 | A | 9/1993 | Clarkson et al. ............... 435/263 |
| 5,475,101 | A | 12/1995 | Ward et al. ................. 536/23.74 |
| 5,648,263 | A | 7/1997 | Schülein et al. .............. 435/263 |
| 5,650,322 | A | 7/1997 | Clarkson et al. ............. 435/263 |
| 5,691,178 | A | 11/1997 | Schülein et al. .............. 435/209 |
| 5,776,757 | A | 7/1998 | Schülein et al. .............. 435/209 |
| 5,861,271 | A | 1/1999 | Fowler et al. ................. 435/69.1 |
| 5,955,270 | A * | 9/1999 | Radford et al. ................... 435/6 |
| 6,162,782 | A | 12/2000 | Clarkson et al. ............. 510/320 |
| 6,255,115 | B1 | 7/2001 | Beijersbergen et al. ...... 435/477 |
| 6,599,722 | B2 | 7/2003 | Boston et al. ................. 435/137 |

FOREIGN PATENT DOCUMENTS

| GB | 1368599 | 10/1974 |
| GB | 2094826 | 9/1982 |
| GB | 2095275 | 9/1992 |
| WO | WO 91/04673 | 4/1991 |
| WO | WO 92/06209 | 4/1992 |
| WO | WO 94/28117 | 12/1994 |
| WO | WO 98/21339 | 5/1998 |
| WO | WO 98/31821 | 7/1998 |
| WO | WO 01/04284 | 1/2001 |
| WO | WO 2004/016760 | 2/2004 |

OTHER PUBLICATIONS

UniProt Accession No. P19355 (Exoglucanase I, a cellobiohydrolase, Nov. 1, 1990).*
Altschul, Stephen F. et al., "Basic Local Alignment Search Tool," *J. Mol. Biol.*, 215:403-410, 1990.
Aro, Nina et al., "ACEII, a Novel Transcriptional Activator Involved in Regulation of Cellulase and Xylanase Genes of *Trichoderma reesei*," *J. Biol. Chem.*, vol. 276, No. 26, pp. 24309-24314, Jun. 29, 2001.
Aubert, et al., Ed., p. 11 et seq., Academic Press, 1988.
Ausubel, et al., Current Protocols in Molecular Biology, Greene Publishing, Associates and Wiley Interscience, N.Y. (1994).
Bajar, Aslam, et al., "Identification of a fungal cutinase promoter that is inducible by a plant signal via a phosphorylated trans-acting factor," *Proc. Natl. Acad. Sci. USA*, vol. 88, pp. 8208-8212, Sep. 1991.
Ballance, D.J., et al., "Transformation of *Aspergillus nidulans* by the Orotidine-5′-Phosphate Decarboxylase Gene of *Neurospora crassa*," *Biochemical and Biophysical Research Communications*, vol. 112, No. 1, pp. 284-289, Apr. 15, 1983.
Baulcombe, D., "Viruses and gene silencing in plants," *Archives of Virology*, Calisher and Horzinek eds., Springer-Verlag, New York, NY 15:189-201, 1999.
Becker, Dieter, et al., "Engineering of a glycosidase Family 7 cellobiohydrolase to more alkaline pH optimum: the pH behaviour of *Trichoderma reesei* Cel7A and its E223S/A224H/L225V/T226A/D262G mutant," *Biochem. J.*, 356:19-30 (2001).
Berges, Thierry et al., "Isolation of uridine auxotrophs from *Trichoderma reesei* and efficient transformation with the cloned *ura3* and *ura5* genes," *Curr. Genet.* vol. 19, pp. 359-365, 1991.
Bhikhabhai, Ramagauri et al., "Isolation of Cellulolytic Enzymes from *Trichoderma reesei* QM 9414,"J. Appl. Biochem. 6:336-345, 1984.
Brumbauer, Aniko et al., "Fractionation of cellulase and β-glucosidase in a *Trichoderma reesei* culture liquid by use of two-phase partitioning," Bioseparation 7:287-295, 1999.
Burley, S.K. et al., "Aromatic-Aromatic Interaction: A Mechanism of Protein Structure Stabilization," *Science* 229:23-28, 1985.
Cadwell, Craig R., et al., "Randominzation of Genes by PCR Mutagenesis," *PCR Methods and Applications*, 2:28-33, 1992.
Campbell, Edward I., et al., "Improved transformation efficiency of *Aspergillus niger* using the homologous *niaD* gene for nitrate reductase," Current Genetics, 16:53-56, 1989.

(Continued)

*Primary Examiner* — Robert Mondesi
*Assistant Examiner* — Iqbal H Chowdhury
(74) *Attorney, Agent, or Firm* — Danisco US Inc.

(57) ABSTRACT

Described herein are variants of *H. jecorina* CBH I, a Cel7 enzyme. The present invention provides novel cellobiohydrolases that have improved thermostability and reversibility.

45 Claims, 39 Drawing Sheets

(56) References Cited

OTHER PUBLICATIONS

Cao, Qing-Na et al., "Penicillopepsin-JT2, a recombinant enzyme from *Penicillium janthinellum* and the contribution of a hydrogen bond in subsite $S_3$ $\kappa_{cat}$," Protein Science, vol. 9, pp. 991-1001, 2000.
Carter, Paul et al., "Improved oligonucleotide site-directed mutagenesis using M13 vectors," *Nucleic Acids Research*, vol. 13, No. 12, pp. 4431-4443, 1985.
Cees, A. M. et at., "Heterologous Gene Expression in Filamentous Fungi," *More Gene Manipulations in Fungi*, Bennett, J.W. et al., ed., pp. 396-428, Academic Press, 1991.
Coligan, J. E. et at., eds., Current Protocols in Immunology, 1991.
Coughlan, Michael, P. et al., "Comparative Biochemistry of Fungal and Bacterial Cellulolytic Enzyme Systems," *Biochemistry and Genetics of Cellulose Degradation*, pp. 11-30 1988.
Cummings, C. et al., "Secretion of *Trichoderma reesei* β-glucosidase by *Saccharomyces cerevisiae*," Curr. Genet. 29:227-233, 1996.
Davies, Gideon J., "Oligosaccharide specificity of a family 7 endoglucanase: insertion of potential sugar-binding subsites," *Journal of Biotechnology*, 57:91-100, 1997.
Deutscher, Murray P., "Rethinking Your Purification Procedure," Methods in Enzymology, vol. 182, No. 57, p. 779, 1990.
Divne, Christina, et al., "High-resolution Crystal Structures Reveal How a Cellulose Chain is Bound in the 50 Å Long Tunnel of Cellobiohydrolase I from *Trichoderma reesei*," *J. Mol. Biol.*, 275:309-325, 1998.
Ellouz, S. et al., "Analytical Separation of *Trichoderma reesei* Cellulases by Ion-Exchange Fast Protein Liquid Chromatography," *Journal of Chromatography*, 396:307-317, 1987.
Eriksson, A. E., et al., "Response of a Protein Structure to Cavity-Creating Mutations and its Relation to the Hydrophobic Effect," *Science*, 255:178-183, 1992.
Filho, Edivaldo X. F., "Purification and characterization of a β-glucosidase from solid-state cultures of *Humicola grisea* var. *thermoidea*," Can. J. Microbiol., 42:1-5, 1996.
Fliess, A., et al., "Characterization of Cellulases by HPLC Separation," Eur. J. Appl. Microbiol. Biotechnol., vol. 17, pp. 314-318, 1983.
Freer, Shelby N., "Kinetic Characterization of a β-Glucosidase from a Yeast, *Candida wickerhamii*," J. Biol. Chem., vol. 268, No. 13, pp. 9337-9342, 1993.
Freshney, R. I., ed., Animal Cell Culture, 1987.
Gloss, Lisa M., et al., "Urea and Thermal Equilibrium Denaturation Studies on the Dimerization Domain of *Escherichia coli* Trp Repressor," *Biochem.*, vol. 36, No. 19, pp. 5612-5623, 1997.
Goedegebuur, Frits, et al., "Cloning and relational analysis of 15 novel fungal endoglucanases from family 12 glycosyl hydrolase," Current Genetics, vol. 41, pp. 89-98, 2002.
Goldman, G. H., et al., "Transformation of *Trichoderma harzianum* by high-voltage electric pulse," *Current Genetics*, 17:169-174, 1990.
Goyal, Anil, et al., "Characteristics of Fungal Cellulases," *Bioresource Technology*, vol. 36, pp. 37-50, 1991.
Hale & Markham, The Harper Collins Dictionary of Biology, Harper Perennial, NY, 1991.
Halldorsdottir, S, et al., "Cloning, sequencing and overexpression of a *Rhodothermus marinus* gene encoding a thermostable cellulase of glycosyl hydrolase family 12," *Appl. Microbiol. Biotechnol.*, 49(3):277-284, 1998.
Hemmpel, W. H., "The surface modification of woven and knitted cellulose fibre fabrics by enzymatic degradation," *ITB Dyeing/Printing/Finishing*, 3:5-14, 1991.
Henikoff, Steven, et al., "Amino acid substitution matrices from protein blocks," *Proc. Natl. Acad. Sci. USA*, 89:10915-10919, Nov. 1992.
Higuchi, Russell, "Recombinant PCR," *PCR Protocols: A Guide to Methods and Applications*, pp. 177-183, Academic Press, Inc. 1990.
Himmel, Michael E., "Adanced Bioethanol Production Technologies: A Perspective," *American Chemical Society*, pp. 2-45, 1997.
Hopwood, et al., "Genetic Manipulation of Streptomyces: A Laboratory Manual," Innes, 1985.

Hu, Qianjin, et al., "Antibodies Specific for the Human Retinoblastoma Protein Identify a Family of Related Polypeptides," *Molecular and Cellular Biology*, vol. 11, No. 11, pp. 5792-5799, Nov. 1991.
Ilmen, Marja, et al., "Regulation of Cellulase Gene Expression in the Filamentous Fungus *Trichoderma reesei*," *Appl. and Envir. Micro.*, vol. 63, No. 4, pp. 1298-1306, Apr. 1997.
Jakobovits, Aya, et at., "Production of Antigen-Specific Human Antibodies from Mice Engineered with Human Heavy and Light Chain YACs[a]," Annals New York Academy of Sciences, 764:525-535, 1995.
Jakobovits, Aya, "Production of fully human antibodies by transgenic mice," Curr. Opin. Biotechnol., 6(5):561-566, 1995.
Jones, Peter T. et al., "Replacing the complementarity—determining regions in a human antibody with those from a mouse," *Nature*, 321:522-525, 1986.
Karlin, Samuel, et al., "Applications and statistics for multiple high-scoring segments in molecular sequences," *Proc. Natl. Acad. Sci. USA*, 90:5873-5877, 1993.
Kawaguchi, Takashi, et al., "Cloning and sequencing of the cDNA encoding β-glucosidase 1 from *Aspergillus aculeatus*," Gene 173(2):287-288, 1996.
Kellis, James T. Jr., et al., "Contribution of hydrophobic interactions to protein stability," *Nature*, 333:784-786, 1988.
Kleywegt, Gerard J., "The Crystal Structure of the Catalytic Core Domain of Endoglucanase I from *Trichoderma reesei* at 3.6 Å Resolution, and a Comparison with Related Enzymes," *J. Mol. Biol.*, 272:383-397, 1997.
Knowles, Jonathan, et al., "Cellulase families and their genes," *TIBTECH* 5, pp. 255-261, 1987.
Kohler, G. et al., "Continuous cultures of fused cells secreting antibody of predefined specificity," *Nature*, vol. 256, pp. 495-499, Aug. 7, 1975.
Kriegler, Gene Transfer and Expression: A Laboratory Manual, 1990.
Krishna, S. Hari, et al., "Simultaneous saccharification and fermentation of lignocellulosic wastes to ethanol using a thermotolerant yeast," *Bioresource Tech.*, 77:193-196, 2001.
Kuhls, K., et al., "Molecular evidence that the asexual industrial fungus *Trichoderma reesei* is a clonal derivative of the ascomycete *Hypocrea jecorina*," *Proc. Natl. Acad. Sci. USA*, vol. 92, pp. 7755-7760, Jul. 1996.
Kumar, Akhil, et al., "Optimizing the Use of Cellulase Enzymes in Finishing Cellulosic Fabrics," *Textile Chemist and Colorist*, 29:37-42, Apr. 1997.
Kunkel, Thomas A., "Rapid and efficient site-specific mutagenesis without phenotypic selection," *Proc. Natl. Acad. Sci. USA*, vol. 82, pp. 488-492, Jan. 1985.
Lazraq, R., et al., "Conjugative transfer of a shuttle plasmid for *Escherichia coli* to *Mycobacterium smegmatis*," *FEMS Microbiology Letters*, 69:135-138, 1990.
Li, Xin-Liang, et al., "Expression of *Aureobasidium pullulans xynA* in, and Secretion of the Xylanase from, *Saccharomyces cerevisiae*," *Applied and Environmental Microbiology*, vol. 62, No. 1, pp. 209-213, 1996.
Linder, Marcus et al., "The roles and function of cellulose-binding domains," Journal of Biotechnol. 57:15-28, 1997.
Linko, Matti, Proceedings of the Second TRICEL Symposium on *Trichoderma reesei* Cellulases and Other Hydrolases, Espoo 1993, ed. by P. Suominen & T. Reinikainen. Foundation for Biotechnical and Industrial Fermentation Research 8, pp. 9-11, 1993.
Luo, J., et al., "Detection of a Stable Intermediate in the Thermal Unfolding of a Cysteine-Free Form of Dihydrofolate Reductase from *Escherichia coli*," *Biochem.*, vol. 34, No. 33, pp. 10669-10675, 1995.
Matthews, Brian W.,"Structural and Genetic Analysis of Protein Stability," *Annu. Rev. Biochem.*, 62:139-160, 1993.
Matthews, B. W., et al., "Enhanced protein thermostability from site-directed mutations that decrease the entropy of unfolding," *Proc. Natl. Acad. Sci. USA*, vol. 84, pp. 6663-6667, 1987.
Medve, Jozsef et al., "Ion-exchange chromatographic purification and quantitative analysis of *Trichoderma reesei* cellulases cellobiohydrolase I, II and endoglucanase II by fast protein liquid chromatography," *J. Chromatography A*, 808:153-165, 1998.

(56) References Cited

OTHER PUBLICATIONS

Mitsuishi, Yasushi, et al., "Site-directed mutagenesis of the putative catalytic residues of *Trichoderma reesei*, cellobiohydrolase I and endoglucanase I," *FEBS*, 275(1.2)135-138, 1990.

Needleman, Saul B., "A General Method Applicable to the Search for Similarities in the Amino Acid Sequence of Two Proteins," *J. Mol. Biol.*, 48:443-453, 1970.

Nidetzky, Bernd, "Specific Quantification of *Trichoderma reesei* Cellulases in Reconstituted Mixtures and its Application to Cellulase-Cellulose Binding Studies," *Biotechnology and Bioengineering*, vol. 44, pp. 961-966, 1994.

Nevalainen, H., et al., "Molecular Biology of Cellulolytic Fungi," The Mycota II, Genetics and Biotechnology, Kück (Ed.), Springer-Verlag Berlin Heidelberg, 1995, pp. 303-319.

Ohmiya, Kunio, et al., "Structure of Cellulases and Their Applications," Biotechnol. Gen. Engineer. Rev., vol. 14, pp. 365-414, 1997.

Ooi, Toshihiko, et al., "Complete nucleotide sequence of a gene coding for *Aspergillus aculeatus* cellulase (FI-CMCase)", Nucleic Acids Research, vol. 18, No. 19, 1990.

Pearson, William R., et al., "Improved tools for biological sequence comparison," *Proc. Natl. Acad. Sci. USA*, vol. 85, pp. 2444-2448, Apr. 1988.

Penttila, Merja E., et al., "A versatile transformation system for the cellulolytic filamentous fungus *Trichoderma reesei*," Gene, vol. 61, pp. 155-164, 1987.

Penttila, Merja E., et al., "Expression of Two *Trichoderma reesei* Endoglucanases in the Yeast *Saccharomyces cerevisiae*," Yeast, vol. 3, pp. 175-185, 1987.

Penttila, Merja E., et al., "Efficient secretion of two fungal cellobiohydrolases by *Saccharomyces cerevisiae*," Gene, 63:103-112, 1988.

Pere J., et al., "Use of Purified Enzymes in Mechanical Pulping," 1996 Tappi Pulping Conference, pp. 693-696, Nashville, TN.

Pourquie, J., et al., "Scale Up of Cellulase Production and Utilization," Biochemistry and Genetics of Cellulose Degradation, Academic Press Ltd., pp. 71-86, 1988.

Riechmann, Lutz, et al., "Reshaping human antibodies for therapy," *Nature*, vol. 332, pp. 323-327, 1988.

Rothstein, Steven J., et al., "Synthesis and secretion of wheat α-amylase in *Saccharomyces cerevisiae*," Gene, 55:353-356, 1987.

Russell, Rupert J. M., et al., "Engineering thermostability: lessons from thermophilic proteins," *Current Opinion in Biotechnology*, 6:370-374, 1995.

Saarilahti, Hannu T., et al., "CelS: a novel endoglycanase identified from *Erwinia carotovora* subsp. *carotovora*," Gene, 90:9-14, 1990.

Sakamoto, S., et al., "Cloning and sequencing of cellulase cDNA from *Aspergillus kawachii* and its expression in *Saccharomyces cerevisiae*," Curr. Genet., 27:435-439, 1995.

Sambrook, et al., Molecular Cloning: A Laboratory Manual (Second Edition), Cold Spring Harbor Press, Plainview, N.Y., 1989.

Saloheimo, M., et al., "EGIII, a new endoglucanase from *Trichoderma reesei*: the characterization of both gene and enzyme," Gene, 63:11-21, 1988.

Sandgren, Mats, et al., "Comparison of family 12 glycoside hydrolases and recruited substitutions important for thermal stability," *Protein Science*, vol. 12, pp. 848-860, 2003.

Sheehan, John, et al., "Enzymes, Energy, and the Environment: A Strategic Perspective on the U.S. Department of Energy's Research and Development Activities for Bioethanol," *Biotechnol. Prog.*, 15:817-827, 1999.

Schülein, Martin, "Cellulases of *Trichoderma reesei*," Methods Enzymol., 160, 25, pp. 234-243, 1988.

Scopes, Robert K., et al. "Purification of All Glycolytic Enzymes from One Muscle Extract," *Methods Enzymol.*, 90:479-491, 1982.

Sheir-Neiss, G., et al., "Characterization of the secreted cellulases of *Trichoderma reesei* wild type and mutants during controlled fermentations," *Appl. Microbiol. Biotechnol.*, vol. 20, pp. 46-53, 1984.

The Shizuoka Prefectural Hammamatsu Textile Industrial Research Institute Report, vol. 24 pp. 54-61 (1986)—listed but not provided.

Shoemaker, S. P., et al., "Enzymic Activities of Endo-1,4-β-D-Glucanases Purified From *Trichoderma viride*," *Biochemica et Biophysica Acta*, 523:133-146, 1978.

Shoemaker, S., et al., "Molecular Cloning of Exo-Cellobiohydrolase I Derived from *Trichoderma reesei* Strain L27," *Bio/Technology*, pp. 691-696, 1983.

Singleton, et al., Dictionary of Microbiology and Molecular Biology, 2D Ed., John Wiley and Sons, New York (1994).

Smith, Temple F., et al., "Comparison of Biosequences," *Advances in Applied Mathematics*, vol. 2, pp. 482-489, 1981.

Spilliaert, Rémi, et al., "Cloning and sequencing of a *Rhodothermus marinus* gene, bglA, coding for a thermostable β-glucanase and its expression in *Escherichia coli*," Eur. J. Biochem., 224(3):923-930, 1994.

Srisodsuk, Malee, et al., "*Trichoderma reesei* cellobiohydrolase I with an endoglucanase cellulose-binding domain: action on bacterial microcrystalline cel ulose," *Journal of Biotechnology*, 57:49-57, 1997.

Stahlberg, Jerry, et al., "A New Model for Enzymatic Hydrolysis of Celluloase Based on the Two-Domain Structure of Cellobiohydrolase I," *Bio/Technol.*, 9:286-290, 1991.

Strathern et al., eds. The Molecular Biology of the Yeast *Saccharomyces*, 1981.

Sulzenbacher, Gerlind, et al., "Structure of the Endoglucanase I from *Fusarium oxysporum*: Native, Cellobiose, and 3,4-Epoxybutyl β-D-Cellobioside-Inhibited Forms, at 2.3 Å Resolution," *Biochemistry*, 36:5902-5911, 1997.

Suurnäkki, A., et al., "*Trichoderma reesei* cellulases and their core domains in the hydrolysis and modification of chemical pulp," *Cellulose* 7:189-209, 2000.

Tanner, John J., et al., "Determinants of Enzyme Thermostability Observed in the Molecular Structure of *Thermus acquaticus* D-Glyceraldehyde-3-phosphate Dehydrogenase at 2.5 Å Resolution," *Biochemistry*, 35(8):2597-2609, 1996.

Teeri, Tuula T., et al., "Homologous domains in *Trichoderma reesei* cellulolytic enzymes: gene sequence and expression of cellobiohydrolase II," Gene, 51:43-52, 1987.

Teeri, Tuula T., "Crystalline cellulose degradation: new insight into the function of cellobiohydrolases," *TIBTECH*, vol. 15, pp. 160-167, 1997.

Teeri, T., T., Spec. Publ.—R. Soc. Chem., 246 (Recent Advances in Carbohydrate Bionginering), pp. 302-308, 1999.

Te'o, Valentino S. J., et al., "Codon optimization of xylanase gene xynB from the thermophilic bacterium *Dictyoglomus thermophilum* for expression in the filamentous fungus *Trichoderma reesei*," *FEMS Microbiology Letters*, 190:13-19, 2000.

Tomaz, Cândida T., et al., "Studies on the chromatographic fractionation of *Trichoderma reesei* cellulases by hydrophobic interaction," *J. Chromatography A*, 865:123-128, 1999.

Tomme, Peter, et al., "Studies of the cellulolytic system of *Trichoderma reesei* QM 9414. Analysis of domain function in two cellobiohydrolases by limited proteolysis," *Eur. J. Biochem.*, 170:575-581, 1988.

Tormo, José, et al., "Crystal structure of a bacterial family-III cellulose-binding domain: a general mechanism for attachment to cellulose," EMBO J. , vol. 15, No. 21, pp. 5739-5751, 1996.

Tyndall, R. M., "Improving the Softness and Surface Appearance of Cotton Fabrics and Garments by Treatment with Cellulase Enzymes," *Textile Chemist and Colorist*, 24(6):23-26, 1992.

Vallette, Francois, et al., "Construction of mutant and chimeric genes using the polymerase chain reaction," *Nucleic Acids Research*, vol. 17, No. 2, pp. 723-733, 1989.

van Hartingsveldt, Wim, et al., "Development of a homologous transformation system for *Aspergillus niger* based on the *pyrG* gene," *Mol. Gen. Genet.*, 206:71-75, 1987.

van Rensburg, Pierre, "Engineering Yeast for Efficient Cellulose Degradation," *Yeast*, 14:67-76, 1998.

van Tilbeurgh, Herman, et al., Separation of endo- and exo-type cellulases using a new affinity chromatography method, *FEBS*, vol. 169, No. 2, pp. 215-218, 1984.

Verhoeyen, Martine, et al., "Reshaping Human Antibodies: Grafting an Antilysozyme Activity," *Science*, vol. 239, pp. 1534-1536, 1986.

(56) References Cited

OTHER PUBLICATIONS

Ward, Michael, et al., "Use of *Aspergillus* overproducing mutants, cured for integrated plasmid, to overproduce heterologous proteins," *Appl. Microbiol. Biotechnol.*, vol. 39, pp. 738-743, 1993.

Watanabe, Kunihiko, et al., "Multiple proline substitutions cumulatively thermostabilize *Bacillus cereus* ATCC7064 oligo-1,6-glucosidase," *Eur. J. Biochem.*, 226:277-283, 1994.

Wells, James A., et al., "Cassette mutagenesis: an efficient method for generation of multiple mutations at defined sites," *Gene*, vol. 34, pp. 315-323, 1985.
Wood, Thomas M., etal., "Properties of cellulolytic enzyme systems," *Biochemical Society Transactions*, $611^{th}$ Meeting, Galway, vol. 13, pp. 407-410, 1985.
Wood, Thomas M., et al., "Methods for Measuring Cellulase Activities," *Methods in Enzymology*, vol. 160, No. 9, pp. 87-116, 1988.
Yelton, M. Melanie, et al, "Transformation of *Aspergillus nidulans* by using a *trpC* plasmid," *Proc. Natl. Acad. Sci.*, vol. 81, pp. 1470-1474, 1984.
Zeng, A.-P, et al., Microbial Conversion of Glycerol to 1,3-Propanediol: Recent Progress, *Fuels and Chemicals from Biomass*, pp. 264-279, 1997.
Zuber, H., "Temperature adaptation of lactate dehydrogenase Structural, functional and genetic aspects," *Biophysical Chemistry*, 29:171-179, 1988.
Ahn, J-H., et al. "Molecular Cloning and Characterization of Ce12 from the Fungus *Cochlibolus carbonum.*" *Biosci. Biotechnol. Biochem*. vol. 65, No. 6, pp. 1406-1411, 2001.
Becker, et al., "Engineering of a glycosidase Family 7 cellobiohydrolase to more Alkaline pH optimum: The pH behaviour of *Trichoderma reesei* Cel7A and its E22/A224H/L225V/T226A/D262G mutant," *Biochemical Journal*, V356:1 (May 15, 2001 pp. 19-30.
Cheng, C., et al. "Nucleotide sequence of the cellobiohydrolase gene from *Trichoderma viride.*" *Nucleic Acids Research*, vol. 18, No. 18, p. 5559, 1990.
Covert, S.F., et al. "Genomic Organizations of a Cellulase Gene Family in *Phanerochaete chrysosporium.*" *Curr. Genet.*, vol. 22, pp. 407-413, 1992.
Covert, S.F., et al. "Structure, Organization, and Transcription of a Cellobiohydrolase Gene Cluster from *Phanerochaete chtysosporium.*" *Appl. Environ. Microbiol.*, vol. 58, No. 7, pp. 2168-2175, Jul. 1992.
Gross, L.S., et al. "Changing the properties of *Hypocrea jecorina* Cel7A (*Trichoderma reesei* CBH1) by single amino acid mutations." *Biophys. J.*, vol. 82, No. part 2, p. 459a, Jan. 2002.
Search Reports for PCT and EP.

* cited by examiner

Figure 1: Amino Acid and Nucleic Acid Sequences of *Hypocrea jecorina* Cel7A

```
     GlnSerAlaCys ThrLeuGln SerGluThr HisProProLeu ThrTrpGln LysCysSer SerGlyGlyThr CysThrGln GlnThrGly SerValValIle.
  1  CAGTCGGCCT GCACTCTCCA ATCGGAGACT CACCCGCCTC TGACATGGCA AAATGCTCG TCTGGTGGCA CTTGCACTCA ACAGACAGGC TCCGTGGTCA

.IAspAlaAsn TrpArgTrp ThrHisAlaThr AsnSerSer ThrAsnCys TyrAspGlyAsn ThrTrpSer SerPheLeu CysProAspAsn GluThrCys.
 101 TCGACGCCAA CTGGCGCTGG ACTCACGCTA CGAACAGCAG CACGAACTGC TACGACGGAA ACACGTGGAG CTCGACCCTA TGTCCTGACA ACAGACCTG

.AlaLysAsn CysCysLeuAsp GlyAlaAla TyrAlaSer ThrTyrGlyVal ThrThrSer GlyAsnSer LeuSerIleGly PheValThr GlnSerAla.
 201 CGCGAAGAAC TGCTGTCTGG ACGGTGCCGC CTACGGTCC ACGTACGGAG TTACCACGAG CGGTAACAGC CTCTCCATTG GCTTTGTCAC CCAGTCTGCG

GlnLysAsnVal GlyAlaArg LeuTyrLeu MetAlaSerAsp ThrThrTyr GlnGluPhe ThrLeuLeuGly AsnGluPhe SerPheAsp ValAspValSer.
 301 CAGAAGAACG TTGGCGCTCG CCTTTACCTT ATGGCGAGCG ACACGACCTA CCAGGAATTC ACCCTGCTTG GCAACGAGTT CTCTTTCGAT GTTGATGTTT

.SGlnLeuPro CysGlyLeu AsnGlyAlaLeu TyrPheVal SerMetAsp AlaAspGlyGly ValSerLys TyrProThr AsnThrAlaGly AlaLysTyr.
 401 CGCAGCTGCC GTGCGGCTTG AACGGAGCTC TCTACTTCGT GTCCATGGAC GCGGATGGTG GCGTGAGCAA GTATCCCACC AACACCGCTG GCGCCAAGTA

.GlyThrGly TyrCysAspSer GlnCysPro ArgAspLeu LysPheIleAsn GlyGlnAla AsnValGlu GlyTrpGluPro SerSerAsn AsnAlaAsn.
 501 CGGCACGGGG TACTGTGACA GCCAGTGTCC CCGGGATCTG AAGTTCATCA ATGGCCAGGC CAACGTTGAG GGCTGGGAGC CGTCATCCAA CAACGCGAAC

ThrGlyIleGly GlyHisGly SerCysCys SerGluMetAsp IleTrpGlu AlaAsnSer IleSerGluAla LeuThrPro HisProCys ThrThrValGly.
 601 ACGGGCATTG GAGGACACGG AAGCTGCTGC TCTGAGATGG ATATCTGGGA GGCCAACTCC ATCTCCGAGG CTCTTACCCC CCACCCTTGC ACGACTGTCG

.GlnGluIle CysGluGly AspGlyCysGly GlyThrTyr SerAspAsn ArgTyrGlyGly ThrCysAsp ProAspGly CysAspTrpAsn ProTyrArg.
 701 GCCAGGAGAT CTGCGAGGGT GATGGGTGCG GCGGAACTTA CTCCGATAAC AGATATGGCG GCACTTGCGA TCCCGATGGC TGCGACTGGA ACCCATACCG

.LeuGlyAsn ThrSerPheTyr GlyProGly SerSerPhe ThrLeuAspThr ThrLysLys LeuThrVal ValThrGlnPhe GluThrSer GlyAlaIle.
 801 CCTGGGCAAC ACCAGCTTCT ACGGCCCTGG CTCAAGCTTC ACCCTCGATA CCACCAAGAA ATTGACCGTT GTCACCCAGT TCGAGACGTC GGGTGCCATC

AsnArgTyrTyr ValGlnAsn GlyValThr PheGlnGlnPro AsnAlaGlu LeuGlySer TyrSerGlyAsn LeuLeuAsn AspAspTyr CysThrAlaGlu.
 901 AACCGATACT ATGTCCAGAA TGGCGTCACT TTCCAGCAGC CCAACGCCGA GCTTGGTAGT TACTCTGGCA ACAGACTCAA CGATGATTAC TGCACAGCTG

.GGluAlaGlu PheGlyGly SerSerPheSer AspLysGly GlnLeuThr GlnPheLysLys AlaThrSer GlyGlyMet ValLeuValMet SerLeuTrp.
1001 AGGAGGCAGA ATTCGGCGGA TCCTCTTTCT CAGACAAGGG CGGCCTGACT CAGTTCAAGA AGGCTACCTC TGGCGGCATG GTTCTGGTCA TGAGTCTGTG

.AspAspTyr TyrAlaAsnMet LeuTrpLeu AspSerThr TyrProThrAsn GluThrSer SerThrPro GlyAlaValArg GlySerCys SerThrSer.
1101 GGATGATTAC TACGCCAACA TGCTGTGGCT GGACTCCACC TACCCGACAA ACGAGACCTC CTCCACACCC GGTGCCGTGC GGGAAGCTG CTCCACCAGC

SerGlyValPro AlaGlnVal GluSerGln SerProAsnAla LysValThr PheSerAsn IleLysPheGly ProIleGly SerThrGly AsnProSerGly.
1201 TCCGGTGTCC CTGCTCAGGT CGAATCTCAG TCTCCCAACG CCAAGGTCAC CTTCTCCAAC ATCAAGTTCG GACCCATTGG CAGCACCGGC AACCCTAGCG

.GGlyAsnPro ProGlyGly AsnProProGly ThrThrThr ThrArgArg ProAlaThrThr ThrGlySer SerProGly ProThrGlnSer HisTyrGly.
1301 GCGGCAACCC TCCCGGCGGA AACCCGCCTG GCACCACCAC CACCCGCCGC CCAGCCACTA CCACTGGAAG CTCTCCCGGA CCTACCCAGT CTCACTACGG

.GlnCysGly GlyIleGlyTyr SerGlyPro ThrValCys AlaSerGlyThr ThrCysGln ValLeuAsn ProTyrTyrSer GlnCysLeu
1401 CCAGTGCGGC GGTATTGGCT ACAGCGGCCC CACCGTCTGC GCCAGCGGCA CAACTTGCCA GGTCCTGAAC CCTTACTACT CTCAGTGCCT G
```

_Hypocrea jecorina_ Cel7A

497 amino acids 1-431 in the catalytic module 432-461 in the linker region 462-497 in the cellulose binding module 12 disulfide bonds--10 in the catalytic module E212 and E217 are the active site residues

Figure 3

C-α trace of the crystal structures from the catalytic domains of four Cel7 homologues aligned and overlaid as described.

Red = α-helix, Cyan = disordered, Blue/Green = turns

Figure 5A: Amino Acid (SEQ ID NO: 8) and Nucleic Acid (SEQ ID NO: 7) Sequence of *Hypocrea jecorina* Cel7A mutant L225F

```
       GlnSerAlaCys ThrLeuGln SerGluThr HisProProLeu ThrTrpGln LysCysSer SerGlyGlyThr CysThrGln GlnThrGly SerValValIle·
   1   CAGTCGGCCT GCACTCTCCA ATCGGAGACT CACCCCCCTC TGACATGGCA GAATGCTCG TCTGGTGGCA CTTGCACTCA ACAGACCGGC TCCGTGGTCA

·IAspAlaAsn TrpArgTrp ThrHisAlaThr AsnSerSer ThrAsnCys TyrAspGlyAsn ThrTrpSer SerThrLeu CysProAspAsn GluThrCys·
 101   TCGACGCCAA CTGGCGCTGG ACTCACGCTA CGAACAGCAG CACGAACTGC TACGATGGCA ACACTTGGAG CTCGACCCTA TGTCCTGACA ACGAGACCTG

·AlaLysAsn CysCysLeuAsp GlyAlaAla TyrAlaSer ThrTyrGlyVal ThrThrSer GlyAsnSer LeuSerIleGly PheValThr GlnSerAla
 201   CGGAAGAAC TGCTGTCTGG ACGGTGCCGC CTACGCGTCC ACGTACGGAG TTACCACGAG CGGTAACAGC CTCTCCATTG GCTTTGTCAC CCAGTCTGCG

GlnLysAsnVal GlyAlaArg LeuTyrLeu MetAlaSerAsp ThrThrTyr GlnGluPhe ThrLeuLeuGly AsnGluAsp SerPheAsp ValAspValSer·
 301   CAGAAGAACG TTGGCGCTCG CCTTTACCTT ATGGCGAGCG ACACGACCTA CCAGGAATTC ACCCTGCTTG GCAACGAGTT CCTTTTCGAT GTTGATGTTT

·SGlnLeuPro CysGlyLeu AsnGlyAlaLeu TyrPheVal SerMetAsp AlaAspGlyGly ValSerLys TyrProThr AsnThrAlaGly AlaLysTyr·
 401   CGCAGCTGCC GTGCGGTCTG AACGGAGCTC TCTACTTCGT GTCCATGGAC GCGGATGGTG GCGTGAGCAA GTATCCCACC AACACCGCTG GCGCCAAGTA

·GlyThrGly TyrCysAspSer GlnCysPro ArgAspLeu LysPheIleAsn GlyGlnAla AsnValGlu GlyTrpGluPro SerSerAsn AsnAlaAsn·
 501   CGGCACGGG TACTGTGACA GCCAGTGTCC CCGGGATCTG AAGTTCATCA ATGGCCAGGC CAACGTTGAG GGCTGGGAGC CGTCATCCAA CAACGCGAAC

ThrGlyIleGly GlyHisGly SerCysCys SerGluMetAsp IleTrpGlu AlaAsnSer IleSerGluAla PheThrPro HisProCys ThrThrValGly·
 601   ACGGGCATTG GAGGACACGG AAGCTGCTGC TCTGAGATGG ATATCTGGGA GGCCAACTCC ATCTCCGAGG CTTTTACCCC CCACCCTTGC ACGACTGTCG

·GGlnGluIle CysGluGly AspGlyCysGly GlyThrTyr SerAspAsn ArgTyrGlyGly ThrCysAsp ProAspGly CysAspTrpAsn ProTyrArg·
 701   GCCAGGAGAT CTGCGAGGGT GATGGGTGCG GCGGAACTTA CTCCGATAAC AGATATGGCG GCACTTGCGA TCCCGATGGC TGCGACTGGA ACCCATACCG

·LeuGlyAsn ThrSerPheTyr GlyProGly SerSerPhe ThrLeuAspThr ThrLysLys LeuThrVal ValThrGlnPhe GluThrSer GlyAlaIle·
 801   CCTGGGCAAC ACCAGCTTCT ACGGCCCTGG CTCAAGCTTC ACCCTCGATA CCACCAAGAA ATTGACCGTT GTCACCCAGT TCGAGACGTC GGGTGCCATC

AsnArgTyrTyr ValGlnAsn GlyValThr PheGlnGlnPro AsnAlaGlu LeuGlySer TyrSerGlyAsn GluLeuAsn AspAspTyr CysThrAlaGlu·
 901   AACCGATACT ATGTCCAGAA TGGCGTCACT TTCCAGCAGC CCAACGCCGA GCTTGGTAGT TACTCTGGAA ACGAGCTCAA CGATGATTAC TGCACAGCTG

·GGluAlaGlu PheGlyGly SerSerPheSer AspLysGly GlnProThr GlnPheLysLys AlaThrSer GlyGlyMet ValLeuValMet SerLeuTrp·
1001   AGGAGGCAGA ATTCGGCGGA TCCTCTTTCT CAGACAAGGG CGGCCTGACT CAGTTCAAGA AGGCTACCTC TGGCGGCATG GTTCTGGTCA TGAGTCTGTG

·AspAspTyr TyrAlaAsnMet LeuTrpLeu AspSerThr TyrProThrAsn GluThrSer SerThrPro GlyAlaValArg GlySerCys SerThrSer
1101   GGATGATTAC TACGCCAACA TGCTCTGGCT GGACTCCACC TACCCGACAA ACGAGACCTC CTCCACACCC GGTGCCGTGC GCGGAAGCTG CTCCACCAGC

SerGlyValPro AlaGlnVal GluSerGln SerProAsnAla LysValThr PheSerAsn IleLysPheGly ProIleGly SerProGly AsnProSerGly·
1201   TCCGGTGTCC CTGCTCAGGT CGAATCTCAG TCTCCCAACG CCAAGGTCAC CTTCTCCAAC ATCAAGTTCG GACCCATTGG CAGCACCGGC AACCCTAGCG

·GGlyAsnPro ProGlyGly AsnProProGly GlyAsnPro ThrThrThr ThrArgArg ProAlaThrThr ThrGlySer SerProGly ProThrGlnSer HisTyrGly·
1301   GCGGCAACCC TCCCGGCGGA AACCCGCCTG GCGGCAACCC CACCACCACC ACCAGGCGCC CCAGCCACTA CCACTGGAAG CTCTCCCGGA CCTACCCAGT CTCACTACGG

·GlnCysGly GlyIleGlyTyr SerGlyPro ThrValCys AlaSerGlyThr ThrCysGln ValLeuAsn ProTyrTyrSer GlnCysLeu
1401   CCAGTGCGGC GGTATTGGCT ACAGCGGCCC CACCGTTTGC GCCAGCGGCA CAACTTGCCA GGTCCTGAAC CCTTACTACT CCCAGTGCCT G
```

Figure 5B: Amino Acid (SEQ ID NO: 10) and Nucleic Acid (SEQ ID NO: 9) Sequence for *Hypocrea jecorina* Cel7A mutant S113D

```
   1  GlnSerAlaCys ThrLeuGln SerGluThr HisProProLeu ThrTrpGln LysCysSer SerGlyGlyThr CysThrGln GlnThrGly SerValVallle·
      CAGTCGGCCT GCACTCTCCA ATCGGAGACT CACCCGCCTC TGACATGGCA GAAATGCTCG TCTGGTGGCA CTTGCACTCA ACAGACCAGG TCCGTGGTCA 101  ·IAspAlaAsn TrpArgTyr ThrHisAlaThr AsnSerCys ThrAsnCys TyrAspGlyAsn ThrTrpSer SerThrLeu CysProAspAsn GluThrCys·
      TCGACGCCAA CTGGCGCTGG ACTCACGCTA CGAACAGCAG CACGAACTGC TACGATGGCA ACACTTGGAG CTCGACCCTA TGTCCTGACA ACGAGACCTG 201  ·AlaLysAsn CysCysLeuAsp GlyAlaAla TyrAlaSer ThrTyrGlyVal ThrThrSer GlyAsnSer LeuSerIleGly PheValThr GlnSerAla·
      CGCGAAGAAC TGCTGTCTCG ACGGTGCCGC CTACGCGTCC AGTACGGAG TTACCACGAG CGGTAACAGC CTCTCCATTG GCTTTGTCAC CCAGTCGCG 301  GlnLysAsnVal GlyAlaArg LeuTyrLeu MetAlaAspAsp ThrThrTyr GlnGluPhe ThrLeuLeuGly AsnGluPhe SerPheAsp ValAspValSer·
      CAGAAGAACG TTGGCGCTCG CCTTTACCTT ATGGCGGATG ACACGACCTA CCAGGAATTC ACCCTGCTTG GCAACGAGTT CTCTTTCGAT GTTGATGTT 401  ·SGlnLeuPro CysGlyLeu AsnGlyAlaLeu TyrPheVal SerMetAsp AlaAspGlyGly ValSerLys TyrProThr AsnThrAlaGly AlaLysTyr·
      CCGCAGCTGCC GTGGGGCTTG AACGGAGCTC TCTACTTCGT GTCCATGGAC GCGGATGGTG GCGTGAGCAA GTATCCCACC AACACCGCTG GCGCCAAGTA 501  ·GlyThrGly TyrCysAspSer GlnCysPro ArgAspLeu LysPheIleAsn GlyGlnAla AsnValGlu GlyTrpGluPro SerSerAsn AsnAlaAsn·
      CGGCACGGGG TACTGTGACA GCCAGTGTCC CCGCGATCTG AAGTTCATCA ATGGCCAGGC CAACGTTGAG GGCTGGGAGC CGTCATCCAA CAACGCGAAC 601  ThrGlyIleGly GlyHisGly SerCysCys SerGluMetAsp IleTrpGlu AlaAsnSer IleSerGluAla LeuThrPro HisProCys ThrThrValGly·
      ACGGGCATTG GAGGACACGG AAGCTGCTGC TCTGAGATGG ATATCTGGGA GGCCAACTCC ATCTCCGAGG CTCTTACCCC CCACCCTTGC ACGACTGTCG 701  ·GGlnGluIle CysGluGly AspGlyCysGly GlyThrTyr SerAspAsn ArgTyrGlyGly ThrCysAsp ProAspGly CysAspTrpAsn ProTyrArg·
      GCCAGGAGAT CTGCGAGGG GATGGGTGC GCGGAACTTA CTCCGATAAC AGATATGGCG GCACTTGCGA TCCCGATGGC TGCGACTGGA ACCCATACCG 801  ·LeuGlyAsn ThrSerPheTyr GlyProGly SerSerPhe ThrLeuAspThr ThrLysLys LeuThrVal ValThrGlnPhe GluThrSer GlyAlaIle·
      CCTGGGCAAC ACCAGCTTCT ACGGCCCTGG CTCAAGCTTT ACCCTCGATA CGACCAAGAA ATTGACCGTT GTCACCCAGT TCGAGACGTC GGGTGCCATC 901  AsnArgTyrTyr ValGlnAsn GlyValThr PheGlnGlnPro AsnAlaGlu LeuGlySer TyrSerGlyAsn GluLeuAsn AspAspTyr CysThrAlaGlu·
      AACCGATACT ATGTCCAGAA TGGCGTCACT TTCCAGCAGC CCAACGCCGA GCTTGGTAGT TACTCTGGCA ACGAGCTCAA CGATGATTAC TGCACAGCTG 1001  ·GGluAlaGlu PheGlyGly SerSerPheSer AspLysGly GlyLeuThr GlnPheLysLys AlaThrGly GlyGlyMet ValLeuValMet SerLeuTrp·
      AGGAGGCAGA ATTCGGCGGA TCCTCTTTCT CAGACAAAGG CGGCCTGACT CAGTTCAAGA AGGCTACCTC TGGCGGCATG GTTCTGGTCA TGAGTCTGTG 1101  ·AspAspTyr TyrAlaAsnMet LeuTrpLeu AspSerThr TyrProThrAsn GluThrSer SerThrPro GlyAlaValArg GlySerCys SerThrSer·
      GGATGATTAC TACGCCAACA TGCTCTGGCT CGACTCCACC TACCCGACAA ACGAGACCTC CTCCACACCC GGTGCCGTGC GGGGAAGCTG CTCCACCAGC 1201  SerGlyValPro AlaGlnVal GluSerGln SerProAsnAla LysValThr PheSerAsn IleLysPheGly ProlleGly SerThrGly AsnProSerGly·
      TCCGGTGTCC CTGCTCAGGT CGAATCTCAG TCTCCCAACG CCAAGGTCAC ATTCAAGTCG GACCCATTGG CAGCACCGGC AACCCTAGCC 1301  ·GGlyAsnPro AlaGlnIleVal GluSerGln SerProAsnAla LysValThr ThrArgArg ThrAlaThrThr ProAlaThr ProProGly SerProSerGly·
      GCGCAACCC TCCCGGCGGA AACCCGCTG GCCAGCGGCC CACGGTCGC GCACCACAC CCGCCCACTA GACCATTCG CAGCACCGGC AACCCTAGCC 1401  ·GlnCysGly GlyIleGlyTyr SerGlyPro ThrValCys AlaSerGlyThr ThrCysGln ValLeuAsn ProTyrTyrSer GlnCysLeu
      CCAGTGCGGC GGTATTGGCT ACAGCGGCCC CACGGTCTGC GCCAGCGGCA CAACTTGCCA GGTCTGAAC CCTACTACT CTCAGTGCCT G
```

Figure 5C: Amino Acid (SEQ ID NO: 12) and Nucleic Acid (SEQ ID NO: 11) Sequence for *Hypocrea jecorina* Cel7A mutant A77D

```
   1  GlnSerAlaCys ThrLeuGln SerGluThr HisProPro Leu ThrTrpGln LysCysSer SerGlyGlyThr CysThrGln GlnThrGly SerValValIle·
      CAGTCGGCCT GCACTCTCCA ATCGGAGACT CACCCCCCTC TGACATGGCA GAATGCTCC TCTGGTGGCA CTTGCACTCA ACAGACAGGC TCCGTGGTCA

101  ·IAspAlaAsn TrpArgTrp ThrHisAlaThr AsnSerSer ThrAsnCys TyrAspGlyAsn ThrTrpSer SerThrLeu CysProAspAsn GluThrCys·
      TCGACGCCAA CTGGCGCTGG ACTCACGCTA CGAACAGCAG ACGAACTGC TACGATGGCA ACACTTGGAG CTCGACCCTA TGTCCTGACA ACGAGACCTG

201  ·AlaLysAsn CysCysLeuAsp GlyAlaAsp TyrAlaSer ThrTyrGlyVal ThrThrSer GlyAsnSer LeuSerIleGly PheValThr GlnSerAla
      CGCTAAGAAC TGCTGTCTGG ACGGTGCCGA CTACGCGTCC ACGTACGGAG TTACCACGAG CGGTAACAGC CTTTCCATTG GCTTTGTCAC CCAGTCTGCG

301  GlnLysAsnVal GlyAlaArg LeuTyrLeu MetAlaSerAsp ThrThrTyr GlnGluPhe ThrLeuLeuLeu GlyAsnGluPhe SerPheAsp ValAspValSer·
      CAGAAGAACG TTGGCGCTCG CCTTTACCTT ATGGCCAGCG ACACGACCTA CCAGGAATTC ACCCTGCTTG GCAACGAGTT CTCTTTCGAT GTTGATGTTT

401  ·SGlnLeuPro CysGlyLeu AsnGlyAlaLeu TyrPheVal SerMetAsp AlaAspGlyGly ValSerLys TyrProThr AsnThrAlaGly AlaLysTyr·
      CGCAGCTGCC GTGCGGCTTG AACGGAGCTC TCTACTTCGT GTCCATGGAC GCGGATGGTG GCGTGAGCAA GTATCCCACC AACACCGCTG GCGCCAAGTA

501  ·GlyThrGly TyrCysAspSer GlnCysPro ArgAspLeu LysPheIleAsn GlyGlnAla AsnValGlu GlyTrpGluPro SerSerAsn AsnAlaAsn·
      CGGAACGGGG TACTGTGACA GCCAGTGTCC CCGGGATCTG AAGTTCATCA ATGGCCAGGC CAACGTTGAG GGCTGGGAGC CGTCATCCAA CAACGCGAAC

601  ThrGlyIleGly GlyHisGly SerCysCys SerGluMetAsp IleTrpGlu AlaAsnSer IleSerGluAla LeuThrPro HisProCys ThrThrValGly·
      ACGGGCATTG GAGGACACGG AAGCTGCTGC TCTGAGATGG ATATCTGGGA GGCCAACTCC ATCTCCGAGG CTCTTACCCC CCACCCTTGC ACGACTGTCG

701  ·GGlnGluIle CysGluGly AspGlyCysGly GlyThrTyr SerAspAsn ArgTyrGlyGly ThrCysAsp ProAspGly CysAspTrpAsn ProTyrArg·
      GCCAAGAGAT CTGCGAGGGT GATGGGTGCG GCGGAACTTA CTCCGATAAC AGATATGGCC GCACTTGCGA TCCCGATGGC TGCGACTGGA ACCCATACCG

801  ·LeuGlyAsn ThrSerPheTyr GlyProGly SerSerPhe ThrLeuAspThr ThrLysLys LeuThrVal ValThrGlnPhe GluThrSer GlyAlaIle·
      CCTGGGCAAC ACCAGCTTCT ACGGCCCTGG CTCAAGCTTT ACCCTCGATA CCACCAAGAA ATTGACCGTT GTCACCCAGT TCGAGACCTC GGGTGCCATC

901  AsnArgTyrTyr ValGlnAsn GlyValThr PheGlnGlnPro AsnAlaGlu LeuGlySer TyrSerGlyAsn GluLeuAsn AspAspTyr CysThrAlaGlu·
      AACCGATACT ATGTCCAGAA TGGCGTCACT TTCCAGCAGC CCAACGCCGA GCTTGGTAGT TACTCTGGCA ACGAGCTCAA CGATGATTAC TGCACAGCTG

1001  ·GGlyAlaGlu PheGlyGly SerSerPheSer AspLysGly GlyLeuThr GlnPheLysLys AlaThrSer AlaGlyMet ValLeuValMet SerLeuTrp·
      AGGGAGCCGA ATTCGGCGGA TCCTCTTTCT CAGACAAGGG CGGCCTGACT CAGTTCAAGA AGGCTACCTC TGGCGGCATG GTTCTGGTCA TGAGTCTGTG

1101  ·AspAspTyr TyrAlaAsnMet LeuTrpLeu AspSerThr TyrProThrAsn GluThrSer SerThrPro GlyAlaValArg GlySerCys SerThrSer·
      GGATGATTAC TACGCCAACA TGCTCTGGCT GGACTCCACC TACCCGACAA ACGAGACCTC CTCCACACCC GGTGCCGTGC GCGGAAGCTG CTCCACCAGC

1201  ·SerGlyValPro AlaGlnVal GluSerGln SerProAsnAla LysValThr PheSerAsn IleLysPheGly ProIleGly SerThrGly AsnProSerGly·
      TCCGGTGTCC CTGCTCAGGT CGAATCTCAG TCTCCCAACG CCAAGGTCAC CTTCTCCAAC ATCAAGTTCG GACCCATTGG CAGCACCGGC AACCCTAGCG

1301  ·GGlyAsnPro ProGlyGly AsnProProGly ThrThrThr ThrArgArg ProAlaThrThr ThrGlySer ProProGly ProThrGlnSer HisTyrGly·
      GCGGCAACCC TCCCGGCGGA AACCCGCCTG GCACCACCAC CACCCGCCGC CCAGCCACTA CCACTGGAAG CCCTCCCGGA CCTACCCAGT CTCACTACGG

1401  ·GlnCysGly GlyIleGlyTyr SerGlyPro ThrValCys AlaSerGlyThr ThrCysGln ValLeuAsn ProTyrTyrSer GlnCysLeu
      CCAGTGCGGC GGTATTGGCT ACAGCGGGCC CACGGTTTGC GCCAGCGGAA CAACTTGCCA GGTCCTGAAC CCTTACTACT CTCAGTGCCT G
```

Figure 5D: Amino Acid (SEQ ID NO: 14) and Nucleic Acid (SEQ ID NO: 13) Sequences of *Hypocrea jecorina* Cel7A mutant L288F

```
   1  GlnSerAlaCys ThrLeuGln SerGluThr HisProProLeu ThrTrpGln LysCysSer SerGlyGlyThr CysThrGln GlnThrGly SerValValIle·
      CAGTCGGCCT GCACTCTCCA ATCGGAGACT CACCCGCCTC TGACATGGCA GAAATGCTCG TCTGGTGGCA CTTGCACTCA ACAGACAGGC TCCGTGGTCA

101  ·IAspAlaAsn TrpArgTrp ThrHisAlaThr AsnSerSer ThrAsnCys TyrAspGlyAsn ThrTrpSer SerThrLeu CysProAspAsn GluThrCys·
      TCGACGCCAA CTGGCGCTGG ACTCACGCTA CGAACAGCAG TACGAACTGC TACGATGGCA ACACTTGGCA CTCGACCCTA TGTCCTGACA ACGAGACCTG

201  ·AlaLysAsn CysCysLeuAsp TyrAlaSer ThrTyrGlyVal ThrThrSer GlyAsnSer LeuSerIleGly PheValThr GlnSerAla
      CGCGAAGAAC TGCTGTCTGG ACGGTGCCGC CTACGGTGTC ACGACATCC GGTAACAGC CTCTCCATTG GCTTTGTCAC CCAGTCTGCG

301  GlnLysAsnVal GlyAlaArg LeuTyrLeu MetAlaSerAsp ThrThrTyr GlnGluPhe ThrLeuLeuGly AsnGluPhe SerPheAsp ValAspValSer·
      CAGAAGAACG TTGGCGCTCG CCTTTACCTT ATGGCGAGCG ACACGACCTA CCAGGAATTC ACCCTGCTTG GCAACGAGTT CTCTTTCGAT GTTGATGTTT

401  ·SGlnGluPro CysGlyLeu AsnGlyAlaLeu TyrPheVal SerMetGly AlaAspGlyGly ValSerLys TyrProThr AsnThrAlaGly AlaLysTyr·
      CGCAGGAGCC GTGCGGCTTG AACGGAGCTC TCTACTTCGT GTCCATGGAC GCGGATGGTG GCGTGAGCAA GTATCCCACC AACACCGCTG GCGCCAAGTA

501  ·GlyThrGly TyrCysAspSer GlnCysPro ArgAspLeu LysPheIleAsn GlyGlnAla AsnValGlu GlyTrpGluPro SerSerAsn AsnAlaAsn
      CGGCACGGG TACTGTGACA GCCAGTGTCC CCGCGATCTG AAGTTCATCA ATGGCCAGGC CAACGTTGAG GGCTGGGAGC CGTCATCCAA CAACGCGAAC

601  ThrGlyIleGly GlyHisGly SerCysCys SerGluMetAsp IleTrpGlu AlaAsnSer IleSerGluAla LeuThrPro HisProCys ThrThrValGly·
      ACGGGCATTG GAGGACACGG AAGCTGCTGC TCTGAGATGG ATATCTGGGA GGCCAACTCC ATCTCCGAGG CTCTTACCCC CCACCCTTGC ACGACTGTCG

701  ·GGlnGluIle CysGluGly AspGlyCysGly GlyThrTyr SerAspAsn ArgTyrGlyGly GlyThrCys SerAspPhe ProAspGly CysAspTrpArg·
      GCCAAGAGAT CTGCGAGGGT GATGGGTGC GGGAACTTA CTCCGATAAC AGATATGGCG GTGGCACCTG CTCCGATTTC CCCGACTGGA ACCCATACCG

801  ·LeuGlyAsn ThrSerPheTyr GlyProGly SerSerPhe ThrLeuAspThr ThrLysLys PheThrVal ValThrGlnPhe GluThrSer GlyAlaIle
      CCTGGGCAAC ACCAGTTCT ACGGCCCTGG CTCAAGCTTC ACCCTCGATA CCACCAAGAA ATTCACCGTT GTCACCCAGT TCGAGACGTC GGGTGCCATC

901  AsnArgTyrTyr ValGlnAsn GlyValThr PheGlnGlnPro AsnAlaGlu LeuGlySer TyrSerGlyAsn GluLeuAsn AspAspTyr CysThrAlaGlu·
      AACCGATACT ATGTCCAGAA TGGGGTCACT TTCCAGCAGC CCAACCCCGA GCTTGGTAGT TACTCTGGCA ACGAGCTCAA CGATGATTAC TGCACAGCTG

1001  ·GGluAlaGlu PheGlyGly SerSerPheSer AspLysLys GlyLeuThr GlnPheLysLys AlaThrSer GlyGlyMet ValLeuValMet SerLeuTrp·
      AGGAAGCAGA ATTCGGCGGA TCCTCTTTCT CAGACAAGG CGGCTGACT CAGTTCAAGA AGGCTACCTC TGGCGGCATG GTTCTGGTCA TGAGTCTGTG

1101  ·AspAspTyr TyrAlaAsnMet LeuTrpLeu AspSerThr TyrProThrAsn GluThrSer SerThrPro GlyAlaValArg GlySerCys SerThrSer
      GGATGATTAC TACGCCAACA TGCTGTGGCT GGACTCCACC TACCCGACAA ACGAGACCTC CTCCACACCC GGTGCCGTGC GCGGAAGCTG CTCCACCAGC

1201  SerGlyValPro AlaGlnVal GluSerGln SerProAsnAla LysValThr PheSerAsn IleLysPheGly ProIleGly SerThrGly AsnProSerGly·
      TCCGGTGTCC CTGCTCAGGT CGAATCTCAG TCTCCCAACG CCAAGGTCAC CTTCTCCAAC ATCAAGTTCG GACCCATTGG CAGCACCGGC AACCCTAGCG

1301  ·GGlyAsnPro ProGlyGly AsnProProGly ThrThrThr ThrArgArg ProAlaThrThr ThrGlySer SerProGly ProThrGlnSer HisTyrGly·
      GCGGCAACCC TCCCGGCGGA AACCCCCCTG GCACCACCAC CACCCGCCGC CCAGCCACTA CCACTGGAAG CTCTCCCGGA CCTACCCAGT CTCACTACGG

1401  ·GlnCysGly GlyIleGlyTyr SerGlyPro ThrValCys AlaSerGlyThr ThrCysGln ValLeuAsn ProTyrTyrSer GlnCysLeu
      CCAGTGCGGC GGTATTGGCT ACAGCGGCCC CACGGTCTGC GCCAGCGGCA CAACTTGCCA GGTCCTGAAC CCTTACTACT CTCAGTGCCT G
```

Figure 5E: Amino Acid (SEQ ID NO: 16) and Nucleic Acid (SEQ ID NO: 15) Sequence of *Hypocrea jecorina* Cel7A mutant A299E

```
         GlnSerAlaCys ThrLeuGln SerGluThr HisProProLeu ThrTrpGln LysCysSer SerGlyGlyThr CysThrGln GlnThrGly SerValValIle·
   1     CAGTCGGCCT GCACTCTCCA ATCGGAGACT CACCCGCCTC TGACATGGCA GAATGCTCG TCTGGTGGCA CTTGCACTCA ACAGACAGGC TCCGTGGTCA

·IAspAlaAsn TrpArgTrp ThrHisAlaThr AsnSerSer TyrAspGlyAsn ThrTrpSer SerThrLeu CysProAspAsn GluThrCys·
  101    TCGACGCCAA CTGGCGCTGG ACTCACGCTA CGAACAGCAG TACGATGGCA ACACTTGGAG CTCGACCCTA TGTCCTGACA ACGAGACCTG

·AlaLysAsn CysCysLeuAsp GlyAlaAla TyrAlaSer ThrTyrGlyVal ThrThrSer GlyAsnSer LeuSerIleGly PheValThr GlnSerAla
  201    CGCGAAGAAC TGCTGTCTGG ACGGTGCCGC CTACGCGTCC ACGTACGGAG TTACCACGAG CGGTAACAGC CTCTCCATTG GCTTTGTCAC CCAGTCTGCG

GlnLysAsnVal GlyAlaArg LeuTyrLeu MetAlaSerAsp ThrTyrTyr GlnGluPhe ThrLeuLeuGly AsnGluPhe SerPheAsp ValAspValSer·
  301    CAGAAGAACG TTGGCGCTCG CCTTTACCTT ATGGCGAGCG ACACGACCTA CCAGGAATTC ACCCTGCTTG GCAACGAGTT CTCTTTCGAT GTTGATGTTT

·SGlnLeuPro CysGlyLeu AsnGlyAlaLeu TyrPheVal SerMetAsp AlaAspGlyGly ValSerLys TyrProThr AsnThrAlaGly AlaLysTyr·
  401    CGCAGCTGCC GTGCGGCTTG AACGGAGCTC TCTACTTCGT GTCCATGGAC GCCGATGGCG GCGTAGCAA GTATCCCACC AACACCGCTG GCGCAAGTA

·GlyThrGly TyrCysAspSer GlnCysPro ArgAspLeu LysPheIleAsn GlyGlnAla AsnValGlu GlyTrpGluPro SerSerAsn AsnAlaAsn
  501    CGGCACGGGG TACTGTGACA GCCAGTGTCC CCGGGATCTG AAGTTCATCA ATGGCCAGGC CAACGTTGAG GGCTGGGAGC CGTCATCCAA CAACGCCAAC

ThrGlyIleGly GlyHisGly SerCysCys SerGluMetAsp IleTrpGlu AlaAsnSer IleSerGluAla LeuThrPro HisProCys ThrThrValGly·
  601    ACCGGCATTG GAGGACACGG AAGCTGCTGC TCTGAGATGG ATATCTGGGA GGCCAACTCC ATCTCCGAGG CTCTTACCCC CCACCCTTGC ACGACTGTCG

·GGlnGluIle CysGluGlyGly AspGlyCysGly GlyThrTyr SerAspAsn ArgTyrGlyGly ThrCysAspLys CysAspAspSer TyrArg·
  701    GCCAGGAGAT CTGCGAGGGT GATGGGTGCG GCGGAACTTA CTCCGATAAC AGATATGGCG GCACTTGCGA TAAGTGCGGA TCCGACTACGG ACCCATACCG

·LeuGlyAsn ThrSerPheTyr GlyProGly SerSerPhe ThrLeuAspPhe ThrLysLys LeuThrVal ValThrGlnPhe GluThrSer GlyIleIle
  801    CCTGGGCAAC ACCAGCTTCT ACGGCCCTGG CTCAAGCTTT ACCCTCGATA CCAAGAAGAA ATTGACCGTT GTCACCCAGT TCGAGACGTC GGGTGAGATC

AsnArgTyrTyr ValGlnAsn GlyValThr PheGlnGlnPro AsnAlaGlu LeuGlySer TyrSerGlyAsn GluLeuAsn AspAspTyr CysThrAlaGlu·
  901    AACCGATACT ATGTCCAGAA TGGCGTCACT TTCCAGCAGC CCAACGCCGA GCTTGGTAGT TACTCCGGCA ACGAGCTCAA CGATGATTAC TGCACAGCTG

·GGluAlaGlu PheGlyGly SerSerPheSer AspLysGly GlyLeuThr GlnPheLysLys AlaThrSer GlyGlyMet ValLeuValMet SerLeuTrp·
 1001    AGGAGGCAGA ATTCGGCGGA TCCTCTTTCT CAGACAAGGG CGGCCTGACT CAGTTCAAGA AGGCTACCTC TGGCGGCATG GTTCTGGTCA TGAGTCTGTG

·AspAspTyr TyrAlaAsnMet LeuTrpLeu AspSerThr TyrProThrAsn GluThrSer SerThrPro GlyAlaValArg GlySerCys SerThrSer
 1101    GGATGATTAC TACGCCAACA TGCTGTGGCT GGACTCCACC TACCCGACAA CCGAGACCTC CTCCACACCC GGGGCCGTGC GGGGAAGCTG CTCCACCAGC

·SerGlyValPro AlaGlnVal GluSerGln SerProAsnAla LysValThr PheSerAsn IleLysPheGly ProIleGly SerProGly AsnProSerGly·
 1201    TCCGGTGTCC CTGCTCAGGT CGAATCTCAG TCTCCCAACG CCAAGGTCAC CTTCTCCAAC ATCAAGTTCG GACCCATTGG CAGCACCGGC AACCCTAGCG

·GGlyAsnPro ProGlyGly AsnProProGly ThrThrThr ThrArgArg ProAlaThrThr ThrGlySer SerProGly ProThrGlnSer HisTyrGly·
 1301    GCGGCAACCC TCCCGGCGGA AACCCGCCTG GCACCACCAC CACCCGCCGC CCAGCCACTA CCACCGGAAG CTCCCCCGGA CCTACCCAGT CTCACTACGG

·GlnCysGly GlyIleGlyTyr SerGlyPro ThrValCys AlaSerGlyThr ThrCysGln ValLeuAsn ProTyrTyrSer GlnCysLeu
 1401    CCAGTGCGGC GGTATTGGCT ACAGCGGCCC CACCGTTTGC GCCAGCGGCA CAACTTGCCA GGTCCTGAAC CCTTACTACT CTCAGTGCCT G
```

Figure 5F: Amino Acid (SEQ ID NO: 18) and Nucleic Acid (SEQ ID NO: 17) Sequence of *Hypocrea jecorina* Cel7A mutant N301K

```
   1  GlnSerAlaCys ThrLeuGln SerGluThr HisProProLeu ThrTrpGln LysCysSer SerGlyGlyThr CysThrGln GlnThrGly SerValIle·
      CAGTCGGCCT GCACTCTCA ATGGAGACT CACCCGCCT TGACATGGCA GAATGTGTC TCTGGTGGCA CTTGCACTCA ACAGACAGG TCCGTGGTCA

101  ·IAspAlaAsn TrpArgTrp ThrHisAlaThr AsnSerSer ThrAsnCys TyrAspGlyAsn ThrThrSer SerThrLeu CysProAspAsn GluThrCys·
      TCGACGCCAA CTGGCGCTGG ACTCACGCTA CGAACAGCAG CGAACTGC TACGATGGCA ACACTTGGCA CTCCACCCTA TGTCCTGACA ACGAACCTG

201  ·AlaLysAsn CysCysLeuAsp GlyAlaAla TyrAlaSer ThrTyrGlyVal ThrThrSer GlyAsnSer LeuSerIleGly PheValThr GlnSerAla·
      CGCGAAGAAC TGCTGTCTG ACGGTGCCGC CTACGCGTC ACGTACGGAG TTACCACGAG CGGTAACAGC CTCTCCATTG GCTTTGTCAC CCAGTCTGCG

301  GlnLysAsnVal GlyAlaArg LeuTyrLeu MetAlaSerAsp ThrThrTyr GlnGluPhe ThrLeuLeuGly AsnGluPhe SerPheAsp ValAspValSer·
      CAGAAGAACG TTGGCGCTCG CCTTTACTT ATGGCCAGCG ACACGACCTA CCAGGAATTC ACCCTGCTTG GCAACGAGTT CTCTTTCGAT GTTGATGTT

401  ·SGlnLeuPro CysGlyLeu AsnGlyAlaLeu TyrPheVal SerMetAsp AlaAspGlyGly ValSerLys TyrProThr AsnThrAlaGly AlaLysTyr·
      CCCAGCTGCC GTGCGGCCTG AACGGAGCTC TCTACTTCGT GTCCATGGAC GCCGATGGTG GCGTGAGCAA GTATCCCACC AACACCGCTG GCGCCAAGTA

501  ·GlyThrGly TyrCysAspSer GlnCysPro ArgAspLeu LysPheIleAsn GlyGlnAla AsnValGlu GlyTrpGluPro SerSerAsn AsnAlaAsn·
      CGGCACGGGG TACTGTGACA GCCAGTGTCC CCGGGATCTG AAGTTCATCA ATGGCCAGGC CAACGTTGAG GGCTGGGAGC CGTCATCCAA CAACGCGAAC

601  ThrGlyIleGly GlyHisGly SerCysCys SerGluMetAsp IleTrpGlu AlaAsnSer IleSerGluAla LeuThrPro HisProCys ThrThrValGly·
      ACGGGCATTG GAGGACACGG AAGCTGCTGC TCTGAGATGG ATATTCTGGGA GGCCAACTCC ATCTCCGAGG CTCTCACCCC CCACCCTTGC ACGACTGTCG

701  ·GGlnGluIle CysGluGly AspGlyCysGly GlyThrTyr SerAspAsn ArgTyrGlyGly ThrCysAspHis ProAspAsp CysAspTrpAsn ProTyrArg·
      GCCAGGAGAT CTGCGAGGGT GATGGGTGCG GGGGAACTTA CTCCGATAAC AGATATGGCG GCACTTGCGA TCACCCTGAC GACTGCGACT GGAACCCATA CCGG

801  ·LeuGlyAsn ThrSerPhe GlyProGly SerSerPhe ThrLeuAspThr ThrLysLys LeuThrVal ValThrGlnPhe GluThrSer GlyAlaIle·
      CCTGGGCAAC ACCAGCTTCT ACGGCCGTGG CTCAAGCTTC ACCCTCGATA CCACCAAGAA ATTGACCGTT GTCACCCAGT TCGAGACGTC GGGTGCCATC

901  LysArgTyrTyr ValGlnAsn GlyValThr PheGlnGlnPro AsnAlaGlu LeuGlySer TyrSerGlyAsn GluLeuAsn AspAspTyr CysThrAlaGlu·
      AAGCGATACT ATGTCCAGAA TGGCGTGACT TTCCAGCAGC CCAACGCCGA GCTTGGTAGT TACTCTGGGA ACGAGCTCAA CGATGATTAC TGCACAGCTG

1001  ·GGluAlaGlu PheGlyGly SerSerPheSer AspLysGly GlyLeuThr GlnPheLysLys AlaThrSer GlyGlyMet ValLeuValMet SerLeuTrp·
      AGGAGGCAGA ATTCGGCGGA TCCTCTTTCT CAGACAAGGG CGGCCTGACT CAGTTCAAGA AGGCTACCTC TGGCGGCATG GTTCTGGTCA TGAGTCTGTG

1101  ·AspAspTyr TyrAlaAsnMet LeuTrpLeu AspSerThr TyrProThrAsn GluThrSer SerThrPro GlyAlaValArg GlySerCys SerThrSer·
      GGATGATTAC TACGCCAACA TGCTCTGGCT GGACTCCACC TACCCGACA ACGAGACCTC CTCCACACC GGTGCCGTGC GCGGAAGCTG CTCCACCAGC

1201  SerGlyValPro AlaGlnVal GluSerGln SerProAsnAla LysValThr PheSerAsn IleLysPheGly ProIleGly SerThrGly AsnProSerGly·
      TCCGGTGTCC CTGCTCAGGT CGAATCTCAG TCTCCCAACG CCAAGGTCAC CTTCTCCAAC ATCAAGTTCG GACCCATTGG CAGCACCGGC AACCCTAGCG

1301  ·GGlyAsnPro ProGlyGly AsnProProGly ThrThrThr ThrArgArg ProAlaThrThr ThrGlySer ProGlySer ProThrGlnSer HisTyrGly·
      GCGGCAACCC TCCCGGCGGA AACCCGCCTG GCACCACCAC CACCCGCCGC CCAGCCACTA CCACTGGAAG CCCTGGGAG CCTACCCAGT CTCACTACGG

1401  ·GlnCysGly GlyIleGlyTyr SerGlyPro ThrValCys AlaSerGlyThr ThrCysGln ValLeuAsn ProTyrTyrSer GlnCysLeu
      CCAGTGCGGC GGTATTGGCT ACAGCGGCCC CACGGTCTGC GCCAGCGGCA CAACTTGCCA GGTCCTGAAC CCTTACTACT CTCAGTGCCT G
```

Figure 5G: Amino Acid (SEQ ID NO: 20) and Nucleic Acid (SEQ ID NO: 19) Sequence of *Hypocrea jecorina* Cel7A mutant T356L.

```
   1  GlnSerAlaCys ThrLeuGln SerGluThr HisProProLeu ThrTrpGln LysCysSer SerGlyGlyThr CysThrGln GlnThrGly SerValValIle·
      CAGTCGGCCT GCACTCTCCA ATCGGAGACT CACCCGCCTC TGACATGGCA GAATGTTCG TCTGGTGGCA CTTGCACTCA ACAGACAGGC TCCGTGGTCA

101  ·IAspAlaAsn TrpArgTrp ThrHisAlaThr AsnSerSer ThrAsnCys TyrAspGlyAsn ThrTrpSer SerThrLeu CysProAspAsn GluThrCys·
      TCGACGCCAA CTGGCGCTGG ACTCACGCTA CCAACAGCAG CACGAACTGC TACGATGGCA ACACTTGGAG CTCGACCCTA TGTCCTGACA ACGAGACCTG

201  ·AlaLysAsn CysCysLeuAsp GlyAlaAla TyrAlaSer ThrTyrGlyVal ThrThrSer GlyAsnSer LeuSerIleGly PheValThr GlnSerAla
      CGGCAAGAAC TGCTGTCTGG ACGGTGCCGC CTACGCGTCC ACGTACGGAG TTACCACGAG CGGTAACAGC CTCTCCATTG GCTTTGTCAC CCAGTCTGCG

301  GlnLysAsnVal GlyAlaArg LeuTyrLeu MetAlaSerAsp ThrThrTyr GlnGluPhe ThrLeuLeuGly AsnGluPhe SerPheAsp ValAspValSer·
      CAGAAGAACG TTGGCGCTCG CCTTTACCTT ATGGCGAGCG ACACGACCTA CCAGGAATTC ACCCTGCTTG GCAACGAGTT CTCTTTCGAT GTTGATGTTT

401  ·SGlnLeuPro CysGlyGlu AsnGlyAlaLeu TyrPheVal SerMetAsp AlaAspGlyGly ValSerLys TyrProThr AsnThrAlaGly AlaLysTyr·
      CGCAGCTGCC GTGCGGCGAG AACGGAGCTC TCTACTTCGT GTCCATGGAC GCCGATGGTG GCGTGAGCAA GTATCCGACC AACACCGCTG GCGCCAAGTA

501  ·GlyThrGly TyrCysAspSer GlnCysPro ArgAspLeu LysPheIleAsn GlyGlnAla AsnValGlu GlyTrpGluPro SerSerAsn AsnAlaAsn
      CGGCACGGGG TACTGTGACA GCCAGTGTCC CCGCGATCTG AAGTTCATCA ATGGCCAGGC CAACGTTGAG GGCTGGGAGC CGTCATCCAA CAACGCGAAC

601  ThrGlyIleGly GlyHisGly SerCysCys SerGluMetAsp IleTrpGlu AlaAsnSer IleSerGluAla LeuThrPro HisProCys ThrThrValGly·
      ACGGGCATTG GAGGACACGG AAGCTGCTGC TCTGAGATGG ATATCTGGGA GGCCAACTCC ATCTCCGAGG CTCTTACCCC CCACCCTTGC ACGACTGTCG

701  ·GGlnGluIle CysGluGly AspGlyCysGly GlyThrTyr SerAspAsn ArgTyrGlyGly ThrCysAsp ProAspGly CysAspTrpAsn ProTyrArg·
      GCCAGGAGAT CTGCGAGGGT GATGGGTGCG GCGGAACTTA CTCCGATAAC AGATATGGCG GCACTTGCGA TCCCGATGGC TGCGACTGGA ACCCATACCG

801  ·LeuGlyAsn ThrSerPheTyr GlyProGly SerSerPhe ThrLysLys ThrLeuAspThr ThrSerGly LeuThrVal ValThrGlnPhe GluThrSer GlyAlaIle
      CCTGGGCAAC ACCAGCTTCT ACGGCCCTGG CTCAAGCTTC ACCCTCGATA CCACCAGCGG GCTTGGTAGT TACTCTGGCA ACGAGTCAA CGATGATTAC TGCACAGCTG

901  AsnArgTyrTyr ValGlnAsn GlyValThr PheGlnGlnPro AsnAlaGlu LeuGlySer TyrSerGlyAsn GluAlaGlu AspAspTyr CysThrAlaGlu·
      AACCGATACT ATGTCCAGAA TGGCGTCACT TTCCAGCAGC CCAACGCCGA GCTTGGTAGT TACTCTGGCA ACGAGTCAA CGATGATTAC TGCACAGCTG

1001  ·GGluAlaGlu PheGlyGly SerSerPheSer AspLysLys GlnPheLysLys AlaLeuSer GlyGlyMet ValLeuValMet SerLeuTrp·
      AGGAGGCAGA ATTCGGCGGA TCCTCTTTCT CAGACAAGGG CGGCCTGACT CAGTTCAAGA AGGCTCTCTC TGGCGGCATG GTTCTGGTCA TGAGTCTGTG

1101  ·AspAspTyr TyrAlaAsnMet LeuTrpLeu AspSerThr TyrProThrAsn GluThrSer SerThrPro GlyAlaValArg GlySerCys SerThrSer
      GGATGATTAC TACGCCAACA TGCTCTGGCT GGACTCCACC TACCCGACAA ACGAGACCTC CTCCACACCC GGTGCCGTGC GGGAAGCTG CTCCACCAGC

1201  SerGlyValPro AlaGlnVal GluSerGln SerProAsnAla LysValThr PheSerAsn IleLysPheGly ProIleGly SerThrGly AsnProSerGly·
      TCCGGTGTCC CTGCTCAAGT CGAATCTCAG TCTCCCAACG CCAAGGTCAC CTTCTCCAAC ATCAAGTTCG GACCCATTGG CAGCACCGGC AACCCTAGCG

1301  ·GGlyAsnPro ProGlyGly AsnProProGly ThrThrThr ThrArgArg ProAlaThrThr ThrGlySer SerProGly ProThrGlnSer HisTyrGly·
      GCGGCAACCC TCCCGGCGGA AACCCGCCTG GCACCACCAC CACCCGCCGC CCAGCCACTA CCACCGGAAG CTCTCCCGGA CCTACCCAGT CTCACTACGG

1401  ·GlnCysGly GlyIleGlyTyr SerGlyPro ThrValCys AlaSerGlyThr ThrCysGln ValLeuAsn ProTyrTyrSer GlnCysLeu
      CCAGTGCGGC GGTATTGGCT ACAGCGGCCC CACGGTCTGC GCCAGCGGCA CAACTTGCCA GGTCCTGAAC CCTTACTACT CTCAGTGCCT G
```

Figure 5H: Amino Acid (SEQ ID NO: 22) and Nucleic Acid (SEQ ID NO: 21) Sequence of *Hypocrea jecorina* Cel7A mutant G430F

```
  1  GlnSerAlaCys ThrLeuGln SerGluThr HisProProLeu ThrTrpLys CysThrGln LysCysGly Thr SerGlyGlyThr CysThrGln GlnThrGly SerValValIle·
     CAGTCGGCCT GCACTCTCCA ATCGGAGACT CACCCGCCCTC TGACATGGCA GAATGTCCG TCTGGTGGCA CTTGCACTCA ACAGACCAGC TCCGTGGTCA

101  ·IlAspAlaAsn TrpArgTrp ThrHisAlaThr AsnSerSer ThrAsnCys TyrAspGlyAsn ThrTrpSer SerThrLeu CysProAspAsn GluThrCys·
     TCGACGCCAA CTGGCGCTGG ACTCACGCTA CGAACAGCAG CACGAACTGC TACGATGGCA ACACTTGGAG CTCGACCCTA TGTCCTGACA ACGAGACCTG

201  ·AlaLysAsn CysCysLeuAsp GlyAlaAla TyrAlaSer ThrTyrGlyVal ThrThrSer GlyAsnSer LeuSerIleGly PheValThr GlnSerAla
     CGGGAAGAAC TGCTGTCTGG ACGGTGCCGC CTACGCGTCC ACGTACGGAG TTACCACGAG CGGTAACAGC CTCTCCATTG GCTTTGTCAC CCAGTCTGCG

301  GlnLysAsnVal GlyAlaArg LeuTyrLeu MetAlaSerAsp ThrThrTyr GlnGluPhe ThrLeuLeuGly AsnGluPhe SerPheAsp ValAspValSer·
     CAGAAGAACG TTGGCGCTCG CCTTTACCTT ATGGCGAGCG ACACGACCTA CCAGGAATTC ACCCTGCTTG GCAACGAGTT CTCTTTCGAT GTTGATGTTT

401  ·SGlnLeuPro CysGlyLeu AsnGlyAlaLeu TyrPheVal SerMetAsp AlaAspGlyGly ValSerLys TyrProThr AsnThrAlaGly AlaLysTyr·
     CGGCACTGCC GTGCGGCTTG AACGGAGCTC TCTACTTCGT GTCCATGGAC GCGGATGGTG GCGTGAGCAA GTATCCCACC AACACCGCTG GCGCCAAGTA

501  ·GlyThrGly TyrCysAspSer GlnCysPro ArgAspLeu LysPheIleAsn GlyGlnAla AsnValGlu GlyTrpGluPro SerSerAsn AsnAlaAsn
     CGGCACCGGG TACTGTGACA GCCAGTGTCC CCGGGATCTG AAGTTCATCA ATGGCCAGGC CAACGTTGAG GGCTGGGAGC CGTCATCAA CAACGCGAAC

601  ThrGlyIleGly GlyHisGly SerCysCys SerGluMetAsp IleTrpGlu AlaAsnSer IleSerGluAla LeuThrPro HisProCys ThrThrValGly·
     ACGGGCATTG GAGGACACGG AAGCTGCTGC TCTGAGATGG ATATCTGGGA GGCCAACTCC ATCTCCGAGG CTCTTACCCC CCACCCTTGC ACGACTGTCG

701  ·GGlnGluIle CysGluGly AspGlyCysGly GlyThrTyr SerAspAsn ArgTyrGlyGly ThrCysAsp ProAspGly CysAspTrpAsn ProTyrArg·
     GCCAGGAGAT CTGCGAGGGT GATGGTTGCG GCGGAACTTA CTCCGATAAC CGCTATGGTGG GCACTTGCGA TCCCGATGGC TGCGACTGGA ACCCATACCG

801  ·LeuGlyAsn ThrSerPheTyr GlyProGly SerSerPhe ThrLeuAspThr ThrLysLys ThrLeuThrVal ValThrGlnPhe GluThrSer GlyAlaIle·
     CCTGGGCAAC ACCAGCTTCT ACGGCCCTGG CTCAAGCTTT ACCCTGGACA CCACCAAGAA ATGACCGTT GTCACCCAGT TCGAGACGTC GGGTGCCATC

901  AsnArgTyrTyr ValGlnAsn GlyValThr PheGlnGlnPro AsnAlaGlu LeuGlySer TyrSerGlyAsn GluLeuAsn AspAspTyr CysThrAlaGlu·
     AACCGATACT ATGTCCAGAA TGGCGTCACT TTCCAGCAGC CCAACGCCGA GCTTGGTAGT TACTCTGGCA ACGAGCTCAA CGATGATTAC TGCACAGCTG

1001 ·GGlnLeuAla PheGlyGly SerSerPheSer AspLysGly GlyLeuThr GlnPheLysLys AlaThrSer GlyGlyMet ValLeuValMet SerLeuTrp·
     AGGAGGCAGA ATTCGGCGGA TCCTCTTTCT CAGACAAGGG CGGCCTGACT CAGTTCAAGA AGGCTACCTC TGGCGGCATG GTTCTGGTCA TGAGTCTGTG

1101 ·AspAspTyr TyrAlaAsnMet LeuTrpLeu AspSerThr TyrProThrAsn GluThrSer SerThrPro GlyAlaValArg GlySerCys SerThrSer
     GGATGATTAC TACGCCAACA TGCTGTGGCT GGACTCCACC TACCCGACAA ACGAGACCTC CTCCACACCC GGTGCCGTGC GGGGAAGCTG CTCCACCAGC

1201 SerGlyValPro AlaGlnVal GluSerGln SerProAsnAla LysValThr PheSerAsn IleLysPheGly AspIleGly SerThrPhe AsnProSerGly·
     TCCGGTGTCC CTGCTCAGGT CGAATCTCAG AGCCCCAAAC GCTAAGGTCAC CTTCTCCAAC ATCAAGTTCG GAGACATTGG CAGCACCTTC AACCCTAGCG

1301 ·GGlyAsnPro ProGlyGly AsnProProGly ThrThrThr ThrArgArg ProAlaThrThr ThrGlySer ProGlySer ProThrGlnSer HisTyrGly·
     GCGGCAACCC TCCCGGCGGA AACCCGCCTG GCACCACCAC CACCCGCCGC CCAGCCACTA CAACTGGAAG CCCTGGGAG CCCACCCAGT CTCACTACGG

1401 ·GlnCysGlyGly GlyIleGlyTyr SerGlyPro ThrValCys AlaSerGlyThr ThrCysGln ValLeuAsn ProTyrTyrSer GlnCysLeu
     CCAGTGCGGC GGTATTGGCT ACAGCGGGCCC CACGGTCTGC GCCAGCGGGCA CAACTTGCCA GGTCCTGAAC CCTTACTACT CTCAGTGCCT G
```

Figure 5I: Amino Acid (SEQ ID NO: 24) and Nucleic Acid (SEQ ID NO: 23) Sequence for *Hypocrea jecorina* Cel7A mutant T246C/Y371C

```
     GlnSerAlaCys ThrLeuGln HisProProLeu ThrThrGln LysCysSer SerGlyGlyThr CysThrGly GlnThrGly SerValValIle·
  1  CAGTCGGGCT GCACTCTCCA ATCGGAGACT CACCCGCCTC TGACACGGCA GAAATGCTCG TCTGGTGGCA CTTGCACTGGA ACAGACAGGC TCCGTGGTCA

·IAspAlaAsn TrpArgTrp ThrHisAlaThr AsnSerSer ThrAsnCys TyrAspGlyAsn ThrTrpSer SerThrLeu CysProAspAsn GluThrCys·
101  TCGCGCCAA CTGGCGCTGG ACTCACGCTA CGAACAGCAG CACGAACTGC TACGATGGCA ACACTTGGAG CTCGACCCTA TGTCCTGACA ACGAGACCTG

·AlaLysAsn CysCysLeuAsp GlyAlaAla TyrAlaSer ThrTyrGlyVal ThrThrSer GlyAsnSer LeuSerIleGly PheValThr GlnSerAla
201  CGGAGAAC TGCTGTGTCG ACGGTGCCGC CTACGCGTCC ACGTACGGAG TTACCACGAG CGGTAACAGC CTTTCCATTG GCTTTGTCAC CCAGTCTGCG

GlnLysAsnVal GlyAlaArg LeuTyrLeu MetAlaSerAsp ThrThrTyr GlnGluPhe ThrLeuLeuGly AsnGluPhe SerPheAsp ValAspValSer·
301  CAGAAGAACG TTGGCGCTCG CCTTTACCTT ATGGCGAGCG ACACGACCTA CCAGGAATTC ACCCTGCTTG GCAACGAGTT CTCTTTCGAT GTTGATGTTT

·SGlnLeuPro CysGlyLeu AsnGlyAlaLeu TyrPheVal SerMetAsp AlaAspGlyGly ValSerLys TyrProThr AsnThrAlaGly AlaLysTyr·
401  CGCAGCTGCC GTGCGGCTTG AACGGAGCTC TCTACTTCGT GTCCATGGAC GCCGATGGTG GCGTGAGCAA GTATCCCACC AACACCGCTG GCGCAAGTA

·GlyThrGly CysGlyAspSer GlnCysPro ArgAspLeu LysPheIleAsn GlyGlnAla AsnValGlu GlyTrpGluPro SerSerAsn AsnAlaAsn
501  CGGCACGGGG TACTGTGACA GCCAGTGTCC CCGGGATCTG AAGTTCATCA ATGGCCAGGC CAACGTTGAG GGCTGGGAGC CGTCATCCAA CAACGCGAAC

ThrGlyIleGly GlyHisSer SerCysCys SerGluMetAsp IleTrpGlu AlaAsnSer IleSerGluAla LeuThrPro HisProCys ThrThrValGly·
601  ACCGGCATTG GAGGACACGG AAGCTGCTGC TCTGAGATGG ATATCTGGGA GGCCAACTCC ATCTCCGAGG CCCTTACCCC ACGACTGTCG

·GGlnGluIle CysGluGly AspGlyCysGly GlyTyrTyr SerAspSer ArgTyrGlyGly ThrCysGly ThrCysGly ProAspTrpAsn ProTyrArg·
701  GCCAGGAGAT CTGCGAGGGT GATGGGTGCG GCGGATATTA CTCCGATAAC AGATACGGCGTT CTCACCCAGT TGCGACTGCG GGGACTGGA ACCCATACCG

·LeuGlyAsn ThrSerPheTyr GlyProGly SerSerPhe ThrLeuAspThr ThrLysLys LeuThrVal ValThrGlnPhe GluThrSer GlyAlaIle·
801  CCTGGGCAAC ACCAGCTTC ACGGCCCTGG CTCCAGCTTT ACCCTCGATA CCACCAAGAA GCTTACGGTT GTCACCCAGT TCGAGACGTC GGGTGCCATC

AsnArgTyrTyr ValGlnAsn GlyValThr PheGlnGlnPro AsnAlaGlu LeuGlySer TyrSerGlyAsn GluLeuAsn AspAspTyr CysThrAlaGlu·
901  AACCGATACT ATGTCCAGAA TGGCGTCACT TTCCAGCAGC CCAACGCCGA GCTTGGTAGT TACTCTGGCA ACGAGCTCAA CGATGATTAC TGCACAGCTG

·GGluAlaGlu PheGlyGly SerSerPheSer AspLysGly GlyLeuThr GlnPheLysLys AlaThrSer GlyGlyMet ValLeuValMet SerLeuTrp·
1001 AGGAGGCAGA ATTCGGCGGA TCCTCTTTCT CAGACAAGGG CGGCCTGACT CAGTTCAAGA AGGCTACCTC TGGCGGCATG GTTCTGGTCA TGAGTCTGTG

·AspAspTyr CysAlaAsnMet LeuTrpLeu AspSerThr TyrProThrAsn GluThrSer SerThrPro GlyAlaValArg GlySerCys SerThrSer
1101 GGATGATTAC TGCGCCAACA TGCTCTGGCT GGACTCCACC TACCCGACAA ACGAGACCTC CTCCACCCC GGTGCCGTGC GGGAAGCTG CTCCACCAGC

SerGlyValPro AlaGlnVal GluSerGln SerProAsnAla LysValThr PheSerAsn IleLysPheGly ProIleGly SerThrGly AsnProSerGly·
1201 TCCGGTGTCC CTGCTCAGGT CGAATCTCAG TCTCCCAACG CCAAGGTCAC CTTCTCCAAC ATCAAGTTCG GACCCATTGG CAGCACCGGG AACCCTAGCG

·GGlyAsnPro ProGlyGly AsnProProGly ThrThrThr ThrArgArg ProAlaThrThr ThrGlySer SerProGly ProThrGlnSer HisTyrGly·
1301 GCGGCAACCC TCCCGGCGGA AACCCGCCTG GCACCACCAC CACCCGCCGC CCAGCCACTA CCACTGGAAG CTCTCCGGGAA CCTACCCAGT CTCACTACGG

·GlnCysGly GlyIleGlyTyr SerGlyPro ThrValCys AlaSerGlyThr ThrCysGln ValLeuAsn ProTyrTyrSer GlnCysLeu
1401 CCAGTGCGGC GGTATTGGCT ACAGCGGGCC CACGGTCTGC GCCAGCGGCA CAACTTGCCA GGTCCTGAAC CCTTACTACT CTCAGTGCCT G
```

Figure 5J: Amino Acid (SEQ ID NO: 26) and Nucleic Acid (SEQ ID NO: 25) Sequence for *Hypocrea jecorina* Cel7A mutant T246A/R251A/Y252A

```
  1  GlnSerAlaCys ThrLeuGln SerGluThr HisProProLeu ThrTrpGln LysCysSer SerGlyGlyThr CysThrGln GlnThrGly SerValValIle
     CAGTCGGCCT GCACTCTCCA ATCGGAGACT CACCCGCCTC TGACATGGCA GAAATGCTCG TCTGGTGGCACT CTTGCACTCA ACAGACAGGC TCCGTGGTCA

101  ·IlAspAlaAsn TrpArgTrp ThrHisAlaThr AsnSerSer ThrAsnCys TyrAspGlyAsn ThrThrSer SerTrpSer CysProAspAsn GluThrCys·
     TCGACGCCAA CTGGCGCTGG ACTCACGCTA CGAACAGCAG CACGAACTGC TACGATGGCA ACACTTGGAG CTCGACCTGT GTCCTGACA ACGAGACCTG

201  ·AlaLysAsn CysCysLeuAsp TyrAlaAla ThrTyrGlyVal ThrThrSer GlyAsnSer LeuSerIleGly PheValThr GlnSerAla
     GCGGAAGAAC TGCTGTCTCG ACGGTGCGCC CTACGCGGCT ACGTACGGAG TTACCACGAG CGGTAACAGC CTCTCCATTG GCTTTGTCAC CCAGTCTGCG

301  GlnLysAsnVal GlyAlaArg LeuTyrLeu MetAlaSerAsp ThrThrTyr GlnGluPhe ThrLeuLeuGly SerPheAsn ValAspValSer·
     CAGAAGAACG TTGGCGCTCG CCTTTACCTT ATGGCGAGCG ACACGACCTA CCAGGAATTC ACCCTGCTTG GCAGCGAGTT CTCTTTCGAT GTTGATGTTT

401  ·SGlnLeuPro CysGlyLeu AsnGlyAlaLeu TyrPheVal SerMetAsp AlaAspGlyGly ValSerLys TyrProThr AsnThrAlaGly AlaLysTyr·
     CCCAGCTGCC GTGCGGCCTG AACGGAGCTC TCTACTTCGT GTCCATGGAC GCGGATGGTG GCGTGAGCAA GTATCCCACC AACACCGCTG GCGCCAAGTA

501  ·GlyThrGly TyrCysAspSer GlnCysPro ArgAspLeu LysPheIleAsn GlyGlnAla AsnValGlu GlyTrpGluPro SerSerAsn AsnAlaAsn·
     CGGAACGGGG TACTGTGACA GCCAGTGTCC CCGCGATCTG AAGTTCATCA ATGGCCAGGC CAACGTTGAG GGCTGGGAGC CGTCATCCAA CAACGCGAAC

601  ·ThrGlyIleGly GlyHisGly SerCysCys SerGluMetAsp IleTrpGlu AlaAsnSer IleSerGluAla LeuThrPro HisThrValGly·
     ACGGGCATTG GAGGACACGG AAGCTGCTGC TCTGAGATGG ATATCTGGGA GGCCAACTCC ATCTCCGAGG CTCTTACCCC CCACCCTGC ACGACTGTCG

701  ·GGlnGluIle CysGluGly AspGlyCysGly GlyAlaTyr SerAspAsn ArgTyrGlyGly ThrCysAsp ProAspGly CysAspTrpAsn ProTyrArg·
     GCCAGGAGAT CTGCGAGGGT GATGGGTGCG GCGGAGCTTA CTCCGATAAC CGATACGGCG GCACTTGCGA TCCCGATGGC TGCGACTGGA ACCCATACCG

801  ·LeuGlyAsn ThrSerPheTyr GlyProGly SerSerPhe ThrLeuAspThr ThrLysLys LeuThrVal ValThrGlnPhe GluThrSer GlyAlaIle·
     CCTGGGCAAC ACCAGCTTCT ACGGCCCTGG CTCAAGCTTT ACCCTCGATA CCACCAAGAA GCTTACTGTT GTCACCCAGT TCGAGACGTC GGGTGCCATC

901  ·AsnArgTyrTyr ValGlnAsn GlyValThr PheGlnGlnPro AsnAlaGlu LeuGlySer TyrSerGlyAsn ThrAspTyr CysThrAlaGlu·
     AACCGATACT ATGTCCAGAA TGGCGTCACT TTCCAGCAGC CCAACGCCGA GCTTGGTAGT TACTCTGGCA ACGAGCTCAA CGATGATTAC TGCACAGCTG

1001 ·GGluAlaGlu PheGlyGly SerSerPheSer AspLysGly GlyLeuThr GlnPheLysLys AlaThrSer GlyGlyMet ValLeuValMet SerLeuTrp·
     AGGAGGCCGA ATTCGGCGGA TCCTCTTTCT CAGACAAGGG CGGCCTGACT CAGTTCAAGA AGGCTACCTC TGGCGGCATG GTTCTGGTCA TGAGTCTGTG

1101 ·AspAspTyr TyrAlaAsnMet LeuTrpLeu AspSerThr TyrProThrAsn GluThrSer SerThrPro GlyAlaValArg GlySerCys SerThrSer·
     GGATGATTAC TACGCCAACA TGCTGTGGCT GGACTCCACC TACCCCACAA ACGAGACCTC CTCCACACCC GGTGCCGTGC GGGGAAGCTG CTCCACCAGC

1201 ·SerGlyValPro AlaGlnVal GluSerGln SerProAsnAla LysValThr PheSerAsn IleLeuLysAspGly SerThrGly AsnProSerGly·
     TCCGGTGTCC CTGCTCAGGT CGAATTCCAG TCTCCCAACG CCAAGGTCAC CTTCTCCAAC ATCAAGTTCG GACCCATTGG CAGCACCGGC AACCCTAGCG

1301 ·GGlyAsnPro ProGlyGly AsnProProGly ThrThrThr ThrArgArg ProAlaThrThr ThrGlySer SerProGly ProThrGlnSer HisTyrGly·
     GCGGCAACCC TCCCGGCGGA AACCCGCCTG GCACCACCAC CACCCGCCGC CCAGCCACTA CCACTGGAAG CTCTCCCGGA CCTACCCAGT CTCACTACGG

1401 ·GlnCysGly GlyIleGlyTyr SerGlyPro ThrValCys AlaSerGlyThr ThrCysGln ValLeuAsn ProTyrTyrSer GlnCysLeu
     CCAGTGCGGC GGTATTGGCT ACAGCGGCCC CACGGTCTGC GCCAGCGGCA CAACTTGCCA GGTCCTGAAC CCTTACTACT CTCAGTGCCT G
```

Figure 5K: Amino Acid (SEQ ID NO: 28) and Nucleic Acid (SEQ ID NO: 27) Sequence of *Hypocrea jecorina* Cel7A mutant T380G/Y381D/R394A

```
   1  GlnSerAlaCys ThrLeuGln SerGluThr HisProProLeu ThrTrpGln LysCysSer SerGlyGlyThr CysThrGln GlnThrGly SerValValIle·
      CAGTCGGCCT GCACTCTCCA ATCGGAGACT CACCCGCCCTC TGACATGGCA GAAATGCTCG TCTCGGTGGA CTTGCACTCA ACAGACAGGC TCCGTGGTCA

101  ·IAspAlaAsn TrpArgTrp ThrHisAlaThr AsnSerSer ThrAlaAsnCys TyrAspGlyAsn ThrTrpSer SerThrLeu CysProAspAsn GluThrCys··
      TCGACGCCAA CTGGCGCTGG ACTCACGCTA CGAACAGCAG CACGGCCAAC TGTTACGATGGCAAC ACACTTGGAG CTCGACCCTA TGTCCTGACA ACAGACCTG

201  ·AlaLysAsn CysCysLeuAsp GlyAlaAla TyrAlaSer ThrTyrGlyVal ThrThrSer GlyAsnSer LeuSerIleGly PheValThr GlnSerAla
      CGGCAAGAAC TGCTGTCTCG ACGGTGCCGC CTACGCGTCC ACGTACGGAG TACCACGAG CGGTAACAGC CTCTCCATTG GCTTTGTCAC CCAGTCTGCG

301  ·GlnLysAsnVal GlyAlaArg LeuTyrLeu MetAlaSerAsp ThrThrTyr GlnLeuPhe ThrLeuLeuGly AsnGluPhe SerPheAsp ValAspValSer·
      CAGAAGAACG TTGGCGCTCG CCTTTACCTT ATGGCGAGCG ACACGACCTA CCAGGAATTC ACCCTGCTTG GCAACGAGTT CTCTTTCGAT GTTGATGTT

401  ·SGlnLeuPro CysGlyLeu AsnGlyAlaLeu TyrPheVal SerMetAsp AlaAspGlyGly ValSerLys TyrProThr AsnThrAlaGly AlaLysTyr·
      CCAGCTGCC GTGCGGCTTG AACGGAGCTC TCTACTTCGT GTCCATGGAC GCGGATGGTG GCGTGAGCAA GTATCCCACC AACACCGCTG GCGCCAAGTA

501  ·GlyThrGly TyrCysAspSer GlnCysPro ArgAspLeu LysPheIleAsn GlyGlnAla AsnValGlu GlyTrpGluPro SerSerAsn AsnAlaAsn
      CGGCACGGG TACTGTGACA GCCAGTGTCC CCGCGATCTG AAGTTCATCA ATGGCCAGGC CAACGTTGAG GGCTGGGAGC CGTCATCCAA CAACGCGAAC

601  ThrGlyIleGly GlyHisGly SerCysCys SerGluMetAsp IleTrpGlu AlaAsnSer IleSerGluAla LeuThrPro HisProCys ThrThrValGly·
      ACGGGCATTG GAGGACACGG AAGCTGCTGC TCTGAGATGG ATATCTGGGA GGCCAACTCG ATCTCCGAGG CTCTTACCCC CCACCCTTGC ACGACTGTCG

701  ·GGlnGluIle CysGluGly AspGlyCysGly GlyThrTyr SerAspAsn ArgTyrGlyGly ThrCysAsp ProAspGly CysAspTrpAsn ProTyrArg·
      GCCAGGAGAT CTGCGAGGGT GATGGGTGCG GCGGAACTTA CTCCGATAAC AGATATGGGG GCACTTGCGA TCCCGATGGC TGCGACTGGA ACCCATACCG

801  ·LeuGlyAsn ThrSerPheTyr GlyProGly SerSerPhe ThrLeuAspThr ThrLysLys AlaThrPhe ThrValValThr GlnThrGlyPhe GlyAlaIle
      CCTCGGCAAC ACCAGCTTCT ACGGCCCTGG CTCAAGCTTT ACCCTCGATA CCACCAAGAA GCTTACTTTC ACCGTCGTCACCCAGACTGGC TTCGGAGCTC GGGTGCCATC

901  AsnArgTyr.ValGlnAsn GlyValThr PheGlnGlnPro AsnAlaGlu LeuGlySer TyrSerGlyAsn GluLeuAsn AspSerTyr CysThrAlaGlu·
      AACCGATACT ATGTCCAGAA TGGCGTCACT TTCCAGCAGC CCAACGCCGA GCTTGGTAGT TACTCTGGCA ACGAGCTCAA CGATGATTAC TGCACAGCTG

1001  ·GGluAlaGlu PheGlyGly SerSerPheSer AspLysLys AspProThrAsn GluThrPro SerThrPro GlyAlaValAla GlySerCys SerThrSer
      AGGGAGCGGA ATTCGGCGGA TCCTCTTTCT CAGACAAGGG CGACCCGACT CAGTTCAAGA AGGCTACCTC TGGCGCCATG GTTCTGGTCA TCAGTCTGTG

1101  ·AspAspTyr· TyrAlaAsnMet LeuTrpLeu AspSerGly AspProThrAsn GluThrPro SerThrPro GlyAlaValAla GlySerCys SerThrSer
      GGATGATTAC TACGCCAACA TGCTGTGGCT GGACTCCGGC GACCCGACAA ACGAGACCTC CCTCACACCC GGTGCCGTGG CCGGAAGCTG CTCCACCAGC

1201  SerGlyValPro AlaGlnVal GluSerGln SerProAsnAla LysValThr PheSerAsn IleLysPheGly ProIleGly SerThrGly AsnProSerGly·
      TCCGGTGTCC CTGCTCAGGT CGAATCCCAG TCTCCCAACG CCAAGGTCAC CTTCTCCAAC ATCAAGTTCG GACCCATTGG CAGCACCGGC AACCCTAGCG

1301  ·GGlyAsnPro ProGlyGly AsnProProGly ThrThrThr ThrArgArg ProAlaThrThr ThrGlySer SerProGly ProThrGlnSer HisTyrGly·
      GCGGCAACCC TCCCGGCGGA AACCCGCCTG GCACCACCAC CACCCGCCGC CCAGCCACTA CCACTGGAAG CTCTCCCGGA CCTACCCCAGT CTCACTACGG

....  ·GlnCysGlyGly GlyIleGlyTyr SerGlyPro ThrValCys AlaSerGlyThr ThrCysGln ValLeuAsn ProTyrTyrSer GlnCysLeu
      CCAGTGCGGC GGTATTGGCT ACAGCGGCCC CACGGTCTGC GCCAGCGGCA CAACTTGCCA GGTCCTGAAC CCTTACTACT CTCAGTGCCT G
```

Figure 5L: Amino Acid (SEQ ID NO: 30) and Nucleic Acid (SEQ ID NO: 29) Sequence of *Hypocrea jecorina* Cel7A mutant T380G/Y381D/R394A with residues 382 through 393 deleted

```
   1  GlnSerAlaCys ThrLeuGln SerGluThr HisProProLeu ThrTrpGln LysCysSer SerGlyGlyThr CysThrGln GlnThrGly SerValValIle·
      CAGTCGGCCT GCACTCTCCA ATCCGAGACT CACCCGCCTC TGCATGGCA GAATGCTCG TCTGGTGGCA CTTGCACTCA ACAGACAGGC TCCGTGGTCA

101  ·IAspAlaAsn TrpArgTrp ThrHisAlaThr AsnSerSer ThrAsnCys TyrAspGlyAsn ThrTrpSer SerThrLeu CysProAspAsn GluThrCys·
      TCGACGCCAA CTGGCGCTGG ACTCACGGTA CGAACAGCAG CACGAACTGC TACGATGGCA ACACTTGGAG CTCGACCCTA TGTCCTGACA ACGAGACCTG

201  ·AlaLysAsn CysCysLeuAsp CysAlaAla TyrAlaSer ThrTyrGlyVal ThrThrSer GlyAsnSer LeuSerIleGly PheValThr GlnSerAla
      CGCCAAGAAC TGCTGTCTCG ACGGTGCCGC CTACGGCTCC ACGTACGGAG TTACCACGAG CGGTAACAGC CTCTCCATTG GCTTTGTCAC CCAGTCTGCG

301  GlnLysAsnVal GlyAlaArg LeuTyrLeu MetAlaSerAsp ThrTyrThr GlnGluPhe ThrLeuLeuGly AsnGluPhe SerPheAsp ValAspValSer·
      CAGAAGAACG TTGGCGCTCG CCTTTACCTT ATGGCAGCGA CACGTACACC CAGGAATTC ACCCTGCTTG GCAACGAGTT CTCTTTCGAT GTTGATGTTT

401  ·SGlnLeuPro CysGlyLeu AsnGlyAlaLeu TyrPheVal SerMetAsp AlaAspGlyGly ValSerLys TyrProThr AsnThrAlaGly AlaLysTyr·
      CGCAGCTGCC GTGCGGCTTG AACGGAGCTC TCTACTTCGT GTCCATGGAC GCGGATGGTG GCGTGAGCAA GTATCCCACC AACACCGCTG GCGCCAAGTA

501  ·GlyThrGly TyrCysAspSer GlnCysPro ArgAspLeu LysPheIleAsn GlyGlnAla AsnValGlu GlyTrpGluPro SerSerAsn AsnAlaAsn
      CGGCACGGGG TACTGTGACA GCCAGTGTCC CCGGGATCTG AAGTTCATCA ATGGCCAGGC CAACGTTGAG GGCTGGGAGC CGTCATCCAA CAACGCGAAC

601  ThrGlyIleGly GlyHisGly SerCysCys SerGluMetAsp IleTrpGlu AlaAsnSer IleSerGluAla LeuThrPro HisProCys ThrThrValGly·
      ACGGGCATTG GAGGACACGG AAGCTGCTGC TCTGAGATGG ATATCTGGGA GGCCAACTCC ATCTCCGAGG CTCTTACCCC CCACCCTTGC ACGACTGTCG

701  ·GGlnGluIle CysGluGly AspGlyCysGly GlyThrTyr SerAspAsn ArgTyrGlyGly ThrCysAsp ProAspGly CysAspTrpArg ProTyrArg·
      GCCAGGAGAT CTGCGAGGGT GATGGGTGCG GCGGAACTTA CTCCGATAAC AGATATGGCG GCACTTGCGA TCCCGATGGC TGCGACTGGA ACCCATACCG

801  ·LeuGlyAsn ThrSerPheTyr GlyProGly SerSerPhe ThrLeuLysThr LeuThrGln AspThrGln SerLysIleVal ValThrGlnPhe GlyAlaIle
      CCTGGGCAAC ACCAGCTTCT ACGGCCCTGG CTCAAGCTTT ACCCTGAAGA CCCTCACCCA GGACACCCAG AGCAAGATTG TCACCCAGT TCGGAGCCATC

901  AsnArgTyrTyr ValGlnAsn GlyValThr PheGlnGlnPro AsnAlaGlu LeuGlySer TyrSerGlyAsn GluLeuAsn AspAspTyr CysThrAlaGlu·
      AACCGATACT ATGTCCAAGA TGGCGTCACT TTCCAGCAGC CCAACGCCGA GCTTGGTAGT TACTCTGGCA ACGAGCTCAA CGATGATTAC TGCACCAGCTG

1001  ·GGluAlaGlu PheGlyGly SerSerPheSer AspLysGly GlyLeuThr GlnPheLysLys AlaThrSer AlaGlyMet ValLeuValMet SerLeuTrp·
      AGGAGGCAGA ATTCGGCGGA TCCTCTTTCT CAGACAAGGG CGGCCTGACT CAGTTCAAGA AGGCTACCTC TGGGCCATG GTTCTGGTCA TGAGTCTGTG

1101  ·AspAspTyr TyrAlaAsnMet LeuTrpLeu AspSerGly AspAlaGlySer CysSerThr SerSerGly ValProAlaGln ValGluSer GlnSerPro
      GGATGATTAC TACGCCAACA TGCTCTGGCT GGACTCCGGA GACGCCGGAA GCTGCTCCAC CAGCTCCGGT GTCCCTGCTC AGGTCGAATC TCAGTCTCCC

1201  AsnAlaLysVal ThrProSer AsnIleLys PheGlyProIle PheGlyGly SerGlyAsnPro GlyAsnPro SerGlyAsnPro ProGlyThrThr·
      AACGCCAAGG TCACCTTCTC CAACATCAAG TTCGGACCCA TTGGCGGCAC CGGCAACCCT AGCGGCGGCA ACCCTCCCGG CACCAACCCG CCTGGCACCA

1301  ·TThrThrArg ArgProAla ThrThrThrGly SerSerPro GlyProThr GlnSerHisTyr GlyGlnCys GlyGlyIle GlyTyrSerGly ProThrVal·
      CCACCACCCG CCGGCCAGCC ACTACCACCG GAAGCTCTCC CGGACCTACC CAGTCTCACT ACGGCCAGTG CGGCGGTATT GGCTACAGCG GCCCCACGGT

1401  ·CysAlaSer GlyThrThrCys GlnValLeu AsnProTyr TyrSerGlnCys Leu
      CTGCGCCCAGC GGCACAACTT GCCAGGTCCT GAACCCTTAC TACTCTCAGT GCCTG
```

Figure 5M: Amino Acid (SEQ ID NO: 32) and Nucleic Acid (SEQ ID NO: 31) Sequence of *Hypocrea jecorina* Cel7A mutant Y252Q/D259W/S342Y

```
   1  GlnSerAlaCys ThrLeuGln SerGluThr HisProProLeu ThrTrpGln LysCysSer SerGlyGlyThr CysThrGln GlnThrGly SerValValIle
      CAGTCGGCCT GCACTCTCCA ATCGGAGACT CACCCGCCTC TGACATGGCA GAAATGCTCG TCTGGTGGCA CTTGCACTCA ACAGACAGGC TCCGTGGTCA

101  ·IleAspAlaAsn TrpArgTrp ThrHisAlaThr AsnSerSer ThrAsnCys TyrAspGlyAsn ThrTrpSer SerThrLeu CysProAspAsn GluThrCys·
      TCGACGCCAA CTGGCGCTGG ACTCACGCTA CGAACAGCAG CACGAACTGC TACGATGGCA ACACTTGGCA CTCGACCCTA TGCCTGACA ACGAGACCTG

201  ·AlaLysAsn CysCysLeuAsp GlyAlaAla TyrAlaSer ThrTyrGlyVal ThrThrSer GlyAsnSer LeuSerIleGly PheValThr GlnSerAla
      CGGCGAAGAAC TGCTGTCTGG ACGGTGCCGC CTACGCGTCC ACGTACGGAG TTACCACGAG CGGTAACAGC CTCTCCATTG GCTTTGTCAC CCAGTCTGCG

301  ·GlnLysAsnVal GlyAlaArg LeuTyrLeu MetAlaSerAsp ThrThrTyr GlnGluPhe ThrLeuLeuGly AsnGluPhe SerPheAsp ValAspValSer·
      CAGAAGAACG TTGGCGCTCG CCTTTACCTT ATGGCGAGCG ACACGACCTA CCAGGAATTC ACCCTGCTTG GCAACGAGTT CTCTTTCGAT GTTGATGTTT

401  ·SGlnLeuPro CysGlyLeu AsnGlyAlaLeu TyrPheVal SerMetAsp AlaAspGlyGly ValSerLys TyrProThr AsnThrAlaGly AlaLysTyr·
      CGGCAGCTGC GTGCGGCTTG AACGGAGCTC TCTACTTCGT GTCCATGGAC GCGGATGGTG GCGTGAGCAA GTATCCCACC AACACCGCTG GCGCCAAGTA

501  ·GlyThrGly CysGlyPro GlnCysSerPro ArgAspLeu LysPheIleAsn GlyGlnAla AsnValGlu GlyTrpGluPro SerSerAsn AsnAlaAsn
      CGGCACGGGG TACTGTGACA GCCAGTCTCC CCGCGATCTG AAGTTCATCA ATGGCCAGGC CAACGTTGAG GGCTGGGAGC CGTCATCCAA CAACGCGAAC

601  ThrGlyIleGly GlyHisGly SerCysCys SerGluMetAsp IleTrpGlu AlaAsnSer IleSerGluAla LeuThrPro HisProCys ThrThrValGly·
      ACGGGCATTG GAGGACACGG AAGCTGCTGC TCTGAGATGG ATATCTGGGA GGCCAACTCG ATCTCCGAGG CTCTTACCCC CCACCCTTGC ACGACTGTCG

701  ·GGlnGluIle CysGluGly AspGlyCysGly GlyThrTyr SerAspAsn ArgGlnGlyGly ThrCysAsp ProTrpGly CysAspTrpArg ProTyrArg·
      GCCAGGAGAT CTGCGAGGGT GATGGGTGCG GCGGAACTTA CTCCGATAAC AGACAGGGCG GCACTTGCGA TCCCTGGGGC TGCGACTGGA ACCCATACCG

801  ·LeuGlyAsn ThrSerPheTyr GlyProGly SerSerPhe ThrLeuAspThr ThrLysLys LeuThrVal ValThrGlnPhe GluThrSer GlyAlaIle
      CCTGGGCAAC ACCAGCTTCT ACGGGCCTGG CTCAAGCTTT ACCCTCGATA CCACCAAGAA ATTGACCGTT GTCACCCAGT TCGAGACGTC GGGTGCCATC

901  AsnArgTyrTyr ValGlnAsn GlyValThr PheGlnLnPro AsnAlaGlu LeuGlySer TyrSerGlyAsn GluLeuAsn AspAspTyr CysThrAlaGlu·
      AACCGATACT ATGTCCAGAA TGGCGTGACT TTCCAGCAGC CCAACGCCGA GCTTGGTAGT TACTCTGGCA ACGAGCTCAA CGATGATTAC TGCACAGCTG

1001  ·GGluAlaGlu PheGlyGly SerTyrPheSer AspLysGly GlyLeuThr GlnPheLysLys AlaThrSer GlyGlyMet ValLeuValMet SerLeuTrp·
      AGGAGGCAGA ATTCGGGGGA TCCTATTTCT CAGACAAGGG CGGCCTGACT CAGTTCAAGA AGGCTACCTC TGGCGGCATG GTTCTGGTCA TGAGTCTGTG

1101  ·AspAspTyr TyrAlaAsnMet LeuTrpLeu AspSerThr TyrProThrAsn GluThrSer ThrHisAla GlyAlaValArg GlySerCys SerThrSer
      GGATGATTAC TACGCCAACA TGCTCTGGCT GGACTCCACC TACCCGACAA ACGAGACCTC CACACACGCC GGTGCCGTGC GGGGAAGCTG CTCCACCAGC

1201  SerGlyValPro AlaGlnVal GluSerGln SerProAsnAla LysValThr PheSerAsn IleLysPheGly ProIleGly SerThrGly AsnProSerGly·
      TCCGGTGTCC CTGCTCAGGT CGAATCTCAG AGCCCCAACG CTAAGGTCAC CTTCTCCAAC ATCAAGTTCG GACCCATTGG CAGCACCGGC AACCCTAGCG

1301  ·GGlyAsnPro ProProGly GlyAsnProPro GlyThrThr ThrArgArg ProAlaThrThr ThrGlySer SerProGly ProThrGlnSer HisTyrGly·
      GCGGCAACCC TCCCCGGA AACCCGCCTG GCACCACAC CCAGGAGGA CGCCACTACC CCACCGGGAAG CTCTCCCGGA CCTACCCAGT CTCACTACGG

1401  ·GlnCysGly GlyIleGlyTyr SerGlyPro ThrValCys AlaSerGlyThr ThrCysGln ValLeuAsn ProTyrTyrSer GlnCysLeu
      CCAGTGCGGC GGTATTGGCT ACAGCGGCCC CACGGTCTGC GCCAGCGGCA CAACTTGCCA GGTCCTGAAC CCTTACTACT CTCAGTGCCT G
```

FIGURE 6A: pTEX2

| | | | | | |
|---|---|---|---|---|---|
| AAGCTTAAGG | TGCACGGCCC | ACGTGGCCAC | TAGTACTTCT | CGAGCTCTGT | 50 |
| ACATGTCCGG | TCGCGACGTA | CGCGTATCGA | TGGCGCCAGC | TGCAGGCGGC | 100 |
| CGCCTGCAGC | CACTTGCAGT | CCCGTGGAAT | TCTCACGGTG | AATGTAGGCC | 150 |
| TTTTGTAGGG | TAGGAATTGT | CACTCAAGCA | CCCCCAACCT | CCATTACGCC | 200 |
| TCCCCCATAG | AGTTCCCAAT | CAGTGAGTCA | TGGCACTGTT | CTCAAATAGA | 250 |
| TTGGGGAGAA | GTTGACTTCC | GCCCAGAGCT | GAAGGTCGCA | CAACCGCATG | 300 |
| ATATAGGGTC | GGCAACGGCA | AAAAGCACG | TGGCTCACCG | AAAAGCAAGA | 350 |
| TGTTTGCGAT | CTAACATCCA | GGAACCTGGA | TACATCCATC | ATCACGCACG | 400 |
| ACCACTTTGA | TCTGCTGGTA | AACTCGTATT | CGCCCTAAAC | CGAAGTGCGT | 450 |
| GGTAAATCTA | CACGTGGGCC | CCTTTCGGTA | TACTGCGTGT | GTCTTCTCTA | 500 |
| GGTGCCATTC | TTTTCCCTTC | CTCTAGTGTT | GAATTGTTTG | TGTTGGAGTC | 550 |
| CGAGCTGTAA | CTACCTCTGA | ATCTCTGGAG | AATGGTGGAC | TAACGACTAC | 600 |
| CGTGCACCTG | CATCATGTAT | ATAATAGTGA | TCCTGAGAAG | GGGGGTTTGG | 650 |
| AGCAATGTGG | GACTTTGATG | GTCATCAAAC | AAAGAACGAA | GACGCCTCTT | 700 |
| TTGCAAAGTT | TTGTTTCGGC | TACGGTGAAG | AACTGGATAC | TTGTTGTGTC | 750 |
| TTCTGTGTAT | TTTTGTGGCA | ACAAGAGGCC | AGAGACAATC | TATTCAAACA | 800 |
| CCAAGCTTGC | TCTTTTGAGC | TACAAGAACC | TGTGGGGTAT | ATATCTAGAG | 850 |
| TTGTGAAGTC | GGTAATCCCG | CTGTATAGTA | ATACGAGTCG | CATCTAAATA | 900 |
| CTCCGAAGCT | GCTGCGAACC | CGGAGAATCG | AGATGTGCTG | GAAAGCTTCT | 950 |
| AGCGAGCGGC | TAAATTAGCA | TGAAAGGCTA | TGAGAAATTC | TGGAGACGGC | 1000 |
| TTGTTGAATC | ATGGCGTTCC | ATTCTTCGAC | AAGCAAAGCG | TTCCGTCGCA | 1050 |
| GTAGCAGGCA | CTCATTCCCG | AAAAAACTCG | GAGATTCCTA | AGTAGCGATG | 1100 |
| GAACCGGAAT | AATATAATAG | GCAATACATT | GAGTTGCCTC | GACGGTTGCA | 1150 |
| ATGCAGGGGT | ACTGAGCTTG | GACATAACTG | TTCCGTACCC | CACCTCTTCT | 1200 |
| CAACCTTTGG | CGTTTCCCTG | ATTCAGCGTA | CCCGTACAAG | TCGTAATCAC | 1250 |
| TATTAACCCA | GACTGACCGG | ACGTGTTTTG | CCCTTCATTT | GGAGAAATAA | 1300 |
| TGTCATTGCG | ATGTGTAATT | TGCCTGCTTG | ACCGACTGGG | GCTGTTCGAA | 1350 |
| GCCCGAATGT | AGGATTGTTA | TCCGAACTCT | GCTCGTAGAG | GCATGTTGTG | 1400 |
| AATCTGTGTC | GGGCAGGACA | CGCCTCGAAG | GTTCACGGCA | AGGGAAACCA | 1450 |
| CCGATAGCAG | TGTCTAGTAG | CAACCTGTAA | AGCCGCAATG | CAGCATCACT | 1500 |
| GGAAAATACA | AACCAATGGC | TAAAAGTACA | TAAGTTAATG | CCTAAAGAAG | 1550 |
| TCATATACCA | GCGGCTAATA | ATTGTACAAT | CAAGTGGCTA | AACGTACCGT | 1600 |
| AATTTGCCAA | CGGCTTGTGG | GGTTGCAGAA | GCAACGGCAA | AGCCCCACTT | 1650 |
| CCCCACGTTT | GTTTCTTCAC | TCAGTCCAAT | CTCAGCTGGT | GATCCCCCAA | 1700 |
| TTGGGTCGCT | TGTTTGTTCC | GGTGAAGTGA | AAGAAGACAG | AGGTAAGAAT | 1750 |
| GTCTGACTCG | GAGCGTTTTG | CATACAACCA | AGGGCAGTGA | TGGAAGACAG | 1800 |
| TGAAATGTTG | ACATTCAAGG | AGTATTTAGC | CAGGGATGCT | TGAGTGTATC | 1850 |
| GTGTAAGGAG | GTTTGTCTGC | CGATACGACG | AATACTGTAT | AGTCACTTCT | 1900 |
| GATGAAGTGG | TCCATATTGA | AATGTAAGTC | GGCACTGAAC | AGGCAAAAGA | 1950 |
| TTGAGTTGAA | ACTGCCTAAG | ATCTCGGGCC | CTCGGGCCTT | CGGCCTTTGG | 2000 |
| GTGTACATGT | TTGTGCTCCG | GCAAATGCA | AAGTGTGGTA | GGATCGAACA | 2050 |
| CACTGCTGCC | TTTACCAAGC | AGCTGAGGGT | ATGTGATAGG | CAAATGTTCA | 2100 |
| GGGGCCACTG | CATGGTTTCG | AATAGAAAGA | GAAGCTTAGC | CAAGAACAAT | 2150 |
| AGCCGATAAA | GATAGCCTCA | TTAAACGGAA | TGAGCTAGTA | GGCAAAGTCA | 2200 |
| GCGAATGTGT | ATATATAAAG | GTTCGAGGTC | CGTGCCTCCC | TCATGCTCTC | 2250 |
| CCCATCTACT | CATCAACTCA | GATCCTCCAG | GAGACTTGTA | CACCATCTTT | 2300 |
| TGAGGCACAG | AAACCCAATA | GTCAACCGCG | GTTTAGGCGC | GCCAGCTCCG | 2350 |
| TGCGAAAGCC | TGACGCACCG | GTAGATTCTT | GGTGAGCCCG | TATCATGACG | 2400 |
| GCGGCGGGAG | CTACATGGCC | CCGGGTGATT | TATTTTTTTT | GTATCTACTT | 2450 |

FIGURE 6B: pTEX2

| | | | | |
|---|---|---|---|---|
| CTGACCCTTT | TCAAATATAC | GGTCAACTCA | TCTTTCACTG | GAGATGCGGC | 2500
| CTGCTTGGTA | TTGCGATGTT | GTCAGCTTGG | CAAATTGTGG | CTTTCGAAAA | 2550
| CACAAAACGA | TTCCTTAGTA | GCCATGCATT | TTAAGATAAC | GGAATAGAAG | 2600
| AAAGAGGAAA | TTAAAAAAAA | AAAAAAAACA | AACATCCCGT | TCATAACCCG | 2650
| TAGAATCGCC | GCTCTTCGTG | TATCCCAGTA | CCAGTTTAAA | CGGATCTCAA | 2700
| GCTTGCATGC | AAAGATACAC | ATCAATCGCA | GCTGGGGTAC | AATCATCCAT | 2750
| CATCCCAACT | GGTACGTCAT | AACAAAAATC | GACAAGATGG | AAAAAGAGGT | 2800
| CGCCTAAATA | CAGCTGCATT | CTATGATGCC | GGGCTTTGGA | CAAGAGCTCT | 2850
| TTCTCAGCTC | CGTTTGTCCT | CCCTCCCTTT | TCCCCCTTCT | TGCTAAATGC | 2900
| CTTTCTTTAC | TTCTTTCTTC | CCTTCCCTCC | CCTATCGCAG | CAGCCTCTCG | 2950
| GTGTAGGCTT | TCCACGCTGC | TGATCGGTAC | CGCTCTGCCT | CCTCTACGGG | 3000
| GTCTGAGGCC | TTGAGGATGC | CCCGGCCCAC | AATGGCAATG | TCGCTGCCGG | 3050
| CGATGCCAAT | CAGCTTGTGC | GGCGTGTTGT | ACTGCTGGCC | CTGGCCGTCT | 3100
| CCACCGACCG | ATCCGTTGGT | CTGCTGGTCC | TCGTCTTCGG | GGGGCAGCTG | 3150
| GCAGCCGGGC | GTCATGTGGA | TAAAGGCATC | GTCGGGCTCG | GTGTTGAGCG | 3200
| TCTCCTGCGA | GATGAAGCCC | ATGACAAAGT | CCTTGTGCTC | CCGGGCGGCC | 3250
| TCGACGCAGG | CCTGCGTGTA | CTCCTTGTTC | ATGAAGTTGC | CCTGGCTGGA | 3300
| CATTTGGGCG | AGGATCAGGA | GGCCTCGGCT | CAGCGGCGCC | TCCTCGATGC | 3350
| CCGGGAAGAG | CGACTCGTCG | CCCTCGGCGA | TGGCCTTTGT | TAACCGGGGC | 3400
| GAGGAGACGG | ACTCGTACTG | CTGGGTGACG | GTGGTGATGG | AGACGATGCT | 3450
| GCCCTTGCGG | CCGTCGCCGG | ACCGGTTCGA | GTAGATGGGC | TTGTCCAGGA | 3500
| CGCCAATGGA | GCCCATGCCG | TTGACGGCGC | CGGCGGGCTC | GGCGTCCCTG | 3550
| GAGTCGGCGT | CGTCGTCAAA | CGAGTCCATG | GTGGGCGTGC | CGACGGTGAC | 3600
| GGACGTCTTG | ACCTCGCAGG | GGTAGCGCTC | GAGCCAGCGC | TTGGCGCCCT | 3650
| GGGCCAGCGA | GGCCACCGAC | GCCTTGCCGG | GCACCATGTT | GACGTTGACA | 3700
| ATGTGCGCCC | AGTCGATGAT | GCGCGCCGAC | CCGCCCGTGT | ACTGCAGCTC | 3750
| GACGGTGTGG | CCAATGTCGC | CAAACTTGCG | GTCCTCGAAG | ATGAGGAAGC | 3800
| CGTGCTTGCG | CGCCAGCGAC | GCCAGCTGGG | CTCCCGTGCC | CGTCTCCGGG | 3850
| TGGAAGTCCC | AGCCCGAGAC | CATGTCGTAG | TGCGTCTTGA | GCACGACAAT | 3900
| CGACGGGCCA | ATCTTGTCGG | CCAGGTACAG | CAGCTCGCGC | GCTGTCGGCA | 3950
| CGTCGGCGCT | CAGGCACAGG | TTGGACGCCT | TGAGGTCCAT | GAGCTTGAAC | 4000
| AGGTAAGCCG | TCAGCGGGTG | CGTCGCCGTC | TCGCTCCTGG | CCGCGAAGGT | 4050
| GGCCTTGAGC | GTCGGGTGTG | GTGCCATGGC | TGATGAGGCT | GAGAGAGGCT | 4100
| GAGGCTGCGG | CTGGTTGGAT | AGTTTAACCC | TTAGGGTGCC | GTTGTGGCGG | 4150
| TTTAGAGGGG | GGGAAAAAAA | AGAGAGAGAT | GGCACAATTC | TGCTGTGCGA | 4200
| ATGACGTTGG | AAGCGCGACA | GCCGTGCGGG | AGGAAGAGGA | GTAGGAACTG | 4250
| TCGGCGATTG | GGAGAATTTC | GTGCGATCCG | AGTCGTCTCG | AGGCGAGGGA | 4300
| GTTGCTTTAA | TGTCGGGCTC | GTCCCTGGT | CAAAATTCTA | GGGAGCAGCG | 4350
| CTGGCAACGA | GAGCAGAGCA | GCAGTAGTCG | ATGCTAGAAA | TCGATAGATC | 4400
| CACGATGCCA | AAAAGCTTGT | TCATTTCGGC | TAGCCCGTGA | TCCTGGCGCT | 4450
| TCTAGGGCTG | AAACTGTGTT | GTTAATGTAT | TATTGGCTGT | GTAACTGACT | 4500
| TGAATGGGGA | ATGAGGAGCG | CGATGGATTC | GCTTGCATGT | CCCCTGGCCA | 4550
| AGACGAGCCG | CTTTGGCGGT | TTGTGATTCG | AAGGTGTGTC | AGCGGAGGCG | 4600
| CCAGGGCAAC | ACGCACTGAG | CCAGCCAACA | TGCATTGCTG | CCGACATGAA | 4650
| TAGACACGCG | CCGAGCAGAC | ATAGGAGACG | TGTTGACTGT | AAAAATTCTA | 4700
| CTGAATATTA | GCACGCATGG | TCTCAATAAG | AGCAATAGGA | ATGCTTGCCA | 4750
| ATCATAAGTA | CGTATGTGCT | TTTTCCTGCA | AATGGTACGT | ACGGACAGTT | 4800
| CATGTTGTCT | GTCATCCCCC | ACTCAGGCTC | TCATGATCAT | TTTATGGGAC | 4850
| TGGGGTTTTG | CTGACTGAAT | GGATTCAGCC | GCACGAAACA | AATTGGGGGC | 4900

FIGURE 6C: pTEX2

| | | | | | |
|---|---|---|---|---|---|
| CATGCAGAAG | GGAAGCCCCC | CCAGCCCCCT | GTTCATAATT | TGTTAAGAGT | 4950 |
| CGGAGAGCTG | CCTAGTATGA | AGCAGCAATT | GATAACGTTG | ACTTTGCGCA | 5000 |
| TGAGCTCTGA | AGCCGGGCAT | ATGTATCACG | TTTCTGCCTA | GAGCCGCACG | 5050 |
| GGACCCAAGA | AGCTCTTGTC | ATAAGGTATT | TATGAGTGTT | CAGCTGCCAA | 5100 |
| CGCTGGTTCT | ACTTTGGCTC | AACCGCATCC | CATAAGCTGA | ACTTTGGGAG | 5150 |
| CTGCCAGAAT | GTCTCTTGAT | GTACAGCGAT | CAACAACCGT | GCGCCGGTCG | 5200 |
| ACAACTGTTC | ACCGATCAGG | GACGCGAAGA | GGACCCAATC | CCGGTTAACG | 5250 |
| CACCTGCTCC | GAAGAAGCAA | AAGGGCTATG | AGGTGGTGCA | GCAAGGAATC | 5300 |
| AAAGAGCTCT | ATCCACTTGA | CAAGGCCAAT | GTCGCTCCCG | ATCTGGAGTA | 5350 |
| AGTCAACCCT | GAAGTGGAAG | TTTGCTTCTC | TGATTAGTAT | GTAGCATCGT | 5400 |
| GTTTGTCCCA | GGACTGGGTG | CAAATCCCGA | AGACAGCTGG | AAGTCCAGCA | 5450 |
| AGACCGACTT | CAATTGGACC | ACGCATACAG | ATGGCCTCCA | GAGAGACTTC | 5500 |
| CCAAGAGCTC | GGTTGCTTCT | GTATATGTAC | GACTCAGCAT | GGACTGGCCA | 5550 |
| GCTCAAAGTA | AAACAATTCA | TGGGCAATAT | CGCGATGGGG | CTCTTGGTTG | 5600 |
| GGCTGAGGAG | CAAGAGAGAG | GTAGGCCAAA | CGCCAGACTC | GAACCGCCAG | 5650 |
| CCAAGTCTCA | AACTGACTGC | AGGCGGCCGC | CATATGCATC | CTAGGCCTAT | 5700 |
| TAATATTCCG | GAGTATACGT | AGCCGGCTAA | CGTTAACAAC | CGGTACCTCT | 5750 |
| AGAACTATAG | CTAGCATGCG | CAAATTTAAA | GCGCTGATAT | CGATCGCGCG | 5800 |
| CAGATCCATA | TATAGGGCCC | GGGTTATAAT | TACCTCAGGT | CGACGTCCCA | 5850 |
| TGGCCATTCG | AATTCGTAAT | CATGGTCATA | GCTGTTTCCT | GTGTGAAATT | 5900 |
| GTTATCCGCT | CACAATTCCA | CACAACATAC | GAGCCGGAAG | CATAAAGTGT | 5950 |
| AAAGCCTGGG | GTGCCTAATG | AGTGAGCTAA | CTCACATTAA | TTGCGTTGCG | 6000 |
| CTCACTGCCC | GCTTTCCAGT | CGGGAAACCT | GTCGTGCCAG | CTGCATTAAT | 6050 |
| GAATCGGCCA | ACGCGCGGGG | AGAGGCGGTT | TGCGTATTGG | GCGCTCTTCC | 6100 |
| GCTTCCTCGC | TCACTGACTC | GCTGCGCTCG | GTCGTTCGGC | TGCGGCGAGC | 6150 |
| GGTATCAGCT | CACTCAAAGG | CGGTAATACG | GTTATCCACA | GAATCAGGGG | 6200 |
| ATAACGCAGG | AAAGAACATG | TGAGCAAAAG | GCCAGCAAAA | GGCCAGGAAC | 6250 |
| CGTAAAAAGG | CCGCGTTGCT | GGCGTTTTTC | CATAGGCTCC | GCCCCCCTGA | 6300 |
| CGAGCATCAC | AAAAATCGAC | GCTCAAGTCA | GAGGTGGCGA | AACCCGACAG | 6350 |
| GACTATAAAG | ATACCAGGCG | TTTCCCCCTG | GAAGCTCCCT | CGTGCGCTCT | 6400 |
| CCTGTTCCGA | CCCTGCCGCT | TACCGGATAC | CTGTCCGCCT | TTCTCCCTTC | 6450 |
| GGGAAGCGTG | GCGCTTTCTC | ATAGCTCACG | CTGTAGGTAT | CTCAGTTCGG | 6500 |
| TGTAGGTCGT | TCGCTCCAAG | CTGGGCTGTG | TGCACGAACC | CCCCGTTCAG | 6550 |
| CCCGACCGCT | GCGCCTTATC | CGGTAACTAT | CGTCTTGAGT | CCAACCCGGT | 6600 |
| AAGACACGAC | TTATCGCCAC | TGGCAGCAGC | CACTGGTAAC | AGGATTAGCA | 6650 |
| GAGCGAGGTA | TGTAGGCGGT | GCTACAGAGT | TCTTGAAGTG | GTGGCCTAAC | 6700 |
| TACGGCTACA | CTAGAAGAAC | AGTATTTGGT | ATCTGCGCTC | TGCTGAAGCC | 6750 |
| AGTTACCTTC | GGAAAAAGAG | TTGGTAGCTC | TTGATCCGGC | AAACAAACCA | 6800 |
| CCGCTGGTAG | CGGTGGTTTT | TTTGTTTGCA | AGCAGCAGAT | TACGCGCAGA | 6850 |
| AAAAAAGGAT | CTCAAGAAGA | TCCTTTGATC | TTTTCTACGG | GGTCTGACGC | 6900 |
| TCAGTGGAAC | GAAAACTCAC | GTTAAGGGAT | TTTGGTCATG | AGATTATCAA | 6950 |
| AAAGGATCTT | CACCTAGATC | CTTTTAAATT | AAAAATGAAG | TTTTAAATCA | 7000 |
| ATCTAAAGTA | TATATGAGTA | AACTTGGTCT | GACAGTTACC | AATGCTTAAT | 7050 |
| CAGTGAGGCA | CCTATCTCAG | CGATCTGTCT | ATTTCGTTCA | TCCATAGTTG | 7100 |
| CCTGACTCCC | CGTCGTGTAG | ATAACTACGA | TACGGGAGGG | CTTACCATCT | 7150 |
| GGCCCCAGTG | CTGCAATGAT | ACCGCGAGAC | CCACGCTCAC | CGGCTCCAGA | 7200 |
| TTTATCAGCA | ATAAACCAGC | CAGCCGGAAG | GGCCGAGCGC | AGAAGTGGTC | 7250 |
| CTGCAACTTT | ATCCGCCTCC | ATCCAGTCTA | TTAATTGTTG | CCGGGAAGCT | 7300 |
| AGAGTAAGTA | GTTCGCCAGT | TAATAGTTTG | CGCAACGTTG | TTGCCATTGC | 7350 |

FIGURE 6D: pTEX2

| | | | | | |
|---|---|---|---|---|---|
| TACAGGCATC | GTGGTGTCAC | GCTCGTCGTT | TGGTATGGCT | TCATTCAGCT | 7400 |
| CCGGTTCCCA | ACGATCAAGG | CGAGTTACAT | GATCCCCCAT | GTTGTGCAAA | 7450 |
| AAAGCGGTTA | GCTCCTTCGG | TCCTCCGATC | GTTGTCAGAA | GTAAGTTGGC | 7500 |
| CGCAGTGTTA | TCACTCATGG | TTATGGCAGC | ACTGCATAAT | TCTCTTACTG | 7550 |
| TCATGCCATC | CGTAAGATGC | TTTTCTGTGA | CTGGTGAGTA | CTCAACCAAG | 7600 |
| TCATTCTGAG | AATAGTGTAT | GCGGCGACCG | AGTTGCTCTT | GCCCGGCGTC | 7650 |
| AATACGGGAT | AATACCGCGC | CACATAGCAG | AACTTTAAAA | GTGCTCATCA | 7700 |
| TTGGAAAACG | TTCTTCGGGG | CGAAAACTCT | CAAGGATCTT | ACCGCTGTTG | 7750 |
| AGATCCAGTT | CGATGTAACC | CACTCGTGCA | CCCAACTGAT | CTTCAGCATC | 7800 |
| TTTTACTTTC | ACCAGCGTTT | CTGGGTGAGC | AAAAACAGGA | AGGCAAAATG | 7850 |
| CCGCAAAAAA | GGGAATAAGG | GCGACACGGA | AATGTTGAAT | ACTCATACTC | 7900 |
| TTCCTTTTTC | AATATTATTG | AAGCATTTAT | CAGGGTTATT | GTCTCATGAG | 7950 |
| CGGATACATA | TTTGAATGTA | TTTAGAAAAA | TAAACAAATA | GGGGTTCCGC | 8000 |
| GCACATTTCC | CCGAAAAGTG | CCACCTGACG | TCTAAGAAAC | CATTATTATC | 8050 |
| ATGACATTAA | CCTATAAAAA | TAGGCGTATC | ACGAGGCCCT | TTCGTCTCGC | 8100 |
| GCGTTTCGGT | GATGACGGTG | AAAACCTCTG | ACACATGCAG | CTCCCGGAGA | 8150 |
| CGGTCACAGC | TTGTCTGTAA | GCGGATGCCG | GGAGCAGACA | AGCCCGTCAG | 8200 |
| GGCGCGTCAG | CGGGTGTTGG | CGGGTGTCGG | GGCTGGCTTA | ACTATGCGGC | 8250 |
| ATCAGAGCAG | ATTGTACTGA | GAGTGCACCA | TAAAATTGTA | AACGTTAATA | 8300 |
| TTTTGTTAAA | ATTCGCGTTA | AATTTTTGTT | AAATCAGCTC | ATTTTTTAAC | 8350 |
| CAATAGGCCG | AAATCGGCAA | AATCCCTTAT | AAATCAAAAG | AATAGCCCGA | 8400 |
| GATAGGGTTG | AGTGTTGTTC | CAGTTTGGAA | CAAGAGTCCA | CTATTAAAGA | 8450 |
| ACGTGGACTC | CAACGTCAAA | GGGCGAAAAA | CCGTCTATCA | GGGCGATGGC | 8500 |
| CCACTACGTG | AACCATCACC | CAAATCAAGT | TTTTTGGGGT | CGAGGTGCCG | 8550 |
| TAAAGCACTA | AATCGGAACC | CTAAAGGGAG | CCCCCGATTT | AGAGCTTGAC | 8600 |
| GGGGAAAGCC | GGCGAACGTG | GCGAGAAAGG | AAGGGAAGAA | AGCGAAAGGA | 8650 |
| GCGGGCGCTA | GGGCGCTGGC | AAGTGTAGCG | GTCACGCTGC | GCGTAACCAC | 8700 |
| CACACCCGCC | GCGCTTAATG | CGCCGCTACA | GGGCGCGTAC | TATGGTTGCT | 8750 |
| TTGACGTATG | CGGTGTGAAA | TACCGCACAG | ATGCGTAAGG | AGAAAATACC | 8800 |
| GCATCAGGCG | CCATTCGCCA | TTCAGGCTGC | GCAACTGTTG | GGAAGGGCGA | 8850 |
| TCGGTGCGGG | CCTCTTCGCT | ATTACGCCAG | CTGGCGAAAG | GGGGATGTGC | 8900 |
| TGCAAGGCGA | TTAAGTTGGG | TAACGCCAGG | GTTTTCCCAG | TCACGACGTT | 8950 |
| GTAAAACGAC | GGCCAGTGCC | | | | 8970 |

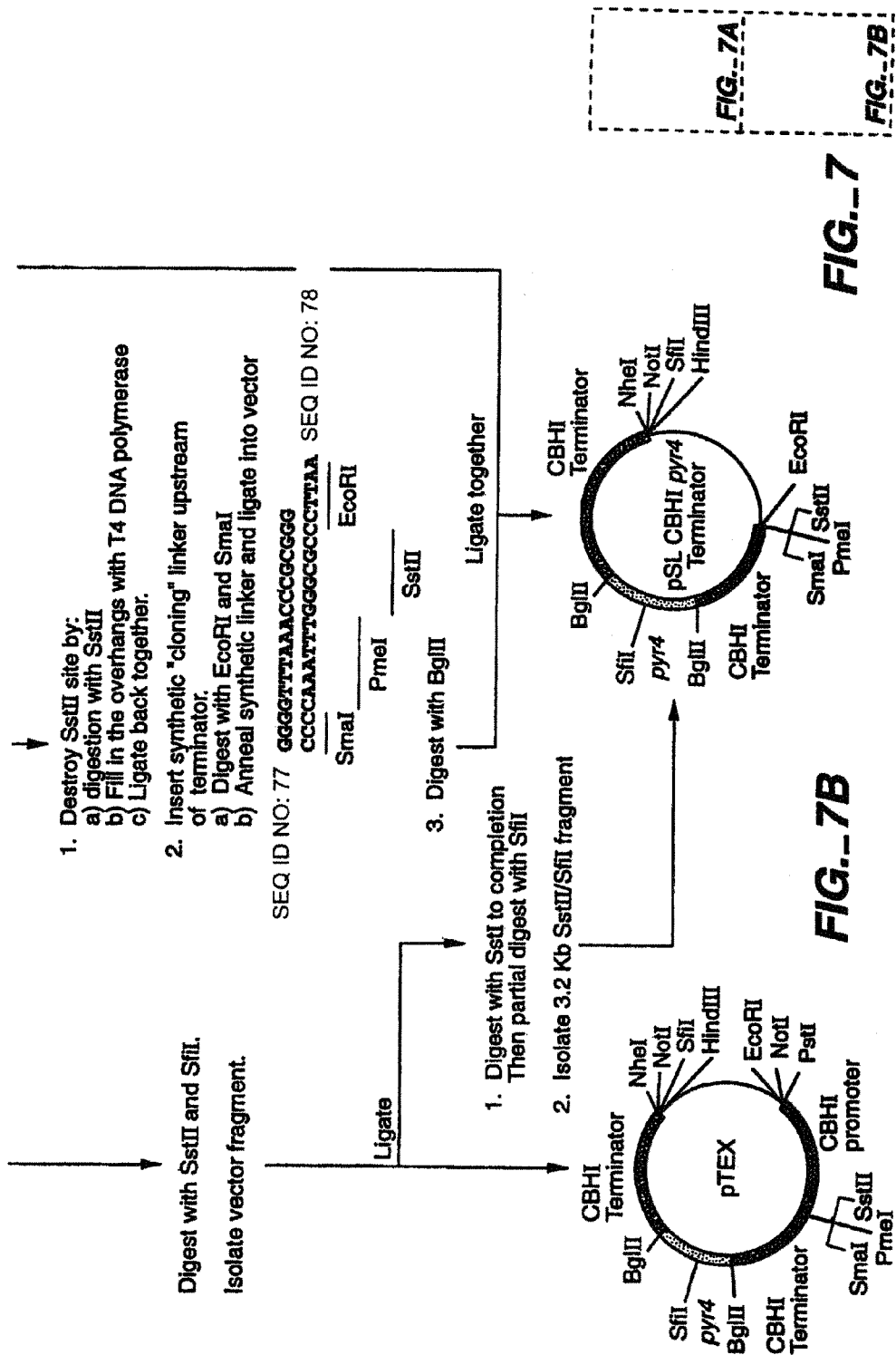

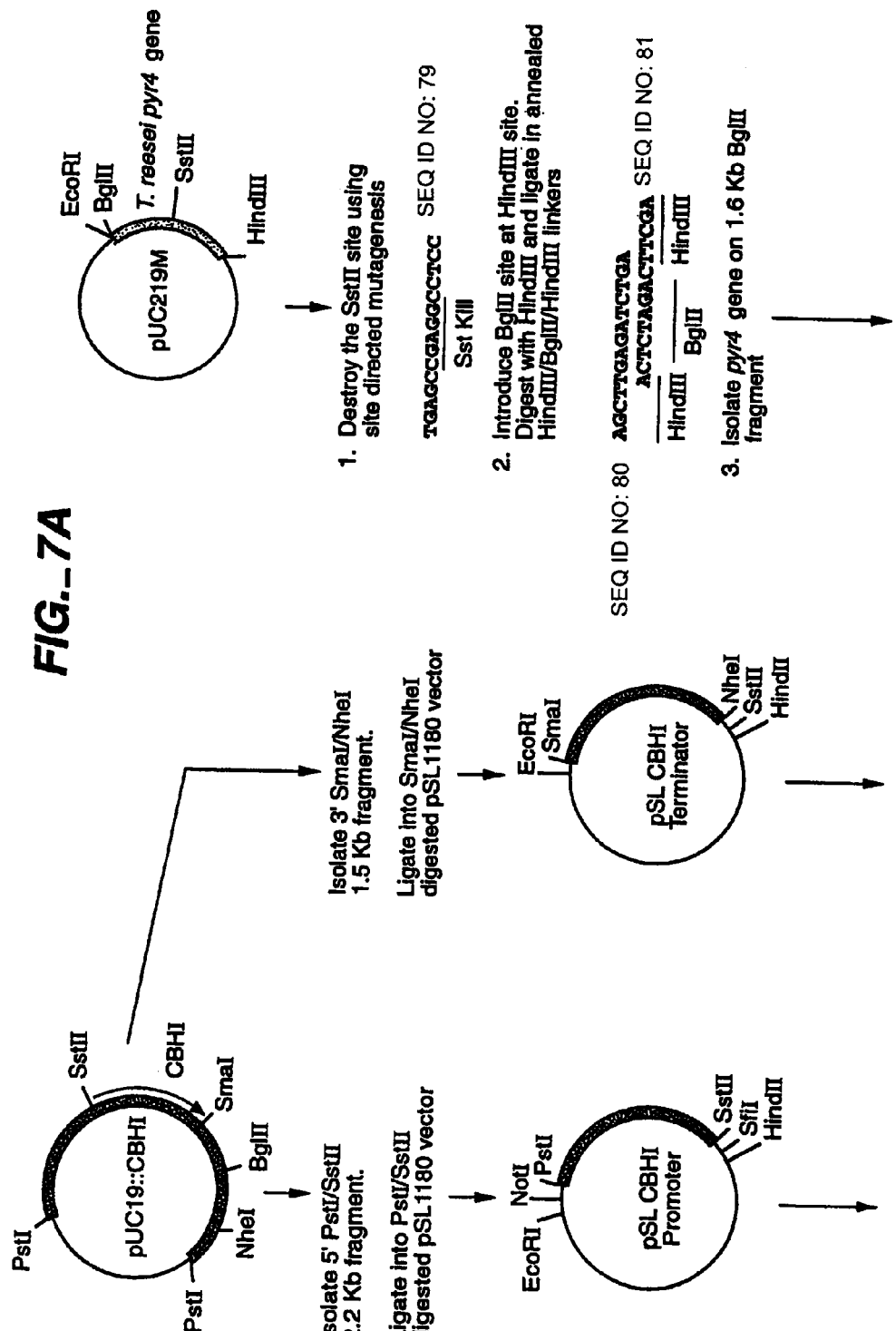
FIG._7A

```
SEQ ID NO: 3    2OVW.A          ---------------------------------TPDK-AKEQHPKLETYRCTKA
SEQ ID NO: 4    1A39            ---------------------------------KPGE-TKEVHPQLTTFRCTKR
SEQ ID NO: 2    6CEL            ---------------------------------SACTLQSETHPPLTWQKCSSG
SEQ ID NO: 5    1EG1.A          ---------------------------------QPGTSTPEVHPKLTTYKCTKS
SEQ ID NO: 34   P_chrysosporium M-----RTALA-LILALAAFS---AVSAQQAGTITAETHPTLTIQQCTQS
SEQ ID NO: 35   P_chrysospori_5 M-----RTALA-LILALAAFS---AVSAQQAGTITAETHPTLTIQQCTQS
SEQ ID NO: 36   P_chrysospori_6 M-----VDIQI-ATFLLLGVV---GVAAQQVGTYIPENHPLLATQSCTAS
SEQ ID NO: 37   P_chrysospori_7 M-----FRTA--TLLAFTMAA---MVFGQQVGTNTAENHRTLTSQKCTKS
SEQ ID NO: 38   P_chrysospori_8 M-----FRTA--TLLAFTMAA---MVFGQQVGTNTAENHRTLTSQKCTKS
SEQ ID NO: 39   P_chrysospori_9 M-----FRTA--TLLAFTMAA---MVFGQQVGTNTARSHPALTSQKCTKS
SEQ ID NO: 40   P_chrysospor_10 M-----FRAA--ALLAFTCLA---MVSGQQAGTNTAENHPQLSQQCTTS
SEQ ID NO: 41   P_chrysospor_11 M-----FRAA--ALLAFTCLA---MVSGQQAGTNTAENHPQLSQQCTTS
SEQ ID NO: 12   P_chrysospor_12 M-----FRAA--ALLAFTCLA---MVSGQQAGTNTAENHPQLSQQCTTS
SEQ ID NO: 43   I_lacteus_45863 M-----FRKA--ALLAFSFLA---IAHGQQVGTNQAENHPSLPSQKCTAS
SEQ ID NO: 44   I_lacteus_45_14 M-----FHKA--VLVAFSLVT---IVHGQQAGTQTAENHPQLSSQKCTAG
SEQ ID NO: 45   I_lacteus_45_15 M-----FPKA--SLIALSFIA---AVYGQQVGTQMAEVHPKLPSQLCTKS
SEQ ID NO: 46   A_alternata_617 ---------------------------------MTWQSCTAK
SEQ ID NO: 47   L_maculans_7804 M-----YRS---LIFATSLLS---LAKGQLVG--------NL-Y--CK--
SEQ ID NO: 48   C_parasitica_39 M-----FSKF--ALTGSLLAG---AVNAQGVGTQQTETHPQMTWQSCTSP
SEQ ID NO: 49   C_carbonum_3913 M-----YRTL--AFASLSLYG---AARAQQVGTSTAENHPKLTWQTCTGT
SEQ ID NO: 50   H_grisea_134622 M-----RTAK--FATLAALVA---SAAAQQACSLTTERHPSLSWNKCTAG
SEQ ID NO: 51   H_grisea_950383 M-----RTAK--FATLAALVA---SAAAQQACSLTTERHPSLSWKKCTAG
SEQ ID NO: 52   F_oxysporum_117 M-----YRIV--ATAS-ALIA---AARAQQVCSLNTETKPALTWSKCTSS
SEQ ID NO: 53   C_purpurea_1906 M-----HPSLQ-TILLSALFT---TAHAQQACSSKPETHPPLSWSRCSRS
SEQ ID NO: 54   H_thermoidea_40 MQIK-SYIQY--LAAALPLLS---SVAAQQAGTITAENHPRMTWKRCSGP
SEQ ID NO: 55   H_thermoidea_74 MQIK-SYIQY--LAAALPLLS---SVAAQQAGTITAENHPRMTWKRCSGP
SEQ ID NO: 56   L_maculans_7_26 M-----LSASK-AAAILAFCA--HTASAWVVGDQQTETHPKLNWQRCTGK
SEQ ID NO: 57   N_crassa_729649 M-----RASL--LAFSLA-AA---VAGGQQAGTLTAKRHPSLTWQKCTRG
SEQ ID NO: 58   A_aculeatus_391 M-VD-SFSIYK-TALLLSMLA---TSNAQQVGTYTAETHPSLTWQTCSGS
SEQ ID NO: 59   A_niger_6164684 M--S-SFQIYR-AALLLSILA---TANAQQVGTYTTETHPSLTWQTCTSD
SEQ ID NO: 60   P_janthinellum  MKGSISYQIYKGALLLSALLN---SVSAQQVGTLTAETHPALTWSKCTA-
SEQ ID NO: 61   A_niger_6164682 M-----HQRA--LLFS-ALLT---AVRAQQAGTLTEEVHPSLTWQKCTSE
SEQ ID NO: 62   H_ceramica_1218 M-----YRKL--AVIS-AFLA---TARAQSACTLQSETHPPLTWQKCSSG
SEQ ID NO: 63   H_jecorina_2238 ---------------------------ESACTLQSETHPPLTWQKCSSG
SEQ ID NO: 64   T_viride_121854 M-----YQKL--ALIS-AFLA---TARAQSACTLQAETHPPLTWQKCSSG
SEQ ID NO: 65   T_viride_406299 M-----YQKL--ALIS-AFLA---TARAQSACTLQAETHPPLTWQKCSSG
SEQ ID NO: 66   T_harzianum_710 M-----YRKL--AVIS-AFLA---AARAQQVCTQQAETHPPLTWQKCTAS
SEQ ID NO: 67   A_bisporus_3913 M-----FPRS--ILLALSLTA---VALGQQVGTNMAENHPSLTWQRCTSS
SEQ ID NO: 68   V_volvacea_5231 M-----RA---SLLAFS-LN---SAAGQQAGTLQTKNHPSLTSQKCRQG
SEQ ID NO: 69   T_longibrachiat M-----APSAT-LPLTTAILAIGRLVAAQPGTSTPEVHPKLTTYKCTTS
SEQ ID NO: 70   H_jecorina_1217 M-----APSVT-LPLTTAILAIARLVAAQPGTSTPEVHPKLTTYKCTTS
SEQ ID NO: 71   A_oryzae_246737 M-----IWTL--APFV-ALLP---LVTAQQVGT-TADAHPRLTTYKCTSQ
                consensus       m-----f-------il---mva-------aqq-gt-tae-hp-ltwqkCt--
```

Figure 8A

```
2OVW.A            S--G--CKKQTNYIVADAGIHGIRQK---NGAGCGDWGQKPNATACPDEASCAKNCILSG
1A39              G--G--CKPATNFIVLDSLWHWIHRAEGLGPGGCGDWGNPPPKDVCPDVESCAKNCIMEG
6CEL              G--T--CTQQTGSVVIDANWRWTHATNSSTNCYDGNT---WSSTLCPDNETCAKNCCLDG
1EG1.A            G--G--CVAQDTSVVLDWNYRWMH-DANYNSCTVNGG---VNTTLCPDEATCGKNCFIEG
P_chrysosporium   G--G--CAPLTTKVVLDVNWRWIHSTTGYTNCYSGNT---WDAILCPDPVTCAANCALDG
P_chrysospori_5   G--G--CAPLTTKVVLDVNWRWIHSTTGYTNCYSGNT---WDAILCPDPVTCAANCALDG
P_chrysospori_6   G--G--CTTSSSKIVLDANRRWIHSTLGTTSCLTANG---WDPTLCPDGITCANYCALDG
P_chrysospori_7   G--G--CSNLNTKIVLDANWRWLHSTSGYTNCYTGNQ---WDATLCPDGKTCAANCALDG
P_chrysospori_8   G--G--CSNLNTKIVLDANWRWLHSTSGYTNCYTGNQ---WDATLCPDGKTCAANCALDG
P_chrysospori_9   G--G--CSNLNTKIVLDANWRWLHSTSGYTNCYTGNQ---WDATLCPDGKTCAANCALDG
P_chrysospor_10   G--G--CKPLSTKVVLDSNWRWVHSTSGYTNCYTGNE---WNTSLCPDGKTCAANCALDG
P_chrysospor_11   G--G--CKPLSTKVVLDSNWRWVHSTSGYTNCYTGNE---WDTSLCPDGKTCAANCALDG
P_chrysospor_12   G--G--CKPLSTKVVLDSNWRWVHSTSGYTNCYTGNE---WDTSLCPDGKTCAANCALDG
I_lacteus_45863   G-----CTTSSTSVVLDANWRWVHTTTGYTNCYTGQT---WDASICPDGVTCAKACALDG
I_lacteus_45_14   G--S--CTSASTSVVLDSNWRWVHTTSGYTNCYTGNT---WDASICSDPVSCAQNCALDG
I_lacteus_45_15   G-----CTNQNTAVVLDANWRWLHTTSGYTNCYTGNS---WDATLCPDATTCAQNCAVDG
A_alternata_617   G--S--CTNKNGKIVIDANWRWLHKKEGYDNCYTGNE---WDATACPDNKACAANCAVDG
L_maculans_7804   G--S--CTAKNGKVVLDANWRWLHVKGGYTNCYTGNE---WNATACPDNKSCATNCAIDG
C_parasitica_39   S--S--CTTNQGEVVIDSNWRWVHDKDGYVNCYTGNT---WNTTLCPDDKTCAANCVLDG
C_carbonum_3913   G--GTNCSNKSGSVVLDSNWRWAHNVGGYTNCYTGNS---WSTQYCPDGDSCTKNCAIDG
H_grisea_134622   G--Q--CQTVQASITLDSNWRWTHQVSGSTNCYTGNK---WDTSICTDAKSCAQNCCVDG
H_grisea_950686   G--Q--CQTVQASITLDSNWRWTHQVSGSTNCYTGNK---WDTSICTDAKSCAQNCCVDG
F_oxysporum_117   G-----CSDVKGSVVIDANWRWTHQTSGSTNCYTGNK---WDTSICTDGKTCAEKCCLDG
C_purpurea_1906   G-----CRSVQGAVTVDANWLWT-TVDGSQNCYTGNR---WDTSICSSEKTCSESCCIDG
H_thermoidea_40   G--N--CQTVQGEVVINK-NG-QNCYEGNK---WTSQ-CSSATDCAQRCALDG
H_thermoidea_74   G--N--CQTVQGEVVIDANWRWLHN-NG-QNCYEGNK---WTSQ-CSSATDCAQRCALDG
L_maculans_7_26   GRSS--CTNVNGEVVIDANWRWLAHRSGYTNCYTGSE---WNQSACPNNEACTKNCAIEG
N_crassa_729649   G-----CPTLNTTMVLDANWRWTHATSGSTKCYTGNK---WQATLCPDGKSCAANCALDG
A_aculeatus_391   G--S--CTTTSGSVVIDANWRWVHEVGGYTNCYSGNT---WDSSICSTDTTCASECALEG
A_niger_6164684   G--S--CTTNDGEVVIDANWRWVHSTSSATNCYTGNE---WDTSICTDDVTCAANCALDG
P_janthinellum_   G--X--CSQVSGSVVIDANWPXVHSTSGSTNCYTGNT---WDATLCPDDVTCAANCAVDG
A_niger_6164682   G--S--CTEQSGSVVIDSNWRWTHSVNDSTNCYTGNT---WDATLCPDDETCAANCALDG
H_ceramica_1218   G--T--CTQQTGSVVIDANWRWTHATNSSTNCYDGNT---WSSTLCPDNETCAKNCCLDG
H_jecorina_2238   G--T--CTQQTGSVVIDANWRWTHATNSSTNCYDGNT---WSSTLCPDNETCAKNCCLDG
T_viride_121854   G--T--CTQQTGSVVIDANWRWTHATNSSTNCYDGNT---WSSTLCPDNETCAKNCCLDG
T_viride_406299   G--T--CTQQTGSVVIDANWRWTHATNSSTNCYDGNT---WSSTLCPDNETCAKNCCLDG
T_harzianum_710   G-----CTPQQGSVVLDANWRWTHDTKSTTNCYDGNT---WSSTLCPDDATCAKNCCLDG
A_bisporus_3913   G-----CQNVNGKVTLDANWRWTHRINDFTNCYTGNE---WDTSICPDGVTCAENCALDG
V_volvacea_5231   G-----CPQVNTTIVLDANWRWTHSTSGSTNCYTGNT---WQATLCPDGKTCAANCALDG
T_longibrachiat   G--G--CVAQDTSVVLDWNYRWMHDAN-YNSCTVNGG---VNTTLCPDEATCGKNCYIEG
H_jecorina_1217   G--G--CVAQDTSVVLDWNYRWMHDAN-YNSCTVNGG---VNTTLCPDEATCGKNCYIEG
A_oryzae_246737   N--G--CTRQNTSLVLDAATHFIHKKGTQTSCTNSNG---LDTAICPDKQTCADNCVVDG
consensus         g-----Ct----gsvvlDanwrwih-t-gytncytgn----wdstlCpd--tCa-nCaldG
```

Figure 8B

```
2OVW.A            -MDSNAYK-NAGITTSGNKLRL-QQLI-N----N-QLVSPRV-YLLEENK-KKYEMLHLT
1A39              -IPD---YS-QYGVTTNGTSLRL-QHILPD-----G-RVPSPRV-YLLDKTK-RRYEMLHLT
6CEL              -A---AYASTYGVTTSGNSLSI-DFVTQSA---Q-KNVGARL-YLMA-SD-TTYQEFTLL
1EG1.A            -V----DYA-ASGVTTSGSSLTM-NQYMPSSSGGY-SSVSPRL-YLLDSD--GEYVMLKLN
P_chrysosporium   -A---DYTGTFGILPSGTSVTL-RPVD-G--------LGLRL-FLLA-DD-SHYQMFQLL
P_chrysospori_5   -A---DYTGTFGILPSGTSVTL-RPVD-G--------LGLRL-FLLA-DD-SHYQMFQLL
P_chrysospori_6   -V---SYSSTYGITTSGSALRL-QFVT-GT-------NIGSRV-FLMA-DD-THYRTFQLL
P_chrysospori_7   -A---DYTGTYGITASGSSLKL-QFVT-GS-------NVGSRV-YLMA-DD-THYQMFQLL
P_chrysospori_8   -A---DYTGTYGITASGSSLKL-QFVT-GS-------NVGSRV-YLMA-DD-THYQMFQLL
P_chrysospori_9   -A---DYTGTYGITASGSSLKL-QFVT-GS-------NVGSRV-YLMA-DD-THYQMFQLL
P_chrysospor_10   -A---DYSGTYGITSTGTALTL-KFVT-GS-------NVGSRV-YLMA-DD-THYQLLKLL
P_chrysospor_11   -A---DYSGTYGITSTGTALTL-KFVT-GS-------NVGSRV-YLMA-DD-THYQLLKLL
P_chrysospor_12   -A---DYSGTYGITSTGTALTL-KFVT-GS-------NVGSRV-YLMA-DD-THYQLLKLL
I_lacteus_45863   -A---DYSGTYGITTSGNALTL-QFVK-GT-------NVGSRV-YLLQ-DA-SNYQMFQLI
I_lacteus_45_14   -A---DYAGTYGITTSGDALTL-KFVT-GS-------NVGSRV-YLME-DE-TNYQMFKLM
I_lacteus_45_15   -A---DYSGTYGITTSGNALTL-KFKT-GT-------NVGSRV-YLMQ-TD-TAYQMFQLL
A_alternata_617   -A---DYSGTYGITAGSNSLKL-KFITKGSY--S-TNIGSRT-YLMK-DD-TTYEMFKFT
L_maculans_7804   -A----DYR-RLRHYCERQLLGT-EVHHQGLY--S-TNIGSRT-YLMQ-DD-STYQLFKFT
C_parasitica_39   -A---DYSSTYGITTSGNALSL-QFVTQSS----G-KNIGSRT-YLME--SS-TKYHLFDLI
C_carbonum_3913   -A---DYSGTYGITTSNNALSL-KFVTKGSF--S-SNIGSRT-YLME-TD-TKYQMFNLI
H_grisea_134622   -A---DYTSTYGITTNGDSLTL-KFVTKGQH---S-TNVGSRT-YLMD-GE-DKYQTFELL
H_grisea_950686   -A---DYTSTYGITTNGDSLSL-KFVTKGQY--S-TNVGSRT-YLMD-GE-DKYQTFELL
F_oxysporum_117   -A---DYSGTYGITSSGNQLSL-GFVTNGPY--S-KNIGSRT-YLME-NE-NTYQMFQLL
C_purpurea_1906   -A---DYAGTYGVTTTGDALSL-KFVQQGPY--S-KNVGSRL-YLMK-DE-SRYEMFTLL
H_thermoidea_40   -A----NYQSTYGASTSGDSLTL-KFVTKHEY--G-TNIGSRF-YLMA-NQ-NKYQMFTLM
H_thermoidea_74   -A----NYQSTYGASTSGDSLTL-KFVTKHEY--G-TNIGSRF-YLMA-NQ-NKYQMFTLM
L_maculans_7_26   -S---DYAGTYGITTSGNQMNI-KFITKRPY--S-TNIGART-YLMK-DE-QNYEMFQLI
N_crassa_729649   -A----DYTGTYGITGSGWSLTL-QFVT-D------NVGARA-YLMA-DD-TQYQMLELL
A_aculeatus_391   -A---TYESTYGVTTSGSSLRL-NFVTQAS-----Q-KNIGSRL-YLLA-DD-STYETFKLF
A_niger_6164684   -A---TYEATYGVTTSGSELRL-NFVTQGS---S-KNIGSRL-YLMS-DD-SNYELFKLL
P_janthinellum_   -A----RRQ--HLRVTTSGNSLRI-NFVTTAS----Q-KNIGSRL-YLLE-ND-TTYQKFNLL
A_niger_6164682   -A---DYESTYGVTTDGDSLTL-KFVT-GS-------NVGSRL-YLMDTSD-EGYQTFNLL
H_ceramica_1218   -A----AYASAYGVTTSGNSLSI-GFVTQSA---Q-KNVGARL-YLMA-SD-TTYQEFTLL
H_jecorina_2238   -A----AYTSAYSSZPGGGGGVV-IFFK---------NVGARL-YLMA-SD-TTYQEFTLL
T_viride_121854   -A---AYASTYGVTTSADSLSI-GFVTQSA---Q-KNVGARL-YLMA-SD-TTYQEFTLL
T_viride_406299   -A---AYASTYGVTTSGNSLSI-GFVTQSA---Q-KNVGARL-YLMA-SD-TTYQEFTLL
T_harzianum_710   -A----NYSGTYGVTTSGDALTL-QFVT-AS------NVGSRL-YLMA-ND-STYQEFTLS
A_bisporus_3913   -A---DYAGTYGVTSSGTALTL-KFVTESQ----Q-KNIGSRL-YLMA-DD-SNYEIFNLL
V_volvacea_5231   -A---DYTGTYGVTTSGNSLTL-QFVT-QS-------NVGARLGYLMA-DD-TTYQMFNLL
T_longibrachiat   -V---DYAAS-GVTASGSTLTLNQYMPSSSG--GYSSVSPRL-YLLG-PD-GEYVMLKLN
H_jecornia_1217   -V---DYAAS-GVTASGSSLTLMQYMPSSSG--GYSSVSPRL-YLLD-SD-GEYVMLKLN
A_oryzae_246737   IT----DYA-SYGVQTKNDTLTLQQYLQTGNA---T-KSLSPRV-YLLA-EDGENYSMLKLL
consensus         -a---dysgtygittsg-slsl--fvt-gs-------nvgsRv-yLma-dd-t-Yqmf-ll
```

Figure 8C

```
2OVW.A            G-TEFSFDVEMEKLPCGMNGALFLSEMPQDGG-K-----STSR---NSKAGAY-------
1A39              G-FEFTFDVDATKLPCGMNSALYLSEMHPTGA-K-----S--K---YNPGGAY-------
6CEL              G-NEFSFDVDVSQLPCGLNGALYFVSMDADGG-V-----SKYP---TNTAGAK-------
1EG1.A            G-QELSFDVDLSALPCGENGSLYLSQMDENGG-A-------NQ---YNTAGAN-------
P_chrysosporium   N-KEFTFDVEMPNMRCGSSGAIHLTAMDADGG-L-----AKYP---GNQAGAK-------
P_chrysospori_5   N-KEFTFDVEMPNMRCGSSGAIHLTAMDADGG-L-----AKYP---GNQAGAK-------
P_chrysospori_6   N-QELAFDVDVSKLPCGLNGALYFVAMDADGG-K-----SKYP---GNRAGAK-------
P_chrysospori_7   N-QEFTFDVDMSNLPCGLNGALYLSAMDADGG-M-----AKYP---TNKAGAK-------
P_chrysospori_8   N-QEFTFDVDMSNLPCGLNGALYLSAMDADGG-M-----AKYP---TNKAGAK-------
P_chrysospori_9   N-QEFTFDVDMSNLPCGLNGALYLSAMDADGG-M-----AKYP---TNKAGAK-------
P_chrysospor_10   N-QEFTFDVDMSNLPCGLNGALYLSAMDADGG-M-----SKYP---GNKAGAK-------
P_chrysospor_11   N-QEFTFDVDMSNLPCGLNGALYLSAMDADGG-M-----SKYP---GNKAGAK-------
P_chrysospor_12   N-QEFTFDVDMSNLPCGLNGALYLSAMDADGG-M-----SKYP---GNKAGAK-------
I_lacteus_45863   N-QEFTFDVDMSNLPCGLNGAVYLSQMDQDGG-V-----SRFP---TNTAGAK-------
I_lacteus_45_14   N-QEFTFDVDVSNLPCGLNGAVYFVQMDQDGG-T-----SKFP---NNKAGAK-------
I_lacteus_45_15   N-QEFTFDVDMSNLPCGLNGALYLSQMDQDGG-L-----SKFP---TNKAGAK-------
A_alternata_617   GNQEFTFDVDVSNLPCGFNGALYFVSMDADGG-L-----KKYS---TNKAGAK-------
L_maculans_7804   GSQEFTFDVDLSNLPCGLNGALYFVSMDADGG-L-----KKYP---TNKAGAK-------
C_parasitica_39   G-NEFAFDVDLSKLPCGLNGALYFVTMDADGG-M-----AKYS---TNTAGAE-------
C_carbonum_3913   N-KEFTFDVDVSKLPCGLNGALYFVEMAADGG-I-----GK-G---NNKAGAK-------
H_grisea_134622   G-NEFTFDVDVSNIGCGLNGALYFVSMDADGG-L-----SRYP---GNKAGAK-------
H_grisea_950686   G-NEFTFDVDVSNIGCGLNGALYFVSMDADGG-L-----SRYP---GNKAGAK-------
F_oxysporum_117   G-NEFTFDVDVSGIGCGLNGAPHFVSMDEDGG-K-----AKYS---GNKAGAK-------
C_purpurea_1906   G-NEFTFDVDVSKLGCGLNGALYFVSMDEDGG-M-----KRFP---MNKAGAK-------
H_thermoidea_40   N-NEFAFDVDLSKVECGINSALYFVAMEEDGG-M-----ASYP---SNRAGAK-------
H_thermoidea_74   N-NEFAFDVDLSKVECGINSALYFVAMEEDGG-M-----ASYP---SNRAGAK-------
L_maculans_7_26   G-NEFTFDVDLSQ-RCGMNGALYFVSMPQKGQ---------------GAPGAK-------
N_crassa_729649   N-QELWFDVDMSNIPCGLNGALYLSAMDADGG-M-----RKYP---TNKAGAK-------
A_aculeatus_391   N-REFTFDVDVSNLPCGLNGALYFVSMDADGG-V-----SRFP---TNKAGAK-------
A_niger_6164684   G-QEFTFDVDVSNLPCGLNGALYFVAMDADGG-T-----SEYS---GNKAGAK-------
P_janthinellum_   N-QEFTFDVDVSNLPCGLNGALYFVDMDADGG-M-----AKYP---TNKAGAK-------
A_niger_6164682   D-AEFTFDVDVSNLPCGLNGALYFTAMDADGG-V-----SKYP---ANKAGAK-------
H_ceramica_1218   G-NEFSFDVDVSQLPCGLNGALYFVSMDADGG-V-----SKYP---TNTAGAK-------
H_jecorina_2238   G-NEFSFDVDVSQLPCGLNGALYFVSMDADGG-V-----SKYP---TNTAGAK-------
T_viride_121854   G-NEFSFDVDVSQLPCGLNGALYFVSMDADGG-V-----TKYP---TNTAGAK-------
T_viride_406299   G-NEFSFDVDVSQLPCGLNGALYFVSMDADGG-V-----SKYP---TNTAGAK-------
T_harzianum_710   G-NEFSFDVDVSQLPCGLNGALYFVSMDADGG-Q-----SKYP---GNAAGAK-------
A_bisporus_3913   N-KEFTFDVDVSKLPCGLNGALYFSEMAADGG-M-----SS-----TNTAGAK-------
V_volvacea_5231   N-QEFWFDVDMSNLPCGLNGALYFSAMARTAAWMPMVVCASTPLISTRRSTARLLRLPVP
T_longibrachiat   G-QELSFDVDLSALPCGENGSLYLSQMDENGG-A-----NQY-----NTAGAN-------
H_jecornia_1217   G-QELSFDVDLSALPCGENGSLYLSQMDENGG-A-----NQY-----NTAGAN-------
A_oryzae_246737   N-QEFTFDVDASTLVCGMNGALYLSEMEASGG-K-----SSL-----NQAGAK-------
consensus         n-nEftFDVdmsnlpCGlngalyfv-Mdadgg-v------skyp----nkagAk-------
```

Figure 8D

```
2OVW.A            ----YGAGYCDAQCYV-TPFINGVGNIK---------------GQGVCCNELDIWEANSRA
1A39              ----YGTGYCDAQCFV-TPFINGLGNIE---------------GKGSCCNEMDIWEANSRA
6CEL              ----YGTGYCDSQCPRDLKFINGQANVEGWEPSSNNANTGIGGHGSCCSQMDIWEANSIS
1EG1.A            ----YGTGYCDAQCPV-QTWRNGTLNTS---------------HQGFCCNEMDILEGNSRA
P_chrysosporium   ----YGTGYCSAQCPKGVKFINGQANVEGWLGTTA--TTGTGFFGSCCTDIALWEANDNS
P_chrysospori_5   ----YGTGYCSAQCPKGVKFINGQANVEGWLGTTA--TTGTGFFGSCCTDIALWEANDNS
P_chrysospori_6   ----YGTGYCDSQCPRDVQFINGQANVQGWNATSA--TTGTGSYGSCCTELDIWEANSNA
P_chrysospori_7   ----YGTGYCDSQCPRDIKFINGEANVEGWNATSA--NAGTGNYGTCCTEMDIWEANNDA
P_chrysospori_8   ----YGTGYCDSQCPRDIKFINGEANVEGWNATSA--NAGTGNYGTCCTEMDIWEANNDA
P_chrysospori_9   ----YGTGYCDSQCPRDIKFINGEANVEGWNATSA--NAGTGNYGTCCTEMDIWEANNDA
P_chrysospor_10   ----YGTGYCDSQCPKDIKFINGEANVGNWTETGS--NTGTGSYGTCCSEMDIWEANNDA
P_chrysospor_11   ----YGTGYCDSQCPKDIKFINGEANVGNWTETGS--NTGTGSYGTCCSEMDIWEANNDA
P_chrysospor_12   ----YGTGYCDSQCPKDIKFINGEANVGNWTETGS--NTGTGSYGTCCSEMDIWEANNDA
I_lacteus_45863   ----YGTGYCDSQCPRDIKFINGEANVEGWTGSSTDSNSGTGNYGTCCSEMDIWEANSVA
I_lacteus_45_14   ----FGTGYCDSQCPQDIKFINGEANIVDWTASAGDANSGTGSFGTCCQEMDIWEANSIS
I_lacteus_45_15   ----YGTGYCDSQCPHDIKFINGMANVAGWAGSASDPNAGSGTLGTCCSEMDIWEANNDA
A_alternata_617   ----YGTGYCDAQCPRDLKFINGEGNVEGWKPSSNDANAGVGGHGSCCAEMDIWEANSVS
L_maculans_7804   ----YGTGYCDAQCPRDLKFINGEGNVEGWQPSKNDQNAGVGGHGSCCAEMDIWEANSVS
C_parasitica_39   ----YGTGYCDSQCPRDLKFINGGNVEGWTPSTNDANAGVGGLGSCCSEMDVWEANSMD
C_carbonum_3913   ----YGTGYCDSQCPHDIKFINGKANVEGWNPSDADPNGGAGKIGACCPEMDIWEANSIS
H_grisea_134622   ----YGTGYCDAQCPRDIKFINGEANIEGWTGSTNDPNAGAGRYGTCCSEMDIWEANNMA
H_grisea_950686   ----YGTGYCDAQCPRDIKFINGEANIEGWTGSTNDPNAGAGRYGTCDSEMDIWEANNMA
F_oxysporum_117   ----YGTGYCDAQCPRDVKFINGVANSEGWKPSDSDVNAGVGNLGTCCPEMDIWEANSIS
C_purpurea_1906   ----FGTGYCDSQCPRDVKFINGMANSKDWIPSKSDANAGIGSLGACCREMDIWEANNIA
H_thermoidea_40   ----YGTGYCDAQCARDLKFIGGKANIEGWRPSTNDPNAGVGPMGACCAEIDVWESNAYA
H_thermoidea_74   ----YGTGYCDAQCARDLKFIGGKANIEGWRPSTNDPNAGVGPMGACCAEIDVWESNAYA
L_maculans_7_26   ----YGTGYCDAQCARDLKFVRGSANAEGWTKSASDPNSGVGKKGACCAQMDVWEANSAA
N_crassa_729649   ----YATGYCDAQCPRDLKYINGIANVEGWTPSTND-ANGIGDHGSCCSEMDIWEANKVS
A_aculeatus_391   ----YGTGYCDSQCPRDLKFIDGQANIEGWEPSSTDVNAGTGNHGSCCPEMDIWEANSIS
A_niger_6164684   ----YGTGYCDSQCPRDLKFINGEANCDGWEPSSNNVNTGVGDHGSCCAEMDVWEANSIS
P_janthinellum    ----YGTGYCDSQCPRDLKFINGGWTPSKNDVNSGIGNHGSCCAEMDIWEANSIS
A_niger_6164682   ----YGTGYCDSQCPRDLKFIDGQANVDGWEPSSNNDNTGIGNHGSCCPEMDIWEANKIS
H_ceramica_1218   ----YGTGYCDSQCPRDLKFINGQANVEGWEPSSNNANTGIGGHGSCCSEMDIWEANSIS
H_jecorina_2238   ----YGTGYCDSQCPRDLKFINGQANVEGWEPSSNNANTGIGGHGSCCSEMDIWEANSIS
T_viride_121854   ----YGTGYCDSQCPRDLKFINGQANVEGWEPSSNNANTGIGGHGSCCSEMDIWEANSIS
T_viride_406299   ----YGTGYCDSQCPRDLKFINGQANVEGWEPSSNNANTGIGGHGSCCSEMDIWEANSIS
T_harzianum_710   ----YGTGYCDSQCPRDLKFINGQANVEGWEPSSNNANTGVGGHGSCCSEMDIWEANSIS
A_bisporus_3913   ----YGTGYCDSQCPRDIKFIDGEANSEGWEGSPNDVNAGTGNPGACCSEMDIWEANSIS
V_volvacea_5231   PRSRYGRGICDSQCPRDIKFINGEANVQGWQPSPNDTNAGTGNYGACCNKMDVWEANSIS
T_longibrachiat   ----YGSGYCDAQCPVQ-TWRNGTLNTSG--------------QGFCCNEMDILEGNSRA
H_jecorina_1217   ----YGSGYCDAQCPVQ-TWRNGTLNTS---------------HQGFCCNEMDILEGNSRA
A_oryzae_246737   ----YGTGYCDAQCYTT-PWINGEGNTE---------------SVGSCCQEMDIWEANARA
consensus         ----ygtGycdsQCprdlkfinG-aNvegw--ss---n-g-g--GsCCsemdiwEaNsia
```

Figure 8E

```
2OVW.A              THIAPHPCSKPGL-YGC-TGDECG-----------SSGICDK-AGCGW-NHNRINVTDFYGR
1A39                SHVAPHTCNKKGL-YLC-EGEECA-----------FEGVCDK-NGCGW-NNYRVNVTDYYGR
6CEL                EALTPHPCTTVGQ-EIC-EGDGCGGTYSD---NRYGGTCDP-DGCDW-NPYRLGNTSFYGP
1EG1.A              NALTPHSCTA-----------------------TACDS-AGCGF-NPYGSGYKSYYGP
P_chrysosporium     ASFAPHPCTTNSQ-TRC-SGSDC----------TADSGLCDA-DGCNF-NSFRMGNTTFFGA
P_chrysospori_5     ASFAPHPCTTNSQ-TRC-SGSDC----------TADSGLCDA-DGCNF-NSFRMGNTTFFGA
P_chrysospori_6     AALTPHTCTNNAQ-TRC-SGSNC----------TSNTGFCDA-DGCDF-NSFRLGNTTFLGA
P_chrysospori_7     AAYTPHPCTTNAQ-TRC-SGSDC----------TRDTGLCDA-DGCDF-NSFRMGDQTFLGK
P_chrysospori_8     AAYTPHPCTTNAQ-TRC-SGSDC----------TRDTGLCDA-DGCDF-NSFRMGDQTFLGK
P_chrysospori_9     AAYTPHPCTTNAQ-TRC-SGSDC----------TRDTGLCDA-DGCDF-NSFRMGDQTFLGK
P_chrysospor_10     AAFTPHPCTTTGQ-TRC-SGDDC----------ARNTGLCDHGDGCDF-NSFRMGDKTFLGK
P_chrysospor_11     AAFTPHPCTTTGQ-TRC-SGDDC----------ARNTGLCDG-DGCDF-NSFRMGDKTFLGK
P_chrysospor_12     AAFTPHPCTTTGQ-TRC-SGDDC----------ARNTGLCDG-DGCDF-NSFRMGDKTFLGK
I_lacteus_45863     AAYTPHPCSVNQQ-TRC-TGADCGQ--GD--DRYDGVCDP-DGCDF-NSFRMGDQTFLGK
I_lacteus_45_14     AAYTPHPCTVTEQ-TRC-SGSDCGQ--GS--DRFNGICDP-DGCDF-NSFRMGNTEFYGK
I_lacteus_45_15     AAFTPHPCSVDGQ-TQC-SGTQCGD--DD--ERYSGLCDK-DGCDF-NSFRMGDKSFLGK
A_alternata_617     TAVTPHSCSTIEQ-SRC-DGDGCGGTYSA---DRYAGVCDP-DGCDF-NSYRMGVRDFYGK
L_maculans_7804     TAVTPHSCSTIEQ-SRC-DGDGCGGTYSA---DRYAGVCDP-DGCDF-NSYRMGVKDFYGK
C_parasitica_39     MAYTPHPCETAAQ-HSC-NADECGGTYS---SRYAGDCDP-DGCDW-NPFRMGNKDFYGS
C_carbonum_3913     TAYTPHPCRGVGL-QECSDAASCGD--GS--NRYDGQCDK-DGCDF-NSYRMGVRDFYGK
H_grisea_134622     TAFTPHPCTIIGQ-SRC-EGDSCGGTYSN---ERYAGVCDP-DGCDF-NSYRQGNKTFYGK
H_grisea_950686     TAFTPHPCTIIGQ-SRC-EGDSCGGTYSN---ERYAGVCDP-DGCDF-NSYRQGNKTFYGK
F_oxysporum_117     TAFTPHPCTKLTQ-HSC-TGDSCGGTYSS---DRYGGTCDA-DGCDF-NAYRQGNRTFYGP
C_purpurea_1906     SAFTPHPCKNSAY-HSC-TGDGCGGTYSK---NRYSGDCDP-DGCDF-NSYRLGNTTFYGP
H_thermoidea_40     YAFTPHACGSKNRYHIC-ETNNCGGTYSD--DRFAGYCDA-NGCDY-NPYRMGNKDFYGK
H_thermoidea_74     YAFTPHACGSKNRYHIC-ETNNCGGTYSD--DRFAGYCDA-NGCDY-NPYRMGNKDFYGK
L_maculans_7_26     TALTPHSCQPAGY-SVC-EDTNCGGTYSE---DRYAGTCDA-NGCDF-NPFRVGVKDFYGK
N_crassa_729649     TAFTPHPCTTIEQ-HMC-EGDSCGGTYSD---DRYGVLCDA-DGCDF-NSYRMGNTTFYGE
A_aculeatus_391     SAFTAHPCDSVQQ-TMC-TGDTCGGTYSDTTDRYSGTCDP-DGCDF-NPYRFGNTNFYGP
A_niger_6164684     NAFTAHPCDSVSQ-TMC-DGDSCGGTYSASGDRYSGTCDP-DGCDY-NPYRLGNTDFYGP
P_janthinellum_     NAVTPHPCDTPSQ-TMC-TGQRCGGTYST--DRYGGTCDP-DGCDF-NPYRMGVTNFYGP
A_niger_6164682     TALTPHPCDSSEQ-TMC-EGNDCGGTYSD---DRYGGTCDP-DGCDF-NPYRMGNDSFYGP
H_ceramica_1218     EALTPHPCTTVGQ-EIC-EGDGCGGTYSD---NRYGGTCDP-DGCDW-NPYRLGNTSFYGP
H_jecorina_2238     EALTPHPCTTVGQ-EIC-EGDGCGGTYS----NRYGGTCDP-DGCDW-NPYRLGNTSFYGP
T_viride_121854     EALTPHPCTTVGQ-EIC-EGDSCGGTYSD---DRYGGTCDP-DGCDW-NPYRLGNTSFYGP
T_viride_406299     EALTPHPCTTVGQ-EIC-DGDSCGGTYSG---DRYGGTCDP-DGCDW-NPYRLGNTSFYGP
T_harzianum_710     EALTPHPCETVGQ-TMC-SGDSCGGTYSN---DRYGGTCDP-DGCDW-NPYRLGNTSFYGP
A_bisporus_3913     SAYTPHPCREPGL-QRC-EGNTCS----VN--DRYATECDP-DGCDF-NSFRMGDKSFYGP
V_volvacea_5231     TAYTPHPCTQRGL-VRC-SGTACGG----GS--NRYGSICDH-DGLGFQNLFGMGRTRVRAR
T_longibrachiat     NALTPHSCTATA------------------------CDS-AGCGF-NPYGSGYPNYFGP
H_jecorina_1217     NALTPHSCTATA------------------------CDS-AGCGF-NPYGSGYKSYYGP
A_oryzae_246737     TGLTPHPCNTTGL-YEC-SGSGCG--------D--SGVCDK-AGCGF-NPYGLGAKDYYGY
consensus           -aftpHpCtt-gq-t-c--gd-cggtys----dry-g-CD--dGcdf-N-yrmgn-sfyg-
```

Figure 8F

```
2OVW.A            -GKQYKTDSTRKFTVTSQFVANK----QGDLI-ELHRHYIQDNKVIESATVNISGPPK-IN
1A39              -GEEFKVNTLKPFTVVTQFLANR---RGKLE-KIHRFYVQDGKVIESFYTNKEGVPY-TN
6CEL              -GSSFTLDTTKKLTVVTQFETS---------G-AINRYYVQNGVTFQQPNAE-LGSYS-GN
1EG1.A            -G---DTVDTSKTFTIITQFNTDNGSPSGNLV-SITRKYQQNGVDIPSAQP------G-GD
P_chrysosporium   -G---MSVDTTKLFTVVTQFITSDNTSMGALV-EIHRLYIQNGQVIQNSVVNIPGINP-AT
P_chrysospori_5   -G---MSVDTTKLFTVVTQFITSDNTSMGALV-EIHRLYIQNGQVIQNSVVNIPGINP-AT
P_chrysospori_6   -G---MSVDTTKTFTVVTQFITSDNTSTGNLT-EIRRFYVQNGNVIPNSVVNVTGIGA-VN
P_chrysospori_7   -G--LTVDTSKPFTVVTQFITNDGTSAGTLT-EIRRLYVQNGKVIQNSSVKIPGIDP-VN
P_chrysospori_8   -G--LTVDTSKPFTVVTQFITNDGTSAGTLT-EIRRLYVQNGKVIQNSSVKIPGIDL-VN
P_chrysospori_9   -G--LTVDTSKPFTVVTQFITNDGTSAGTLT-EIRRLYVQNGKVIQNSSVKIPGIDP-VN
P_chrysospor_10   -G--MTVDTSKPFTDVTQFLTNDNTSTGTLS-EIRRIYIQNGKVIQNSVANIPGVDP-VN
P_chrysospor_11   -G--MTVDTSKPFTVVTQFLTNDNTSTGTLS-EIRRIYIQNGKVIQNSVANIPGVDP-VN
P_chrysospor_12   -G--MTVDTSKPFTVVTQFLTNDNTSTGTLS-EIRRIYIQNGKVIQNSVANIPGVDP-VN
I_lacteus_45863   -G--LTVDTSRKFTIVTQFISDDGTTSGNLA-EIRRFYVQDGNVIPNSKVSIAGIDA-VN
I_lacteus_45_14   -G--LTVDTSQKFTIVTQFISDDGTADGNLA-EIRRFYVQNGKVIPNSVVQITGIDP-VN
I_lacteus_45_15   -G--MTVDTSRKFTVVTQFVTTDGTTNGDLH-EIRRLYVQDGKVIQNSVVSIPGIDA-VD
A_alternata_617   -G--KTVDTSKKFTVVTQFI-----GTGDAM-EIKRFYVQNGKTIAQPASAVPGVEG--N
L_maculans_7804   -G--KTVDTSKKFTVVTQFI-----GSGDAM-EIKRFYVQNGKTIPQPDSTIPGVTG--N
C_parasitica_39   -G--DTVDTSQKFTVVTQF-HG---SGSSLT-EISQYYIQGGTKIQQPNSTWPTLTG-YN
C_carbonum_3913   -G--ATLDTTKKMTVITQFL-G---SGSSLS-EIKRFYVQNGKVYKNSQSAVAGVTG--N
H_grisea_134622   -G--MTVDTTKKITVVTQFLKD---ANGDLG-EIKRFYVQDGKIIPNSESTIPGVEG--N
H_grisea_950686   -G--MTVDTTKKITVVTQFLKD---ANGDLG-EIKRFYVQDGKIIPNSESTIPGVEG---N
F_oxysporum_117   -GSNFNIDTTKKMTVVTQFHKG---SNGRLS-EITRLYVQNGKVIANSESKIAGNPG--S
C_purpurea_1906   -GPKFTIDTTRKISVVTQFLKG---RDGSLR-EIKRFYVQNGKVIPNSVSRVRGVPG--N
H_thermoidea_40   -G--KTVDTNRKFTVVSRF------ERNR----LSQFFVQDGRKIEVPPPTWPGLPN-SA
H_thermoidea_74   -G--KTVDTNRKFTVVSRF------ERNR----LSQFFVQDGRKIEVPPPTWPGLPN-SA
L_maculans_7_26   -G--KTVDTTKKMTVVTQFV-G---SGNQLS-EIKRFYVQDGKVIANPEPTIPGM-----
N_crassa_729649   -G--KTVDTSSKFTVVTQFIKD---SAGDLA-EIKAFYVQNGKVIENSQSNVDGVSG--N
A_aculeatus_391   -G--KTVDNSKPFTVVTQFITHDGTDTGTLT-EIRRLYVQNGVVIGNGPSTYTAASG--N
A_niger_6164684   -G--LTVDTNSPFTVVTQFITDDGTSSGTLT-EIKRLYVQNGEVIANGASTYSSVNG--S
P_janthinellum_   -G--ETIDTKSPFTVVTQFLTNDGTSTGTLS-EIKRFYVQGGKVIGNPQSTIVGVSG--N
A_niger_6164682   -G--KTIDTGSKMTVVTQFITD---GSGSLS-EIKRYYVQNGNVIANADSNISGVTG--N
H_ceramica_1218   -GSSFTLDTTKKLTVVTQF--E---TSGA-----INRYYVQNGVTFQQPNAELGSYSG--N
H_jecorina_2238   -GSSFTLDTTKKLTVVTQF--E---TSGA-----INRYYVQDGVTFQQPNAELGSYSG--N
T_viride_121854   -GSSFTLDTTKKLTVVTQF--E---TSGA-----INRYYVQNGVTFQQPNAELGDYSG--N
T_viride_406299   -GSSFTLDTTKKLTVVTQF--E---TSGA-----INRYYVQNGVTFQQPNAELGDYSG--N
T_harzianum_710   -GSSFALDTTKKLTVVTQFA------TDGS----ISRYYVQNGVKFQQPNAQVGSYSG--N
A_bisporus_3913   -G--MTVDTNQPITVVTQFITDNGSDNGNLQ-EIRRIYVQNGQVIQNSNVNIPGIDS-GN
V_volvacea_5231   VGRVKQFNRSSRVVEPISWTKQTTLHLGNLPWKSADCNVQNGRVIQNSKVNIPGMPSTMD
T_longibrachiat   -G---DTVDTSKTFTIITQFNTDNGSPSGNLV-SITRKYRQNGVDIPSAK---PG--G--D
H_jecorina_1217   -G---DTVDTSKTFTIITQFNTDNGSPSGNLV-SITRKYQQNGVDIPSAQ---PG--G--D
A_oryzae_246737   -G---LKVNTNETFTVVTQFLTNDNTTSGQLS-EIRRLYIQNGQVIQNAAVTSGGKTV--D
consensus         -G---tvdttkkftvvtqfvt----s-g-l--eirrfyvQngkvi-n----ipgv-g--n
```

Figure 8G

```
2OVW.A              FINDKYCAATG----ANE---YMRLGGTKQMGDAMSRGMVLAMSVWWSEGDFMAWLDQG--
1A39                MIDDEFCEATG----SRK---YMELGATQGMGEALTRGMVLAMSIWWDQGGNMEWLDHG--
6CEL                ELNDDYCTAEEAEFGGSS--FSDKGGLTQFKKATSGGMVLVMSLWDDYYANMLWLDSTYP
1EG1.A              TISSC----------PS--ASAYGGLATMGKALSSGMVLVFSIWNDNSQYMNWLDSG--
P_chrysosporium     SITDDLCAQENAAFGGTSS-FAQHGGLAQVGEALRSGMVLALSIVNS-AADTLWLDSNYP
P_chrysospori_5     SITDDLCAQENAAFGGTSS-FAQHGGLAQVGEALRSGMVLALSIVNS-AADTLWLDSNYP
P_chrysospori_6     SITDPFCSQQKKAFIETNY-FAQHGGLAQLGQALRTGMVLAFSISDDPANHMLWLDSNFP
P_chrysospori_7     SITDNFCSQQKTAFGDTNY-FAQHGGLKQVGEALRTGMVLALSIWDDYAANMLWLDSNYP
P_chrysospori_8     SITDNFCSQQKTAFGDTNY-FAQHGGLKQVGEALRTGMVLALSIWDDYAANMLWLDSNYP
P_chrysospori_9     SITDNFCSQQKTAFGDTNY-FAQHGGLKQVGEALRTGMVLALSIWDDYAANMLWLDSNYP
P_chrysospor_10     SITDNFCAQQKTAFGDTNW-FAQKGGLKQMGEALGNGMVLALSIWDDHAANMLWLDSDYP
P_chrysospor_11     SITDNFCAQQKTAFGDTNW-FAQKGGLKQMGEALGNGMVLALSIWDDHAANMLWLDSDYP
P_chrysospor_12     SITDNFCAQQKTAFGDTNW-FAQKGGLKQMGEALGNGMVLALSIWDDHAANMLWLDSDYP
I_lacteus_45863     SITDDFCTQQKTAFGDTNR-FAAQGGLKQMGAALKSGMVLALSLWDDHAANMLWLDSDYP
I_lacteus_45_14     SITEDFCTQQKTVFGDTNN-FAAKGGLKQMGEAVKNGMVLALSLWDDYAAQMLWLDSDYP
I_lacteus_45_15     SITDNFCAQQKSVFGDTNY-FATLGGLKKMGAALKSGMVLAMSVWDDHAASMQWLDSNYP
A_alternata_617     SITTKFCDQQKAVFGDTYT-FKDKGGMANMAKALANGMVLVMSLWDDHYSNMLWLDSTYP
L_maculans_7804     SITTFFCDAQKKAFGDKYT-FKDKGGMANM-PSTCNGMVLVMSLWDDHYSNMLWLDSTYP
C_parasitica_39     SITDDFCKAQKVEFNDTDV-FSEKGGLAQMGAGMADGMVLVMSLWDDHYANMLWLDSTYP
C_carbonum_3913     SITESFCTAQKKAFGDTSS-FAALGGLNEMGASLARGHVLIMSLWGDHAVNMLWLDSTYP
H_grisea_134622     SITQDWCDRQKVAFGDIDD-FNRKGGMKQMGKALAGPMVLVMSIWDDHASNMLWLDSTFP
H_grisea_950686     SITQDWCDRQKVAFGDIDD--FNRKGGMKQMGKALAGPMVLVMSIWDDHASNMLWLDSTFP
F_oxysporum_117     SLTSDFCSKQKSVFGDIDD-FSRKGGWNGMSDALSAPMVLVMSLWHDHHSNMLWLDSTYP
C_purpurea_1906     SITQGFCNAQKKMFGAHES-FNAKGGMKGMSAAVSKPMVLVMSLWDDHNSNMLWLDSTYP
H_thermoidea_40     DITPELCDAQFRVFDDRNR-FAETGGFDALNEALTIPMVLVMSIWDDHHSNMLWLDSSYP
H_thermoidea_74     DITPELCDAQFRVFDDRNR-FAETGGFDALNEALTIPMVLVMSIWDDHHSNMLWLDSSYP
L_maculans_7_26     -----EWCNTQKKVFQEEAYPFNEFGGMASMSEGMSQGMVLVMSLWDDHYANMLWLDSNWP
N_crassa_729649     SITQSFCKSQKTAFGDIDD-FNKKGGLKQMGKALAQAMVLVMSIWDDHAANMLWLDSTYP
A_aculeatus_391     SITESFCKAEKTLFGDTNV-FETHGGLSAMGDALGDGMVLVLSLWDDHAADMLWLDSDYP
A_niger_6164684     SITSAFCESEKTLFGDENV-FDRHGGLEGMGEAMAKGMVLVLSLWDDYAADMLWLDSDYP
P_janthinellum_     SITDSWCNAQKSAFGDTNE-FSKHGGMAGMGAGLADGMVLVMSLWDDHASDMLWLDSTYP
A_niger_6164682     SITTDFCTAQKKAFGDEDI-FAEHNGLAGISDAMSS-MVLILSLWDDYYASMEWLDSDYP
H_ceramica_1218     ELNDDYCTAEEAEFGGSS--FSDKGGLTQFKKATSGGMVLVMSLWDDYYANMLWLDSTYP
H_jecorina_2238     ELNDDYCTAEEAEFGGSS--FSDKGGLTQFXXATSGGMVLVMSLWDDYYANMLWLDSTYP
T_viride_121854     SLDDDYCAAEEAEFGGSS--FDKGGLTQFKKATSGGMVLVMSLWDDYYANMLWLDSTYP
T_viride_406299     SLDDDYCAAEEAEFGGSS--FSDKGGLTQFKKATSGGMVLVMSLWDDYYANMLWLDSTYP
T_harzianum_710     TINTDYCAAEQTAFGGTS--FTDKGGLAQINKAFQGGMVLVMSLWDDYAVNMLWLDSTYP
A_bisporus_3913     SISAEFCDQAKEAFGDERS-FQDRGGLSGMGSALDRGMVLVLSIWDDHAVNMLWLDSDYP
V_volvacea_5231     SVTTEFCNAQKTAFNDTFS-FQQKGGMANMSEALRRGMVLVLSIWDDHAANMLWLDSITS
T_longibrachiat     TISS--CPSASA---------Y---GGLATMGKALSSGMVLVFSIWNDNSQYMNWLDS---
H_jecornia_1217     TISS--CPSASA---------Y---GGLATMGKALSSGMVLVFSIWNDNSQYMNWLDS----
A_oryzae_246737     SITKDFCSGE----GSA---FNRLGGLEEMGHALGRGMVLALSIWNDAGSFMQWLD----
consensus           sitdefc--qk--fgds----f----ggl-qmg-al--gmVLvmSiwddhaanmlWLDs-yp
```

Figure 8H

```
2OVW.A            -----------VAGPCDATEGDPKNIVKVQPNPEVTFSNIRIGEIG-STS
1A39              -----------EAGPCAKGEGAPSNIVQVEPFPEVTYTNLRWGEIG-STY-------QELQ
6CEL              TNETS-STPGAVRGSCSTSSGVPAQVESQSPNAKVTFSNIKFGPIG-STG-------NPSG
1EG1.A            -----------NAGPCSSTEGNPSNILANNPNTHVVFSNIRWGDIG-STT
P_chrysosporium   ADADP-SAPGVARGTCPQDS---ASIP-EAPTPSVVFSNIKLGDIG-TTF--G----AGS
P_chrysospori_5   ADADP-SAPGVARGTCPQDS---ASIP-EAPTPSVVFSNIKLGDIG-TTF--G----AGS
P_chrysospori_6   PSANP-AVPGVARGMCSITSGNPADVGILNPSPYVSFLNIKFGSIG-TTF-------RPA
P_chrysospori_7   TNKDP-STPGVARGTCATTSGVPAQIEAQSPNAYVVFSNIKFGDLN-TTYT-GT--VSSS
P_chrysospori_8   TNKDP-STPGVARGTCATTSGVPAQIEAQSPNAYVVFSNIKFGDLN-TTYT-GT--VSSS
P_chrysospori_9   TNKDP-STPGVARGTCATTSGVPAQIEAQSPNAYVVFSNIKFGDLN-TTYT-GT--VSSS
P_chrysospor_10   TDKDP-SAPGVARGTCATTSGVPSDVESQVPNSQVVFSNIKFGDIG-STFS-G----TSS
P_chrysospor_11   TDKDP-SAPGVARGTCATTSGVPSDVESQVPNSQVVFSNIKFGDIG-STFS-G----TSS
P_chrysospor_12   TDKDP-SAPGVARGTCATTSGVPSDVESQVPNSQVVFSNIKFGDIG-STFS-G----TSS
I_lacteus_45863   TTADA-SNPGVARGTCPTTSGFPRDVESQSGSATVTYSNIKWGDLN-STFT-GTL-TTPS
I_lacteus_45_14   TTADP-SQPGVARGTCPTTSGVPSQVEGQEGSSSVIYSNIKFGDLN-STFT-GTLTNPSS
I_lacteus_45_15   ADGDA-TKPGVARGTCSADSGLPTNVESQSASASVTFSNIKWGDIN-TTFT-G----TGS
A_alternata_617   TDKNPDTDLGTGRGECETSSGVPADVESQHADATVVYSNIKFGPLN-STF---G
L_maculans_7804   TDKNPDTDAGSGRGECAITSGVPADVESQHPDASVIYSNIKFGPIN-TTF--G
C_parasitica_39   VDADA-SSPGKQRGTCATTSGVPADVESSDASATVIYSNIKFGPIG-ATY
C_carbonum_3913   TDADP-SKPGAARGTCPTTSGKPEDVEKNSPDATVVFSNIKFGPIG-STF--A----QPA
H_grisea_134622   VDAAG--KPGAERGACPTTSGVPAEVEAEAPNSNVVFSNIRFGPIG-STVA-GLPGAGNG
H_grisea_950686   VDAAG--KPGAERGACPTTSGVPAEVEAEAPNSNVVFSNIRFGPIG-STVA-GLPGAGNG
F_oxysporum_117   TDST---KVGSQRGSCATTSGKPSDLERDVPNSKVSFSNIKFGPIG-STY-------KSD
C_purpurea_1906   TNSR---QRGSKRGSCPASSGRPTDVESSAPDSTVVFSNIKFGPIG-STF-------SRG
H_thermoidea_40   PEKAG--LPGGDRGPCPTTSGVPAEVEAQYPNAQVVWSNIRFGPIG-STV--------NV
H_thermoidea_74   PEKAG--LPGGDRGPCPTTSGVPAEVEAQYPDAQVVWSNIRFGPIG-STV--------NV
L_maculans_7_26   READP-AKPGVARRDCPTSGGKPSEVEAANPNAQVMFSNIKFGPIG-STF-------AHA
N_crassa_729649   V---P-KVPGAYRGSGPTTSGVPAEVDANAPNSKVAFSNIKFGHLGISPFS-GGS-SGTP
A_aculeatus_391   TTSCA-SSPGVARGTCPTTTGNATYVEANYPNSYVTYSNIKFGTLN-STYS-GTSSGGSS
A_niger_6164684   VNSSA-STPGVARGTCSTDSGVPATVEAESPNAYVTYSNIKFGPIG-STYSSGS--SSGS
P_janthinellum_   TNATS-TTPGAKRGTCDISRR-PNTVESTYPNAYVIYSNIKTGPLN-STFT-GGTTSSSS
A_niger_6164682   ENATA-TDPGVARGTCDSESGVPATVEGAHPDSSVTFSNIKFGPIN-STF--------SAS
H_ceramica_1216   TNETS-STPGAVRGSCSTSSGVPAQVESQSPNAKVTFSNIKFGPIG-ST---G----NPS
H_jecorina_2238   TNETS-STPGAVRGSCSTSSGVPAQVESQSPNAKVTFSNIKFGPIG-ST---G----NPS
T_viride_121854   TDETS-STPGAVRGSSSTSSGVPAQLESNSPNAKVVYSNIKFGPIG-ST---G----NPS
T_viride_406299   TNETS-STPGAVRGSCSTSSGVPAQLESNSPNAKVVYSNIKFGPIG-ST---G----NSS
T_harzianum_710   TNATA-STPGAKRGSCSTSSGVPAQVEAQSPNSKVIYSNIRFGPIG-ST---G----GNT
A_bisporus_3913   LDASP-SQPGISRGTCSRDSGKPEDVEANAGGVQVVYSNIKFGDIN-STF--N----NNG
V_volvacea_5231   AAACR-STPSEVHATPLRESQIRSSHSRQT--RYVTFTNIKFGPFN-ST---G----TTY
T_longibrachiat   ---------G-RAGPCSSTEGNPSNILANNPGTHVVYSNIRWGDIG-STTN-ST---GGN
H_jecorina_1217   ---------G-NAGPCSSTEGNPSNILANNPNTHVVFSNIRWGDIG-STT--N----STA
A_oryzae_246737   ---------GGSAGPCNATEGNPALIEKLYPDTHVKFSKIRWGDIG-STY-------RH
consensus         t------s-pq--rgsc-ttsgvpa-ve-q-pn--VvfsnikFgpig-sty--g------s
```

Figure 8I

```
2OVW.A
1A39
6CEL
1EG1.A
P_chrysosporium    AL-------FS-GRSPPGPVPGS-APAS--S----ATA---TAPP-FGSQCGGLGYAGPTG
P_chrysospori_5    AL-------F--SGRS
P_chrysospori_6
P_chrysospori_7    SV-------SSSHSSTSTSSSHS-SSST--PPTQPTGV---TVPQ-WG-QCGGIGYTGST-
P_chrysospori_8    SV-------SSSHSSTSTSSSHS-SSST--PPTQPTGV---TVPQ-WG-QCGGIGYTGST-
P_chrysospori_9    SV-------SSSHSSTSTSSSHS-SSST--PPTQPTGV---TVPQ-WG-QCGGIGYTGST-
P_chrysospor_10    P--------NPPGGST-TSSPVT-TSPT--PP--PTGP----TVPQ-WG-QCGGIGYSGST-
P_chrysospor_11    P--------NPPGGST-TSSPVT-TSPT--PP--PTGP----TVPQ-WG-QCGGIGYSGST-
P_chrysospor_12    P--------NPPGGST-TSSPVT-TSPT--PP--PTGP----TVPQ-WG-QCGGIGYSGST-
I_lacteus_45863    GS-------SSPSSPASTSGSST-SASS--SASVPTQS--GTVAQ-WA-QCGGIGYSGAT-
I_lacteus_45_14    PA-------GPPVTSSPSEPSQS-TQPS--QPAQPTQPA-GTAAQ-WA-QCGGMGFTGPT-
I_lacteus_45_15    T--------SPSSPAGPVSSSTS-VASQ--PT-QPAQG---TVAQ-WG-QCGGTGFTGPT-
A_alternata_617
L_maculans_7804
C_parasitica_39
C_carbonum_3913
H_grisea_134622    GN-------NGGNPPPPTTTTSS-APAT--TTTASAGP---KAGR-WQ-QCGGIGFTGPT-
H_grisea_950686    GN-------NGGNPPPPTTTTSS-APAT--TTTASAGP---KAGR-WQ-QCGGIGFTGPT-
F_oxysporum_117    G--------TTPNPPASSSTTGS-STPT--NP--PAG----SVDQ-WG-QCGGQNYSGPT-
C_purpurea_1906    K
H_thermoidea_40
H_thermoidea_74
L_maculans_7_26    A
N_crassa_729649    PS-------NPSSSASPTSSTAKPSSTS--TASNPSGT---GAAH-WA-QCGGIGFSGPT-
A_aculeatus_391    SSSTTLTTKASTSTTSSKTTTT-TSKT--STTSSSST---NVAQLYG-QCGGQGWTGPT-
A_niger_6164684    GS-------SSSSSTTTKATST-TLKT--TSTTSSGSSSTSAAQAYG-QCGGQGWTGPT-
P_janthinellum_    TT-------TTTSKSTSTSSSSK-TTTTVTTTTSSGSS-GTGARDWA-QCGGNGWTGPT-
A_niger_6164682    A
H_ceramica_1218    GG-------NPPGGNR-GTTTTR-RPAT--TTGSSPGP---TQSH-YG-QCGGIGYSGPT-
H_jecorina_2238    GG-------NPPGGNPPGTTTTT-TTSS--SZ-PPPG----AHRR-YG-QCGGIGYSGPT-
T_viride_121854    GG-------NPPGGNPPGTTT-P-RPAT--STGSSPGP---TQTH-YG-QCGGIGYIGPT-
T_viride_406299    GG-------NPPGGNPPGTTTTR-RPAT--STGSSPGP---TQTH-YG-QCGGIGYSGPT-
T_harzianum_710    GS-------NPPGTSTTRAPPSS-TGSS------PTA----TQTH-YG-QCGGTGWTGPT-
A_bisporus_3913    G-----------GGGNPSPTTTR-----------PNSP---AQTM-WG-QCGGQGWTGPT-
V_volvacea_5231    T--------TGSVPTTSTSTGTT-GSST--PP-QPTGV---TVPQ--G-QCGGIGYTGPT-
T_longibrachiat    PP-------PPPPPASSTTFSTT-RRSS--TTSSSPSC---TQTH-WG-QCGGIGYTGCK-
H_jecorina_1217    PP-------PFPASSTTFSTTRR-SSTT--SS---SPSC---TQTH-WG-QCGGIGYSGCK-
A_oryzae_246737
consensus          -----------------------s-------------------fg-qcgg-qytg-t-
```

Figure 8J

```
2OVW.A
1A39
6CEL
1EG1.A
P_chrysosporium      VCPSPYTCQALNIYYSQ-CI
P_chrysospori_5
P_chrysospori_6
P_chrysospori_7      TCASPYTCHVLNPYYSQ-CY
P_chrysospori_8      TCASPYTCHVLNPYYSQ-CY
P_chrysospori_9      TCASPYTCHVLNPYYSQ-CY
P_chrysospor_10      TCASPYTCHVLNPYYSQ-CY
P_chrysospor_11      TCASPYTCHVLNPYYSQ-CY
P_chrysospor_12      TCASPYTCHVLNPCESILSLQRSSNADQYLQTTRSATKRRLDTALQPRK
I_lacteus_45863      TCVSPYTCHVVNAYYSQ-CY
I_lacteus_45_14      VCASPFTCHVLNPYYSQ-CY
I_lacteus_45_15      VCASPFTCHVVNPYYSQ-CY
A_alternata_617
L_maculans_7804
C_parasitica_39
C_carbonum_3913
H_grisea_134622      QCEEPYICTKLNDWYSQ-CL
H_grisea_950686      QCEEPYICTKLNDWYSQ-CL
F_oxysporum_117      TCKSPFTCKKINDFYSQ-CQ
C_purpurea_1906
H_thermoidea_40
H_thermoidea_74
L_maculans_7_26
N_crassa_729649      TCPEPYTCAKDHDIYSQ-CV
A_aculeatus_391      TCASG-TCTKQNDYYSQ-CL
A_niger_6164684      TCVSGYTCTYENAYYSQ-CL
P_janthinellum       TCVSPYTCTKQNDWYSQ-CL
A_niger_6164682
H_ceramica_1218      VCASGTTCQVLNPYYSQ-CL
H_jecorina_2238      VCASGTTCQVLNPYYSQ-CL
T_viride_121854      VCASGSTCQVLNPYYSQ-CL
T_viride_406299      VCASGSTCQVLNPYYSQ-CL
T_harzianum_710      RCASGYTCQVLNPFYSQ-CL
A_bisporus_3913      ACQSPSTCHVINDFYSQ-CF
V_volvacea_5231      TCASPTTCHVLNPYYSQ-CY
T_longibrachiat      TCTSGTTCQYGNDYYS QCL
H_jecorina_1217      TCTSGTTCQYGNDYYS QCL
A_oryzae_246737
consensus            -c-s--tc---n-ttsq-c-
```

Figure 8K

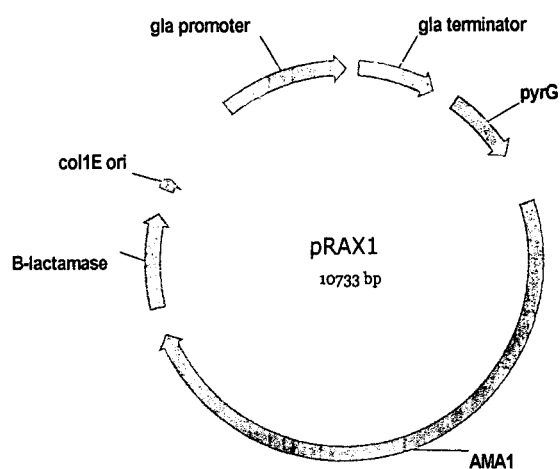
Figure 10: pRAX1

Figure 11: Destination vector pRAXdes2 for expression in *A. niger*
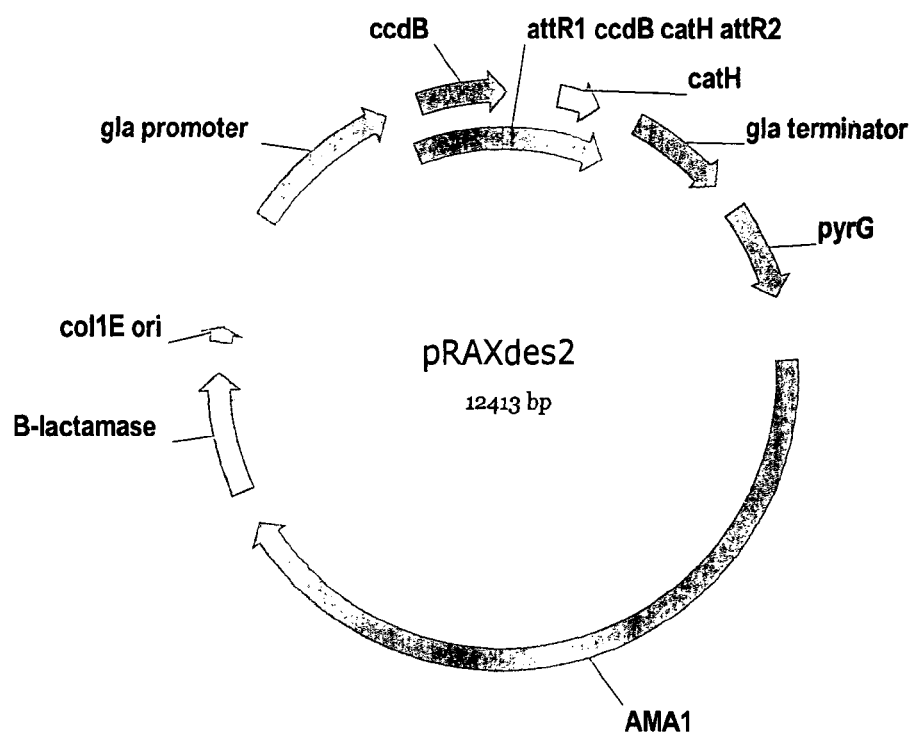

Figure 12: Replicative expression pRAXdesCBH1 vector of CBH1 genes under the control of the glucoamylase promotor.
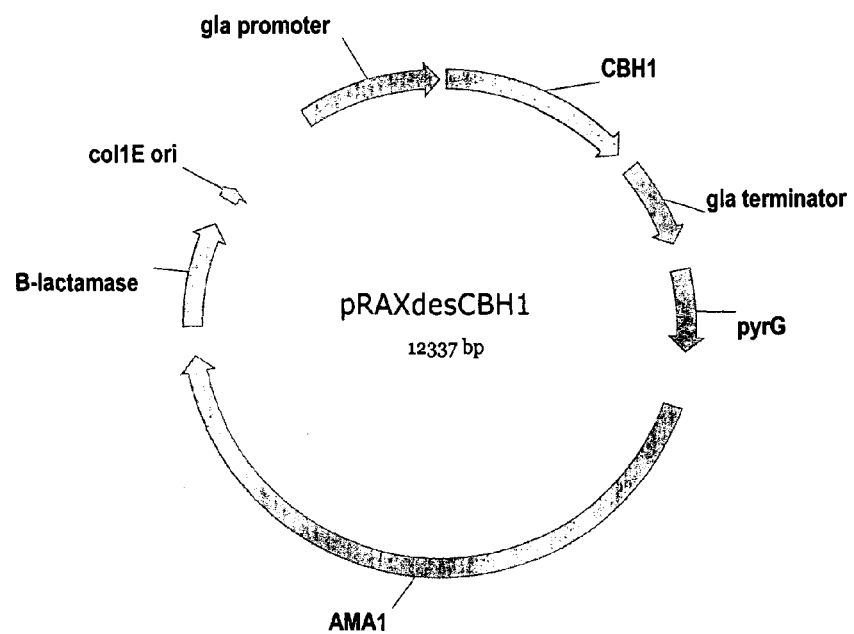

VARIANT *HYPOCREA JERCORINA* CBH1 CELLULASES

CROSS-REFERENCE TO RELATED APPLICATIONS

This application is a divisional of U.S. application Ser. No. 10/641,678, filed Aug. 15, 2003 and claims priority to U.S. Provisional Application No. 60/404,063, filed Aug. 16, 2002, to U.S. Provisional Application No. 60/458,853 filed Mar. 27, 2003, to U.S. Provisional Application No. 60/456,368 filed Mar. 21, 2003, and to U.S. Provisional Application No. 60/458,696 filed Mar. 27, 2003, all each of which is herein incorporated by reference in its entirety.

STATEMENT AS TO RIGHTS TO INVENTIONS MADE UNDER FEDERALLY SPONSORED RESEARCH AND DEVELOPMENT

Portions of this work were funded by Subcontract No. ZCO-0-30017-01 with the National Renewable Energy Laboratory under Prime Contract No. DE-AC36-99G10337 with the U.S. Department of Energy. Accordingly, the United States Government may have certain rights in this invention.

FIELD OF THE INVENTION

The present invention relates to variant cellobiohydrolase enzymes and isolated nucleic acid sequences which encode polypeptides having cellobiohydrolase activity. The invention also relates to nucleic acid constructs, vectors, and host cells comprising the nucleic acid sequences as well as methods for producing recombinant variant CBH polypeptides.

REFERENCES

1. Sheehan and Himmel *Biotechnology Progress* 15, pp 817-827 (1999)
2. Matti Linko Proceedings of the Second TRICEL Symposium on *Trichoderma reesei* Cellulases and Other Hydrolases pp 9-11 (1993)
3. Tuula T. Teeri *Trends in Biotechnology* 15, pp 160-167 (1997)
4. T. T. Teeri et al. Spec. Publ.-R. Soc. Chem., 246 (Recent Advances in Carbohydrate Bioengineering), pp 302-308. (1999)
5. PDB reference 2OVW: Sulzenbacher, G., Schulein, M., Davies, G. J. *Biochemistry* 36 pp. 5902 (1997)
PDB reference 1A39: Davies, G. J., Ducros, V., Lewis, R. J., Borchert, T. V., Schulein, M. *Journal of Biotechnology* 57 pp. 91 (1997)
7. PDB reference 6CEL: Divne, C., Stahlberg, J., Teeri, T. T., Jones, T. A. *Journal of Molecular Biology* 275 pp. 309 (1998)
8. PDB reference 1EG1: Kleywegt, G. J., Zou, J. Y., Divne, C., Davies, G. J., Sinning, I., Stahlberg, J., Reinikainen, T., Srisodsuk, M., Teeri, T. T., Jones, T. A. *Journal of Molecular. Biology* 272 pp. 383 (1997)
9. PDB reference 1DY4 (8CEL): J. Stahlberg, H. Henriksson, C. Divne, R. Isaksson, G. Pettersson, G. Johansson, T. A. Jones

BACKGROUND OF THE INVENTION

Cellulose and hemicellulose are the most abundant plant materials produced by photosynthesis. They can be degraded and used as an energy source by numerous microorganisms, including bacteria, yeast and fungi, that produce extracellular enzymes capable of hydrolysis of the polymeric substrates to monomeric sugars (Aro et al., J. Biol. Chem., vol. 276, no. 26, pp. 24309-24314, Jun. 29, 2001). As the limits of non-renewable resources approach, the potential of cellulose to become a major renewable energy resource is enormous (Krishna et al., Bioresource Tech. 77:193-196, 2001). The effective utilization of cellulose through biological processes is one approach to overcoming the shortage of foods, feeds, and fuels (Ohmiya et al., Biotechnol. Gen. Engineer. Rev. vol. 14, pp. 365-414, 1997).

Cellulases are enzymes that hydrolyze cellulose (beta-1,4-glucan or beta D-glucosidic linkages) resulting in the formation of glucose, cellobiose, cellooligosaccharides, and the like. Cellulases have been traditionally divided into three major classes: endoglucanases (EC 3.2.1.4) ("EG"), exoglucanases or cellobiohydrolases (EC 3.2.1.91) ("CBH") and beta-glucosidases ([beta]-D-glucoside glucohydrolase; EC 3.2.1.21) ("BG"). (Knowles et al., TIBTECH 5, 255-261, 1987; Shulein, Methods Enzymol., 160, 25, pp. 234-243, 1988). Endoglucanases act mainly on the amorphous parts of the cellulose fibre, whereas cellobiohydrolases are also able to degrade crystalline cellulose (Nevalainen and Penttila, Mycota, 303-319, 1995). Thus, the presence of a cellobiohydrolase in a cellulase system is required for efficient solubilization of crystalline cellulose (Suurnakki, et al. Cellulose 7:189-209, 2000). Beta-glucosidase acts to liberate D-glucose units from cellobiose, cello-oligosaccharides, and other glucosides (Freer, J. Biol. Chem. vol. 268, no. 13, pp. 9337-9342, 1993).

Cellulases are known to be produced by a large number of bacteria, yeast and fungi. Certain fungi produce a complete cellulase system capable of degrading crystalline forms of cellulose, such that the cellulases are readily produced in large quantities via fermentation. Filamentous fungi play a special role since many yeast, such as *Saccharomyces cerevisiae*, lack the ability to hydrolyze cellulose. See, e.g., Aro et al., 2001; Aubert et al., 1988; Wood et al., Methods in Enzymology, vol. 160, no. 9, pp. 87-116, 1988, and Coughlan, et al., "Comparative Biochemistry of Fungal and Bacterial Cellulolytic Enzyme Systems" Biochemistry and Genetics of Cellulose Degradation, pp. 11-30 1988.

The fungal cellulase classifications of CBH, EG and BG can be further expanded to include multiple components within each classification. For example, multiple CBHs, EGs and BGs have been isolated from a variety of fungal sources including *Trichoderma reesei* which contains known genes for 2 CBHs, i.e., CBH I and CBH II, at least 8 EGs, i.e., EG I, EG II, EG III, EGIV, EGV, EGVI, EGVII and EGVIII, and at least 5 BGs, i.e., BG1, BG2, BG3, BG4 and BG5.

In order to efficiently convert crystalline cellulose to glucose the complete celluiase system comprising components from each of the CBH, EG and BG classifications is required, with isolated components less effective in hydrolyzing crystalline cellulose (Filho et a., Can. J. Microbiol. 42:1-5, 1996). A synergistic relationship has been observed between cellulase components from different classifications. In particular, the EG-type cellulases and CBH-type cellulases synergistically interact to more efficiently degrade cellulose. See, e.g., Wood, Biochemical Society Transactions, 611th Meeting, Galway, vol. 13, pp. 407-410, 1985.

Cellulases are known in the art to be useful in the treatment of textiles for the purposes of enhancing the cleaning ability of detergent compositions, for use as a softening agent, for improving the feel and appearance of cotton fabrics, and the like (Kumar et al., Textile Chemist and Colorist, 29:37-42, 1997).

Cellulase-containing detergent compositions with improved cleaning performance (U.S. Pat. No. 4,435,307; GB App. Nos. 2,095,275 and 2,094,826) and for use in the treatment of fabric to improve the feel and appearance of the textile (U.S. Pat. Nos. 5,648,263, 5,691,178, and 5,776,757; GB App. No. 1,358,599; The Shizuoka Prefectural Hammamatsu Textile Industrial Research Institute Report, Vol. 24, pp. 54-61, 1986), have been described.

Hence, cellulases produced in fungi and bacteria have received significant attention. In particular, fermentation of Trichoderma spp. (e.g., Trichoderma longibrachiatum or Trichoderma reesei) has been shown to produce a complete cellulase system capable of degrading crystalline forms of cellulose.

Although cellulase compositions have been previously described, there remains a need for new and improved cellulase compositions for use in household detergents, stonewashing compositions or laundry detergents, etc. Cellulases that exhibit improved performance are of particular interest.

BRIEF SUMMARY OF THE INVENTION

The invention provides an isolated cellulase protein, identified herein as variant CBH I, and nucleic acids which encode a variant CBH I.

In one embodiment the invention is directed to a variant CBH I cellulase, wherein said variant comprises a substitution or deletion at a position corresponding to one or more of residues S8, Q17, G22, T41, N49, S57, N64, A68, A77, N89, S92, N103, A112, S113, E193, S196, M213, L225, T226, P227, T246, D249, R251, Y252, T255, D257, D259, S278, S279, K286, L288, E295, T296, S297, A299, N301, E325, T332, F338, S342, F352, T356, Y371, T380, Y381, V393, R394, S398, V403, S411, G430, G440, T445, T462, T484, Q487, and P491 in CBH I from Hypocrea jecorina (SEQ ID NO: 2). In first aspect, the invention encompasses an isolated nucleic acid encoding a polypeptide having cellobiohydrolase activity, which polypeptide is a variant of a glycosyl hydrolase of family 7, and wherein said nucleic acid encodes a substitution at a residue which is sensitive to temperature stress in the polypeptide encoded by said nucleic acid, wherein said variant cellobiohydrolase is derived from H. jecorina cellobiohydrolase. In second aspect, the invention encompasses an isolated nucleic acid encoding a polypeptide having cellobiohydrolase activity, which polypeptide is a variant of a glycosyl hydrolase of family 7, and wherein said nucleic acid encodes a substitution at a residue which affects enzyme processivity in the polypeptide encoded by said nucleic acid, wherein said variant cellobiohydrolase is derived from H. jecorina cellobiohydrolase. In third aspect, the invention encompasses an isolated nucleic acid encoding a polypeptide having cellobiohydrolase activity, which polypeptide is a variant of a glycosyl hydrolase of family 7, and wherein said nucleic acid encodes a substitution at a residue which affects product inhibition in the polypeptide encoded by said nucleic acid, wherein said variant cellobiohydrolase is derived from H. jecorina cellobiohydrolase.

In a second embodiment the invention is directed to a variant CBH I cellulose comprising a substitution at a position corresponding to one or more of residues S8P, Q17L, G22D, T41I, N49S, S57N, N64D, A68T, A77D, N89D, S92T, N103I, A112E, S113(T/N/D), E193V, S196T, M213I, L225F, T226A, P227(L/T/A), T246(C/A), D249K, R251A, Y252(A/Q), T255P, D257E, D259W, S278P, S279N, L288F, E295K, T296P, S297T, A299E, N301(R/K), E325K, T332(K/Y/H), F338Y, S342Y, F352L, T356L, Y371C, T380G, Y381D, V393G, R394A, S398T, V403D, S411F, G430F, G440R, T462I, T484S, Q487L and/or P491L in CBH I from Hypocrea jecorina (SEQ ID NO: 2). In one aspect of this embodiment the variant CBH I cellulase further comprises a deletion at a position corresponding to T445 in CBH I from Hypocrea jecorina (SEQ ID NO: 2). In a second aspect of this embodiment the variant CBH I cellulase further comprises the deletion of residues corresponding to residues 382-393 in CBH I of Hypocrea jecorina (SEQ ID NO: 2).

In a third embodiment the invention is directed to a variant CBH I cellulase, wherein said variant comprises a substitution at a position corresponding to a residue selected from the group consisting of S8P, N49S, A68T, A77D, N89D, S92T, S113(N/D), L225F, P227(A/L/T), D249K, T255P, D257E, S279N, L288F, E295K, S297T, A299E, N301K, T332(K/Y/H), F338Y, T356L, V393G, G430F in CBH I from Hypocrea jecorina (SEQ ID NO: 2).

In a fourth embodiment the invention is directed to a variant CBH I consists essentially of the mutations selected from the group consisting of
  i. A112E/T226A;
  ii. S196T/S411F;
  iii. E295K/S398T;
  iv. T246C/Y371C;
  v. T41I plus deletion at T445
  vi. A68T/G440R/P491L;
  vii. G22D/S278P/T296P;
  viii. T246A/R251A/Y252A;
  ix. T380G/Y381D/R394A;
  x. T380G/Y381D/R394A plus deletion of 382-393, inclusive;
  xi. Y252Q/D259W/S342Y;
  xii. S113T/T255P/K286M;
  xiii. P227L/E325K/Q487L;
  xiv. P227T/T484S/F352L;
  xv. Q17L/E193V/M213I/F352L;
  xvi. S8P/N49S/A68T/S113N;
  xvii. S8P/N49S/A68T/S113N/P227L;
  xviii. T41I/A112E/P227L/S278P/T296P;
  xix. S8P/N49S/A68T/A112E/T226A;
  xx. S8P/N49S/A68T/A112E/P227L;
  xxi. S8P/T41I/N49S/A68T/A112E/P227L;
  xxii. G22D/N49S/A68T/P227L/S278P/T296P;
  xxiii. S8P/G22D/T41I/N49S/A68T/N103I/S113N/P227L/S278P/T296P;
  xxiv. G22D/N49S/A68T/N103I/S113N/P227L/S278P/T296P;
  xxv. G22D/N49S/A68T/N 103I/A112E/P227L/S278P/T296P;
  xxvi. G22D/N49S/N64D/A68T/N 103I/S113N/S278P/T296P;
  xxvii. S8P/G22D/T41I/N49S/A68T/N 103I/S113N/P227L/D249K/S278P/T296P;
  xxviii. S8P/G22D/T41I/N49S/A68T/N103I/S113N/P227L/S278P/T296P/N301R;
  xxix. S8P/G22D/T41I/N49S/A68T/N103I/S113N/P227L/D249K/S278P/T296P/N301R
  xxx. S8P/G22D/T41I/N49S/A68T/S113N/P227L/D249K/S278P/T296P/N301R;
  xxxi. S8P/T41I/N49S/S57N/A68T/S113N/P227L/D249K/S278PIT296P/N301R;
  xxxii. S8P/G22D/T41I/N49S/A68T/S113N/P227L/D249K/S278P/N301R;
  xxxiii. S8P/T41I/N49S/A68T/S92T/S113N/P227L/D249K/V403D/T462I;
  xxxiv. S8P/G22DIT41I/N49S/A68T/S92T/S 113N/P227L/D249K/V403D/T462I xxxv. S8P/T41I/N49S/A68T/S92T/S113N/P227L/D249K/S411F;
xxxvi. S8P/G22D/T41I/N49S/A68T/S92T/S113N/P227L/D249K/S411F;
xxxvii. S8P/G22D/T41I/N49S/A68T/S92T/S113N/S196T/P227L/D249K/T255P/S278P/T296P/N301R/E325K/S411F;
xxxviii. S8P/T41I/N49S/A68T/S92T/S113N/S196T/P227L/D249K/T255P/S278P/T296P/N301R/E325K/V403D/S411F/T462I;
xxxix. S8P/G22D/T41I/N49S/A68T/S92T/S113N/S196T/P227L/D249K/T255P/S278P/T296P/N301R/E325K/V403D/S411F/T462I;

in CBH I from Hypocrea jecorina (SEQ ID NO:2).

In an fifth embodiment the invention is directed to a vector comprising a nucleic acid encoding a variant CBH I. In another aspect there is a construct comprising the nucleic acid of encoding the variant CBH I operably linked to a regulatory sequence.

In a sixth embodiment the invention is directed to a host cell transformed with the vector comprising a nucleic acid encoding a CBH I variant.

In a seventh embodiment the invention is directed to a method of producing a CBH I variant comprising the steps of:
(a) culturing a host cell transformed with the vector comprising a nucleic acid encoding a CBH I variant in a suitable culture medium under suitable conditions to produce CBH I variant;
(b) obtaining said produced CBH I variant.

In an eighth embodiment the invention is directed to a detergent composition comprising a surfactant and a CBH I variant. In one aspect of this embodiment the detergent is a laundry detergent. In a second aspect of this embodiment the detergent is a dish detergent. In third aspect of this invention, the variant CBH I cellulase is used in the treatment of a cellulose containing textile, in particular, in the stonewashing or indigo dyed denim.

In a ninth embodiment the invention is directed to a feed additive comprising a CBH I variant.

In a tenth embodiment the invention is directed to a method of treating wood pulp comprising contacting said wood pulp with a CBH I variant.

In a eleventh embodiment the invention is directed to a method of converting biomass to sugars comprising contacting said biomass with a CBH I variant.

In an embodiment, the cellulase is derived from a fungus, bacteria or Actinomycete. In another aspect, the cellulase is derived from a fungus. In a most preferred embodiment, the fungus is a filamentous fungus. It is preferred the filamentous fungus belong to Euascomycete, in particular, *Aspergillus* spp., *Gliocladium* spp., *Fusarium* spp., *Acremonium* spp., *Myceliophtora* spp., *Verticillium* spp., *Myrothecium* spp., or *Penicillium* spp. In a further aspect of this embodiment, the cellulase is a cellobiohydrolase.

Other objects, features and advantages of the present invention will become apparent from the following detailed description. It should be understood, however, that the detailed description and specific examples, while indicating preferred embodiments of the invention, are given by way of illustration only, since various changes and modifications within the scope and spirit of the invention will become apparent to one skilled in the art from this detailed description.

BRIEF DESCRIPTION OF THE DRAWINGS

FIG. 1 is the nucleic acid (lower line; SEQ ID NO: 1) and amino acid (upper line; SEQ ID NO: 2) sequence of the wild type Cel7A (CBH I) from *H. jecorina*.

Figure 3:
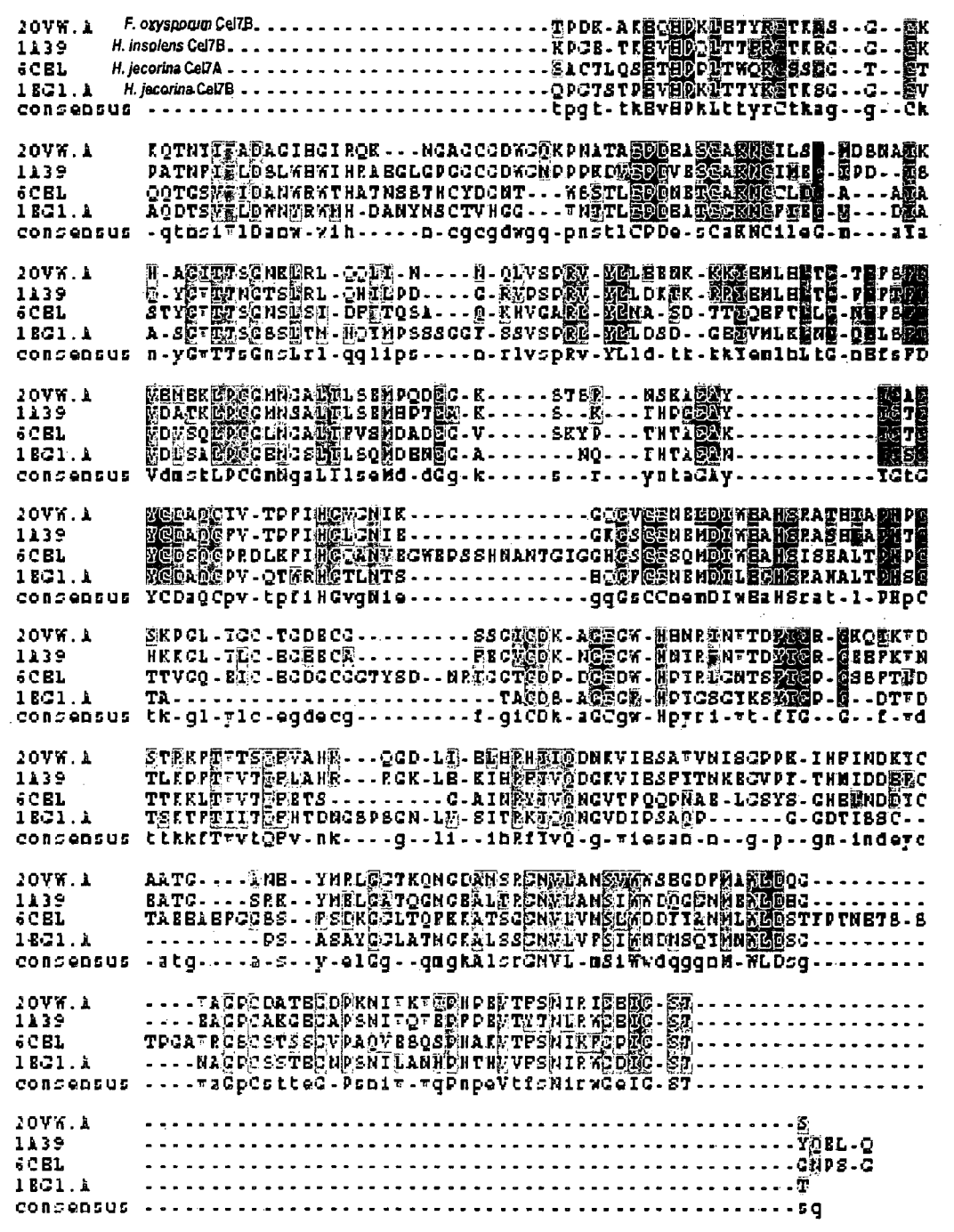

FIG. 3 shows the amino acid alignment of the Cel7 family members for which there were crystal structures available. The sequences are: 2OVW—*Fusarium oxysporum* Cel7B (SEQ ID NO:3), 1A39—*Humicola insolens* Cel7B (SEQ ID NO:4), 6CEL—*Hypocrea jecorina* Cel7A (amino acids 2 to 434 of SEQ ID NO:2), 1 EG1—*Hypocrea jecorina* Cel7B (SEQ ID NO:5) and a consensus sequence (SEQ ID NO:6).

FIG. 5 A-M is the nucleic acid sequence and deduced amino acid sequence for eight single residue mutations and five multiple mutation variants.

FIG. 6 A-D is the nucleic acid sequence for pTrex2 (SEQ ID NO:33).

FIGS. 7 A & B depicts the construction of the expression plasmid pTEX.

FIG. 8 A-J is the amino acid alignment of all 42 members of the Cel7 family.

FIG. 10 is the pRAX1 vector. This vector is based on the plasmid pGAPT2 except a 5259 bp HindIII fragment of *Aspergillus nidulans* genomic DNA fragment AMA1 sequence (Molecular Microbiology 1996 19:565-574) was inserted. Base 1 to 1134 contains *Aspergillus niger* glucoamylase gene promoter. Base 3098 to 3356 and 4950 to 4971 contains *Aspergillus niger* glucoamylase terminator. *Aspergillus nidulans* pyrG gene was inserted from 3357 to 4949 as a marker for fungal transformation. There is a multiple cloning site (MCS) into which genes may be inserted.

FIG. 11 is the pRAXdes2 vector backbone. This vector is based on the plasmid vector pRAX1. A Gateway cassette has been inserted into pRAX1 vector (indicated by the arrow on the interior of the circular plasmid). This cassette contains recombination sequence attR1 and attR2 and the selection marker catH and ccdB. The vector has been made according to the manual given in Gateway™ Cloning Technology: version 1 page 34-38 and can only replicate in *E. coli* DB3.1 from Invitrogen; in other *E. coli* hosts the ccdB gene is lethal. First a PCR fragment is made with primers containing attB1/2 recombination sequences. This fragment is recombined with pDONR201 (commercially available from Invitrogen); this vector contains attP1/2 recombination sequences with catH and ccdB in between the recombination sites. The BP clonase enzymes from Invitrogen are used to recombine the PCR fragment in this so-called ENTRY vector, clones with the PCR fragment inserted can be selected at 50 µg/ml kanamycin because clones expressing ccdB do not survive. Now the att sequences are altered and called attL1 and attL2. The second step is to recombine this clone with the pRAXdbs2 vector (containing attR1 and attR2 catH and ccdB in between the recombination sites). The LR clonase enzymes from Invitrogen are used to recombine the insert from the ENTRY vector in the destination vector. Only pRAXCBH1 vectors are selected using 100 µg/ml ampicilliri because ccdB is lethal and the ENTRY vector is sensitive to ampicillin. By this method the expression vector is now prepared and can be used to transform *A. niger*.

FIG. 12 provides an illustration of the pRAXdes2cbh1 vector which was used for expression of the nucleic acids encoding the CBH1 variants in *Aspergillus*. A nucleic acid encoding a CBH1 enzyme homolog or variant was cloned into the vector by homologous recombination of the att sequences.

DETAILED DESCRIPTION

Figure 2:
FIG. 2 is the 3-D structure of *H. jecorina* CBH I.
Figure 4:
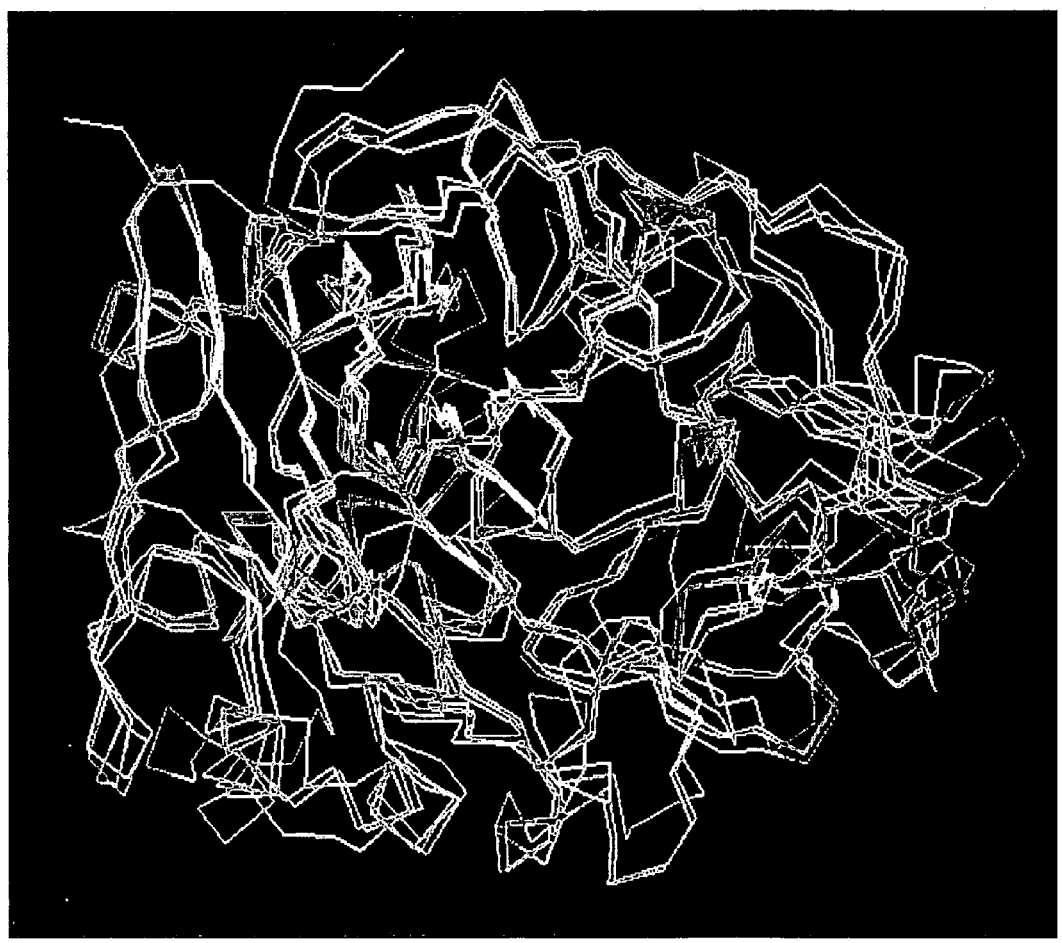
FIG. 4 illustrates the crystal structures from the catalytic domains of these four Cel7 homologues aligned and overlayed as described herein.

The invention will now be described in detail by way of reference only using the following definitions and examples. All patents and publications, including all sequences disclosed within such patents and publications, referred to herein are expressly incorporated by reference.

Unless defined otherwise herein, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Marham, THE HARPER COLLINS DICTIONARY OF BIOLOGY, Harper Perennial, N.Y. (1991) provide one of skill with a general dictionary of many of the terms used in this invention. Although any methods and materials similar or equivalent to those described herein can be used in the practice or testing of the present invention, the preferred methods and materials are described. Numeric ranges are inclusive of the numbers defining the range. Unless otherwise indicated, nucleic acids are written left to right in 5' to 3' orientation; amino acid sequences are written left to right in amino to carboxy orientation, respectively. Practitioners are particularly directed to Sambrook et al., MOLECULAR CLONING: A LABORATORY MANUAL (Second Edition), Cold Spring Harbor Press, Plainview, N.Y., 1989, and Ausubel F M et al., Current Protocols in Molecular Biology, John Wiley & Sons, New York, N.Y., 1993, for definitions and terms of the art. It is to be understood that this invention is not limited to the particular methodology, protocols, and reagents described, as these may vary.

The headings provided herein are not limitations of the various aspects or embodiments of the invention which can be had by reference to the specification as a whole. Accordingly, the terms defined immediately below are more fully defined by reference to the specification as a whole.

All publications cited herein are expressly incorporated herein by reference for the purpose of describing and disclosing compositions and methodologies which might be used in connection with the invention.

I. DEFINITIONS

The term "polypeptide" as used herein refers to a compound made up of a single chain of amino acid residues linked by peptide bonds. The term "protein" as used herein may be synonymous with the term "polypeptide" or may refer, in addition, to a complex of two or more polypeptides.

"Variant" means a protein which is derived from a precursor protein (e.g., the native protein) by addition of one or more amino acids to either or both the C- and N-terminal end, substitution of one or more amino acids at one or a number of different sites in the amino acid sequence, or deletion of one or more amino acids at either or both ends of the protein or at one or more sites in the amino acid sequence. The preparation of an enzyme variant is preferably achieved by modifying a DNA sequence which encodes for the native protein, transformation of that DNA sequence into a suitable host, and expression of the modified DNA sequence to form the derivative enzyme. The variant CBH I enzyme of the invention includes peptides comprising altered amino acid sequences in comparison with a precursor enzyme amino acid sequence wherein the variant CBH enzyme retains the characteristic cellulolytic nature of the precursor enzyme but which may have altered properties in some specific aspect. For example, a variant CBH enzyme may have an increased pH optimum or increased temperature or oxidative stability but will retain its characteristic cellulolytic activity. It is contemplated that the variants according to the present invention may be derived from a DNA fragment encoding a cellulase variant CBH enzyme wherein the functional activity of the expressed cellulase derivative is retained. For example, a DNA-fragment encoding a cellulase may further include a DNA sequence or portion thereof encoding a hinge or linker attached to the cellulase DNA sequence at either the 5' or 3' end wherein the functional activity of the encoded cellulase domain is retained.

"Equivalent residues" may also be defined by determining homology at the level of tertiary structure for a precursor cellulase whose tertiary structure has been determined by x-ray crystallography. Equivalent residues are defined as those for which the atomic coordinates of two or more of the main chain atoms of a particular amino acid residue of a cellulase and *Hypocrea jecorina* CBH (N on N, CA on CA, C on C and O on O) are within 0.13 nm and preferably 0.1 nm after alignment. Alignment is achieved after the best model has been oriented and positioned to give the maximum overlap of atomic coordinates of non-hydrogen protein atoms of the cellulase in question to the *H. jecorina* CBH I. The best model is the crystallographic model giving the lowest R factor for experimental diffraction data at the highest resolution available.

$$R \text{ factor} = \frac{\sum_h |Fo(h)| - |Fc(h)|}{\sum_h |Fo(h)|}$$

Equivalent residues which are functionally analogous to a specific residue of *H. jecorina* CBH I are defined as those amino acids of a cellulase which may adopt a conformation such that they either. alter, modify or contribute to protein structure, substrate binding or catalysis in a manner defined and attributed to a specific residue of the *H. jecorina* CBH I. Further, they are those residues of the cellulase (for which a tertiary structure has been obtained by x-ray crystallography) which occupy an analogous position to the extent that, although the main chain atoms of the given residue may not satisfy the criteria of equivalence on the basis of occupying a homologous position, the atomic coordinates of at least two of the side chain atoms of the residue lie with 0.13 nm of the corresponding side chain atoms of *H. jecorina* CBH. The crystal structure of *H. jecorina* CBH I is shown in FIG. 2.

The term "nucleic acid molecule" includes RNA, DNA and cDNA molecules. It will be understood that, as a result of the degeneracy of the genetic code, a multitude of nucleotide sequences encoding a given protein such as CBH I may be produced. The present invention contemplates every possible variant nucleotide sequence, encoding CBH 1, all of which are possible given the degeneracy of the genetic code.

"heterologous" nucleic acid construct or sequence has a portion of the sequence which is not native to the cell in which it is expressed. Heterologous, with respect to a control sequence refers to a control sequence (i.e. promoter or enhancer) that does not function in nature to regulate the same gene the expression of which it is currently regulating. Generally, heterologous nucleic acid sequences are not endogenous to the cell or part of the genome in which they are present, and have been added to the cell, by infection, transfection, transformation, microinjection, electroporation, or the like. A "heterologous" nucleic acid construct may contain a control sequence/DNA coding sequence combination that is the same as, or different from a control sequence/DNA coding sequence combination found in the native cell.

As used herein, the term "vector" refers to a nucleic acid construct designed for transfer between different host cells. An "expression vector" refers to a vector that has the ability to incorporate and express heterologous DNA fragments in a foreign cell. Many prokaryotic and eukaryotic expression vectors are commercially available. Selection of appropriate expression vectors is within the knowledge of those having skill in the art.

Accordingly, an "expression cassette" or "expression vector" is a nucleic acid construct generated recombinantly or synthetically, with a series of specified nucleic acid elements that permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter.

As used herein, the term "plasmid" refers to a circular double-stranded (ds) DNA construct used as a cloning vector, and which forms an extrachromosomal self-replicating genetic element in many bacteria and some eukaryotes.

As used herein, the term "selectable marker-encoding nucleotide sequence" refers to a nucleotide sequence which is capable of expression in cells and where expression of the selectable marker confers to cells containing the expressed gene the ability to grow in the presence of a corresponding selective agent, or under corresponding selective growth conditions.

As used herein, the term "promoter" refers to a nucleic acid sequence that functions to direct transcription of a downstream gene. The promoter will generally be appropriate to the host cell in which the target gene is being expressed. The promoter together with other transcriptional and translational regulatory nucleic acid sequences (also termed "control sequences") are necessary to express a given gene. In general, the transcriptional and translational regulatory sequences include, but are not limited to, promoter sequences, ribosomal binding sites, transcriptional start and stop sequences, translational start and stop sequences, and enhancer or activator sequences.

"Chimeric gene" or "heterologous nucleic acid construct", as defined herein refers to a non-native gene (i.e., one that has been introduced into a host) that may be composed of parts of different genes, including regulatory elements. A chimeric gene construct for transformation of a host cell is typically composed of a transcriptional regulatory region (promoter) operably linked to a heterologous protein coding sequence, or, in a selectable marker chimeric gene, to a selectable marker gene encoding a protein conferring antibiotic resistance to transformed cells. A typical chimeric gene of the present invention, for transformation into a host cell, includes a transcriptional regulatory region that is constitutive or inducible, a protein coding sequence, and a terminator sequence. A chimeric gene construct may also include a second DNA sequence encoding a signal peptide if secretion of the target protein is desired.

A nucleic acid is "operably linked" when it is placed into a functional relationship with another nucleic acid sequence. For example, DNA encoding a secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading frame. However, enhancers do not have to be contiguous. Linking is accomplished by ligation at convenient restriction sites. If such sites do not exist, the synthetic oligonucleotide adaptors, linkers or primers for PCR are used in accordance with conventional practice.

As used herein, the term "gene" means the segment of DNA involved in producing a polypeptide chain, that may or may not include regions preceding and following the coding region, e.g. 5' untranslated (5' UTR) or "leader" sequences and 3' UTR or "trailer" sequences, as well as intervening sequences (introns) between individual coding segments (exons).

In general, nucleic acid molecules which encode the variant CBH I will hybridize, under moderate to high stringency conditions to the wild type sequence provided herein as SEQ ID NO:1. However, in some cases a CBH I-encoding nucleotide sequence is employed that possesses a substantially different codon usage, while the protein encoded by the CBH I-encoding nucleotide sequence has the same or substantially the same amino acid sequence as the native protein. For example, the coding sequence may be modified to facilitate faster expression of CBH I in a particular prokaryotic or eukaryotic expression system, in accordance with the frequency with which a particular codon is utilized by the host. Te'o, et al. (FEMS Microbiology Letters 190:13-19, 2000), for example, describes the optimization of genes for expression in filamentous fungi.

A nucleic acid sequence is considered to be "selectively hybridizable" to a reference nucleic acid sequence if the two sequences specifically hybridize to one another under moderate to high stringency hybridization and wash conditions. Hybridization conditions are based on the melting temperature (Tm) of the nucleic acid binding complex or probe. For example, "maximum stringency" typically occurs at about Tm-5° C. (5° below the Tm of the probe); "high stringency" at about 5-10° below the Tm; "moderate" or "intermediate stringency" at about 10-20° below the Tm of the probe; and "low stringency" at about 20-25° below the Tm. Functionally, maximum stringency conditions may be used to identify sequences having strict identity or near-strict identity with the hybridization probe; while high stringency conditions are used to identify sequences having about 80% or more sequence identity with the probe.

Moderate and high stringency hybridization conditions are well known in the art (see, for example, Sambrook, et al, 1989, Chapters 9 and 11, and in Ausubel, F. M., et al., 1993, expressly incorporated by reference herein). An example of high stringency conditions includes hybridization at about 42° C. in 50% formamide, 5×SSC, 5×Denhardt's solution, 0.5% SDS and 100 µg/ml denatured carrier DNA followed by washing two times in 2×SSC and 0.5% SDS at room temperature and two additional times in 0.1×SSC and 0.5% SDS at 42° C.

As used herein, "recombinant" includes reference to a cell or vector, that has been modified by the introduction of a heterologous nucleic acid sequence or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention.

As used herein, the terms "transformed", "stably transformed" or "transgenic" with reference to a cell means the cell has a non-native (heterologous) nucleic acid sequence integrated into its genome or as an episomal plasmid that is maintained through multiple generations.

As used herein, the term "expression" refers to the process by which a polypeptide is produced based on the nucleic acid sequence of a gene. The process includes both transcription and translation.

The term "introduced" in the context of inserting a nucleic acid sequence into a cell, means "transfection", or "transformation" or "transduction" and includes reference to the incorporation of a nucleic acid sequence into a eukaryotic or prokaryotic cell where the nucleic acid sequence may be incorporated into the genome of the cell (for example, chromosome, plasmid, plastid, or mitochondrial DNA), converted into an autonomous replicon, or transiently expressed (for example, transfected mRNA).

It follows that the term "CBH I expression" refers to transcription and translation of the cbh I gene, the products of which include precursor RNA, mRNA, polypeptide, post-translationally processed polypeptides, and derivatives thereof, including CBH I from related species such as *Trichoderma koningii, Hypocrea jecorina* (also known as *Trichoderma longibrachiatum, Trichoderma reesei* or *Trichoderma viride*) and *Hypocrea schweinitzii*. By way of example, assays for CBH I expression include Western blot for CBH I protein, Northern blot analysis and reverse transcriptase polymerase chain reaction (RT-PCR) assays for CBH I mRNA, and endoglucanase activity assays as described in Shoemaker S. P. and Brown R. D. Jr. (Biochim. Biophys. Acta, 1978, 523:133-146) and Schulein (Methods Enzymol., 160, 25, pp. 234-243, 1988).

The term "alternative splicing" refers to the process whereby multiple polypeptide isoforms are generated from a single gene, and involves the splicing together of nonconsecutive exons during the processing of some, but not all, transcripts of the gene. Thus a particular exon may be connected to any one of several alternative exons to form messenger RNAs. The alternatively-spliced mRNAs produce polypeptides ("splice variants") in which some parts are common while other parts are different.

The term "signal sequence" refers to a sequence of amino acids at the N-terminal portion of a protein which facilitates the secretion of the mature form of the protein outside the cell. The mature form of the extracellular protein lacks the signal sequence which is cleaved off during the secretion process.

By the term "host cell" is meant a cell that contains a vector and supports the replication, and/or transcription or transcription and translation (expression) of the expression construct. Host cells for use in the present invention can be prokaryotic cells, such as *E. coli*, or eukaryotic cells such as yeast, plant, insect, amphibian, or mammalian cells. In general, host cells are filamentous fungi.

The term "filamentous fungi" means any and all filamentous fungi recognized by those of skill in the art. A preferred fungus is selected from the group consisting of *Aspergillus, Trichoderma, Fusarium, Chrysosporium, Penicillium, Humicola, Neurospora*, or alternative sexual forms thereof such as *Emericella, Hypocrea*. It has now been demonstrated that the asexual industrial fungus *Trichoderma reesei* is a clonal derivative of the ascomycete *Hypocrea jecorina*. See Kuhls et al., PNAS (1996) 93:7755-7760.

The term "cellooligosaccharide" refers to oligosaccharide groups containing from 2-8 glucose units and having β-1,4 linkages, e.g., cellobiose.

The term "cellulase" refers to a category of enzymes capable of hydrolyzing cellulose polymers to shorter cello-oligosaccharide oligomers, cellobiose and/or glucose. Numerous examples of cellulases, such as exoglucanases, exocellobiohydrolases, endoglucanases, and glucosidases have been obtained from cellulolytic organisms, particularly including fungi, plants and bacteria.

CBH I from *Hypocrea jecorina* is a member of the Glycosyl Hydrolase Family 7 (hence Cel 7) and, specifically, was the first member of that family identified in *Hypocrea jecorina* (hence Cel 7A). The Glycosyl Hydrolase Family 7 contains both Endoglucanases and Cellobiohydrolases/exoglucanases, and that CBH I is the latter. Thus, the phrases CBH I, CBH I-type protein and Cel 7 cellobiohydrolases may be used interchangeably herein.

The term "cellulose binding domain" as used herein refers to portion of the amino acid sequence of a cellulase or a region of the enzyme that is involved in the cellulose binding activity of a cellulase or derivative thereof. Cellulose binding domains generally function by non-covalently binding the cellulase to cellulose, a cellulose derivative or other polysaccharide equivalent thereof. Cellulose binding domains permit or facilitate hydrolysis of cellulose fibers by the structurally distinct catalytic core region, and typically function independent of the catalytic core. Thus, a cellulose binding domain will not possess the significant hydrolytic activity attributable to a catalytic core. In other words, a cellulose binding domain is a structural element of the cellulase enzyme protein tertiary structure that is distinct from the structural element which possesses catalytic activity. Cellulose binding domain and cellulose binding module may be used interchangeably herein.

As used herein, the term "surfactant" refers to any compound generally recognized in the art as having surface active qualities. Thus, for example, surfactants comprise anionic, cationic and nonionic surfactants such as those commonly found in detergents. Anionic surfactants include linear or branched alkylbenzenesulfonates; alkyl or alkenyl ether sulfates having linear or branched alkyl groups or alkenyl groups; alkyl or alkenyl sulfates; olefinsulfonates; and alkanesulfonates. Ampholytic surfactants include quaternary ammonium salt sulfonates, and betaine-type ampholytic surfactants. Such ampholytic surfactants have both the positive and negative charged groups in the same molecule. Nonionic surfactants may comprise polyoxyalkylene ethers, as well as higher fatty acid alkanolamides or alkylene oxide adduct thereof, fatty acid glycerine monoesters, and the like.

As used herein, the term "cellulose containing fabric" refers to any sewn or unsewn fabrics, yarns or fibers made of cotton or non-cotton containing cellulose or cotton or non-cotton containing cellulose blends including natural cellulosics and manmade cellulosics (such as jute, flax, ramie, rayon, and lyocell).

As used herein, the term "cotton-containing fabric" refers to sewn or unsewn fabrics, yarns or fibers made of pure cotton or cotton blends including cotton woven fabrics, cotton knits, cotton denims, cotton yarns, raw cotton and the like.

As used herein, the term "stonewashing composition" refers to a formulation for use in stonewashing cellulose containing fabrics. Stonewashing compositions are used to modify cellulose containing fabrics prior to sale, i.e., during the manufacturing process. In contrast, detergent compositions are intended for the cleaning of soiled garments and are not used during the manufacturing process.

As used herein, the term "detergent composition" refers to a mixture which is intended for use in a wash medium for the laundering of soiled cellulose containing fabrics. In the context of the present invention, such compositions may include, in addition to cellulases and surfactants, additional hydrolytic enzymes, builders, bleaching agents, bleach activators, bluing agents and fluorescent dyes, caking inhibitors, masking agents, cellulase activators, antioxidants, and solubilizers.

As used herein, the term "decrease or elimination in expression of the cbh1 gene" means that either that the cbh1 gene has been deleted from the genome and therefore cannot be expressed by the recombinant host microorganism; or that the cbh1 gene has been modified such that a functional CBH1 enzyme is not produced by the host microorganism.

The term "variant cbh1 gene" or "variant CBH1" means, respectively, that the nucleic acid sequence of the cbh1 gene from *H. jecorina* has been altered by removing, adding, and/or manipulating the coding sequence or the amino acid sequence of the expressed protein has been modified consistent with the invention described herein.

As used herein, the term "purifying" generally refers to subjecting transgenic nucleic acid or protein containing cells to biochemical purification and/or column chromatography.

As used herein, the terms "active" and "biologically active" refer to a biological activity associated with a particular protein and are used interchangeably herein. For example, the enzymatic activity associated with a protease is proteolysis and, thus, an active protease has proteolytic activity. It follows that the biological activity of a given protein refers to any, biological activity typically attributed to that protein by those of skill in the art.

As used herein, the term "enriched" means that the CBH is found in a concentration that is greater relative to the CBH concentration found in a wild-type, or naturally occurring, fungal cellulase composition. The terms enriched, elevated and enhanced may be used interchangeably herein.

A wild type fungal cellulase composition is one produced by a naturally occurring fungal source and which comprises one or more BGL, CBH and EG components wherein each of these components is found at the ratio produced by the fungal source. Thus, an enriched CBH composition would have CBH at an altered ratio wherein the ratio of CBH to other cellulase components (i.e., EGs, beta-glucosidases and other endoglucanases) is elevated. This ratio may be increased by either increasing CBH or decreasing (or eliminating) at least one other component by any means known in the art.

Thus, to illustrate, a naturally occurring cellulase system may be purified into. substantially pure components by recognized separation techniques well published in the literature, including ion exchange chromatography at a suitable pH, affinity chromatography, size exclusion and the like. For example, in ion exchange chromatography (usually anion exchange chromatography), it is possible to separate the cellulase components by eluting with a pH gradient, or a salt gradient, or both a pH and a salt gradient. The purified CBH may then be added to the enzymatic solution resulting in an enriched CBH solution. It is also possible to elevate the amount of CBH I produced by a microbe using molecular genetics methods to overexpress the gene encoding CBH, possibly in conjunction with deletion of one or more genes encoding other cellulases.

Fungal cellulases may contain more than one CBH component. The different components generally have different isoelectric points which allow for their separation via ion exchange chromatography and the like. Either a single CBH component or a combination of CBH components may be employed in an enzymatic solution.

When employed in enzymatic solutions, the homolog or variant CBH1 component is generally added in an amount sufficient to allow the highest rate of release of soluble sugars from the biomass. The amount of homolog or variant CBH1 component added depends upon the type of biomass to be saccharified which can be readily determined by the skilled artisan. However, when employed, the weight percent of the homolog or variant CBH1 component relative to any EG type components present in the cellulase composition is from preferably about 1, preferably about 5, preferably about 10, preferably about 15, or preferably about 20 weight percent to preferably about 25, preferably about 30, preferably about 35, preferably about 40, preferably about 45 or preferably about 50 weight percent. Furthermore, preferred ranges may be about 0.5 to about 15 weight percent, about 0.5 to about 20 weight percent, from about 1 to about 10 weight percent, from about 1 to about 15 weight percent, from about 1 to about 20 weight percent, from about 1 to about 25 weight percent, from about 5 to about 20 weight percent, from about 5 to about 25 weight percent, from about 5 to about 30 weight percent, from about 5 to about 35 weight percent, from about 5 to about 40 weight percent, from about 5 to about 45 weight percent, from about 5 to about 50 weight percent, from about 10 to about 20 weight percent, from about 10 to about 25 weight percent, from about 10 to about 30 weight percent, from about 10 to about 35 weight percent, from about 10 to about 40 weight percent, from about 10 to about 45 weight percent, from about 10 to about 50 weight percent, from about 15 to about 20 weight percent, from about 15 to about 25 weight percent, from about 15 to about 30 weight percent, from about 15 to about 35 weight percent, from about 15 to about 30 weight percent, from about 15 to about 45 weight percent, from about 15 to about 50 weight percent.

II. HOST ORGANISMS

Filamentous fungi include all filamentous forms of the subdivision Eumycota and Oomycota. The filamentous fungi are characterized by vegetative mycelium having a cell wall composed of chitin, glucan, chitosan, mannan, and other complex polysaccharides, with vegetative growth by hyphal elongation and carbon catabolism that is obligately aerobic.

In the present invention, the filamentous fungal parent cell may be a cell of a species of, but not limited to, *Trichoderma*, e.g., *Trichoderma longibrachiatum, Trichoderma viride, Trichoderma koningii, Trichoderma harzianum; Penicillium* sp.; *Humicola* sp., including *Humicola insolens* and *Humicola grisea; Chrysosporium* sp., including *C. lucknowense; Gliocladium* sp.; *Aspergillus* sp.; *Fusarium* sp., *Neurospora* sp., *Hypocrea* sp., and *Emericella* sp. As used herein, the term "*Trichoderma*" or "*Trichoderma* sp." refers to any fungal strains which have previously been classified as *Trichoderma* or are currently classified as *Trichoderma*.

In one preferred embodiment, the filamentous fungal parent cell is an *Aspergillus niger, Aspergillus awamori, Aspergillus aculeatus*, or *Aspergillus nidulans* cell.

In another preferred embodiment, the filamentous fungal parent cell is a *Trichoderma reesei* cell.

III. CELLULASES

Cellulases are known in the art as enzymes that hydrolyze cellulose (beta-1,4-glucan or beta D-glucosidic linkages) resulting in the formation of glucose, cellobiose, cellooligosaccharides, and the like. As set forth above, cellulases have been traditionally divided into three major classes: endoglucanases (EC 3.2.1.4) ("EG"), exoglucanases or cellobiohydrolases (EC 3.2.1.91) ("CBH") and beta-glucosidases (EC 3.2.1.21) ("BG"). (Knowles, et al., TIBTECH 5, 255-261, 1987; Schulein, 1988).

Certain fungi produce complete cellulase systems which include exo-cellobiohydrolases or CBH-type cellulases, endoglucanases or EG-type cellulases and beta-glucosidases or BG-type cellulases (Schulein, 1988). However, sometimes these systems lack CBH-type cellulases and bacterial cellulases also typically include little or no CBH-type cellulases. In addition, it has been shown that the EG components and CBH components synergistically interact to more efficiently degrade cellulose. See, e.g., Wood, 1985. The different components, i.e., the various endoglucanases and exocellobiohydrolases in a multi-component or complete cellulase system, generally have different properties, such as isoelectric point, molecular weight, degree of glycosylation, substrate specificity and enzymatic action patterns.

It is believed that endoglucanase-type cellulases hydrolyze internal beta-1,4-glucosidic bonds in regions of low crystallinity of the cellulose and exo-cellobiohydrolase-type cellulases hydrolyze cellobiose from the reducing or non-reducing end of cellulose. It follows that the action of endoglucanase components can greatly facilitate the action of exo-cellobiohydrolases by creating new chain ends which are recognized by exo-cellobiohydrolase components. Further, beta-glucosidase-type cellulases have been shown to catalyze the hydrolysis of alkyl and/or aryl β-D-glucosides such as methyl β-D-glucoside and p-nitrophenyl glucoside as well as glycosides containing only carbohydrate residues, such as cellobiose. This yields glucose as the sole product for the microorganism and reduces or eliminates cellobiose which inhibits cellobiohydrolases and endoglucanases.

Cellulases also find a number of uses in detergent compositions including to enhance cleaning ability, as a softening agent and to improve the feel of cotton fabrics (Hemmpel, ITB Dyeing/Printing/Finishing 3:5-14, 1991; Tyndall, Textile Chemist and Colorist 24:23-26, 1992; Kumar et al., Textile Chemist and Colorist, 29:37-42, 1997). While the mechanism is not part of the invention, softening and color restoration properties of cellulase have been attributed to the alkaline endoglucanase components in cellulase compositions, as exemplified by U.S. Pat. Nos. 5,648,263, 5,691,178, and 5,776,757, which disclose that detergent compositions containing a cellulase composition enriched in a specified alkaline endoglucanase component impart color restoration and improved softening to treated garments as compared to cellulase compositions not enriched in such a component. In addition, the use of such alkaline endoglucanase components in detergent compositions has been shown to complement the pH requirements of the detergent composition (e.g., by exhibiting maximal activity at an alkaline pH of 7.5 to 10, as described in U.S. Pat. Nos. 5,648,263, 5,691,178, and 5,776,757).

Cellulase compositions have also been shown to degrade cotton-containing fabrics, resulting in reduced strength loss in the fabric (U.S. Pat. No. 4,822,516), contributing to reluctance to use cellulase compositions in commercial detergent applications. Cellulase compositions comprising endoglucanase components have been suggested to exhibit reduced strength loss for cotton-containing fabrics as compared to compositions comprising a complete cellulase system.

Cellulases have also been shown to be useful in degradation of cellulase biomass to ethanol (wherein the cellulase degrades cellulose to glucose and yeast or other microbes further ferment the glucose into ethanol), in the treatment of mechanical pulp (Pere et al., 1996), for use as a feed additive (WO 91/04673) and in grain wet milling.

Most CBHs and EGs have a multidomain structure consisting of a core domain separated from a cellulose binding domain (CBD) by a linker peptide (Suurnakki et al., 2000). The core domain contains the active site whereas the CBD interacts with cellulose by binding the enzyme to it (van Tilbeurgh et al., 1986; Tomme et al., Eur. J. Biochem. 170: 575-581, 1988). The CBDs are particularly important in the hydrolysis of crystalline cellulose. It has been shown that the ability of cellobiohydrolases to degrade crystalline cellulose clearly decreases when the CBD is absent (Linder and Teeri, J. Biotechnol. 57:15-28, 1997). However, the exact role and action mechanism of CBDs is still a matter of speculation. It has been suggested that the CBD enhances the enzymatic activity merely by increasing the effective enzyme concentration at the surface of cellulose (Stahlberg et al., Bio/Technol. 9:286-290, 1991), and/or by loosening single cellulose chains from the cellulose surface (Tormo et al., EMBO J. vol. 15, no. 21, pp. 5739-5751, 1996). Most studies concerning the effects of cellulase domains on different substrates have been-carried out with core proteins of cellobiohydrolases, as their core proteins can easily be produced by limited proteolysis with papain (Tomme et al., 1988). Numerous cellulases have been described in the scientific literature, examples of which include: from *Trichoderma reesei*. Shoemaker, S. et al., Bio/Technology, 1:691-696, 1983, which discloses CBHI; Teeri, T. et al., Gene, 51:43-52, 1987, which discloses CBHII. Cellulases from species other than *Trichoderma* have also been described e.g., Ooi et al., Nucleic Acids Research, vol. 18, no. 19, 1990, which discloses the cDNA sequence coding for endoglucanase F1-CMC produced by *Aspergillus aculeatus*; Kawaguchi T et al., Gene 173(2):287-8, 1996, which discloses the cloning and sequencing of the cDNA encoding beta-glucosidase 1 from *Aspergillus aculeatus*; Sakamoto et al., Curr. Genet. 27:435-439, 1995, which discloses the cDNA sequence encoding the endoglucanase CMCase-1 from *Aspergillus kawachii* IFO 4308; Saarilahti et al., Gene 90:9-14, 1990, which discloses an endoglucanase from *Erwinia carotovara*; Spilliaert R, et al., Eur J Biochem. 224(3):923-30, 1994, which discloses the cloning and sequencing of bglA, coding for a thermostable beta-glucanase from *Rhodothermus marinu*; and Halldorsdottir S et al., Appl Microbiol Biotechnol. 49(3):277-84, 1998, which discloses the cloning, sequencing and overexpression of a *Rhodothermus marinus* gene encoding a thermostable cellulase of glycosyl hydrolase family 12. However, there remains a need for identification and characterization of novel cellulases, with improved properties, such as improved performance under conditions of thermal stress or in the presence of surfactants, increased specific activity, altered substrate cleavage pattern, and/or high level expression in vitro.

The development of new and improved cellulase compositions that comprise varying amounts CBH-type, EG-type and BG-type cellulases is of interest for use: (1) in detergent compositions that exhibit enhanced cleaning ability, function as a softening agent and/or improve the feel of cotton fabrics (e.g., "stone washing" or "biopolishing"); (2) in compositions for degrading wood pulp or other biomass into sugars (e.g., for bio-ethanol production); and/or (3) in feed compositions.

IV. MOLECULAR BIOLOGY

In one embodiment this invention provides for the expression of variant CBH I genes under control of a promoter functional in a filamentous fungus. Therefore, this invention relies on routine techniques in the field of recombinant genetics. Basic texts disclosing the general methods of use in this invention include Sambrook et al., *Molecular Cloning, A Laboratory Manual* (2nd ed. 1989); Kriegler, *Gene Transfer and Expression: A Laboratory Manual* (1990); and Ausubel et al., eds., *Current Protocols in Molecular Biology* (1994)).

A. Methods for Identifying Homologous CBH1 Genes

The nucleic acid sequence for the wild type *H. jecorina* CBH1 is shown in FIG. 1. The invention, in one aspect, encompasses a nucleic acid molecule encoding a CBH1 homolog described herein. The nucleic acid may be a DNA molecule.

Techniques that can be used to isolate CBH I encoding DNA sequences are well known in the art and include, but are not limited to, cDNA and/or genomic library screening with a homologous DNA probe and expression screening with activity assays or antibodies against CBH I. Any of these methods can be found in Sambrook, et al. or in CURRENT PROTOCOLS IN MOLECULAR BIOLOGY, F. Ausubel, et al., ed. Greene Publishing and Wiley-Interscience, New York (1987) ("Ausubel").

B. Methods of Mutating CBH I Nucleic Acid Sequences

Any method known in the art that can introduce mutations is contemplated by the present invention.

The present invention relates to the expression, purification and/or isolation and use of variant CBH1. These enzymes are preferably prepared by recombinant methods utilizing the cbh gene from *H. jecorina*.

After the isolation and cloning of the cbh1 gene from *H. jecorina*, other methods known in the art, such as site directed mutagenesis, are used to make the substitutions, additions or deletions that correspond to substituted amino acids in the expressed CBH1 variant. Again, site directed mutagenesis and other methods of incorporating amino acid changes in expressed proteins at the DNA level can be found in Sambrook, et al. and Ausubel, et al.

DNA encoding an amino acid sequence variant of the *H. jecorina* CBH1 is prepared by a variety of methods known in the art. These methods include, but are not limited to, preparation by site-directed (or oligonucleotide-mediated) mutagenesis, PCR mutagenesis, and cassette mutagenesis of an earlier prepared DNA encoding the *H. jecorina* CBH1.

Site-directed mutagenesis is a preferred method for preparing substitution variants. This technique is well known in the art (see, e.g., Carter et al. Nucleic Acids Res. 13:4431-4443 (1985) and Kunkel et al., Proc. Natl. Acad. Sci. USA 82:488 (1987)). Briefly, in carrying out site-directed mutagene sis of DNA, the starting DNA is altered by first hybridizing an oligonucleotide encoding the desired mutation to a single strand of such starting DNA. After hybridization, a DNA polymerase is used to synthesize an entire second strand, using the hybridized oligonucleotide as a primer, and using the single strand of the starting DNA as a template. Thus, the oligonucleotide encoding the desired mutation is incorporated in the resulting double-stranded DNA.

PCR mutagenesis is also suitable for making amino acid sequence variants of the starting polypeptide, i.e., *H. jecorina* CBH1. See Higuchi, in PCR Protocols, pp. 177-183 (Academic Press, 1990); and Vallette et al., Nuc. Acids Res. 17:723-733 (1989). See, also, for example Cadwell et al., PCR Methods and Applications, Vol 2, 28-33 (1992). Briefly, when small amounts of template DNA are used as starting material in a PCR, primers that differ slightly in sequence from the corresponding. region in a template DNA can be used to generate relatively large quantities of a specific DNA fragment that differs from the template sequence only at the positions where the primers differ from the template.

Another method for preparing variants, cassette mutagenesis, is based on the technique described by Wells et al., Gene 34:315-323 (1985). The starting material is the plasmid (or other vector) comprising the starting polypeptide DNA to be mutated. The codon(s) in the starting DNA to be mutated are identified. There must be a unique restriction endonuclease site on each side of the identified mutation site(s). If no such restriction sites exist, they may be generated using the above-described oligonucleotide-mediated mutagenesis method to introduce them at appropriate locations in the starting polypeptide DNA. The plasmid DNA is cut at these sites to linearize it. A double-stranded oligonucleotide encoding the sequence of the DNA between the restriction sites but containing the desired mutation(s) is synthesized using standard procedures, wherein the two strands of the oligonucleotide are synthesized separately and then hybridized together using standard techniques. This double-stranded oligonucleotide is referred to as the cassette. This cassette is designed to have 5' and 3' ends that are compatible with the ends of the linearized plasmid, such that it can be directly ligated to the plasmid. This plasmid now contains the mutated DNA sequence.

Alternatively, or additionally, the desired amino acid sequence encoding a variant CBH I can be determined, and a nucleic acid sequence encoding such amino acid sequence variant can be generated synthetically.

The variant CBH I(s) so prepared may be subjected to further modifications, oftentimes depending on the intended use of the cellulase. Such modifications may involve further alteration of the amino acid sequence, fusion to heterologous polypeptide(s) and/or covalent modifications.

V. cbh1 NUCLEIC ACIDS AND CBH1 POLYPEPTIDES

A. Variant cbh-Type Nucleic Acids

The nucleic acid sequence for the wild type *H. jecorina* CBH I is shown in FIG. 1. The invention encompasses a nucleic acid molecule encoding the variant cellulases described herein. The nucleic acid may be a DNA molecule.

After the isolation and cloning of the CBH I, other methods known in the art, such as site directed mutagenesis, are used to make the substitutions, additions or deletions that correspond to substituted amino acids in the expressed CBH I variant. Again, site directed mutagenesis and other methods of incorporating amino acid changes in expressed proteins at the DNA level can be found in Sambrook, et al. and Ausubel, et al.

After DNA sequences that encode the CBH1 variants have been cloned into DNA constructs, the DNA is used to transform microorganisms. The microorganism to be transformed for the purpose of expressing a variant CBH1 according to the present invention may advantageously comprise a strain derived from *Trichoderma* sp. Thus, a preferred mode for preparing variant CBH1 cellulases according to the present invention comprises transforming a *Trichoderma* sp. host cell with a DNA construct comprising at least a fragment of DNA encoding a portion or all of the variant CBH1. The DNA construct will generally be functionally attached to a promoter. The transformed host cell is then grown under conditions so as to express the desired protein. Subsequently, the desired protein product is purified to substantial homogeneity.

However, it may in fact be that the best expression vehicle for a given DNA encoding a variant CBH1 may differ from *H. jecorina*. Thus, it may be that it will be most advantageous to express a protein in a transformation host that bears phylogenetic similarity to the source organism for the variant CBH1. In an alternative embodiment, *Aspergillus niger* can be used as an expression vehicle. For a description of transformation techniques with *A. niger*, see WO 98/31821, the disclosure of which is incorporated by reference in its entirety.

Accordingly, the present description of a *Trichoderma* spp. expression system is provided for illustrative purposes only and as one option for expressing the variant CBH1 of the invention. One of skill in the art, however, may be inclined to express the DNA encoding variant CBH1 in a different host cell if appropriate and it should be understood that the source of the variant CBH1 should be considered in determining the optimal expression host. Additionally, the skilled worker in the field will be capable of selecting the best expression system for a particular gene through routine techniques utilizing the tools available in the art.

B. Variant CBH1 Polypeptides

The amino acid sequence for the wild type *H. jecorina* CBH I is shown in FIG. 1. The variant CBH I polypeptides comprises a substitution or deletion at a position corresponding to one or more of residues S8, Q17, G22, T41, N49, S57, N64, A68, A77, N89, S92, N103, A112, S113, E193, S196, M213, L225, T226, P227, T246, D249, R251, Y252, T255, D257, D259, S278, S279, K286, L288, E295, T296, S297, A299, N301, E325, T332, F338, S342, F352, T356, Y371, T380, Y381, V393, R394, S398, V403, S411, G430, G440, T445, T462, T484, Q487, and P491 in CBH I from *Hypocrea jecorina*. Furthermore, the variant may further comprises a deletion of residues corresponding to residues 382-393 in CBH I from *Hypocrea jecorina*.

The variant CBH I's of this invention have amino acid sequences that are derived from the amino acid sequence of a precursor CBH I. The amino acid sequence of the CBH I variant differs from the precursor CBH I amino acid sequence by the substitution, deletion or insertion of one or more amino acids of the precursor amino acid sequence. In a preferred embodiment, the precursor CBH I is *Hypocrea jecorina* CBH I. The mature amino acid sequence of *H. jecorina* CBH I is shown in FIG. 1. Thus, this invention is directed to CBH I variants which contain amino acid residues at positions which are equivalent to the particular identified residue in *H. jecorina* CBH I. A residue (amino acid) of an CBH I homolog is equivalent to a residue of *Hypocrea jecorina* CBH I if it is either homologous (i.e., corresponding in position in either primary or tertiary structure) or is functionally analogous to a specific residue or portion of that residue in *Hypocrea jecorina* CBH I (ie., having the same or similar functional capacity to combine, react, or interact chemically or structurally). As used herein, numbering is intended to correspond to that of the mature CBH I amino acid sequence as illustrated in FIG. 1. In addition to locations within the precursor CBH I, specific residues in the precursor CBH I corresponding to the amino acid positions that are responsible for instability when the precursor CBH I is under thermal stress are identified herein for substitution or deletion. The amino acid position number (e.g., +51) refers to the number assigned to the mature *Hypocrea jecorina* CBH I sequence presented in FIG. 1.

The variant CBH1's of this invention have amino acid sequences that are derived from the amino acid sequence of a precursor *H. jecorina* CBH1. The amino acid sequence of the CBH1 variant differs from the precursor CBH1 amino acid sequence by the substitution, deletion or insertion of one or more amino acids of the precursor amino acid sequence. The mature amino acid sequence of *H. jecorina* CBH1 is shown in FIG. 1. Thus, this invention is directed to CBH1 variants which contain amino acid residues at positions which are equivalent to the particular identified residue in *H. jecorina* CBH1. A residue (amino acid) of an CBH1 variant is equivalent to a residue of *Hypocrea jecorina* CBH1 if it is either homologous (i.e., corresponding in position in either primary or tertiary structure) or is functionally analogous to a specific residue or portion of that residue in *Hypocrea jecorina* CBH1 (i.e., having the same or similar functional capacity to combine, react, or interact chemically or structurally). As used herein, numbering is intended to correspond to that of the mature CBH1 amino acid sequence as illustrated in FIG. 1. In addition to locations within the precursor CBH1, specific residues in the precursor CBH1 corresponding to the amino acid positions that are responsible for instability when the precursor CBH1 is under thermal stress are identified herein for substitution or deletion. The amino acid position number (e.g., +51) refers to the number assigned to the mature *Hypocrea jecorina* CBH1 sequence presented in FIG. 1.

Alignment of amino acid sequences to determine homology is preferably determined by using a "sequence comparison algorithm." Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), by visual inspection or MOE by Chemical Computing Group, Montreal Canada.

An example of an algorithm that is suitable for determining sequence similarity is the BLAST algorithm, which is described in Altschul, et al., *J. Mol. Biol.* 215:403-410 (1990). Software for performing BLAST analyses is publicly available through the National Center for Biotechnology Information (<www.ncbi.nlm.nih.gov>). This algorithm involves first identifying high scoring sequence pairs (HSPs) by identifying short words of length W in the query. sequence that either match or satisfy some positive-valued threshold score T when aligned with a word of the same length in a database sequence. These initial neighborhood word hits act as starting points to find longer HSPs containing them. The word hits are expanded in both directions along each of the two sequences being compared for as far as the cumulative alignment score can be increased. Extension of the word hits is stopped when: the cumulative alignment score falls off by the quantity X from a maximum achieved value; the cumulative score goes to zero or below; or the end of either sequence is reached. The BLAST algorithm parameters W, T, and X determine the sensitivity and speed of the alignment. The BLAST program uses as defaults a word length (W) of 11, the BLOSUM62 scoring matrix (see Henikoff & Henikoff, *Proc. Natl. Acad. Sci. USA* 89:10915 (1989)) alignments (B) of 50, expectation (E) of 10, M'5, N'-4, and a comparison of both strands.

The BLAST algorithm then performs a statistical analysis of the similarity between two sequences (see, e.g., Karlin & Altschul, *Proc. Nat'l. Acad. Sci. USA*. 90:5873-5787 (1993)). One measure of similarity provided by the BLAST algorithm is the smallest sum probability (P(N)), which provides an indication of the probability by which a match between two nucleotide or amino acid sequences would occur by chance. For example, an amino acid sequence is considered similar to a protease if the smallest sum probability in a comparison of the test amino acid sequence to a protease amino acid sequence is less than about 0.1, more preferably less than about 0.01, and most preferably less than about 0.001.

Additional specific strategies for modifying stability of CBH1 cellulases are provided below:

(1) Decreasing the entropy of main-chain unfolding may introduce stability to the enzyme. For example, the introduction of proline residues may significantly stabilize the protein by decreasing the entropy of the unfolding (see, e.g., Watanabe, et al., *Eur. J. Biochem.* 226:277-283 (1994)). Similarly, glycine residues have no β-carbon, and thus have considerably greater backbone conformational freedom than many other residues. Replacement of glycines, preferably with alanines, may reduce the entropy of unfolding and improve stability (see, e.g., Matthews, et al., *Proc. Natl. Acad. Sci. USA* 84; 6663-6667 (1987)). Additionally, by shortening external loops it may be possible to improve stability. It has been observed that hyperthermophile produced proteins have shorter external loops than their mesophilic homologues (see, e.g., Russel, et al., *Current Opinions in Biotechnology* 6:370-374 (1995)). The introduction of disulfide bonds may also be effective to stabilize distinct tertiary structures in relation to each other. Thus, the introduction of cysteines at residues accessible to existing cysteines or the introduction of pairs of cysteines that could form disulfide bonds would alter the stability of a CBH1 variant.

(2) Decreasing internal cavities by increasing side-chain hydrophobicity may alter the stability of an enzyme. Reducing the number and volume of internal cavities increases the stability of enzyme by maximizing hydrophobic interactions and reducing packing defects (see, e.g., Matthews, *Ann. Rev. Biochem.* 62:139-160 (1993); Burley, et al., *Science* 229:23-29 (1985); Zuber, *Biophys. Chem.* 29:171-179 (1988); Kellis, et al., *Nature* 333:784-786 (1988)). It is known that multimeric proteins from thermophiles often have more hydrophobic sub-unit interfaces with greater surface complementarity than their mesophilic counterparts (Russel, et al., supra). This principle is believed to be applicable to domain interfaces of monomeric proteins. Specific substitutions that may improve stability by increasing hydrophobicity include lysine to arginine, serine to alanine and threonine to alanine (Russel, et al., supra). Modification by substitution to alanine or proline may increase side-chain size with resultant reduction in cavities, better packing and increased hydrophobicity. Substitutions to reduce the size of the cavity, increase hydrophobicity and improve the complementarity the interfaces between the domains of CBH1 may improve stability of the enzyme. Specifically, modification of the specific residue at these positions with a different residue selected from any of phenylalanine, tryptophan, tyrosine, leucine and isoleucine may improve performance.

(3) Balancing charge in rigid secondary structure, i.e., α-helices and β-turns may improve stability. For example, neutralizing partial positive charges on a helix N-terminus with negative charge on aspartic acid may improve stability of the structure (see, e.g., Eriksson, et al., *Science* 255:178-183 (1992)). Similarly, neutralizing partial negative charges on helix C-terminus with positive charge may improve stability. Removing positive charge from interacting with peptide N-terminus in β-turns should be effective in conferring tertiary structure stability. Substitution with a non-positively charged residue could remove an unfavorable positive charge from interacting with an amide nitrogen present in a turn.

(4) Introducing salt bridges and hydrogen bonds to stabilize tertiary structures may be effective. For example, ion pair interactions, e.g., between aspartic acid or glutamic acid and lysine, arginine or histidine, may introduce strong stabilizing effects and may be used to attach different tertiary structure elements with a resultant improvement in thermostability. Additionally, increases in the number of charged residue/non-charged residue hydrogen bonds, and the number of hydrogen-bonds generally, may improve thermostability (see, e.g., Tanner, et al., *Biochemistry* 35:2597-2609 (1996)). Substitution with aspartic acid, asparagine, glutamic acid or glutamine may introduce a hydrogen bond with a backbone amide. Substitution with arginine may improve a salt bridge and introduce an H-bond into a backbone carbonyl.

(5) Avoiding thermolabile residues in general may increase thermal stability. For example, asparagine and glutamine are susceptible to deamidation and cysteine is susceptible to oxidation at high temperatures. Reducing the number of these residues in sensitive positions may result in improved thermostability (Russel, et al., supra). Substitution or deletion by any residue other than glutamine or cysteine may increase stability by avoidance of a thermolabile residue.

(6) Stabilization or destabilization of binding of a ligand that confers modified stability to CBH1 variants. For example, a component of the matrix in which the CBH1 variants of this invention are used may bind to a specific surfactant/thermal sensitivity site of the CBH1 variant. By modifying the site through substitution, binding of the component to the variant may be strengthened or diminished. For example, a non-aromatic residue in the binding crevice of CBH1 may be substituted with phenylalanine or tyrosine to introduce aromatic side-chain stabilization where interaction of the cellulose substrate may interact favorably with the benzyl rings, increasing the stability of the CBH1 variant.

(7) Increasing the electronegativity of any of the surfactant/thermal sensitivity ligands may improve stability under surfactant or thermal stress. For example, substitution with phenylalanine or tyrosine may increase the electronegativity of D (aspartate) residues by improving shielding from solvent, thereby improving stability.

C. Anti-CBH Antibodies

The present invention further provides anti-CBH antibodies. The antibodies may be polyclonal, monoclonal, humanized, bispecific or heteroconjugate antibodies.

Methods of preparing polyclonal antibodies are known to the skilled artisan. The immunizing agent may be an CBH polypeptide or a fusion protein thereof. It may be useful to conjugate the antigen to a protein known to be immunogenic in the mammal being immunized. The immunization protocol may be determined by one skilled in the art based on standard protocols or routine experimentation.

Alternatively, the anti-CBH antibodies may be monoclonal antibodies. Monoclonal antibodies may be produced by cells immunized in an animal or using recombinant DNA methods. (See, e.g., Kohler et al., *Nature*, vol. 256, pp. 495-499, Aug. 7, 1975; U.S. Pat. No. 4,816,567).

An anti-CBH antibody of the invention may further comprise a humanized or human antibody. The term "humanized antibody" refers to humanized forms of non-human (e.g., murine) antibodies that are chimeric antibodies, immunoglobulin chains or fragments thereof (such as Fv, Fab, Fab', $F(ab')_2$ or other antigen-binding partial sequences of antibodies) which contain some portion of the sequence derived from non-human antibody. Methods for humanizing non-human antibodies are well known in the art, as further detailed in Jones et al., Nature 321:522-525, 1986; Riechmann et al., Nature, vol. 332, pp. 323-327, 1988; and Verhoeyen et al., Science, vol. 239, pp. 1534-1536, 1988. Methods for producing human antibodies are also known in the art. See, e.g., Jakobovits, A, et al., Annals New York Academy of Sciences, 764:525-535, 1995 and Jakobovits, A, Curr Opin Biotechnol 6(5):561-6, 1995.

VI. EXPRESSION OF RECOMBINANT CBH1 VARIANTS

The methods of the invention rely on the use cells to express variant CBH I, with no particular method of CBH I expression required.

The invention provides host cells which have been transduced, transformed or transfected with an expression vector comprising a variant CBH-encoding nucleic acid sequence. The culture conditions, such as temperature, pH and the like, are those previously used for the parental host cell prior to transduction, transformation or transfection and will be apparent to those skilled in the art.

In one approach, a filamentous fungal cell or yeast cell is transfected with an expression vector having a promoter or biologically active promoter fragment or one or more (e.g., a series) of enhancers which functions in the host cell line, operably linked to a DNA segment encoding CBH, such that CBH is expressed in the cell line.

A. Nucleic Acid Constructs/Expression Vectors.

Natural or synthetic polynucleotide fragments encoding CBH I ("CBH I-encoding nucleic acid sequences") may be incorporated into heterologous nucleic acid constructs or vectors, capable of introduction into, and replication in, a filamentous fungal or yeast cell. The vectors and methods disclosed herein are suitable for use in host cells for the expression of CBH I. Any vector may be used as long as it is replicable and viable in the cells into which it is introduced. Large numbers of suitable vectors and promoters are known to those of skill in the art, and are commercially available. Cloning and expression vectors are also described in Sambrook et al., 1989, Ausubel F M et al., 1989, and Strathern et al., The Molecular Biology of the Yeast *Saccharomyces*, 1981, each of which is expressly incorporated by reference herein. Appropriate expression vectors for fungi are described in van den Hondel, C.A.M.J.J. et al. (1991) In: Bennett, J. W. and Lasure, L. L. (eds.) More Gene Manipulations in Fungi. Academic Press, pp. 396-428. The appropriate DNA sequence may be inserted into a plasmid or vector (collectively referred to herein as "vectors") by a variety of procedures. In general, the DNA sequence is inserted into an appropriate restriction endonuclease site(s) by standard procedures. Such procedures and related sub-cloning procedures are deemed to be within the scope of knowledge of those skilled in the art.

Recombinant filamentous fungi comprising the coding sequence for variant CBH I may be produced by introducing a heterologous nucleic acid construct comprising the variant CBH I coding sequence into the cells of a selected strain of the filamentous fungi.

Once the desired form of a variant cbh nucleic acid sequence is obtained, it may be modified in a variety of ways. Where the sequence involves non-coding flanking regions, the flanking regions may be subjected to resection, mutagenesis, etc. Thus, transitions, transversions, deletions, and insertions may be performed on the naturally occurring sequence.

A selected variant cbh coding sequence may be inserted into a suitable vector according to well-known recombinant techniques and used to transform filamentous fungi capable of CBH I expression. Due to the inherent degeneracy of the genetic code, other nucleic acid sequences which encode substantially the same or a functionally equivalent amino acid sequence may be used to clone and express variant CBH I. Therefore it is appreciated that such substitutions in the coding region fall within the sequence variants covered by the present invention. Any and all of these sequence variants can be utilized in the same way as described herein for a parent CBH I-encoding-nucleic acid sequence.

The present invention also includes recombinant nucleic acid constructs comprising one or more of the variant CBH I-encoding nucleic acid sequences as described above. The constructs comprise a vector, such as a plasmid or viral vector, into which a sequence of the invention has been inserted, in a forward or reverse orientation.

Heterologous nucleic acid constructs may include the coding sequence for variant cbh: (i) in isolation; (ii) in combination with additional coding sequences; such as fusion protein or signal peptide coding sequences, where the cbh coding sequence is the dominant coding sequence; (iii) in combination with non-coding sequences, such as introns and control elements, such as promoter and terminator elements or 5' and/or 3' untranslated regions, effective for expression of the coding sequence in a suitable host; and/or (iv) in a vector or host environment in which the cbh coding sequence is a heterologous gene.

In one aspect of the present invention, a heterologous nucleic acid construct is employed to transfer a variant CBH I-encoding nucleic acid sequence into a cell in vitro, with established filamentous fungal and yeast lines preferred. For long-term, production of variant CBH I, stable expression is preferred. It follows that any method effective to generate stable transformants may be used in practicing the invention.

Appropriate vectors are typically equipped with a selectable marker-encoding nucleic acid sequence, insertion sites, and suitable control elements, such as promoter and termination sequences. The vector may comprise regulatory sequences, including, for example, non-coding sequences, such as introns and control elements, i.e., promoter and terminator elements or 5' and/or 3' untranslated regions, effective for expression of the coding sequence in host cells (and/or in a vector or host cell environment in which a modified soluble protein antigen coding sequence is not normally expressed), operably linked to the coding sequence. Large numbers of suitable vectors and promoters are known to those of skill in the art, many of which are commercially available and/or are described in Sambrook, et al., (supra).

Exemplary promoters include both constitutive promoters and inducible promoters, examples of which include a CMV promoter, an SV40 early promoter, an RSV promoter, an EF-1α promoter, a promoter containing the tet responsive element (TRE) in the tet-on or tet-off system as described (ClonTech and BASF), the beta actin promoter and the metallothionine promoter that can upregulated by addition of certain metal salts. A promoter sequence is a DNA sequence which is recognized by the particular filamentous fungus for expression purposes. It is operably linked to DNA sequence encoding a variant CBH I polypeptide. Such linkage comprises positioning of the promoter with respect to the initiation codon of the DNA sequence encoding the variant CBH I polypeptide in the disclosed expression vectors. The promoter sequence contains transcription and translation control sequence which mediate the expression of the variant CBH I polypeptide. Examples include the promoters from the *Aspergillus niger*, *A. awamori* or *A. oryzae* glucoamylase, alpha-amylase, or alpha-glucosidase encoding genes; the *A. nidulans* gpdA or trpC Genes; the *Neurospora crassa* cbh1 or trp1 genes; the *A. niger* or *Rhizomucor miehei* aspartic proteinase encoding genes; the *H. jecorina* (*T. reesei*) cbh1, cbh2, egl1, egl2, or other cellulase encoding genes.

The choice of the proper selectable marker will depend on the host cell, and appropriate markers for different hosts are well known in the art. Typical selectable marker genes include argB from *A. nidulans* or *T. reesei*, amdS from *A. nidulans*, pyr4 from *Neurospora crassa* or *T. reesei*, pyrG from *Aspergillus niger* or *A. nidulans*. Additional exemplary selectable markers include, but are not limited to trpc, trp1, oliC31, niaD or leu2, which are included in heterologous nucleic acid constructs used to transform a mutant strain such as trp-, pyr-, leu- and the like.

Such selectable markers confer to transformants the ability to utilize a metabolite that is usually not metabolized by the filamentous fungi. For example, the amdS gene from *H. jecorina* which encodes the enzyme acetamidase that allows transformant cells to grow on acetamide as a nitrogen source. The selectable marker (e.g. pyrG) may restore the ability of an auxotrophic mutant strain to grow on a selective minimal medium or the selectable marker (e.g. olic31) may confer to. transformants the ability to grow in the presence of an inhibitory drug or antibiotic.

The selectable marker coding sequence is cloned into any suitable plasmid using methods generally employed in the art. Exemplary plasmids include pUC18, pBR322, pRAX and pUC100. The pRAX plasmid contains AMA1 sequences from A. nidulans, which make it possible to replicate in *A. niger*.

The practice of the present invention will employ, unless otherwise indicated, conventional techniques of molecular biology, microbiology, recombinant DNA, and immunology, which are within the skill of the art. Such techniques are explained fully in the literature. See, for example, Sambrook et al., 1989; Freshney, Animal Cell Culture, 1987; Ausubel, et al., 1993; and Coligan et al., Current Protocols in Immunology, 1991.

B. Host Cells and Culture Conditions for CBH1 Production (i) Filamentous Fungi

Thus, the present invention provides filamentous fungi comprising cells which have been modified, selected and cultured in a manner effective to result in variant CBH I production or expression relative to the corresponding non-transformed parental fungi.

Examples of species of parental filamentous fungi that may be treated and/or modified for variant CBH I expression include, but are not limited to *Trichoderma*, e.g., *Trichoderma reesei, Trichoderma longibrachiatum, Trichoderma viride, Trichoderma koningii; Penicillium* sp., *Humicola* sp., including *Humicola insolens; Aspergillus* sp., *Chrysosporium* sp., *Fusarium* sp., *Hypocrea* sp., and *Emericella* sp.

CBH I expressing cells are cultured under conditions typically employed to culture the parental fungal line. Generally, cells are cultured in a standard medium containing physiological salts and nutrients, such as described in Pourquie, J. et al., Biochemistry and Genetics of Cellulose Degradation, eds. Aubert, J. P. et al., Academic Press, pp. 71-86, 1988 and Ilmen, M. et al., Appl. Environ. Microbiol. 63:1298-1306, 1997. Culture conditions are also standard, e.g., cultures are incubated at 28° C. in shaker cultures or fermenters until desired levels of CBH I expression are achieved.

Preferred culture conditions for a given filamentous fungus may be found in the scientific literature and/or from the source of the fungi such as the American Type Culture Collection (ATCC; "www.atcc.org"). After fungal growth has been established, the cells are exposed to conditions effective to cause or permit the expression of variant CBH I.

In cases where a CBH I coding sequence is under the control of an inducible promoter, the inducing agent, e.g., a sugar, metal salt or antibiotics, is added to the medium at a concentration effective to induce CBH I expression.

In one embodiment, the strain comprises *Aspergillus niger*, which is a useful strain for obtaining overexpressed protein. For example *A. niger* var *awamori* dgr246 is known to secrete elevated amounts of secreted cellulases (Goedegebuur et al, Curr. Genet (2002) 41: 89-98). Other strains of *Aspergillus niger* var *awamori* such as GCDAP3, GCDAP4 and GAP3-4 are known Ward et al (Ward, M, Wilson, L. J. and Kodama, K. H., 1993, Appl. Microbiol. Biotechnol. 39:738-743).

In another embodiment, the strain comprises Trichoderma reesei, which is a useful strain for obtaining overexpressed protein. For example, RL-P37, described by Sheir-Neiss, et al., *Appl. Microbiol. Biotechnol.* 20:46-53 (1984) is known to secrete elevated amounts of cellulase enzymes. Functional equivalents of RL-P37 include *Trichoderma reesei* strain RUT-C30 (ATCC No. 56765) and strain QM9414 (ATCC No. 26921). It is contemplated that these strains would also be useful in overexpressing variant CBH1.

Where it is desired to obtain the variant CBH I in the absence of potentially detrimental native cellulolytic activity, it is useful to obtain a *Trichoderma* host cell strain which has had one or more cellulase genes deleted prior to introduction of a DNA construct or plasmid containing the DNA fragment encoding the variant CBH I. Such strains may be prepared by the method disclosed in U.S. Pat. No. 5,246,853 and WO 92/06209, which disclosures are hereby incorporated by reference. By expressing a variant CBH I cellulase in a host microorganism that is missing one or more cellulase genes, the identification and subsequent purification procedures are simplified. Any gene from *Trichoderma* sp. which has been cloned can be deleted, for example, the cbh1, cbh2, egl1, and egl2 genes as well as those encoding EG III and/or EGV protein (see e.g., U.S. Pat. No. 5,475,101 and WO 94/28117, respectively).

Gene deletion may be accomplished by inserting a form of the desired gene to be deleted or disrupted into a plasmid by methods known in the art. The deletion plasmid is then cut at an appropriate restriction enzyme site(s), internal to the desired gene coding region, and the gene coding sequence or part thereof replaced with a selectable marker. Flanking DNA sequences from the locus of the gene to be deleted or disrupted, preferably between about 0.5 to 2.0 kb, remain on either side of the selectable marker gene. An appropriate deletion plasmid will generally have unique restriction enzyme sites present therein to enable the fragment containing the deleted gene, including flanking DNA sequences, and the selectable marker gene to be removed as a single linear piece.

A selectable marker must be chosen so as to enable detection of the transformed microorganism. Any selectable marker gene that is expressed in the selected microorganism will be suitable. For example, with *Aspergillus* sp., the selectable marker is chosen so that the presence of the selectable marker in the transformants will not significantly affect the properties thereof. Such a selectable marker may be a gene that encodes an assayable product. For example, a functional copy of a *Aspergillus* sp. gene may be used which if lacking in the host strain results in the host strain displaying an auxotrophic phenotype. Similarly, selectable markers exist for *Trichoderma* sp.

In one embodiment, a pyrG⁻ derivative strain of *Aspergillus* sp. is transformed with a functional pyrG gene, which thus provides a selectable marker for transformation. A pyrG⁻ derivative strain may be obtained by selection of *Aspergillus* sp. strains that are resistant to fluoroorotic acid (FOA). The pyrG gene encodes orotidine-5'-monophosphate decarboxylase, an enzyme required for the biosynthesis of uridine. Strains with an intact pyrG gene grow in a medium lacking uridine but are sensitive to fluoroorotic acid. It is possible to select pyrG⁻ derivative strains that lack a functional orotidine monophosphate. decarboxylase enzyme and require uridine for growth by selecting for FOA resistance. Using the FOA selection technique it is also possible to obtain uridine-requiring strains which lack a functional orotate pyrophosphoribosyl transferase. It is possible to transform these cells with a functional copy of the gene encoding this enzyme (Berges &

Barreau, *Curr. Genet.* 19:359-365 (1991), and van Hartingsveldte et al., (1986) Development of a homologous transformation system for *Aspergillus niger* based on the pyrG gene. Mol. Gen. Genet. 206:71-75). Selection of derivative strains is easily performed using the FOA resistance technique referred to above, and thus, the pyrG gene is preferably employed as a selectable marker.

In a second embodiment, a pyr4⁻ derivative strain of *Hyrocrea* sp. (*Hyrocrea* sp. (*Trichoderma* sp.)) is transformed with a functional pyr4 gene, which thus provides a selectable marker for transformation. A pyr4⁻ derivative strain may be obtained by selection of *Hyrocrea* sp. (*Trichoderma* sp.) strains that are resistant to fluoroorotic acid (FOA). The pyr4 gene encodes orotidine-5'-monophosphate decarboxylase, an enzyme required for the biosynthesis of uridine. Strains with an intact pyr4 gene grow in a medium lacking uridine but are sensitive to fluoroorotic acid. It is possible to select pyr4⁻ derivative strains that lack a functional orotidine monophosphate decarboxylase enzyme and require uridine for growth by selecting for FOA resistance. Using the FOA selection technique it is also possible to obtain uridine-requiring strains which lack a functional orotate pyrophosphoribosyl transferase. It is possible to transform these cells with a functional copy of the gene encoding this enzyme (Berges & Barreau, *Curr. Genet.* 19:359-365 (1991)). Selection of derivative strains is easily performed using the FOA resistance technique referred to above, and thus, the pyr4 gene is preferably employed as a selectable marker.

To transform pyrG⁻ *Aspergillus* sp. or pyr4⁻ *Hyrocrea* sp. (*Trichoderma* sp.) so as to be lacking in the ability to express one or more cellulase genes, a single DNA fragment comprising a disrupted or deleted cellulase gene is then isolated from the deletion plasmid and used to transform an appropriate pyr⁻ *Aspergillus* or pyr⁻ *Trichoderma* host. Transformants are then identified and selected based on their ability to express the pyrG or pyr4, respectively, gene product and thus compliment the uridine auxotrophy of the host strain. Southern blot analysis is then carried out on the resultant transformants to identify and confirm a double crossover integration event that replaces part or all of the coding region of the genomic copy of the gene to be deleted with the appropriate pyr selectable markers.

Although the specific plasmid vectors described above relate to preparation of pyr⁻ transformants, the present invention is not limited to these vectors. Various genes can be deleted and replaced in the *Aspergillus* sp. or *Hyrocrea* sp. (*Trichoderma* sp.) strain using the above techniques. In addition, any available selectable markers can be used, as discussed above. In fact, any host, e.g., *Aspergillus* sp. or *Hyrocrea* sp., gene that has been cloned, and thus identified, can be deleted from the genome using the above-described strategy.

As stated above, the host strains used may be derivatives of *Hyrocrea* sp. (*Trichoderma* sp.) that lack or have a nonfunctional gene or genes corresponding to the selectable marker chosen. For example, if the selectable marker of pyrG is chosen for *Aspergillus* sp., then a specific pyrG⁻ derivative strain is used as a recipient in the transformation procedure. Also, for example, if the selectable marker of pyr4 is chosen for a *Hyrocrea* sp., then a specific pyr4⁻ derivative strain is used as a recipient in the transformation procedure. Similarly, selectable markers comprising *Hyrocrea* sp. (*Trichoderma* sp.) genes equivalent to the *Aspergillus nidulans* genes amdS, argB, trpC, niaD may be used. The corresponding recipient strain must therefore be a derivative strain such as argB⁻, trpC⁻, niaD⁻, respectively.

DNA encoding the CBH I variant is then prepared for insertion into an appropriate microorganism. According to the present invention, DNA encoding a CBH I variant comprises the DNA necessary to encode for a protein that has functional cellulolytic activity. The DNA fragment encoding the CBH I variant may be functionally attached to a fungal promoter sequence, for example, the promoter of the glaA gene in *Aspergillus* or the promoter of the cbh1 or egl1 genes in *Trichoderma*.

It is also contemplated that more than one copy of DNA encoding a CBH I variant may be recombined into the strain to facilitate overexpression. The DNA encoding the CBH I variant may be prepared by the construction of an expression vector carrying the DNA encoding the variant. The expression vector carrying the inserted DNA fragment encoding the CBH I variant may be any vector which is capable of replicating autonomously in a given host organism or of integrating into the DNA of the host, typically a plasmid. In preferred embodiments two types of expression vectors for obtaining expression of genes are contemplated. The first contains DNA sequences in which the promoter, gene-coding region, and terminator sequence all originate from the gene to be expressed. Gene truncation may be obtained where desired by deleting undesired DNA sequences (e.g., coding for unwanted domains) to leave the domain to be expressed under control of its own transcriptional and translational regulatory sequences. A selectable marker may also be contained on the vector allowing the selection for integration into the host of multiple copies of the novel gene sequences.

The second type of expression vector is preassembled and contains sequences required for high-level transcription and a selectable marker. It is contemplated that the coding region for a gene or part thereof can be inserted into this general-purpose expression vector such that it is under the transcriptional control of the expression cassettes promoter and terminator sequences.

For example, in, *Aspergillus*, pRAX is such a general-purpose expression vector. Genes or part thereof can be inserted downstream of the strong glaA promoter.

For example, in *Hypocrea*, pTEX is such a general-purpose expression vector. Genes or part thereof can be inserted downstream of the strong cbh1 promoter.

In the vector, the DNA sequence encoding the CBH I variant of the present invention should be operably linked to transcriptional and translational sequences, i.e., a suitable promoter sequence and signal sequence in reading frame to the structural gene. The promoter may be any DNA sequence that shows transcriptional activity in the host cell and may be derived from genes encoding proteins either homologous or heterologous to the host cell. An optional signal peptide provides for extracellular production of the CBH I variant. The DNA encoding the signal sequence is preferably that which is naturally associated with the gene to be expressed, however the signal sequence from any suitable source, for example an exo-cellobiohydrolase or endoglucanase from *Trichoderma*, is contemplated in the present invention.

The procedures used to ligate the DNA sequences coding for the variant CBH I of the present invention with the promoter, and insertion into suitable vectors are well known in the art.

The DNA vector or construct described above may be introduced in the host cell in accordance with known techniques such as transformation, transfection, microinjection, microporation, biolistic bombardment and the like.

In the preferred transformation technique, it must be taken into account that the permeability of the cell wall to DNA in *Hyrocrea* sp. (*Trichoderma* sp.) is very low. Accordingly, uptake of the desired DNA sequence, gene or gene fragment is at best minimal. There are a number of methods to increase the permeability of the *Hyrocrea* sp. (*Trichoderma* sp.) cell wall in the derivative strain (i.e., lacking a functional gene corresponding to the used selectable marker) prior to the transformation process.

The preferred method in the present invention to prepare *Aspergillus* sp. or *Hyrocrea* sp. (*Trichoderma* sp.) for transformation involves the preparation of protoplasts from fungal mycelium. See Campbell et al. Improved transformation efficiency of *A. niger* using homologous niaD gene for nitrate reductase. Curr. Genet. 16:53-56; 1989. The mycelium can be obtained from germinated vegetative spores. The mycelium is treated with an enzyme that digests the cell wall resulting in protoplasts. The protoplasts are then protected by the presence of an osmotic stabilizer in the suspending medium. These stabilizers include sorbitol, mannitol, potassium chloride, magnesium sulfate and the like. Usually the concentration of these stabilizers varies between 0.8 M and 1.2 M. It is preferable to use about a 1.2 M solution of sorbitol in the suspension medium.

Uptake of the DNA into the host strain, (*Aspergillus* sp. or *Hyrocrea* sp. (*Trichoderma* sp.), is dependent upon the calcium ion concentration. Generally between about 10 mM $CaCl_2$ and 50 mM $CaCl_2$ is used in an uptake solution. Besides the need for the calcium ion in the uptake solution, other items generally included are a buffering system such as TE buffer (10 Mm Tris, pH 7.4; 1 mM EDTA) or 10 mM MOPS, pH 6.0 buffer (morpholinepropanesulfonic acid) and polyethylene glycol (PEG). It is believed that the polyethylene glycol acts to fuse the cell membranes thus permitting the contents of the medium to be delivered into the cytoplasm of the host cell, by way of example either *Aspergillus* sp. or *Hyrocrea* sp. strain, and the plasmid DNA is transferred to the nucleus. This fusion frequently leaves multiple copies of the plasmid DNA tenderly integrated into the host chromosome.

Usually a suspension containing the *Aspergillus* sp. protoplasts or cells that have been subjected to a permeability treatment at a density of $10^5$ to $10^6$/mL, preferably $2 \times 10^5$/mL are used in transformation. Similarly, a suspension containing the *Hyrocrea* sp. (*Trichoderma* sp.) protoplasts or cells that have been subjected to a permeability treatment at a density of $10^8$ to $10^9$/mL, preferably $2 \times 10^8$/mL are used in transformation. A volume of 100 µL of these protoplasts or cells in an appropriate solution (e.g., 1.2 M sorbitol; 50 mM $CaCl_2$) are mixed with the desired DNA. Generally a high concentration of PEG is added to the uptake solution. From 0.1 to 1 volume of 25% PEG 4000 can be added to the protoplast suspension. However, it is preferable to add about 0.25 volumes to the protoplast suspension. Additives such as dimethyl sulfoxide, heparin, spermidine, potassium chloride and the like may also be added to the uptake solution and aid in transformation.

Generally, the mixture is then incubated at approximately 0° C. for a period of between 10 to 30 minutes. Additional PEG is then added to the mixture to further enhance the uptake of the desired gene or DNA sequence. The 25% PEG 4000 is generally added in volumes of 5 to 15 times the volume of the transformation mixture; however, greater and lesser volumes may be suitable. The 25% PEG 4000 is preferably about 10 times the volume of the transformation mixture. After the PEG is added, the transformation mixture is then incubated either at room temperature or on ice before the addition of a sorbitol and $CaCl_2$ solution. The protoplast suspension is then further added to molten aliquots of a growth medium. This growth medium permits the growth of transformants only. Any growth medium can be used in the present invention that is suitable to grow the desired transformants. However, if $Pyr^+$ transformants are being selected it is preferable to use a growth medium that contains no uridine.

The subsequent colonies are transferred and purified on a growth medium depleted of uridine.

At this stage, stable transformants may be distinguished from unstable transformants by their faster growth rate and the formation of circular colonies with a smooth, rather than ragged outline on solid culture medium lacking uridine. Additionally, in some cases a further test of stability may made by growing the transformants on solid non-selective medium (i.e. containing uridine), harvesting spores from this culture medium and determining the percentage of these spores which will subsequently germinate and grow on selective medium lacking uridine.

In a particular embodiment of the above method, the CBH I variant(s) are recovered in active form from the host cell after growth in liquid media either as a result of the appropriate post translational processing of the CBH I variant.

(ii) Yeast

The present invention also contemplates the use of yeast as a host cell for CBH I production. Several other genes encoding hydrolytic enzymes have been expressed in various strains of the yeast *S. cerevisiae*. These include sequences encoding for two endoglucanases (Penttila et al., Yeast vol. 3, pp 175-185, 1987), two cellobiohydrolases (Penttila et al., Gene, 63: 103-112, 1988) and one beta-glucosidase from *Trichoderma reesei* (Cummings and Fowler, Curr. Genet. 29:227-233, 1996), a xylanase from *Aureobasidlium pullulans* (Li and Ljungdahl, Appl. Environ. Microbiol. 62, no. 1, pp. 209-213, 1996), an alpha-amylase from wheat (Rothstein et al., Gene 55:353-356, 1987), etc. In addition, a cellulase gene cassette encoding the *Butyrivibrio fibrisolvens* endo-[beta]-1,4-glucanase (END1), *Phanerochaete chrysosporium* cellobiohydrolase (CBH1), the *Ruminococcus flavefaciens* cellodextrinase (CELL) and the *Endomyces fibrilizer* cellobiase (Bgl1) was successfully expressed in a laboratory strain of *S. cerevisiae* (Van Rensburg et al., Yeast, vol. 14, pp. 67-76, 1998).

C. Introduction of an CBH I-Encoding Nucleic Acid Sequence into Host Cells.

The invention further provides cells and cell compositions which have been genetically modified to comprise an exogenously provided variant CBH I-encoding nucleic acid sequence. A parental cell or cell line may be genetically modified (i.e., transduced, transformed or transfected) with a cloning vector or an expression vector. The vector may be, for example, in the form of a plasmid, a viral particle, a phage, etc, as further described above.

The methods of transformation of the present invention may result in the stable integration of all or part of the transformation vector into the genome of the filamentous fungus. However, transformation resulting in the maintenance of a self-replicating extra-chromosomal transformation vector is also contemplated.

Many standard transfection methods can be used to produce *Trichoderma reesei* cell lines that express large quantities of the heterologus protein. Some of the published methods for the introduction of DNA constructs into cellulase-producing strains of *Trichoderma* include Lorito, Hayes, DiPietro and Harman, 1993, Curr. Genet. 24: 349-356; Goldman, VanMontagu and Herrera-Estrella, 1990, Curr. Genet. 17:169-174; Penttila, Nevalainen, Ratto, Salminen and Knowles, 1987, Gene 6: 155-164, for *Aspergillus* Yelton, Hamer and Timberlake, 1984, Proc. Natl. Acad. Sci. USA 81: 1470-1474, for *Fusarium* Bajar, Podila and Kolattukudy, 1991, Proc. Natl. Acad. Sci. USA 88: 8202-8212, for *Streptomyces* Hopwood et al., 1985, The John Innes Foundation, Norwich, UK and for *Bacillus* Brigidi, DeRossi, Bertarini, Riccardi and Matteuzzi, 1990, FEMS Microbiol. Lett. 55: 135-138).

Other methods for introducing a heterologous nucleic acid construct (expression vector) into filamentous fungi (e.g., *H. jecorina*) include, but are not limited to the use of a particle or gene gun, permeabilization of filamentous fungi cells walls prior to the strasformation process (e.g., by use of high concentrations of alkali, e.g., 0.05 M to 0.4 M $CaCl_2$ or lithium acetate), protoplast fusion or agrobacterium mediated transformation. An exemplary method for transformation of filamentous fungi by treatment of protoplasts or spheroplasts with polyethylene glycol and $CaCl_2$ is described in Campbell, E. I. et al., Curr. Genet. 16:53-56, 1989 and Penttila, M. et al., Gene, 63:11-22, 1988.

Any of the well-known procedures for introducing foreign nucleotide sequences into host cells may be used. These include the use of calcium phosphate transfection, polybrene, protoplast fusion, electroporation, biolistics, liposomes, microinjection, plasma vectors, viral vectors and any of the other well known methods for introducing cloned genomic DNA, cDNA, synthetic DNA or other foreign genetic material into a host cell (see, e.g., Sambrook et al., supra). Also of use is the Agrobacterium-mediated transfection method described in U.S. Pat. No. 6,255,115. It is only necessary that the particular genetic engineering procedure used be capable of successfully introducing at least one gene into the host cell capable of expressing the heterologous gene.

In addition, heterologous nucleic acid constructs comprising a variant CBH I-encoding nucleic acid sequence can be transcribed in vitro, and the resulting RNA introduced into the host cell by well-known methods, e.g., by injection.

The invention further includes novel and useful transformants of filamentous fungi such as *H. jecorina* and *A. niger* for use in producing fungal cellulase compositions. The invention includes transformants of filamentous fungi especially fungi comprising the variant CBH I coding sequence, or deletion of the endogenous cbh coding sequence.

Following introduction of a heterologous nucleic acid construct comprising the coding sequence for a variant cbh 1, the genetically modified cells can be cultured in conventional nutrient media modified as appropriate for activating promoters, selecting transformants or amplifying expression of a variant CBH I-encoding nucleic acid sequence. The culture conditions, such as temperature, pH and the like, are those previously used for the host cell selected for expression, and will be apparent to those skilled in the art.

The progeny of cells into which such heterologous nucleic acid constructs have been introduced are generally considered to comprise the variant CBH I-encoding nucleic acid sequence found in the heterologous nucleic acid construct.

The invention further includes novel and useful transformants of filamentous fungi such as *H. jecorina* for use in producing fungal cellulase compositions. The invention includes transformants of filamentous fungi especially fungi comprising the variant cbh 1 coding sequence, or deletion of the endogenous cbh coding sequence.

Stable transformants of filamentous fungi can generally be distinguished from unstable transformants by their faster growth rate and the formation of circular colonies with a smooth rather than ragged outline on solid culture medium. Additionally, in some cases, a further test of stability can be made by growing the transformants on solid non-selective medium, harvesting the spores from this culture medium and determining the percentage of these spores which will subsequently germinate and grow on selective medium.

VII. ANALYSIS FOR CBH1 NUCLEIC ACID CODING SEQUENCES AND/OR PROTEIN EXPRESSION

In order to evaluate the expression of a variant CBH I by a cell line that has been transformed with a variant CBH I-encoding nucleic acid construct, assays can be carried out at the protein level, the RNA level or by use of functional bioassays particular to cellobiohydrolase activity and/or production.

In one exemplary application of the variant cbh 1 nucleic acid and protein sequences described herein, a genetically modified strain of filamentous fungi, e.g., *Trichoderma reesei*, is engineered to produce an increased amount of CBH I. Such genetically modified filamentous fungi would be useful to produce a cellulase product with greater increased cellulolytic capacity. In one approach, this is accomplished by introducing the coding sequence for cbh 1 into a suitable host, e.g., a filamentous fungi such as *Aspergillus niger*.

Accordingly, the invention includes methods for expressing variant CBH I in a filamentous fungus or other suitable host by introducing an expression vector containing the DNA sequence encoding variant CBH I into cells of the filamentous fungus or other suitable host.

In another aspect, the invention includes methods for modifying the expression of CBH I in a filamentous fungus or other suitable host. Such modification includes a decrease or elimination in expression of the endogenous CBH.

In general, assays employed to analyze the expression of variant CBH I include, Northern blotting, dot blotting (DNA or RNA analysis), RT-PCR (reverse transcriptase polymerase chain reaction), or in situ hybridization, using an appropriately labeled probe (based on the nucleic acid coding sequence) and conventional Southern blotting and autoradiography.

In addition, the production and/or expression of variant CBH I may be measured in a sample directly, for example, by assays for cellobiohydrolase activity, expression and/or production. Such assays are described, for example, in Becker et al., Biochem J. (2001) 356:19-30 and Mitsuishi et al., FEBS (1990) 275:135-138, each of which is expressly incorporated by reference herein. The ability of CBH I to hydrolyze isolated soluble and insoluble substrates can be measured using assays described in Srisodsuk et al., J. Biotech. (1997) 57:49-57 and Nidetzky and Claeyssens Biotech. Bioeng. (1994) 44:961-966. Substrates useful for assaying cellobiohydrolase, endoglucanase or β-glucosidase activities include crystalline cellulose, filter paper, phosphoric acid swollen cellulose, cellooligosaccharides, methylumbelliferyl lactoside, methylumbelliferyl cellobioside, orthonitrophenyl lactoside, paranitrophenyl lactoside, orthonitrophenyl cellobioside, paranitrophenyl cellobioside.

In addition, protein expression, may be evaluated by immunological methods, such as immunohistochemical staining of cells, tissue sections or immunoassay of tissue culture medium, e.g., by Western blot or ELISA. Such immunoassays can be used to qualitatively and quantitatively evaluate expression of a CBH I variant. The details of such methods are known to those of skill in the art and many reagents for practicing such methods are commercially available.

A purified form of a variant CBH I may be used to produce either monoclonal or polyclonal antibodies specific to the expressed protein for use in various immunoassays. (See, e.g., Hu et al., Mol Cell Biol. vol. 11, no. 11, pp. 5792-5799, 1991). Exemplary assays include ELISA, competitive immunoassays, radioimmunoassays, Western blot, indirect immunofluorescent assays and the like. In general, commercially available antibodies and/or kits may be used for the quantitative immunoassay of the expression level of cellobiohydrolase proteins.

VIII. ISOLATION AND PURIFICATION OF RECOMBINANT CBH1 PROTEIN

In general, a variant CBH I protein produced in cell culture is secreted into the medium and may be purified or isolated, e.g., by removing unwanted components from the cell culture medium. However, in some cases, a variant CBH I protein may be produced in a cellular form necessitating recovery from a cell lysate. In such cases the variant CBH I protein is purified from the cells in which it was produced using techniques routinely employed by those of skill in the art. Examples include, but are not limited to, affinity chromatography (Tilbeurgh et al., FEBS Lett. 16:215, 1984), ion-exchange chromatographic methods (Goyal et al., Bioresource Technol. 36:37-50, 1991; Fliess et al., Eur. J. Appl. Microbiol. Biotechnol. 17:314-318, 1983; Bhikhabhai et al., J. Appl. Biochem. 6:336-345, 1984; Ellouz et al., J. Chromatography 396:307-317, 1987), including ion-exchange using materials with high resolution power (Medve et al., J. Chromatography A 808:153-165, 1998), hydrophobic interaction chromatography (Tomaz and Queiroz, J. Chromatography A 865:123-128, 1999), and two-phase partitioning (Brumbauer, et al., Bioseparation 7:287-295, 1999).

Typically, the variant CBH I protein is fractionated to segregate proteins having selected properties, such as binding affinity to particular binding agents, e.g., antibodies or receptors; or which have a selected molecular weight range, or range of isoelectric points.

Once expression of a given variant CBH I protein is achieved, the CBH I protein thereby produced is purified from the cells or cell culture. Exemplary procedures suitable for such purification include the following: antibody-affinity column chromatography, ion exchange chromatography; ethanol precipitation; reverse phase HPLC; chromatography on silica or on a cation-exchange resin such as DEAE; chromatofocusing; SDS-PAGE; ammonium sulfate precipitation; and gel filtration using, e.g., Sephadex G-75. Various methods of protein purification may be employed and such methods are known in the art and described e.g. in Deutscher, Methods in Enzymology, vol. 182, no. 57, pp. 779, 1990; Scopes, Methods Enzymol. 90: 479-91, 1982. The purification step(s) selected will depend, e.g., on the nature of the production process used and the particular protein produced.

IX. UTILITY OF cbh1 AND CBH1

It can be appreciated that the variant cbh nucleic acids, the variant CBH I protein and compositions comprising variant CBH I protein activity find utility in a wide variety applications, some of which are described below.

New and improved cellulase compositions that comprise varying amounts BG-type, EG-type and variant CBH-type cellulases find utility in detergent compositions that exhibit enhanced cleaning ability, function as a softening agent and/or improve the feel of cotton fabrics (e.g., "stone washing" or "biopolishing"), in compositions for degrading wood pulp into sugars (e.g., for bio-ethanol production), and/or in feed compositions. The isolation and characterization of cellulase of each type provides the ability to control the aspects of such compositions.

Variant (or mutant) CBHs with increased thermostability find uses in all of the above areas due to their ability to retain activity at elevated temperatures.

Variant (or mutant) CBHs with decreased thermostability find uses, for example, in areas where the enzyme activity is required to be neutralized at lower temperatures so that other enzymes that may be present are left unaffected. In addition, the enzymes may find utility in the limited conversion of cellulosics, for example, in controlling the degree of crystallinity or of cellulosic chain-length. After reaching the desired extent of conversion the saccharifying temperature can be raised above the survival temperature of the de-stabilized CBH I. As the CBH I activity is essential for hydrolysis of crystalline cellulose, conversion of crystalline cellulose will cease at the elevated temperature.

Variant (or mutant) CBHs with increased reversibility, i.e., enhanced refolding and retention of activity, also find use in similar areas. Depending upon the conditions of thermal inactivation, reversible denaturation can compete with, or dominate over, the irreversible process. Variants with increased reversibility would, under these conditions, exhibit increased resistance to thermal inactivation. Increased reversibility would also be of potential benefit in any process in which an inactivation event was followed by a treatment under non-inactivating conditions. For instance, in a Hybrid Hydrolysis and Fermentation (HHF) process for biomass conversion to ethanol, the biomass would first be incompletely saccharified by cellulases at elevated temperature (say 50° C. or higher), then the temperature would be dropped (to 30° C., for instance) to allow a fermentative organism to be introduced to convert the sugars to ethanol. If, upon decrease of process temperature, thermally inactivated cellulase reversibly refolded and recovered activity then saccharification could continue to higher levels of conversion during the low temperature fermentation process.

In one approach, the cellulase of the invention finds utility in detergent compositions or in the treatment of fabrics to improve the feel and appearance.

Since the rate of hydrolysis of cellulosic products may be increased by using a transformant having at least one additional copy of the cbh gene inserted into the genome, products that contain cellulose or heteroglycans can be degraded at a faster rate and to a greater extent. Products made from cellulose such as paper, cotton, cellulosic diapers and the like can be degraded more efficiently in a landfill. Thus, the fermentation product obtainable from the transformants or the transformants alone may be used in compositions to help degrade by liquefaction a variety of cellulose products that add to the overcrowded landfills.

Separate saccharification and fermentation is a process whereby cellulose present in biomass, e.g., corn stover, is converted to glucose and subsequently yeast strains convert glucose into ethanol. Simultaneous saccharification and fermentation is a process-whereby cellulose present in biomass, e.g., corn stover, is converted to glucose and, at the same time and in the same reactor, yeast strains convert glucose into ethanol. Thus, in another approach, the variant CBH type cellulase of the invention finds utility in the degradation of biomass to ethanol. Ethanol production from readily available sources of cellulose provides a stable, renewable fuel source.

Cellulose-based feedstocks are comprised of agricultural wastes, grasses and woods and other low-value biomass such as municipal waste (e.g., recycled paper, yard clippings, etc.). Ethanol may be produced from the fermentation of any of these cellulosic feedstocks. However, the cellulose must first be converted to sugars before there can be conversion to ethanol.

A large variety of feedstocks may be used with the inventive variant CBH and the one selected for use may depend on the region where the conversion is being done. For example, in the Midwestern United States agricultural wastes such as wheat straw, corn stover and bagasse may predominate while in California rice straw may predominate. However, it should be understood that any available cellulosic biomass may be used in any region.

A cellulase composition containing an enhanced amount of cellobiohydrolase finds utility in ethanol production. Ethanol from this process can be further used as an octane enhancer or directly as a fuel in lieu of gasoline which is advantageous because ethanol as a fuel source is more environmentally friendly than petroleum derived products. It is known that the use of ethanol will improve air quality and possibly reduce local ozone levels and smog. Moreover, utilization of ethanol in lieu of gasoline can be of strategic importance in buffering the impact of sudden shifts in non-renewable energy and petro-chemical supplies.

Ethanol can be produced via saccharification and fermentation processes from cellulosic biomass such as trees, herbaceous plants, municipal solid waste and agricultural and forestry residues. However, the ratio of individual cellulase enzymes within a naturally occurring cellulase mixture produced by a microbe may not be the most efficient for rapid conversion of cellulose in biomass to glucose. It is known that endoglucanases act to produce new cellulose chain ends which themselves are substrates for the action of cellobiohydrolases and thereby improve the efficiency of hydrolysis of the entire cellulase system. Therefore, the use of increased or optimized cellobiohydrolase activity may greatly enhance the production of ethanol.

Thus, the inventive cellobiohydrolase finds use in the hydrolysis of cellulose to its sugar components. In one embodiment, a variant cellobiohydrolase is added to the biomass prior to the addition of a fermentative organism. In a second embodiment, a variant cellobiohydrolase is added to the biomass at the same time as a fermentative organism. Optionally, there may be other cellulase components present in either embodiment.

In another embodiment the cellulosic feedstock may be pretreated. Pretreatment may be by elevated temperature and the addition of either of dilute acid, concentrated acid or dilute alkali solution. The pretreatment solution is added for a time sufficient to at least partially hydrolyze the hemicellulose components and then neutralized.

The major product of CBHI action on cellulose is cellobiose which is available for conversion to glucose by BG activity (for instance in a fungal cellulase product). Either by the pretreatment of the cellulosic biomass or by the enzymatic action on the biomass, other sugars, in addition to glucose and cellobiose, can be made available from the biomass. The hemi-cellulose content of the biomass can be converted (by hemi-cellulases) to sugars such as xylose, galactose, mannose and arabinose. Thus, in a biomass conversion process, enzymatic saccharification can produce sugars that are made available for biological or chemical conversions to other intermediates or end-products. Therefore, the sugars generated from biomass find use in a variety of processes in addition to the generation of ethanol. Examples of such conversions are fermentation of glucose to ethanol (as reviewed by M. E. Himmel et aL pp2-45, in "Fuels and Chemicals from Biomass", ACS Symposium Series 666, ed B. C. Saha and J. Woodward, 1997) and other biological conversions of glucose to 2,5-diketo-D-gluconate (U.S. Pat. No. 6,599,722), lactic acid (R. Datta and S-P. Tsai pp224-236, ibid), succinate (R. R. Gokarn, M. A. Eiteman and J. Sridhar pp237-263, ibid), 1,3-propanediol (A-P. Zheng, H. Biebl and W-D. Deckwer pp264-279, ibid), 2,3-butanediol (C. S. Gong, N. Cao and G. T. Tsao pp280-293, ibid), and the chemical and biological conversions of xylose to xylitol (B. C. Saha and R. J. Bothast pp307-319, ibid). See also, for example, WO 98/21339.

The detergent compositions of this invention may employ besides the cellulase composition (irrespective of the cellobiohydrolase content, i.e., cellobiohydrolase—free, substantially cellobiohydrolase—free, or cellobiohydrolase enhanced), a surfactant, including anionic, non-ionic and ampholytic surfactants, a hydrolase, building agents, bleaching agents, bluing agents and fluorescent dyes, caking inhibitors, solubilizers, cationic surfactants and the like. All of these components are known in the detergent art. The cellulase composition as described above can be added to the detergent composition either in a liquid diluent, in granules, in emulsions, in gels, in pastes, and the like. Such forms are well known to the skilled artisan. When a solid detergent composition is employed, the cellulase composition is preferably formulated as granules. Preferably, the granules can be formulated so as to contain a cellulase protecting agent. For a more thorough discussion, see U.S. Pat. No. 6,162,782 entitled "Detergent compositions containing cellulase compositions deficient in CBH I type components," which is incorporated herein by reference.

Preferably the cellulase compositions are employed from about 0.00005 weight percent to about 5 weight percent relative to the total detergent composition. More preferably, the cellulase compositions are employed from about 0.0002 weight percent to about 2 weight percent relative to the total detergent composition.

In addition the variant cbh I nucleic acid sequence finds utility in the identification and characterization of related nucleic acid sequences. A number of techniques useful for determining (predicting or confirming) the function of related genes or gene products include, but are not limited to, (A) DNA/RNA analysis, such as (1) overexpression, ectopic expression, and expression in other species; (2) gene knockout (reverse genetics, targeted knock-out, viral induced gene silencing (VIGS, see Baulcombe, 100 Years of Virology, Calisher and Horzinek eds., Springer-Verlag, New York, N.Y. 15:189-201, 1999); (3) analysis of the methylation status of the gene, especially flanking regulatory regions; and (4) in situ hybridization; (B) gene product analysis such as (1) recombinant protein expression; (2) antisera production, (3) immunolocalization; (4) biochemical assays for catalytic or other activity; (5) phosphorylation status; and (6) interaction with other proteins via yeast two-hybrid analysis; (C) pathway analysis, such as placing a gene or gene product within a particular biochemical or signaling pathway based on its overexpression phenotype or by sequence homology with related genes; and (D) other analyses which may also be performed to determine or confirm the participation of the isolated gene and its product in a particular metabolic or signaling pathway, and help determine gene function.

All patents, patent applications, articles and publications mentioned herein, are hereby expressly incorporated herein by reference.

EXAMPLES

The present invention is described in further detain in the following examples which are not in any way intended to limit the scope of the invention as claimed. The attached Figures are meant to be considered as integral parts of the specification and description of the invention. All references cited are herein specifically incorporated by reference for all that is described therein.

Example 1

Alignment of Known Cel7A Cellulases

The choice of several of the mutations was determined by first aligning *Hypocrea jecorina* Cel7A to its 41 family members using structural information and a modeling program. The alignment of the primary amino acid sequence of all 42 family members is shown in FIG. 8.

For four of the members (i.e., 2OVW. 1, 1A39, 6CEL and 1EG1.1), the crystal structure had been previously determined. The 4 aligned proteins for which there were published structures had their alignment locked for all residues whose backbone atoms were within a specific RMS deviation (RMS less than or equal to 2.0 Å). The tertiary structural alignment of the four sequences was performed using MOE version 2001.01 by Chemical Computing Group, Montreal Canada. The overlapping structural elements were used to freeze the primary structures of the four sequences. The remaining 38 sequences then had their primary amino acid structure aligned with the frozen four using MOE with secondary structure prediction on and other parameters set to their default settings.

Based on the alignments, various single and multiple amino acid mutations were made in the protein by site mutagenesis.

Single amino acid mutations were based on the following rationale (see also Table 1): After examining the conservation of amino acids between the homologues, sites were picked in the *H. jecorina* sequence where a statistical preference for another amino acid was seen amongst the other 41 sequences (e.g.: at position 77 the Ala, only present in *H. jecorina* and 3 other homologues, was changed to Asp, present in 22 others). The effect of each substitution on the structure was then modeled.

TABLE 1

Cel7A Variants and Rationale for Change

| Cel7A Variants and Rationale for Change | | Tm | ΔTm |
|---|---|---|---|
| Wild Type H. jecorina | | 62.5 | |
| (4)A77D(22) | 3 possible H-bonds to Q7 and I80 | 62.2 | −0.3 |
| (7)S113D(18) | numerous new H-bonds to backbone to stabilize turn | 62.8 | 0.3 |
| (8)L225F(13) | better internal packing | 61.6 | −0.9 |
| (5)L288F(17) | better internal packing | 62.4 | −0.1 |
| (1)A299E(24) | extra ligand to cobalt atom observed in crystal structure | 61.2 | −1.3 |
| (4)N301K(11) | salt bridges to E295 and E325 | 63.5 | 1.0 |
| (5)T356L(20) | better internal packing | 62.6 | 0.1 |
| (2)G430F(17) | better surface packing | 61.7 | −0.8 |

Multiple amino acid mutations were based on a desire to affect the stability, processivity, and product inhibition of the enzyme. The following multiple site changes in the *H. jecorina* sequence were constructed:
1) Thr 246 Cys+Tyr 371 Cys
2) Thr 246 Ala+Arg 251 Ala+Tyr 252 Ala
3) Thr 380 Gly+Tyr 381 Asp+Arg 394 Ala+deletion of Residues 382 to 393, inclusive
4) Thr 380 Gly+Tyr 381 Asp+Arg 394 Ala
5) Tyr 252 Gln+Asp 259 Trp+Ser 342 Tyr The T246A/R251 A/Y252A and the other triple+deletion mutant are both predicted to decrease the product inhibition of the enzyme. The Thr246Cys+Tyr371Cys is predicted to increase the stability of the enzyme and increase the processivity of it. The D259W/Y252Q/S342Y variant is predicted to affect the product inhibition of the enzyme.

Other single and multiple mutations were constructed using methods well known in the art (see references above) and are presented in Table 2.

TABLE 2

H. jecorina CBH I variants

Mutations

S8P
N49S
A68T
A77D
N89D
S92T
S113N
S113D
L225F
P227A
P227L
D249K
T255P
D257E
S279N
L288F
E295K
S297T
A299E
N301K
T332K
T332Y
T332H
T356L

TABLE 2-continued

H. jecorina CBH I variants

Mutations

F338Y
V393G
G430F
T41I (plus deletion of Thr @ 445)
V403D/T462I
S196T/S411F
E295K/S398T
A112E/T226A
T246C/Y371C
G22D/S278P/T296P
S8P/N103I/S113N
S113T/T255P/K286M
P227L/E325K/Q487L
P227T/T484S/F352L
T246A/R251A/Y252A
T380G/Y381D/R394A
Y252Q/D259W/S342Y
A68T/G440R/P491L
Q17L/E193V/M213I/F352L
S8P/N49S/A68T/S113N
A112E/P227L/S278P/T296P
S8P/N49S/A68T/N103I/S113N
S8P/N49S/A68T/S278P/T296P
G22D/N49S/A68T/S278P/T296P
G22D/N103I/S113N/S278P/T296P
S8P/N49S/A68T/S113N/P227L
S8P/N49S/A68T/A112E/T226A
S8P/N49S/A68T/A112E/P227L
T41I/A112E/P227L/S278P/T296P
S8P/T41I/N49S/A68T/S113N/P227L
S8P/T41I/N49S/A68T/A112E/P227L
G22D/N49S/A68T/P227L/S278P/T296P
G22D/N49S/A68T/N103I/S113N/S278P/T296P
G22D/N49S/A68T/N103I/S113N/P227L/S278P/T296P
G22D/N49S/A68T/N103I/A112E/P227L/S278P/T296P
G22D/N49S/N64D/A68T/N103I/S113N/S278P/T296P
S8P/T41I/N49S/A68T/S92T/S113N/P227L/D249K/S411F
S8P/G22D/T41I/N49S/A68T/N103I/S113N/S278P/T296P
S8P/G22D/T41I/N49S/A68T/N103I/S113N/P227L/S278P/T296P
S8P/G22D/T41I/N49S/A68T/S113N/P227L/D249K/S278P/N301R
S8P/G22D/T41I/N49S/A68T/S92T/S113N/P227L/D249K/S411F
S8P/T41I/N49S/A68T/S92T/S113N/P227L/D249K/V403D/T462I
S8P/G22D/T41I/N49S/A68T/N103I/S113N/P227L/D249K/S278P/T296P
S8P/G22D/T41I/N49S/A68T/N103I/S113N/P227L/S278P/T296P/N301R
S8P/G22D/T41I/N49S/A68T/S113N/P227L/D249K/S278P/T296P/N301R
S8P/T41I/N49S/S57N/A68T/S113N/P227L/D249K/S278P/T296P/N301R
S8P/G22D/T41I/N49S/A68T/S92T/S113N/P227L/D249K/V403D/T462I
S8P/G22D/T41I/N49S/A68T/N103I/S113N/P227L/D249K/S278P/T296P/N301R
S8P/G22D/T41I/N49S/A68T/S92T/S113N/S196T/P227L/D249K/T255P/S278P/T296P/N301R/E325K/S411F
S8P/T41I/N49S/A68T/S92T/S113N/S196T/P227L/D249K/T255P/S278P/T296P/N301R/E325K/V403D/S411F/T462I
S8P/G22D/T41I/N49S/A68T/S92T/S113N/S196T/P227L/D249K/T255P/S278P/T296P/N301R/E325K/V403D/S411F/T462I

Example 2

Cloning and Expression of CBHI Variants in *H. jecorina*

A. Construction of the *H. jecorina* General-Purpose Expression Plasmid-PTEX.

The plasmid, pTEX was constructed following the methods of Sambrook et al. (1989), supra, and is illustrated in FIG. 7. This plasmid has been designed as a multi-purpose expression vector for use in the filamentous fungus *Trichoderma longibrachiatum*. The expression cassette has several unique features that make it useful for this function. Transcription is regulated using the strong CBH I gene promoter and terminator sequences for *T. longibrachiatum*. Between the CBHI promoter and terminator there are unique PmeI and SstI restriction sites that are used to insert the gene to be expressed. The *T. longibrachiatum* pyr4 selectable marker gene has been inserted into the CBHI terminator and the whole expression cassette (CBHI promoter-insertion sites-CBHI terminator-pyr4 gene-CBHI terminator) can be excised utilizing the unique NotI restriction site or the unique NotI and NheI restriction sites.

This vector is based on the bacterial vector, pSL1180 (Pharmacia Inc., Piscataway, N.J.), which is a PUC-type vector with an extended multiple cloning site. One skilled in the art would be able to construct this vector based on the flow diagram illustrated in FIG. 7.

The vector pTrex2L was constructed from pTrex2, a derivative of pTEX. The sequence for pTrex2 is given in FIG. 6.

The exact plasmid used is not that important as long as the variant protein is expressed at a useful level. However, maximizing the expression level by forcing integration at the cbh1 locus is advantageous.

B. Cloning

Using methods known in the art a skilled person can clone the desired CBH I variant into an appropriate vector. As noted above, the exact plasmid used is not that important as long as the variant protein is expressed at a useful level. The following description of the preparation of one of the inventive variant CBH I enzymes can be utilized to prepare any of the inventive variants described herein.

The variant cbh 1 genes were cloned into the pTrex2L vector.

Construction of plasmid pTrex2L was done as follows: The 6 nucleotides between the unique Sac II and Asc I sites of pTrex2 were replaced with a synthetic linker containing a BstE II and BamH I sites to produce plasmid Trex2L. The complementary synthetic linkers 21-mer synthetic oligo CBHlink1+: GGTTTGGATCCGGTCACCAGG (SEQ ID NO: 73) And 27-mer synthetic oligo CBHlink−: CGCGC-CTGGTGACCGGATCCAAACCGC (SEQ ID NO: 74) were annealed.

The pTrex2 was digested with Sac II and Asc I. The annealed linker was then ligated into pTrex2 to create pTrex2L. The plasmid was then digested with an appropriate restriction enzyme(s) and a wild type CBH I gene was ligated into the plasmid.

Primers were used to introduce the desired mutations into the wild-type gene. It will be understood that any method that results in the introduction of a desired alteration or mutation in the gene may be used. Synthetic DNA primers were used as PCR templates for mutant constructions. It is well within the knowledge of the skilled artisan to design the primers based on the desired mutation to be introduced.

The mutagenic templates were extended and made double stranded by PCR using the synthetic DNA oligonucleotides. After 25 PCR cycles the final product was primarily a 58 bp double stranded product comprising the desired mutation. The mutagenic fragments were subsequently attached to wild-type CBH I fragments and ligated into the plasmid using standard techniques.

C. Transformation and Expression

The prepared vector for the desired variant was transformed into the uridine auxotroph version of the double or quad deleted Trichoderma strains (see Table 3; see also U.S. Pat. Nos. 5,861,271 and 5,650,322) and stable transformants were identified.

TABLE 3

| CBH I Variant | Transformation/Expression strain |
|---|---|
|  | Expression Strain |
| A77D | quad-delete strain (1A52) |
| S113D | double-delete strain |
| L225F | double-delete strain |
| L288F | double-delete strain |
| A299E | quad-delete strain (1A52) |
| N301K | quad-delete strain (1A52) |
| T356L | double-delete strain |
| G430F | quad-delete strain (1A52) |
| T246C/Y371C | quad-delete strain (1A52) |
| T246A/R251A/Y252A | quad-delete strain (1A52) |

TABLE 3-continued

| CBH I Variant | Transformation/Expression strain |
|---|---|
|  | Expression Strain |
| Y252Q/D259W/S342Y | quad-delete strain (1A52) |
| T380G/Y381D/R394A | quad-delete strain (1A52) |
| T380G/Y381D/R394A plus deletion of 382-393 | quad-delete strain (1A52) |

"double-delete" (Δ CBHI & Δ CBHII) and the "quad-delete" (Δ CBHI & Δ CBHII, Δ EGI & Δ EGII) T.reesei host strains To select which transformants expressed variant CBH I, DNA was isolated from strains following growth on Vogels+1% glucose and Southern blot experiments performed using an isolated DNA fragment containing only the variant CBH I. Transformants were isolated having a copy of the variant CBH I expression cassette integrated into the genome of the host cell. Total mRNA was isolated from the strains following growth for 1 day on Vogels+1% lactose. The mRNA was subjected to Northern analysis using the variant CBH I coding region as a probe. Transformants expressing variant CBH I mRNA were identified.

One may obtain any other novel variant CBH I cellulases or derivative thereof by employing the methods described above.

Example 3

Expression of CBH1 Variants in *A. niger*

The PCR fragments were obtained using the following primers and protocols

The following DNA primers were constructed for use in amplification of homologous CBH1 genes from genomic DNA's isolated from various microorganisms. All symbols used herein for protein and DNA sequences correspond to IUPAC IUB Biochemical Nomenclature Commission codes.

Homologous 5' (FRG192) and 3' (FRG193) primers were developed based on the sequence of CBH1 from *Trichoderma reesei*. Both primers contained Gateway cloning sequences from Invitrogen® at the 5' of the primer. Primer FRG192 contained attB1 sequence and primer FRG193 contained attB2 sequence.

Sequence of FRG192 without the attB1:

```
                              (SEQ ID NO: 75)
ATGTATCGGAAGTTGGCCG
(signal sequence of CBH1 H. jecorina)
```

Sequence of FRG193 without the attB2:

```
                              (SEQ ID NO: 76)
TTACAGGCACTGAGAGTAG
(cellulose binding module of CBH1 H. jecorina)
```

The *H. jecorina* CBH I cDNA clone served as template.

PCR conditions were as follows: 10 µL of 10× reaction buffer (10× reaction buffer comprising 100 mM Tris HCl, pH 8-8.5; 250 mM KCl; 50 mM $(NH_4)_2SO_4$; 20 mM $MgSO_4$); 0.2 mM each of dATP, dTTP, dGTP, dCTP (final concentration), 1 µL of 100 ng/µL genomic DNA, 0.5 µL of PWO polymerase (Boehringer Mannheim, Cat #1644-947) at 1 unit per µL, 0.2 µM of each primer, FRG192 and FRG193, (final concentration), 4 µl DMSO and water to 100 µL.

Various sites in *H. jecorina* CBH1 may be involved in the thermostability of the variants and the *H. jecorina* CBH1 gene was therefore subjected to mutagenesis.

The fragments encoding the variants were purified from an agarose gel using the Qiagen Gel extraction KIT. The purified fragments were used to perform a clonase reaction with the pDONR™201 vector from Invitrogen® using the Gateway™ Technology instruction manual (version C) from Invitrogen®, hereby incorporated by reference herein. Genes were then transferred from this ENTRY vector to the destination vector (pRAXdes2) to obtain the expression vector pRAX-CBH1.

Cells were transformed with an expression vector comprising a variant CBH I cellulase encoding nucleic acid. The constructs were transformed into *A. niger* var. *awamori* according to the method described by Cao et al (Cao Q-N, Stubbs M, Ngo KQP, Ward M, Cunningham A, Pai EF, Tu G-C and Hofmann T (2000) Penicillopepsin-JT2 a recombinant enzyme from *Penicillium janthinellum* and contribution of a hydrogen bond in subsite S3 to kcat Protein Science 9:991-1001).

Transformants were streaked on minimal medium plates (Ballance D J, Buxton F P, and Turner G (1983) Transformation of *Aspergillus nidulans* by the orotidine-5'-phosphate decarboxylase gene of *Neurospora crassa* Biochem Biophys Res Commun 112:284-289) and grown for 4 days at 30° C. Spores were collected using methods well known in the art (See <www.fgsc.net/fgn48/Kaminskyi.htm>). *A. nidulans* conidia are harvested in water (by rubbing the surface of a conidiating culture with a sterile bent glass rod to dislodge the spores) and can be stored for weeks to months at 4° C. without a serious loss of viability. However, freshly harvested spores germinate more reproducibly. For long-term storage, spores can be stored in 50% glycerol at −20° C., or in 15-20% glycerol at −80° C. Glycerol is more easily pipetted as an 80% solution in water. 800 µl of aqueous conidial suspension (as made for 4° C. storage) added to 200 µl 80% glycerol is used for a −80° C. stock; 400 µl suspension added to 600 µl 80% glycerol is used for a −20° C. stock. Vortex before freezing. For mutant collections, small pieces of conidiating cultures can be excised and placed in 20% glycerol, vortexed, and frozen as −80° C. stocks. In our case we store them in 50% glycerol at −80° C.

*A. niger* var *awamori* transformants were grown on minimal medium lacking uridine (Ballance et al. 1983). Transformants were screened for cellulase activity by inoculating 1 $cm^2$ of spore suspension from the sporulated grown agar plate into 100 ml shake flasks for 3 days at 37° C. as described by Cao et al. (2000).

The CBHI activity assay is based on the hydrolysis of the nonfluorescent 4-methylumbelliferyl-β-lactoside to the products lactose and 7-hydroxy-4-methylcoumarin, the latter product is responsible for the fluorescent signal. Pipette 170 µl 50 mM NaAc buffer pH 4.5 in a 96-well microtiter plate (MTP) (Greiner, Fluotrac 200, art. nr. 655076) suitable for fluorescence. Add 10 µl of supernatant and then add 10 µl of MUL (1 mM 4-methylumbelliferyl-β-lactoside (MUL) in milliQ water) and put the MTP in the Fluostar Galaxy (BMG Labtechnologies; D-77656 Offenburg). Measure the kinetics for 16 min. (8 cycles of 120s each) using $\lambda_{320\ nm}$ (excitation) and $\lambda_{460\ nm}$ (emission) at 50° C. Supernatents having CBH activity were then subjected to Hydrophobic Interaction Chromatography.

Example 4

Stability of CBH 1 Variants

CBH I cellulase variants were cloned and expressed as above (see Examples 2 and 3). Cel7A wild type and variants were then purified from cell-free supernatants of these cultures by column chromatography. Proteins were purified using hydrophobic interaction chromatography (HIC). Columns were run on a BioCAD® Sprint Perfusion Chromatography System using Poros® 20 HP2 resin both made by Applied Biosystems.

HIC columns were equilibrated with 5 column volumes of 0.020 M sodium phosphate, 0.5 M ammonium sulfate at pH 6.8. Ammonium sulfate was added to the supernatants to a final concentration of approximately 0.5 M and the pH was adjusted to 6.8. After filtration, the supernatant was loaded onto the column. After loading, the column was washed with 10 column volumes of equilibration buffer and then eluted with a 10 column volume gradient from 0.5 M ammonium sulfate to zero ammonium sulfate in 0.02 M sodium phosphate pH 6.8. Cel7A eluted approximately mid-gradient. Fractions were collected and pooled on the basis of reduced, SDS-PAGE gel analysis.

The melting points were determined according to the methods of Luo, et al., *Biochemistry* 34:10669 and Gloss, et al., *Biochemistry* 36:5612. See also Sandgren at al. (2003) Protein Science 12(4) pp848.

Data was collected on the Aviv 215 circular dichroism spectrophotometer. The native spectra of the variants between 210 and 260 nanometers were taken at 25° C. Buffer conditions were 50 mM Bis Tris Propane/50 mM ammonium acetate/glacial acetic acid at pH 5.5. The protein concentration was kept between 0.25 and 0.5 mgs/mL. After determining the optimal wavelength to monitor unfolding, the samples were thermally denatured by ramping the temperature from 25° C. to 75° C. under the same buffer conditions. Data was collected for 5 seconds every 2 degrees. Partially reversible unfolding was monitored at 230 nanometers in a 0.1 centimeter path length cell. While at 75° C., an unfolded spectra was collected as described above. The sample was then cooled to 25° C. to collect a refolded spectra. The difference between the three spectra at 230 nm was used to assess the variants reversibility.

Figure 9A:
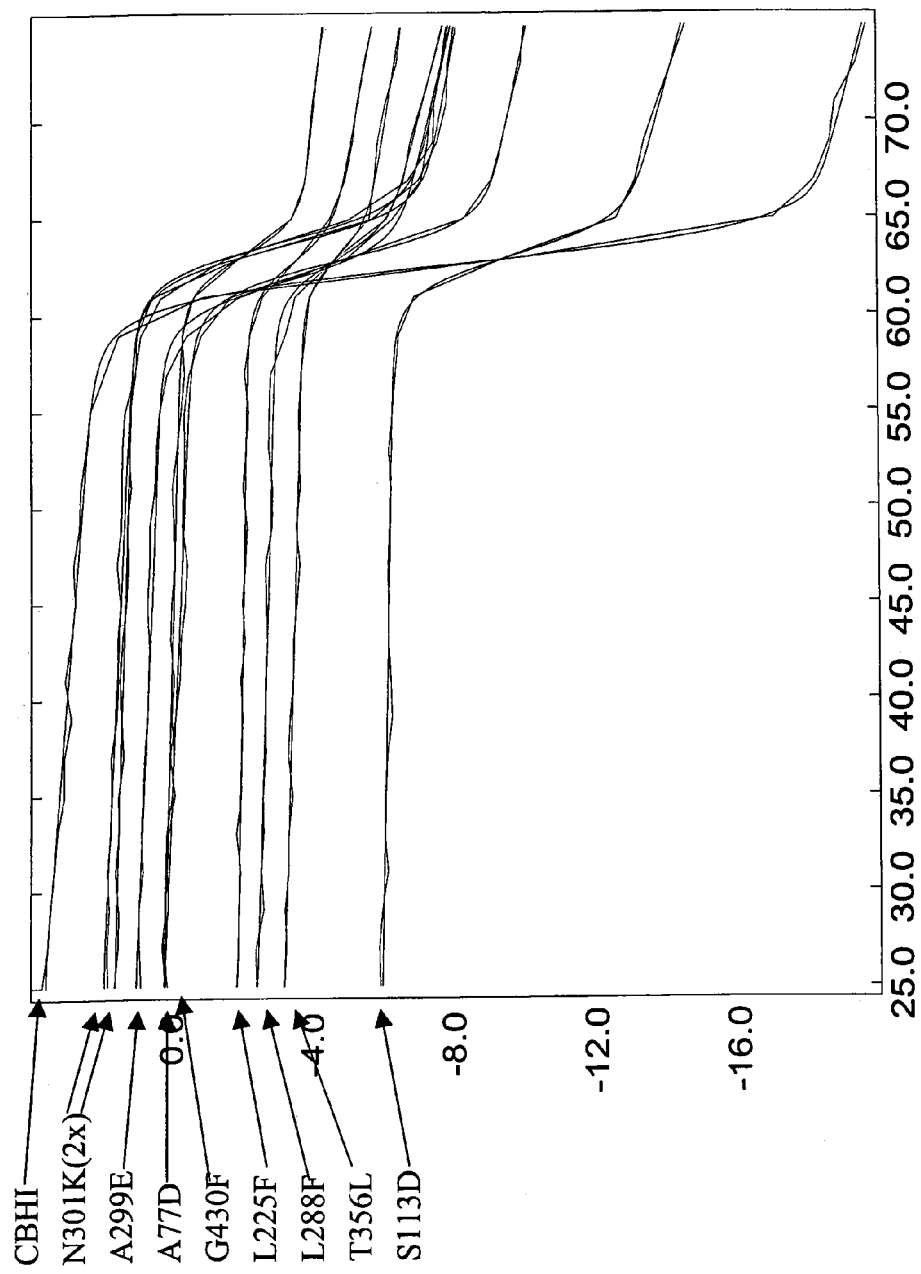
FIG. 9A is a representation of the thermal profiles of the wild type and eight single residue variants.
Figure 9B:
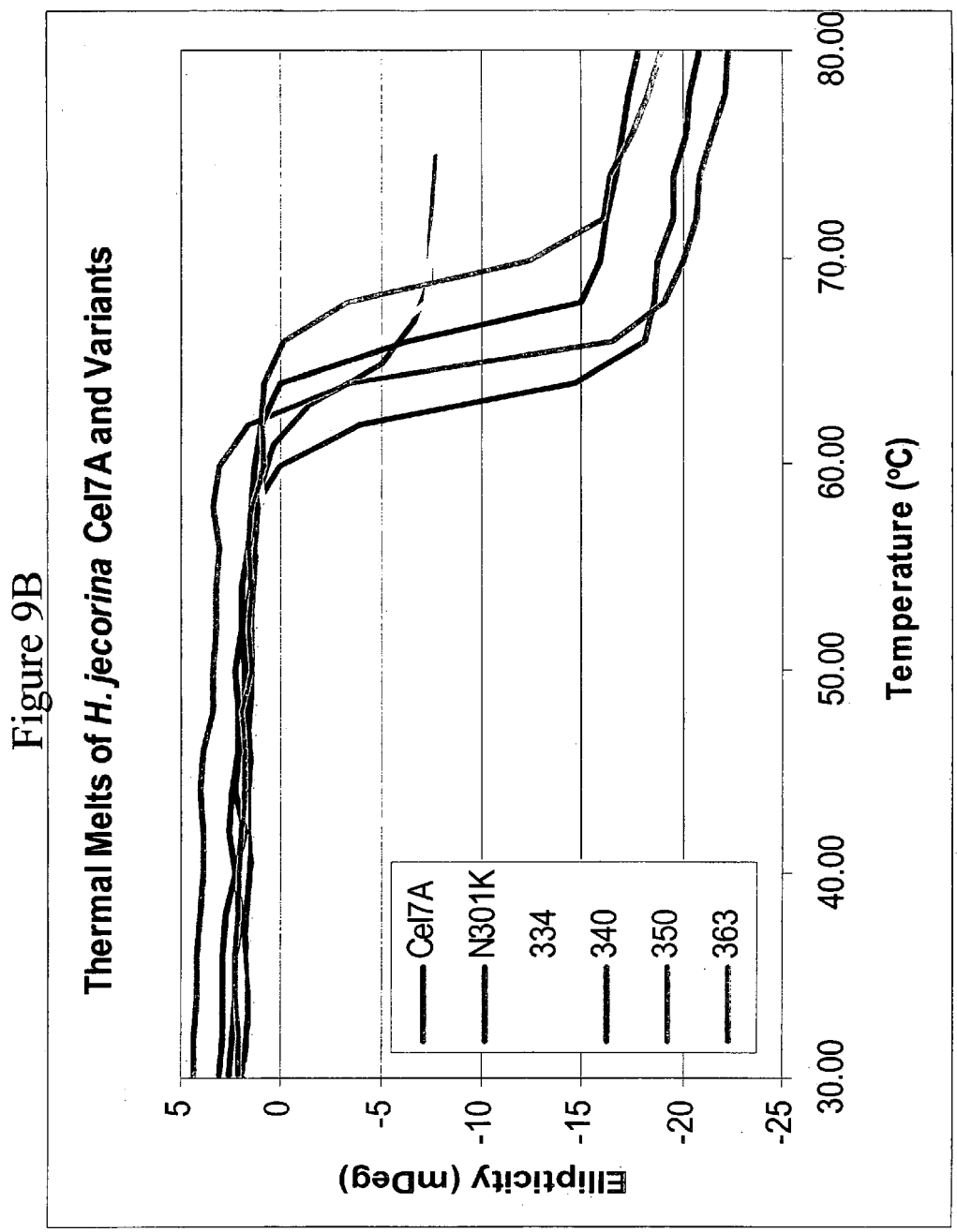
FIG. 9B is a representation of the thermal profiles of the wild type and five variants. Legend for FIG. 9B: Cel7A=wild-type *H. jecorina* CBH I; N301K=N301K variant; 334=P227L variant; 340=S8P/N49S/A68T/S113N variant; 350=S8P/N49S/A68T/S113N/P227L variant; and 363=S8P/G22D/T41I/N49S/A68T/N103I/S113N/P227L/S278P/T296P variant.

The thermal denaturation profiles are shown in FIGS. 9A and 9B for wildtype CBH I and various variant CBH 1's. See also Table 4.

TABLE 4

Thermal Stability of Variant CBH I cellulases

| H. jecorina CBH I Residue Substitution | Tm | delta Tm | % rev 230 nm |
|---|---|---|---|
| Wild type | 62.5 | | 23 |
| S8P | 63.1 | 0.6 | |
| N49S | 63.7 | 1.2 | |
| A68T | 63.7 | 1.2 | 32 |
| A77D | 62.2 | −0.3 | |
| N89D | 63.6 | 1.1 | 50 |
| S92T | 64.4 | 1.9 | 25 |

TABLE 4-continued

Thermal Stability of Variant CBH I cellulases

| H. jecorina CBH I Residue Substitution | Tm | delta Tm | % rev 230 nm |
|---|---|---|---|
| S113D | 62.8 | 0.3 | |
| S113N | 64.0 | 1.5 | |
| L225F | 61.6 | −0.9 | |
| P227A | 64.8 | 2.3 | 49 |
| P227L | 65.2 | 2.7 | 45 |
| D249K | 64.0 | 1.5 | 39 |
| T255P | 64.4 | 1.9 | 35 |
| S279N | 62.4 | −0.1 | −95 |
| E295K | 64.0 | 1.5 | −95 |
| T332K | 63.3 | 0.8 | 37 |
| T332Y | 63.3 | 0.8 | 37 |
| T332H | 62.7 | 0.2 | 64 |
| F338Y | 60.8 | −1.7 | −95 |
| G430F | 61.7 | −0.8 | |
| L288F | 62.4 | −0.1 | |
| A299E | 61.2 | −1.3 | |
| N301K | 63.5 | 1.0 | |
| T356L | 62.6 | 0.1 | |
| D257E | 61.8 | −0.7 | 45 |
| V393G | 61.7 | −0.8 | 43 |
| S297T | 63.3 | 0.8 | 31 |
| T41I plus deletion @ T445 | 64.2 | 1.7 | |
| T246C/Y371C | 65.0 | 2.5 | |
| S196T/S411F | 65.3 | 2.8 | 27 |
| E295K/S398T | 63.9 | 1.4 | 36 |
| V403D/T462I | 64.5 | 2 | 53 |
| A112E/T226A | 63.5 | 1.0 | |
| A68T/G440R/P491L | 63.1 | 0.6 | 32 |
| G22D/S278P/T296P | 63.6 | 1.1 | |
| T246A/R251A/Y252A | 63.5 | 1.0 | |
| T380G/Y381D/R394A | 58.1 | −4.4 | |
| Y252Q/D259W/S342Y | 59.9 | −2.6 | 50 |
| S113T/T255P/K286M | 63.8 | 1.3 | 16 |
| P227L/E325K/Q487L | 64.5 | 2.0 | 22 |
| P227T/T484S/F352L | 64.2 | 1.7 | 45 |
| Q17L/E193V/M213I/F352L | 64.0 | 1.5 | 34 |
| S8P/N49S/A68T/S113N | 64.5 | 2.0 | 90 |
| S8P/N49S/A68T/S113N/P227L | 66.0 | 3.5 | 86 |
| T41I/A112E/P227L/S278P/T296P | 66.1 | 3.6 | 48 |
| S8P/N49S/A68T/A112E/T226A | 64.6 | 2.1 | 46 |
| S8P/N49S/A68T/A112E/P227L | 65.2 | 2.7 | 32 |
| S8P/T41I/N49S/A68T/A112E/P227L | 67.6 | 5.1 | 40 |
| G22D/N49S/A68T/P227L/S278P/T296P | 65.9 | 3.4 | 26 |
| G22D/N49S/A68T/N103I/S113N/P227L/S278P/T296P | 65.3 | 2.8 | 72 |
| G22D/N49S/A68T/N103I/A112E/P227L/S278P/T296P | 65.1 | 2.6 | 20 |
| G22D/N49S/N64D/A68T/N103I/S113N/S278P/T296P | 61.4 | −1.1 | 75 |
| S8P/G22D/T41I/N49S/A68T/N103I/S113N/P227L/S278P/T296P | 68.8 | 6.3 | 56 |
| S8P/G22D/T41I/N49S/A68T/N103I/S113N/P227L/D249K/S278P/T296P | 69.0 | 6.5 | 71 |
| S8P/G22D/T41I/N49S/A68T/N103I/S113N/P227L/S278P/T296P/N301R | 68.7 | 6.2 | 70 |
| S8P/G22D/T41I/N49S/A68T/N103I/S113N/P227L/D249K/S278P/T296P/N301R | 68.8 | 6.3 | 74 |
| S8P/G22D/T41I/N49S/A68T/S113N/P227L/D249K/S278P/T296P/N301R | 69.9 | 7.4 | 88 |
| S8P/T41I/N49S/S57N/A68T/S113N/P227L/D249K/S278P/T296P/N301R | 68.9 | 6.4 | ~100 |
| S8P/G22D/T41I/N49S/A68T/S113N/P227L/D249K/S278P/N301R | 68.7 | 6.2 | 92 |
| S8P/T41I/N49S/A68T/S92T/S113N/P227L/D249K/V403D/T462I | 68.8 | 6.3 | ~100 |
| S8P/G22D/T41I/N49S/A68T/S92T/S113N/P227L/D249K/V403D/T462I | 68.5 | 6.0 | ~100 |
| S8P/T41I/N49S/A68T/S92T/S113N/P227L/D249K/S411F | 68.6 | 6.1 | ~100 |
| S8P/G22D/T41I/N49S/A68T/S92T/S113N/P227L/D249K/S411F | 69.5 | 7.0 | ~100 |
| S8P/G22D/T41I/N49S/A68T/S92T/S113N/S196T/P227L/D249K/T255P/S278P/T296P/N301R/E325K/S411F | 70.7 | 8.2 | ~100 |
| S8P/T41I/N49S/A68T/S92T/S113N/S196T/P227L/D249K/T255P/S278P/T296P/N301R/E325K/V403D/S411F/T462I | 71.0 | 8.5 | ~100 |
| S8P/G22D/T41I/N49S/A68T/S92T/S113N/S196T/P227L/D249K/T255P/S278P/T296P/N301R/E325K/V403D/S411F/T462I | 70.9 | 8.4 | ~100 |

Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled id molecular biology or related fields are intended to be within the scope of the claims.

What is claimed:

1. A nucleic acid encoding a *Hypocrea jecorina* CBH I variant consisting essentially of an amino acid sequence having at least 96.4% sequence identity to the amino acid sequence of SEQ ID NO:2, and comprising one or more alterations as compared to SEQ ID NO:2, wherein said one or more alterations is selected from the group consisting of:
   i. A112E/T226A;
   ii. S196T/S411F;
   iii. E295K/S398T;
   iv. T246C/Y371C;
   v. V403D/T462I;
   vi. T41I plus deletion at T445;
   vii. A68T/G440R/P491L;
   viii. G22D/S278P/T296P;
   ix. T246A/R251A/Y252A;
   x. T380G/Y381D/R394A;
   xi. Y252Q/D259W/S342Y;
   xii. S113T/T255P/K286M;
   xiii. P227L/E325K/Q487L;
   xiv. P227T/T484S/F352L;
   xv. Q17L/E193V/M213I/F352L;
   xvi. S8P/N49S/A68T/S113N;
   xvii. S8P/N49S/A68T/S113N/P227L;
   xviii. T41I/A112E/P227L/S278P/T296P;
   xix. S8P/N49S/A68T/A112E/T226A;
   xx. S8P/N49S/A68T/A112E/P227L;
   xxi. S8P/T41I/N49S/A68T/A112E/P227L;
   xxii. G22D/N49S/A68T/P227L/S278P/T296P;
   xxiii. S8P/G22D/T41I/N49S/A68T/N103I/S113N/P227L/S278P/T296P;
   xxiv. G22D/N49S/A68T/N103I/S113N/P227L/S278P/T296P;
   xxv. G22D/N49S/A68T/N103I/A112E/P227L/S278P/T296P;
   xxvi. G22D/N49S/N64D/A68T/N103I/S113N/S278P/T296P;
   xxvii. S8P/G22D/T41I/N49S/A68T/N103I/S113N/P227L/D249K/S278P/T296P;
   xxviii. S8P/G22D/T41I/N49S/A68T/N103I/S113N/P227L/S278P/T296P/N301R;
   xxix. S8P/G22D/T41I/N49S/A68T/N103I/S113N/P227L/D249K/S278P/T296P/N301R;
   xxx. S8P/G22D/T41I/N49S/A68T/S113N/P227L/D249K/S278P/T296P/N301R;
   xxxi. S8P/T41I/N49S/S57N/A68T/S113N/P227L/D249K/S278P/T296P/N301R;
   xxxii. S8P/G22D/T41I/N49S/A68T/S113N/P227L/D249K/S278P/N301R;
   xxxiii. S8P/T41I/N49S/A68T/S92T/S113N/P227L/D249K/V403D/T462I;
   xxxiv. S8P/G22D/T41I/N49S/A68T/S92T/S113N/P227L/D249K/V403D/T462I;
   xxxv. S8P/T41I/N49S/A68T/S92T/S113N/P227L/D249K/S411F;
   xxxvi. S 8P/G22D/T41I/N49S/A68T/S 92T/S113N/P227L/D249K/S411F;
   xxxvii. S8P/G22D/T41I/N49S/A68T/S92T/S113N/S196T/P227L/D249K/T255P/S278P/T296P/N301R/E325K/S411F;
   xxxviii. S8P/T41I/N49S/A68T/S92T/S113N/S196T/P227L/D249K/T255P/S278P/T296P/N301R/E325K/V403D/S411F/T462I; and
   xxxix. S8P/G22D/T41I/N49S/A68T/S92T/S113N/S196T/P227L/D249K/T255P/S278P/T296P/N301R/E325K/V403D/S411F/T462I.

2. A vector comprising a nucleic acid of claim 1.

3. A host cell transformed with the vector of claim 2.

4. A method of producing a CBH I variant comprising the steps of:
   (a) culturing the host cell according to claim 3 in a suitable culture medium under suitable conditions to produce a CBH I variant; and
   (b) obtaining said produced CBH I variant.

5. The nucleic acid of claim 1 wherein said one or more alterations consists essentially of A112E/T226A.

6. The nucleic acid of claim 1 wherein said one or more alterations consists essentially of S196T/S411F.

7. The nucleic acid of claim 1 wherein said one or more alterations consists essentially of E295K/S398T.

8. The nucleic acid of claim 1 wherein said one or more alterations consists essentially of T246C/Y371C.

9. The nucleic acid of claim 1 wherein said one or more alterations consists essentially of V403D/T462I.

10. The nucleic acid of claim 1 wherein said one or more alterations consists essentially of T41I plus deletion at T445.

11. The nucleic acid of claim 1 wherein said one or more alterations consists essentially of A68T/G440R/P491L.

12. The nucleic acid of claim 1 wherein said one or more alterations consists essentially of G22D/S278P/T296P.

13. The nucleic acid of claim 1 wherein said one or more alterations consists essentially of T246A/R251A/Y252A.

14. The nucleic acid of claim 1 wherein said one or more alterations consists essentially of T380G/Y381D/R394A.

15. The nucleic acid of claim 1 wherein said one or more alterations consists essentially of Y252Q/D259W/S342Y.

16. The nucleic acid of claim 1 wherein said one or more alterations consists essentially of S113T/T255P/K286M.

17. The nucleic acid of claim 1 wherein said one or more alterations comprises P227L/E325K/Q487L.

18. The nucleic acid of claim 1 wherein said one or more alterations comprises P227T/T484S/F352L.

19. The nucleic acid of claim 1 wherein said one or more alterations consists essentially of Q17L/E193V/M213I/F352L.

20. The nucleic acid of claim 1 wherein said one or more alterations comprises consists essentially of S8P/N49S/A68T/S113N.

21. The nucleic acid of claim 1 wherein said one or more alterations comprises S8P/N49S/A68T/S113N/P227L.

22. The nucleic acid of claim 1 wherein said one or more alterations comprises T41I/A112E/P227L/S278P/T296P.

23. The nucleic acid of claim 1 wherein said one or more alterations consists essentially of S8P/N49S/A68T/A112E/T226A.

24. The nucleic acid of claim 1 wherein said one or more alterations comprises S8P/N49S/A68T/A112E/P227L.

25. The nucleic acid of claim 1 wherein said one or more alterations comprises S8P/T41I/N49S/A68T/A112E/P227L.

26. The nucleic acid of claim 1 wherein said one or more alterations comprises G22D/N49S/A68T/P227L/S278P/T296P.

27. The nucleic acid of claim 1 wherein said one or more alterations comprises S8P/G22D/T41I/N49S/A68T/N103I/S113N/P227L/S278P/T296P.

28. The nucleic acid of claim 1 wherein said one or more alterations comprises G22D/N49S/A68T/N103I/S113N/P227L/S278P/T296P.

29. The nucleic acid of claim 1 wherein said one or more alterations comprises G22D/N49S/A68T/N103I/A112E/P227L/S278P/T296P.

30. The nucleic acid of claim 4 wherein said one or more alterations consists essentially of G22D/N49S/N64D/A68T/N103I/S113N/S278P/T296P.

31. The nucleic acid of claim 1 wherein said one or more alterations comprises S8P/G22D/T41I/N49S/A68T/N103I/S113N/P227L/D249K/S278P/T296P.

32. The nucleic acid of claim 1 wherein said one or more alterations comprises S8P/G22D/T41I/N49S/A68T/N103I/S113N/P227L/S278P/T296P/N301R.

33. The nucleic acid of claim 1 wherein said one or more alterations comprises S8P/G22D/T41I/N49S/A68T/N103I/S113N/P227L/D249K/S278P/T296P/N301R.

34. The nucleic acid of claim 1 wherein said one or more alterations comprises S8P/G22D/T41I/N49S/A68T/S113N/P227L/D249K/S278P/T296P/N301R.

35. The nucleic acid of claim 1 wherein said one or more alterations comprises S8P/T41I/N49S/S57N/A68T/S113N/P227L/D249K/S278P/T296P/N301R.

36. The nucleic acid of claim 1 wherein said one or more alterations comprises S8P/G22D/T41I/N49S/A68T/S113N/P227L/D249K/S278P/N301R.

37. The nucleic acid of claim 1 wherein said one or more alterations comprises S8P/T41I/N49S/A68T/S92T/S113N/P227L/D249K/V403D/T462I.

38. The nucleic acid of claim 1 wherein said one or more alterations consists essentially of comprises S8P/G22D/T41I/N49S/A68T/S92T/S113N/P227L/D249K/V403D/T462I.

39. The nucleic acid of claim 1 wherein said one or more alterations comprises S8P/T41I/N49S/A68T/S92T/S113N/P227L/D249K/S411F.

40. The nucleic acid of claim 1 wherein said one or more alterations comprises S8P/G22D/T41I/N49S/A68T/S92T/S113N/P227L/D249K/S411F.

41. The nucleic acid of claim 1 wherein said one or more alterations comprises S8P/G22D/T41I/N49S/A68T/S92T/S113N/S196T/P227L/D249K/T255P/S278P/T296P/N301R/E325K/S411F.

42. The nucleic acid of claim 1 wherein said one or more alterations comprises S8P/T41I/N49S/A68T/S92T/S113N/S196T/P227L/D249K/T255P/S278P/T296P/N301R/E325K/V403D/S411F/T462I.

43. The nucleic acid of claim 1 wherein said one or more alterations comprises S8P/G22D/T41I/N49S/A68T/S92T/S113N/S196T/P227L/D249K/T255P/S278P/T296P/N301R/E325K/V403D/S411F/T462I.

44. A recombinant filamentous fungal cell engineered to be capable of expressing a CBH I variant encoded by the nucleic acid of claim 1.

45. A method of producing a CBH I variant comprising the steps of:
 (a) culturing the recombinant filamentous fungal cell according to claim 44 in a suitable culture medium under suitable conditions to express a CBH I variant; and
 (b) obtaining said CBH I variant.

* * * * *

```
                            SEQUENCE LISTING

<160> NUMBER OF SEQ ID NOS: 81

<210> SEQ ID NO 1
<211> LENGTH: 1491
<212> TYPE: DNA
<213> ORGANISM: Hypocrea jecorina
<220> FEATURE:
<221> NAME/KEY: CDS
<222> LOCATION: (1)..(1491)

<400> SEQUENCE: 1 cag tcg gcc tgc act ctc caa tcg gag act cac ccg cct ctg aca tgg        48
Gln Ser Ala Cys Thr Leu Gln Ser Glu Thr His Pro Pro Leu Thr Trp
1               5                   10                  15 cag aaa tgc tcg tct ggt ggc act tgc act caa cag aca ggc tcc gtg        96
Gln Lys Cys Ser Ser Gly Gly Thr Cys Thr Gln Gln Thr Gly Ser Val
            20                  25                  30 gtc atc gac gcc aac tgg cgc tgg act cac gct acg aac agc agc acg       144
Val Ile Asp Ala Asn Trp Arg Trp Thr His Ala Thr Asn Ser Ser Thr
        35                  40                  45 aac tgc tac gat ggc aac act tgg agc tcg acc cta tgt cct gac aac       192
Asn Cys Tyr Asp Gly Asn Thr Trp Ser Ser Thr Leu Cys Pro Asp Asn
    50                  55                  60 gag acc tgc gcg aag aac tgc tgt ctg gac ggt gcc gcc tac gcg tcc       240
Glu Thr Cys Ala Lys Asn Cys Cys Leu Asp Gly Ala Ala Tyr Ala Ser
65                  70                  75                  80 acg tac gga gtt acc acg agc ggt aac agc ctc tcc att ggc ttt gtc       288
Thr Tyr Gly Val Thr Thr Ser Gly Asn Ser Leu Ser Ile Gly Phe Val
                85                  90                  95 acc cag tct gcg cag aag aac gtt ggc gct cgc ctt tac ctt atg gcg       336
Thr Gln Ser Ala Gln Lys Asn Val Gly Ala Arg Leu Tyr Leu Met Ala
            100                 105                 110 agc gac acg acc tac cag gaa ttc acc ctg ctt ggc aac gag ttc tct       384
Ser Asp Thr Thr Tyr Gln Glu Phe Thr Leu Leu Gly Asn Glu Phe Ser
        115                 120                 125 ttc gat gtt gat gtt tcg cag ctg ccg tgc ggc ttg aac gga gct ctc       432
Phe Asp Val Asp Val Ser Gln Leu Pro Cys Gly Leu Asn Gly Ala Leu
    130                 135                 140 tac ttc gtg tcc atg gac gcg gat ggt ggc gtg agc aag tat ccc acc       480
Tyr Phe Val Ser Met Asp Ala Asp Gly Gly Val Ser Lys Tyr Pro Thr
145                 150                 155                 160 aac acc gct ggc gcc aag tac ggc acg ggg tac tgt gac agc cag tgt       528
Asn Thr Ala Gly Ala Lys Tyr Gly Thr Gly Tyr Cys Asp Ser Gln Cys
                165                 170                 175 ccc cgc gat ctg aag ttc atc aat ggc cag gcc aac gtt gag ggc tgg       576
Pro Arg Asp Leu Lys Phe Ile Asn Gly Gln Ala Asn Val Glu Gly Trp
            180                 185                 190 gag ccg tca tcc aac aac gcg aac acg ggc att gga gga cac gga agc       624
Glu Pro Ser Ser Asn Asn Ala Asn Thr Gly Ile Gly Gly His Gly Ser
        195                 200                 205 tgc tgc tct gag atg gat atc tgg gag gcc aac tcc atc tcc gag gct       672
Cys Cys Ser Glu Met Asp Ile Trp Glu Ala Asn Ser Ile Ser Glu Ala
    210                 215                 220 ctt acc ccc cac cct tgc acg act gtc ggc cag gag atc tgc gag ggt       720
Leu Thr Pro His Pro Cys Thr Thr Val Gly Gln Glu Ile Cys Glu Gly
```

```
                225                 230                 235                 240
gat ggg tgc ggc gga act tac tcc gat aac aga tat ggc ggc act tgc       768
Asp Gly Cys Gly Gly Thr Tyr Ser Asp Asn Arg Tyr Gly Gly Thr Cys
                245                 250                 255 gat ccc gat ggc tgc gac tgg aac cca tac cgc ctg ggc aac acc agc       816
Asp Pro Asp Gly Cys Asp Trp Asn Pro Tyr Arg Leu Gly Asn Thr Ser
            260                 265                 270 ttc tac ggc cct ggc tca agc ttt acc ctc gat acc acc aag aaa ttg       864
Phe Tyr Gly Pro Gly Ser Ser Phe Thr Leu Asp Thr Thr Lys Lys Leu
        275                 280                 285 acc gtt gtc acc cag ttc gag acg tcg ggt gcc atc aac cga tac tat       912
Thr Val Val Thr Gln Phe Glu Thr Ser Gly Ala Ile Asn Arg Tyr Tyr
    290                 295                 300 gtc cag aat ggc gtc act ttc cag cag ccc aac gcc gag ctt ggt agt       960
Val Gln Asn Gly Val Thr Phe Gln Gln Pro Asn Ala Glu Leu Gly Ser
305                 310                 315                 320 tac tct ggc aac gag ctc aac gat gat tac tgc aca gct gag gag gca      1008
Tyr Ser Gly Asn Glu Leu Asn Asp Asp Tyr Cys Thr Ala Glu Glu Ala
                325                 330                 335 gaa ttc ggc gga tcc tct ttc tca gac aag ggc ggc ctg act cag ttc      1056
Glu Phe Gly Gly Ser Ser Phe Ser Asp Lys Gly Gly Leu Thr Gln Phe
            340                 345                 350 aag aag gct acc tct ggc ggc atg gtt ctg gtc atg agt ctg tgg gat      1104
Lys Lys Ala Thr Ser Gly Gly Met Val Leu Val Met Ser Leu Trp Asp
        355                 360                 365 gat tac tac gcc aac atg ctg tgg ctg gac tcc acc tac ccg aca aac      1152
Asp Tyr Tyr Ala Asn Met Leu Trp Leu Asp Ser Thr Tyr Pro Thr Asn
    370                 375                 380 gag acc tcc tcc aca ccc ggt gcc gtg cgc gga agc tgc tcc acc agc      1200
Glu Thr Ser Ser Thr Pro Gly Ala Val Arg Gly Ser Cys Ser Thr Ser
385                 390                 395                 400 tcc ggt gtc cct gct cag gtc gaa tct cag tct ccc aac gcc aag gtc      1248
Ser Gly Val Pro Ala Gln Val Glu Ser Gln Ser Pro Asn Ala Lys Val
                405                 410                 415 acc ttc tcc aac atc aag ttc gga ccc att ggc agc acc ggc aac cct      1296
Thr Phe Ser Asn Ile Lys Phe Gly Pro Ile Gly Ser Thr Gly Asn Pro
            420                 425                 430 agc ggc ggc aac cct ccc ggc gga aac ccg cct ggc acc acc acc acc      1344
Ser Gly Gly Asn Pro Pro Gly Gly Asn Pro Pro Gly Thr Thr Thr Thr
        435                 440                 445 cgc cgc cca gcc act acc act gga agc tct ccc gga cct acc cag tct      1392
Arg Arg Pro Ala Thr Thr Thr Gly Ser Ser Pro Gly Pro Thr Gln Ser
    450                 455                 460 cac tac ggc cag tgc ggc ggt att ggc tac agc ggc ccc acg gtc tgc      1440
His Tyr Gly Gln Cys Gly Gly Ile Gly Tyr Ser Gly Pro Thr Val Cys
465                 470                 475                 480 gcc agc ggc aca act tgc cag gtc ctg aac cct tac tac tct cag tgc      1488
Ala Ser Gly Thr Thr Cys Gln Val Leu Asn Pro Tyr Tyr Ser Gln Cys
                485                 490                 495 ctg                                                                   1491
Leu

<210> SEQ ID NO 2
<211> LENGTH: 497
<212> TYPE: PRT
<213> ORGANISM: Hypocrea jecorina

<400> SEQUENCE: 2

Gln Ser Ala Cys Thr Leu Gln Ser Glu Thr His Pro Pro Leu Thr Trp
1               5                   10                  15
```

```
Gln Lys Cys Ser Ser Gly Gly Thr Cys Thr Gln Gln Thr Gly Ser Val
            20                  25                  30

Val Ile Asp Ala Asn Trp Arg Trp Thr His Ala Thr Asn Ser Ser Thr
        35                  40                  45

Asn Cys Tyr Asp Gly Asn Thr Trp Ser Ser Thr Leu Cys Pro Asp Asn
50                      55                  60

Glu Thr Cys Ala Lys Asn Cys Cys Leu Asp Gly Ala Ala Tyr Ala Ser
65                      70                  75                  80

Thr Tyr Gly Val Thr Thr Ser Gly Asn Ser Leu Ser Ile Gly Phe Val
                    85                  90                  95

Thr Gln Ser Ala Gln Lys Asn Val Gly Ala Arg Leu Tyr Leu Met Ala
                100                 105                 110

Ser Asp Thr Thr Tyr Gln Glu Phe Thr Leu Leu Gly Asn Glu Phe Ser
            115                 120                 125

Phe Asp Val Asp Val Ser Gln Leu Pro Cys Gly Leu Asn Gly Ala Leu
        130                 135                 140

Tyr Phe Val Ser Met Asp Ala Asp Gly Gly Val Ser Lys Tyr Pro Thr
145                 150                 155                 160

Asn Thr Ala Gly Ala Lys Tyr Gly Thr Gly Tyr Cys Asp Ser Gln Cys
                    165                 170                 175

Pro Arg Asp Leu Lys Phe Ile Asn Gly Gln Ala Asn Val Glu Gly Trp
                180                 185                 190

Glu Pro Ser Ser Asn Asn Ala Asn Thr Gly Ile Gly Gly His Gly Ser
            195                 200                 205

Cys Cys Ser Glu Met Asp Ile Trp Glu Ala Asn Ser Ile Ser Glu Ala
        210                 215                 220

Leu Thr Pro His Pro Cys Thr Thr Val Gly Gln Glu Ile Cys Glu Gly
225                 230                 235                 240

Asp Gly Cys Gly Gly Thr Tyr Ser Asp Asn Arg Tyr Gly Gly Thr Cys
                    245                 250                 255

Asp Pro Asp Gly Cys Asp Trp Asn Pro Tyr Arg Leu Gly Asn Thr Ser
                260                 265                 270

Phe Tyr Gly Pro Gly Ser Ser Phe Thr Leu Asp Thr Thr Lys Lys Leu
            275                 280                 285

Thr Val Val Thr Gln Phe Glu Thr Ser Gly Ala Ile Asn Arg Tyr Tyr
290                 295                 300

Val Gln Asn Gly Val Thr Phe Gln Gln Pro Asn Ala Glu Leu Gly Ser
305                 310                 315                 320

Tyr Ser Gly Asn Glu Leu Asn Asp Asp Tyr Cys Thr Ala Glu Glu Ala
                325                 330                 335

Glu Phe Gly Gly Ser Ser Phe Ser Asp Lys Gly Gly Leu Thr Gln Phe
            340                 345                 350

Lys Lys Ala Thr Ser Gly Gly Met Val Leu Val Met Ser Leu Trp Asp
                355                 360                 365

Asp Tyr Tyr Ala Asn Met Leu Trp Leu Asp Ser Thr Tyr Pro Thr Asn
        370                 375                 380

Glu Thr Ser Ser Thr Pro Gly Ala Val Arg Gly Ser Cys Ser Thr Ser
385                 390                 395                 400

Ser Gly Val Pro Ala Gln Val Glu Ser Gln Ser Pro Asn Ala Lys Val
                405                 410                 415

Thr Phe Ser Asn Ile Lys Phe Gly Pro Ile Gly Ser Thr Gly Asn Pro
                420                 425                 430

Ser Gly Gly Asn Pro Pro Gly Gly Asn Pro Pro Gly Thr Thr Thr Thr
            435                 440                 445
```

```
Arg Arg Pro Ala Thr Thr Thr Gly Ser Ser Pro Gly Pro Thr Gln Ser
    450                 455                 460

His Tyr Gly Gln Cys Gly Gly Ile Gly Tyr Ser Gly Pro Thr Val Cys
465                 470                 475                 480

Ala Ser Gly Thr Thr Cys Gln Val Leu Asn Pro Tyr Tyr Ser Gln Cys
                485                 490                 495

Leu

<210> SEQ ID NO 3
<211> LENGTH: 397
<212> TYPE: PRT
<213> ORGANISM: Fusarium oxysporum

<400> SEQUENCE: 3

Thr Pro Asp Lys Ala Lys Glu Gln His Pro Lys Leu Glu Thr Tyr Arg
1               5                   10                  15

Cys Thr Lys Ala Ser Gly Cys Lys Lys Gln Thr Asn Tyr Ile Val Ala
                20                  25                  30

Asp Ala Gly Ile His Gly Ile Arg Gln Lys Asn Gly Ala Gly Cys Gly
            35                  40                  45

Asp Trp Gly Gln Lys Pro Asn Ala Thr Ala Cys Pro Asp Glu Ala Ser
50                  55                  60

Cys Ala Lys Asn Cys Ile Leu Ser Gly Met Asp Ser Asn Ala Tyr Lys
65                  70                  75                  80

Asn Ala Gly Ile Thr Thr Ser Gly Asn Lys Leu Arg Leu Gln Gln Leu
                85                  90                  95

Ile Asn Asn Gln Leu Val Ser Pro Arg Val Tyr Leu Leu Glu Glu Asn
                100                 105                 110

Lys Lys Lys Tyr Glu Met Leu His Leu Thr Gly Thr Glu Phe Ser Phe
            115                 120                 125

Asp Val Glu Met Glu Lys Leu Pro Cys Gly Met Asn Gly Ala Leu Phe
130                 135                 140

Leu Ser Glu Met Pro Gln Asp Gly Gly Lys Ser Thr Ser Arg Asn Ser
145                 150                 155                 160

Lys Ala Gly Ala Tyr Tyr Gly Ala Gly Tyr Cys Asp Ala Gln Cys Tyr
                165                 170                 175

Val Thr Pro Phe Ile Asn Gly Val Gly Asn Ile Lys Gly Gln Gly Val
                180                 185                 190

Cys Cys Asn Glu Leu Asp Ile Trp Glu Ala Asn Ser Arg Ala Thr His
            195                 200                 205

Ile Ala Pro His Pro Cys Ser Lys Pro Gly Leu Tyr Gly Cys Thr Gly
210                 215                 220

Asp Glu Cys Gly Ser Ser Gly Ile Cys Asp Lys Ala Gly Cys Gly Trp
225                 230                 235                 240

Asn His Asn Arg Ile Asn Val Thr Asp Phe Tyr Gly Arg Gly Lys Gln
                245                 250                 255

Tyr Lys Thr Asp Ser Thr Arg Lys Phe Thr Val Thr Ser Gln Phe Val
            260                 265                 270

Ala Asn Lys Gln Gly Asp Leu Ile Glu Leu His Arg His Tyr Ile Gln
        275                 280                 285

Asp Asn Lys Val Ile Glu Ser Ala Thr Val Asn Ile Ser Gly Pro Pro
290                 295                 300

Lys Ile Asn Phe Ile Asn Asp Lys Tyr Cys Ala Ala Thr Gly Ala Asn
305                 310                 315                 320
```

-continued

```
Glu Tyr Met Arg Leu Gly Gly Thr Lys Gln Met Gly Asp Ala Met Ser
                325                 330                 335

Arg Gly Met Val Leu Ala Met Ser Val Trp Trp Ser Glu Gly Asp Phe
            340                 345                 350

Met Ala Trp Leu Asp Gln Gly Val Ala Gly Pro Cys Asp Ala Thr Glu
        355                 360                 365

Gly Asp Pro Lys Asn Ile Val Lys Val Gln Pro Asn Pro Glu Val Thr
    370                 375                 380

Phe Ser Asn Ile Arg Ile Gly Glu Ile Gly Ser Thr Ser
385                 390                 395

<210> SEQ ID NO 4
<211> LENGTH: 401
<212> TYPE: PRT
<213> ORGANISM: Humicola insolens

<400> SEQUENCE: 4

Lys Pro Gly Glu Thr Lys Glu Val His Pro Gln Leu Thr Thr Phe Arg
1               5                   10                  15

Cys Thr Lys Arg Gly Gly Cys Lys Pro Ala Thr Asn Phe Ile Val Leu
            20                  25                  30

Asp Ser Leu Trp His Trp Ile His Arg Ala Glu Gly Leu Gly Pro Gly
        35                  40                  45

Gly Cys Gly Asp Trp Gly Asn Pro Pro Lys Asp Val Cys Pro Asp
    50                  55                  60

Val Glu Ser Cys Ala Lys Asn Cys Ile Met Glu Gly Ile Pro Asp Tyr
65                  70                  75                  80

Ser Gln Tyr Gly Val Thr Thr Asn Gly Thr Ser Leu Arg Leu Gln His
                85                  90                  95

Ile Leu Pro Asp Gly Arg Val Pro Ser Pro Arg Val Tyr Leu Leu Asp
            100                 105                 110

Lys Thr Lys Arg Arg Tyr Glu Met Leu His Leu Thr Gly Phe Glu Phe
        115                 120                 125

Thr Phe Asp Val Asp Ala Thr Lys Leu Pro Cys Gly Met Asn Ser Ala
    130                 135                 140

Leu Tyr Leu Ser Glu Met His Pro Thr Gly Ala Lys Ser Lys Tyr Asn
145                 150                 155                 160

Pro Gly Gly Ala Tyr Tyr Gly Thr Gly Tyr Cys Asp Ala Gln Cys Phe
                165                 170                 175

Val Thr Pro Phe Ile Asn Gly Leu Gly Asn Ile Glu Gly Lys Gly Ser
            180                 185                 190

Cys Cys Asn Glu Met Asp Ile Trp Glu Ala Asn Ser Arg Ala Ser His
        195                 200                 205

Val Ala Pro His Thr Cys Asn Lys Lys Gly Leu Tyr Leu Cys Glu Gly
    210                 215                 220

Glu Glu Cys Ala Phe Glu Gly Val Cys Asp Lys Asn Gly Cys Gly Trp
225                 230                 235                 240

Asn Asn Tyr Arg Val Asn Val Thr Asp Tyr Tyr Gly Arg Gly Glu Glu
                245                 250                 255

Phe Lys Val Asn Thr Leu Lys Pro Phe Thr Val Val Thr Gln Phe Leu
            260                 265                 270

Ala Asn Arg Arg Gly Lys Leu Glu Lys Ile His Arg Phe Tyr Val Gln
        275                 280                 285

Asp Gly Lys Val Ile Glu Ser Phe Tyr Thr Asn Lys Glu Gly Val Pro
    290                 295                 300
```

```
Tyr Thr Asn Met Ile Asp Asp Glu Phe Cys Glu Ala Thr Gly Ser Arg
305                 310                 315                 320

Lys Tyr Met Glu Leu Gly Ala Thr Gln Gly Met Gly Glu Ala Leu Thr
                325                 330                 335

Arg Gly Met Val Leu Ala Met Ser Ile Trp Trp Asp Gln Gly Gly Asn
            340                 345                 350

Met Glu Trp Leu Asp His Gly Glu Ala Gly Pro Cys Ala Lys Gly Glu
        355                 360                 365

Gly Ala Pro Ser Asn Ile Val Gln Val Glu Pro Phe Pro Glu Val Thr
    370                 375                 380

Tyr Thr Asn Leu Arg Trp Gly Glu Ile Gly Ser Thr Tyr Gln Glu Leu
385                 390                 395                 400

Gln

<210> SEQ ID NO 5
<211> LENGTH: 370
<212> TYPE: PRT
<213> ORGANISM: Hypocrea jecorina

<400> SEQUENCE: 5

Gln Pro Gly Thr Ser Thr Pro Glu Val His Pro Lys Leu Thr Thr Tyr
1               5                   10                  15

Lys Cys Thr Lys Ser Gly Gly Cys Val Ala Gln Asp Thr Ser Val Val
                20                  25                  30

Leu Asp Trp Asn Tyr Arg Trp Met His Asp Ala Asn Tyr Asn Ser Cys
            35                  40                  45

Thr Val Asn Gly Gly Val Asn Thr Thr Leu Cys Pro Asp Glu Ala Thr
    50                  55                  60

Cys Gly Lys Asn Cys Phe Ile Glu Gly Val Asp Tyr Ala Ala Ser Gly
65                  70                  75                  80

Val Thr Thr Ser Gly Ser Ser Leu Thr Met Asn Gln Tyr Met Pro Ser
                85                  90                  95

Ser Ser Gly Gly Tyr Ser Ser Val Ser Pro Arg Leu Tyr Leu Leu Asp
            100                 105                 110

Ser Asp Gly Glu Tyr Val Met Leu Lys Leu Asn Gly Gln Glu Leu Ser
        115                 120                 125

Phe Asp Val Asp Leu Ser Ala Leu Pro Cys Gly Glu Asn Gly Ser Leu
    130                 135                 140

Tyr Leu Ser Gln Met Asp Glu Asn Gly Gly Ala Asn Gln Tyr Asn Thr
145                 150                 155                 160

Ala Gly Ala Asn Tyr Gly Gly Gly Tyr Cys Asp Ala Gln Cys Pro Val
                165                 170                 175

Gln Thr Trp Arg Asn Gly Thr Leu Asn Thr Ser His Gln Gly Phe Cys
            180                 185                 190

Cys Asn Glu Met Asp Ile Leu Glu Gly Asn Ser Arg Ala Asn Ala Leu
        195                 200                 205

Thr Pro His Ser Cys Thr Ala Thr Ala Cys Asp Ser Ala Gly Cys Gly
    210                 215                 220

Phe Asn Pro Tyr Gly Ser Gly Tyr Lys Ser Tyr Tyr Gly Pro Gly Asp
225                 230                 235                 240

Thr Val Asp Thr Ser Lys Thr Phe Thr Ile Thr Gln Phe Asn Thr
                245                 250                 255

Asp Asn Gly Ser Pro Ser Gly Asn Leu Val Ser Ile Thr Arg Lys Tyr
            260                 265                 270

Gln Gln Asn Gly Val Asp Ile Pro Ser Ala Gln Pro Gly Gly Asp Thr
```

```
                275                 280                 285
Ile Ser Ser Cys Pro Ser Ala Ser Ala Tyr Gly Gly Leu Ala Thr Met
290                 295                 300

Gly Lys Ala Leu Ser Ser Gly Met Val Leu Val Phe Ser Ile Trp Asn
305                 310                 315                 320

Asp Asn Ser Gln Tyr Met Asn Trp Leu Asp Ser Gly Asn Ala Gly Pro
                325                 330                 335

Cys Ser Ser Thr Glu Gly Asn Pro Ser Asn Ile Leu Ala Asn Asn Pro
                340                 345                 350

Asn Thr His Val Val Phe Ser Asn Ile Arg Trp Gly Asp Ile Gly Ser
                355                 360                 365

Thr Thr
370

<210> SEQ ID NO 6
<211> LENGTH: 356
<212> TYPE: PRT
<213> ORGANISM: Artificial
<220> FEATURE:
<223> OTHER INFORMATION: consensus sequence

<400> SEQUENCE: 6

Thr Pro Gly Thr Thr Lys Glu Val His Pro Lys Leu Thr Thr Tyr Arg
1               5                   10                  15

Cys Thr Lys Ala Gly Gly Cys Lys Gln Thr Asn Ser Ile Thr Leu Asp
                20                  25                  30

Ala Asn Trp Trp Ile His Asn Cys Gly Cys Gly Asp Trp Gly Gln Pro
                35                  40                  45

Asn Ser Thr Leu Cys Pro Asp Glu Ser Cys Ala Lys Asn Cys Ile Leu
50                  55                  60

Glu Gly Asn Ala Tyr Ala Asn Tyr Gly Val Thr Thr Ser Gly Asn Ser
65                  70                  75                  80

Leu Arg Leu Gln Gln Leu Ile Pro Ser Asn Arg Leu Val Ser Pro Arg
                85                  90                  95

Val Tyr Leu Leu Asp Thr Lys Lys Lys Tyr Glu Asn Leu His Leu Thr
                100                 105                 110

Gly Asn Glu Phe Ser Phe Asp Val Asp Met Ser Lys Leu Pro Cys Gly
                115                 120                 125

Met Asn Gly Ala Leu Tyr Leu Ser Glu Met Asp Asp Gly Gly Lys Ser
130                 135                 140

Arg Tyr Asn Thr Ala Gly Ala Tyr Tyr Gly Thr Gly Tyr Cys Asp Ala
145                 150                 155                 160

Gln Cys Pro Val Thr Pro Phe Ile Asn Gly Val Gly Asn Ile Glu Gly
                165                 170                 175

Gln Gly Ser Cys Cys Asn Glu Met Asp Ile Trp Glu Ala Asn Ser Arg
                180                 185                 190

Ala Thr Leu Pro His Pro Cys Thr Lys Gly Leu Tyr Leu Cys Glu Gly
                195                 200                 205

Asp Glu Cys Gly Phe Gly Ile Cys Asp Lys Ala Gly Cys Gly Trp Asn
                210                 215                 220

Pro Tyr Arg Ile Val Thr Phe Tyr Gly Gly Phe Val Asp Thr Thr Lys
225                 230                 235                 240

Lys Phe Thr Val Val Thr Gln Phe Val Asn Lys Gly Leu Ile Ile His
                245                 250                 255

Arg Phe Tyr Val Gln Gly Val Ile Glu Ser Ala Asn Asn Gly Pro Gly
                260                 265                 270
```

```
Asn Ile Asn Asp Glu Tyr Cys Ala Thr Gly Ala Ser Tyr Glu Leu Gly
        275                 280                 285

Gly Glu Glu Gln Met Gly Lys Ala Leu Ser Arg Gly Met Val Leu Met
    290                 295                 300

Ser Ile Trp Trp Asp Gln Gly Gly Asn Met Trp Leu Asp Ser Gly Val
305                 310                 315                 320

Ala Gly Pro Cys Ser Thr Thr Glu Gly Pro Ser Asn Ile Val Val Gln
                325                 330                 335

Pro Asn Pro Glu Val Thr Phe Ser Asn Ile Arg Trp Gly Glu Ile Gly
            340                 345                 350

Ser Thr Ser Gln
        355

<210> SEQ ID NO 7
<211> LENGTH: 1491
<212> TYPE: DNA
<213> ORGANISM: Hypocrea jecorina
<220> FEATURE:
<221> NAME/KEY: CDS
<222> LOCATION: (1)..(1491)

<400> SEQUENCE: 7 cag tcg gcc tgc act ctc caa tcg gag act cac ccg cct ctg aca tgg      48
Gln Ser Ala Cys Thr Leu Gln Ser Glu Thr His Pro Pro Leu Thr Trp
1               5                   10                  15 cag aaa tgc tcg tct ggt ggc act tgc act caa cag aca ggc tcc gtg      96
Gln Lys Cys Ser Ser Gly Gly Thr Cys Thr Gln Gln Thr Gly Ser Val
            20                  25                  30 gtc atc gac gcc aac tgg cgc tgg act cac gct acg aac agc agc acg     144
Val Ile Asp Ala Asn Trp Arg Trp Thr His Ala Thr Asn Ser Ser Thr
        35                  40                  45 aac tgc tac gat ggc aac act tgg agc tcg acc cta tgt cct gac aac     192
Asn Cys Tyr Asp Gly Asn Thr Trp Ser Ser Thr Leu Cys Pro Asp Asn
    50                  55                  60 gag acc tgc gcg aag aac tgc tgt ctg gac ggt gcc gcc tac gcg tcc     240
Glu Thr Cys Ala Lys Asn Cys Cys Leu Asp Gly Ala Ala Tyr Ala Ser
65                  70                  75                  80 acg tac gga gtt acc acg agc ggt aac agc ctc tcc att ggc ttt gtc     288
Thr Tyr Gly Val Thr Thr Ser Gly Asn Ser Leu Ser Ile Gly Phe Val
                85                  90                  95 acc cag tct gcg cag aag aac gtt ggc gct cgc ctt tac ctt atg gcg     336
Thr Gln Ser Ala Gln Lys Asn Val Gly Ala Arg Leu Tyr Leu Met Ala
            100                 105                 110 agc gac acg acc tac cag gaa ttc acc ctg ctt ggc aac gag ttc tct     384
Ser Asp Thr Thr Tyr Gln Glu Phe Thr Leu Leu Gly Asn Glu Phe Ser
        115                 120                 125 ttc gat gtt gat gtt tcg cag ctg ccg tgc ggc ttg aac gga gct ctc     432
Phe Asp Val Asp Val Ser Gln Leu Pro Cys Gly Leu Asn Gly Ala Leu
    130                 135                 140 tac ttc gtg tcc atg gac gcg gat ggt ggc gtg agc aag tat ccc acc     480
Tyr Phe Val Ser Met Asp Ala Asp Gly Gly Val Ser Lys Tyr Pro Thr
145                 150                 155                 160 aac acc gct ggc gcc aag tac ggc acg ggg tac tgt gac agc cag tgt     528
Asn Thr Ala Gly Ala Lys Tyr Gly Thr Gly Tyr Cys Asp Ser Gln Cys
                165                 170                 175 ccc cgc gat ctg aag ttc atc aat ggc cag gcc aac gtt gag ggc tgg     576
Pro Arg Asp Leu Lys Phe Ile Asn Gly Gln Ala Asn Val Glu Gly Trp
            180                 185                 190 gag ccg tca tcc aac aac gcg aac acg ggc att gga gga cac gga agc     624
Glu Pro Ser Ser Asn Asn Ala Asn Thr Gly Ile Gly Gly His Gly Ser
```

```
                195                 200                 205
tgc tgc tct gag atg gat atc tgg gag gcc aac tcc atc tcc gag gct       672
Cys Cys Ser Glu Met Asp Ile Trp Glu Ala Asn Ser Ile Ser Glu Ala
210                 215                 220 ttt acc ccc cac cct tgc acg act gtc ggc cag gag atc tgc gag ggt       720
Phe Thr Pro His Pro Cys Thr Thr Val Gly Gln Glu Ile Cys Glu Gly
225                 230                 235                 240 gat ggg tgc ggc gga act tac tcc gat aac aga tat ggc ggc act tgc       768
Asp Gly Cys Gly Gly Thr Tyr Ser Asp Asn Arg Tyr Gly Gly Thr Cys
                245                 250                 255 gat ccc gat ggc tgc gac tgg aac cca tac cgc ctg ggc aac acc agc       816
Asp Pro Asp Gly Cys Asp Trp Asn Pro Tyr Arg Leu Gly Asn Thr Ser
            260                 265                 270 ttc tac ggc cct ggc tca agc ttt acc ctc gat acc acc aag aaa ttg       864
Phe Tyr Gly Pro Gly Ser Ser Phe Thr Leu Asp Thr Thr Lys Lys Leu
        275                 280                 285 acc gtt gtc acc cag ttc gag acg tcg ggt gcc atc aac cga tac tat       912
Thr Val Val Thr Gln Phe Glu Thr Ser Gly Ala Ile Asn Arg Tyr Tyr
    290                 295                 300 gtc cag aat ggc gtc act ttc cag cag ccc aac gcc gag ctt ggt agt       960
Val Gln Asn Gly Val Thr Phe Gln Gln Pro Asn Ala Glu Leu Gly Ser
305                 310                 315                 320 tac tct ggc aac gag ctc aac gat gat tac tgc aca gct gag gag gca      1008
Tyr Ser Gly Asn Glu Leu Asn Asp Asp Tyr Cys Thr Ala Glu Glu Ala
                325                 330                 335 gaa ttc ggc gga tcc tct ttc tca gac aag ggc ggc ctg act cag ttc      1056
Glu Phe Gly Gly Ser Ser Phe Ser Asp Lys Gly Gly Leu Thr Gln Phe
            340                 345                 350 aag aag gct acc tct ggc ggc atg gtt ctg gtc atg agt ctg tgg gat      1104
Lys Lys Ala Thr Ser Gly Gly Met Val Leu Val Met Ser Leu Trp Asp
        355                 360                 365 gat tac tac gcc aac atg ctg tgg ctg gac tcc acc tac ccg aca aac      1152
Asp Tyr Tyr Ala Asn Met Leu Trp Leu Asp Ser Thr Tyr Pro Thr Asn
    370                 375                 380 gag acc tcc tcc aca ccc ggt gcc gtg cgc gga agc tgc tcc acc agc      1200
Glu Thr Ser Ser Thr Pro Gly Ala Val Arg Gly Ser Cys Ser Thr Ser
385                 390                 395                 400 tcc ggt gtc cct gct cag gtc gaa tct cag tct ccc aac gcc aag gtc      1248
Ser Gly Val Pro Ala Gln Val Glu Ser Gln Ser Pro Asn Ala Lys Val
                405                 410                 415 acc ttc tcc aac atc aag ttc gga ccc att ggc agc acc ggc aac cct      1296
Thr Phe Ser Asn Ile Lys Phe Gly Pro Ile Gly Ser Thr Gly Asn Pro
            420                 425                 430 agc ggc ggc aac cct ccc ggc gga aac ccg cct ggc acc acc acc acc      1344
Ser Gly Gly Asn Pro Pro Gly Gly Asn Pro Pro Gly Thr Thr Thr Thr
        435                 440                 445 cgc cgc cca gcc act acc act gga agc tct ccc gga cct acc cag tct      1392
Arg Arg Pro Ala Thr Thr Thr Gly Ser Ser Pro Gly Pro Thr Gln Ser
    450                 455                 460 cac tac ggc cag tgc ggc ggt att ggc tac agc ggc ccc acg gtc tgc      1440
His Tyr Gly Gln Cys Gly Gly Ile Gly Tyr Ser Gly Pro Thr Val Cys
465                 470                 475                 480 gcc agc ggc aca act tgc cag gtc ctg aac cct tac tac tct cag tgc      1488
Ala Ser Gly Thr Thr Cys Gln Val Leu Asn Pro Tyr Tyr Ser Gln Cys
                485                 490                 495 ctg                                                                  1491
Leu

<210> SEQ ID NO 8
<211> LENGTH: 497
```

```
<212> TYPE: PRT
<213> ORGANISM: Hypocrea jecorina

<400> SEQUENCE: 8

Gln Ser Ala Cys Thr Leu Gln Ser Glu Thr His Pro Pro Leu Thr Trp
1               5                   10                  15

Gln Lys Cys Ser Ser Gly Gly Thr Cys Thr Gln Gln Thr Gly Ser Val
            20                  25                  30

Val Ile Asp Ala Asn Trp Arg Trp Thr His Ala Thr Asn Ser Ser Thr
        35                  40                  45

Asn Cys Tyr Asp Gly Asn Thr Trp Ser Ser Thr Leu Cys Pro Asp Asn
    50                  55                  60

Glu Thr Cys Ala Lys Asn Cys Cys Leu Asp Gly Ala Ala Tyr Ala Ser
65                  70                  75                  80

Thr Tyr Gly Val Thr Thr Ser Gly Asn Ser Leu Ser Ile Gly Phe Val
                85                  90                  95

Thr Gln Ser Ala Gln Lys Asn Val Gly Ala Arg Leu Tyr Leu Met Ala
            100                 105                 110

Ser Asp Thr Thr Tyr Gln Glu Phe Thr Leu Leu Gly Asn Glu Phe Ser
        115                 120                 125

Phe Asp Val Asp Val Ser Gln Leu Pro Cys Gly Leu Asn Gly Ala Leu
    130                 135                 140

Tyr Phe Val Ser Met Asp Ala Asp Gly Gly Val Ser Lys Tyr Pro Thr
145                 150                 155                 160

Asn Thr Ala Gly Ala Lys Tyr Gly Thr Gly Tyr Cys Asp Ser Gln Cys
                165                 170                 175

Pro Arg Asp Leu Lys Phe Ile Asn Gly Gln Ala Asn Val Glu Gly Trp
            180                 185                 190

Glu Pro Ser Ser Asn Asn Ala Asn Thr Gly Ile Gly Gly His Gly Ser
        195                 200                 205

Cys Cys Ser Glu Met Asp Ile Trp Glu Ala Asn Ser Ile Ser Glu Ala
    210                 215                 220

Phe Thr Pro His Pro Cys Thr Thr Val Gly Gln Glu Ile Cys Glu Gly
225                 230                 235                 240

Asp Gly Cys Gly Gly Thr Tyr Ser Asp Asn Arg Tyr Gly Gly Thr Cys
                245                 250                 255

Asp Pro Asp Gly Cys Asp Trp Asn Pro Tyr Arg Leu Gly Asn Thr Ser
            260                 265                 270

Phe Tyr Gly Pro Gly Ser Ser Phe Thr Leu Asp Thr Thr Lys Lys Leu
        275                 280                 285

Thr Val Val Thr Gln Phe Glu Thr Ser Gly Ala Ile Asn Arg Tyr Tyr
290                 295                 300

Val Gln Asn Gly Val Thr Phe Gln Gln Pro Asn Ala Glu Leu Gly Ser
305                 310                 315                 320

Tyr Ser Gly Asn Glu Leu Asn Asp Asp Tyr Cys Thr Ala Glu Glu Ala
                325                 330                 335

Glu Phe Gly Gly Ser Ser Phe Ser Asp Lys Gly Gly Leu Thr Gln Phe
            340                 345                 350

Lys Lys Ala Thr Ser Gly Gly Met Val Leu Val Met Ser Leu Trp Asp
        355                 360                 365

Asp Tyr Tyr Ala Asn Met Leu Trp Leu Asp Ser Thr Tyr Pro Thr Asn
370                 375                 380

Glu Thr Ser Ser Thr Pro Gly Ala Val Arg Gly Ser Cys Ser Thr Ser
385                 390                 395                 400
```

```
Ser Gly Val Pro Ala Gln Val Glu Ser Gln Ser Pro Asn Ala Lys Val
            405                 410                 415

Thr Phe Ser Asn Ile Lys Phe Gly Pro Ile Gly Ser Thr Gly Asn Pro
        420                 425                 430

Ser Gly Gly Asn Pro Pro Gly Gly Asn Pro Pro Gly Thr Thr Thr Thr
    435                 440                 445

Arg Arg Pro Ala Thr Thr Thr Gly Ser Ser Pro Gly Pro Thr Gln Ser
450                 455                 460

His Tyr Gly Gln Cys Gly Gly Ile Gly Tyr Ser Gly Pro Thr Val Cys
465                 470                 475                 480

Ala Ser Gly Thr Thr Cys Gln Val Leu Asn Pro Tyr Tyr Ser Gln Cys
            485                 490                 495

Leu

<210> SEQ ID NO 9
<211> LENGTH: 1491
<212> TYPE: DNA
<213> ORGANISM: Hypocrea jecorina
<220> FEATURE:
<221> NAME/KEY: CDS
<222> LOCATION: (1)..(1491)

<400> SEQUENCE: 9 cag tcg gcc tgc act ctc caa tcg gag act cac ccg cct ctg aca tgg     48
Gln Ser Ala Cys Thr Leu Gln Ser Glu Thr His Pro Pro Leu Thr Trp
1               5                   10                  15 cag aaa tgc tcg tct ggt ggc act tgc act caa cag aca ggc tcc gtg     96
Gln Lys Cys Ser Ser Gly Gly Thr Cys Thr Gln Gln Thr Gly Ser Val
            20                  25                  30 gtc atc gac gcc aac tgg cgc tgg act cac gct acg aac agc agc acg    144
Val Ile Asp Ala Asn Trp Arg Trp Thr His Ala Thr Asn Ser Ser Thr
        35                  40                  45 aac tgc tac gat ggc aac act tgg agc tcg acc cta tgt cct gac aac    192
Asn Cys Tyr Asp Gly Asn Thr Trp Ser Ser Thr Leu Cys Pro Asp Asn
    50                  55                  60 gag acc tgc gcg aag aac tgc tgt ctg gac ggt gcc gcc tac gcg tcc    240
Glu Thr Cys Ala Lys Asn Cys Cys Leu Asp Gly Ala Ala Tyr Ala Ser
65                  70                  75                  80 acg tac gga gtt acc acg agc ggt aac agc ctc tcc att ggc ttt gtc    288
Thr Tyr Gly Val Thr Thr Ser Gly Asn Ser Leu Ser Ile Gly Phe Val
                85                  90                  95 acc cag tct gcg cag aag aac gtt ggc gct cgc ctt tac ctt atg gcg    336
Thr Gln Ser Ala Gln Lys Asn Val Gly Ala Arg Leu Tyr Leu Met Ala
            100                 105                 110 gac gac acg acc tac cag gaa ttc acc ctg ctt ggc aac gag ttc tct    384
Asp Asp Thr Thr Tyr Gln Glu Phe Thr Leu Leu Gly Asn Glu Phe Ser
        115                 120                 125 ttc gat gtt gat gtt tcg cag ctg ccg tgc ggc ttg aac gga gct ctc    432
Phe Asp Val Asp Val Ser Gln Leu Pro Cys Gly Leu Asn Gly Ala Leu
    130                 135                 140 tac ttc gtg tcc atg gac gcg gat ggt ggc gtg agc aag tat ccc acc    480
Tyr Phe Val Ser Met Asp Ala Asp Gly Gly Val Ser Lys Tyr Pro Thr
145                 150                 155                 160 aac acc gct ggc gcc aag tac ggc acg ggg tac tgt gac agc cag tgt    528
Asn Thr Ala Gly Ala Lys Tyr Gly Thr Gly Tyr Cys Asp Ser Gln Cys
                165                 170                 175 ccc cgc gat ctg aag ttc atc aat ggc cag gcc aac gtt gag ggc tgg    576
Pro Arg Asp Leu Lys Phe Ile Asn Gly Gln Ala Asn Val Glu Gly Trp
            180                 185                 190 gag ccg tca tcc aac aac gcg aac acg ggc att gga gga cac gga agc    624
```

```
Glu Pro Ser Ser Asn Asn Ala Asn Thr Gly Ile Gly Gly His Gly Ser
        195                 200                 205 tgc tgc tct gag atg gat atc tgg gag gcc aac tcc atc tcc gag gct       672
Cys Cys Ser Glu Met Asp Ile Trp Glu Ala Asn Ser Ile Ser Glu Ala
    210                 215                 220 ctt acc ccc cac cct tgc acg act gtc ggc cag gag atc tgc gag ggt       720
Leu Thr Pro His Pro Cys Thr Thr Val Gly Gln Glu Ile Cys Glu Gly
225                 230                 235                 240 gat ggg tgc ggc gga act tac tcc gat aac aga tat ggc ggc act tgc       768
Asp Gly Cys Gly Gly Thr Tyr Ser Asp Asn Arg Tyr Gly Gly Thr Cys
                245                 250                 255 gat ccc gat ggc tgc gac tgg aac cca tac cgc ctg ggc aac acc agc       816
Asp Pro Asp Gly Cys Asp Trp Asn Pro Tyr Arg Leu Gly Asn Thr Ser
            260                 265                 270 ttc tac ggc cct ggc tca agc ttt acc ctc gat acc acc aag aaa ttg       864
Phe Tyr Gly Pro Gly Ser Ser Phe Thr Leu Asp Thr Thr Lys Lys Leu
        275                 280                 285 acc gtt gtc acc cag ttc gag acg tcg ggt gcc atc aac cga tac tat       912
Thr Val Val Thr Gln Phe Glu Thr Ser Gly Ala Ile Asn Arg Tyr Tyr
    290                 295                 300 gtc cag aat ggc gtc act ttc cag cag ccc aac gcc gag ctt ggt agt       960
Val Gln Asn Gly Val Thr Phe Gln Gln Pro Asn Ala Glu Leu Gly Ser
305                 310                 315                 320 tac tct ggc aac gag ctc aac gat gat tac tgc aca gct gag gag gca      1008
Tyr Ser Gly Asn Glu Leu Asn Asp Asp Tyr Cys Thr Ala Glu Glu Ala
                325                 330                 335 gaa ttc ggc gga tcc tct ttc tca gac aag ggc ggc ctg act cag ttc      1056
Glu Phe Gly Gly Ser Ser Phe Ser Asp Lys Gly Gly Leu Thr Gln Phe
            340                 345                 350 aag aag gct acc tct ggc ggc atg gtt ctg gtc atg agt ctg tgg gat      1104
Lys Lys Ala Thr Ser Gly Gly Met Val Leu Val Met Ser Leu Trp Asp
        355                 360                 365 gat tac tac gcc aac atg ctg tgg ctg gac tcc acc tac ccg aca aac      1152
Asp Tyr Tyr Ala Asn Met Leu Trp Leu Asp Ser Thr Tyr Pro Thr Asn
    370                 375                 380 gag acc tcc tcc aca ccc ggt gcc gtg cgc gga agc tgc tcc acc agc      1200
Glu Thr Ser Ser Thr Pro Gly Ala Val Arg Gly Ser Cys Ser Thr Ser
385                 390                 395                 400 tcc ggt gtc cct gct cag gtc gaa tct cag tct ccc aac gcc aag gtc      1248
Ser Gly Val Pro Ala Gln Val Glu Ser Gln Ser Pro Asn Ala Lys Val
                405                 410                 415 acc ttc tcc aac atc aag ttc gga ccc att ggc agc acc ggc aac cct      1296
Thr Phe Ser Asn Ile Lys Phe Gly Pro Ile Gly Ser Thr Gly Asn Pro
            420                 425                 430 agc ggc ggc aac cct ccc ggc gga aac ccg cct ggc acc acc acc acc      1344
Ser Gly Gly Asn Pro Pro Gly Gly Asn Pro Pro Gly Thr Thr Thr Thr
        435                 440                 445 cgc cgc cca gcc act acc act gga agc tct ccc gga cct acc cag tct      1392
Arg Arg Pro Ala Thr Thr Thr Gly Ser Ser Pro Gly Pro Thr Gln Ser
450                 455                 460 cac tac ggc cag tgc ggc ggt att ggc tac agc ggc ccc acg gtc tgc      1440
His Tyr Gly Gln Cys Gly Gly Ile Gly Tyr Ser Gly Pro Thr Val Cys
465                 470                 475                 480 gcc agc ggc aca act tgc cag gtc ctg aac cct tac tac tct cag tgc      1488
Ala Ser Gly Thr Thr Cys Gln Val Leu Asn Pro Tyr Tyr Ser Gln Cys
                485                 490                 495 ctg                                                                  1491
Leu

<210> SEQ ID NO 10
```

<211> LENGTH: 497
<212> TYPE: PRT
<213> ORGANISM: Hypocrea jecorina

<400> SEQUENCE: 10

```
Gln Ser Ala Cys Thr Leu Gln Ser Glu Thr His Pro Pro Leu Thr Trp
1               5                   10                  15

Gln Lys Cys Ser Ser Gly Gly Thr Cys Thr Gln Gln Thr Gly Ser Val
            20                  25                  30

Val Ile Asp Ala Asn Trp Arg Trp Thr His Ala Thr Asn Ser Ser Thr
        35                  40                  45

Asn Cys Tyr Asp Gly Asn Thr Trp Ser Ser Thr Leu Cys Pro Asp Asn
50                  55                  60

Glu Thr Cys Ala Lys Asn Cys Cys Leu Asp Gly Ala Ala Tyr Ala Ser
65                  70                  75                  80

Thr Tyr Gly Val Thr Thr Ser Gly Asn Ser Leu Ser Ile Gly Phe Val
                85                  90                  95

Thr Gln Ser Ala Gln Lys Asn Val Gly Ala Arg Leu Tyr Leu Met Ala
            100                 105                 110

Asp Asp Thr Thr Tyr Gln Glu Phe Thr Leu Leu Gly Asn Glu Phe Ser
        115                 120                 125

Phe Asp Val Asp Val Ser Gln Leu Pro Cys Gly Leu Asn Gly Ala Leu
130                 135                 140

Tyr Phe Val Ser Met Asp Ala Asp Gly Gly Val Ser Lys Tyr Pro Thr
145                 150                 155                 160

Asn Thr Ala Gly Ala Lys Tyr Gly Thr Gly Tyr Cys Asp Ser Gln Cys
                165                 170                 175

Pro Arg Asp Leu Lys Phe Ile Asn Gly Gln Ala Asn Val Glu Gly Trp
            180                 185                 190

Glu Pro Ser Ser Asn Asn Ala Asn Thr Gly Ile Gly Gly His Gly Ser
        195                 200                 205

Cys Cys Ser Glu Met Asp Ile Trp Glu Ala Asn Ser Ile Ser Glu Ala
210                 215                 220

Leu Thr Pro His Pro Cys Thr Thr Val Gly Gln Glu Ile Cys Glu Gly
225                 230                 235                 240

Asp Gly Cys Gly Gly Thr Tyr Ser Asp Asn Arg Tyr Gly Gly Thr Cys
                245                 250                 255

Asp Pro Asp Gly Cys Asp Trp Asn Pro Tyr Arg Leu Gly Asn Thr Ser
            260                 265                 270

Phe Tyr Gly Pro Gly Ser Ser Phe Thr Leu Asp Thr Thr Lys Lys Leu
        275                 280                 285

Thr Val Val Thr Gln Phe Glu Thr Ser Gly Ala Ile Asn Arg Tyr Tyr
290                 295                 300

Val Gln Asn Gly Val Thr Phe Gln Gln Pro Asn Ala Glu Leu Gly Ser
305                 310                 315                 320

Tyr Ser Gly Asn Glu Leu Asn Asp Asp Tyr Cys Thr Ala Glu Glu Ala
                325                 330                 335

Glu Phe Gly Gly Ser Ser Phe Ser Asp Lys Gly Gly Leu Thr Gln Phe
            340                 345                 350

Lys Lys Ala Thr Ser Gly Gly Met Val Leu Val Met Ser Leu Trp Asp
        355                 360                 365

Asp Tyr Tyr Ala Asn Met Leu Trp Leu Asp Ser Thr Tyr Pro Thr Asn
370                 375                 380

Glu Thr Ser Ser Thr Pro Gly Ala Val Arg Gly Ser Cys Ser Thr Ser
385                 390                 395                 400
```

```
Ser Gly Val Pro Ala Gln Val Glu Ser Gln Ser Pro Asn Ala Lys Val
            405                 410                 415

Thr Phe Ser Asn Ile Lys Phe Gly Pro Ile Gly Ser Thr Gly Asn Pro
            420                 425                 430

Ser Gly Gly Asn Pro Pro Gly Gly Asn Pro Pro Gly Thr Thr Thr
            435                 440                 445

Arg Arg Pro Ala Thr Thr Thr Gly Ser Ser Pro Gly Pro Thr Gln Ser
450                 455                 460

His Tyr Gly Gln Cys Gly Gly Ile Gly Tyr Ser Gly Pro Thr Val Cys
465                 470                 475                 480

Ala Ser Gly Thr Thr Cys Gln Val Leu Asn Pro Tyr Tyr Ser Gln Cys
            485                 490                 495

Leu

<210> SEQ ID NO 11
<211> LENGTH: 1491
<212> TYPE: DNA
<213> ORGANISM: Hypocrea jecorina
<220> FEATURE:
<221> NAME/KEY: CDS
<222> LOCATION: (1)..(1491)

<400> SEQUENCE: 11 cag tcg gcc tgc act ctc caa tcg gag act cac ccg cct ctg aca tgg      48
Gln Ser Ala Cys Thr Leu Gln Ser Glu Thr His Pro Pro Leu Thr Trp
1               5                  10                  15 cag aaa tgc tcg tct ggt ggc act tgc act caa cag aca ggc tcc gtg     96
Gln Lys Cys Ser Ser Gly Gly Thr Cys Thr Gln Gln Thr Gly Ser Val
            20                  25                  30 gtc atc gac gcc aac tgg cgc tgg act cac gct acg aac agc agc acg    144
Val Ile Asp Ala Asn Trp Arg Trp Thr His Ala Thr Asn Ser Ser Thr
        35                  40                  45 aac tgc tac gat ggc aac act tgg agc tcg acc cta tgt cct gac aac    192
Asn Cys Tyr Asp Gly Asn Thr Trp Ser Ser Thr Leu Cys Pro Asp Asn
    50                  55                  60 gag acc tgc gcg aag aac tgc tgt ctg gac ggt gcc gac tac gcg tcc    240
Glu Thr Cys Ala Lys Asn Cys Cys Leu Asp Gly Ala Asp Tyr Ala Ser
65                  70                  75                  80 acg tac gga gtt acc acg agc ggt aac agc ctc tcc att ggc ttt gtc    288
Thr Tyr Gly Val Thr Thr Ser Gly Asn Ser Leu Ser Ile Gly Phe Val
                85                  90                  95 acc cag tct gcg cag aag aac gtt ggc gct cgc ctt tac ctt atg gcg    336
Thr Gln Ser Ala Gln Lys Asn Val Gly Ala Arg Leu Tyr Leu Met Ala
            100                 105                 110 agc gac acg acc tac cag gaa ttc acc ctg ctt ggc aac gag ttc tct    384
Ser Asp Thr Thr Tyr Gln Glu Phe Thr Leu Leu Gly Asn Glu Phe Ser
        115                 120                 125 ttc gat gtt gat gtt tcg cag ctg ccg tgc ggc ttg aac gga gct ctc    432
Phe Asp Val Asp Val Ser Gln Leu Pro Cys Gly Leu Asn Gly Ala Leu
    130                 135                 140 tac ttc gtg tcc atg gac gcg gat ggt ggc gtg agc aag tat ccc acc    480
Tyr Phe Val Ser Met Asp Ala Asp Gly Gly Val Ser Lys Tyr Pro Thr
145                 150                 155                 160 aac acc gct ggc gcc aag tac ggc acg ggg tac tgt gac agc cag tgt    528
Asn Thr Ala Gly Ala Lys Tyr Gly Thr Gly Tyr Cys Asp Ser Gln Cys
                165                 170                 175 ccc cgc gat ctg aag ttc atc aat ggc cag gcc aac gtt gag ggc tgg    576
Pro Arg Asp Leu Lys Phe Ile Asn Gly Gln Ala Asn Val Glu Gly Trp
            180                 185                 190
```

```
gag ccg tca tcc aac aac gcg aac acg ggc att gga gga cac gga agc       624
Glu Pro Ser Ser Asn Asn Ala Asn Thr Gly Ile Gly Gly His Gly Ser
        195                 200                 205 tgc tgc tct gag atg gat atc tgg gag gcc aac tcc atc tcc gag gct       672
Cys Cys Ser Glu Met Asp Ile Trp Glu Ala Asn Ser Ile Ser Glu Ala
210                 215                 220 ctt acc ccc cac cct tgc acg act gtc ggc cag gag atc tgc gag ggt       720
Leu Thr Pro His Pro Cys Thr Thr Val Gly Gln Glu Ile Cys Glu Gly
225                 230                 235                 240 gat ggg tgc ggc gga act tac tcc gat aac aga tat ggc ggc act tgc       768
Asp Gly Cys Gly Gly Thr Tyr Ser Asp Asn Arg Tyr Gly Gly Thr Cys
                245                 250                 255 gat ccc gat ggc tgc gac tgg aac cca tac cgc ctg ggc aac acc agc       816
Asp Pro Asp Gly Cys Asp Trp Asn Pro Tyr Arg Leu Gly Asn Thr Ser
            260                 265                 270 ttc tac ggc cct ggc tca agc ttt acc ctc gat acc acc aag aaa ttg       864
Phe Tyr Gly Pro Gly Ser Ser Phe Thr Leu Asp Thr Thr Lys Lys Leu
        275                 280                 285 acc gtt gtc acc cag ttc gag acg tcg ggt gcc atc aac cga tac tat       912
Thr Val Val Thr Gln Phe Glu Thr Ser Gly Ala Ile Asn Arg Tyr Tyr
    290                 295                 300 gtc cag aat ggc gtc act ttc cag cag ccc aac gcc gag ctt ggt agt       960
Val Gln Asn Gly Val Thr Phe Gln Gln Pro Asn Ala Glu Leu Gly Ser
305                 310                 315                 320 tac tct ggc aac gag ctc aac gat gat tac tgc aca gct gag gag gca      1008
Tyr Ser Gly Asn Glu Leu Asn Asp Asp Tyr Cys Thr Ala Glu Glu Ala
                325                 330                 335 gaa ttc ggc gga tcc tct ttc tca gac aag ggc ggc ctg act cag ttc      1056
Glu Phe Gly Gly Ser Ser Phe Ser Asp Lys Gly Gly Leu Thr Gln Phe
            340                 345                 350 aag aag gct acc tct ggc ggc atg gtt ctg gtc atg agt ctg tgg gat      1104
Lys Lys Ala Thr Ser Gly Gly Met Val Leu Val Met Ser Leu Trp Asp
        355                 360                 365 gat tac tac gcc aac atg ctg tgg ctg gac tcc acc tac ccg aca aac      1152
Asp Tyr Tyr Ala Asn Met Leu Trp Leu Asp Ser Thr Tyr Pro Thr Asn
370                 375                 380 gag acc tcc tcc aca ccc ggt gcc gtg cgc gga agc tgc tcc acc agc      1200
Glu Thr Ser Ser Thr Pro Gly Ala Val Arg Gly Ser Cys Ser Thr Ser
385                 390                 395                 400 tcc ggt gtc cct gct cag gtc gaa tct cag tct ccc aac gcc aag gtc      1248
Ser Gly Val Pro Ala Gln Val Glu Ser Gln Ser Pro Asn Ala Lys Val
                405                 410                 415 acc ttc tcc aac atc aag ttc gga ccc att ggc agc acc ggc aac cct      1296
Thr Phe Ser Asn Ile Lys Phe Gly Pro Ile Gly Ser Thr Gly Asn Pro
            420                 425                 430 agc ggc ggc aac cct ccc ggc gga aac ccg cct ggc acc acc acc acc      1344
Ser Gly Gly Asn Pro Pro Gly Gly Asn Pro Pro Gly Thr Thr Thr Thr
        435                 440                 445 cgc cgc cca gcc act acc act gga agc tct ccc gga cct acc cag tct      1392
Arg Arg Pro Ala Thr Thr Thr Gly Ser Ser Pro Gly Pro Thr Gln Ser
450                 455                 460 cac tac ggc cag tgc ggc ggt att gga tac agc ggc ccc acg gtc tgc      1440
His Tyr Gly Gln Cys Gly Gly Ile Gly Tyr Ser Gly Pro Thr Val Cys
465                 470                 475                 480 gcc agc ggc aca act tgc cag gtc ctg aac cct tac tac tct cag tgc      1488
Ala Ser Gly Thr Thr Cys Gln Val Leu Asn Pro Tyr Tyr Ser Gln Cys
                485                 490                 495 ctg                                                                   1491
Leu
```

```
<210> SEQ ID NO 12
<211> LENGTH: 497
<212> TYPE: PRT
<213> ORGANISM: Hypocrea jecorina

<400> SEQUENCE: 12

Gln Ser Ala Cys Thr Leu Gln Ser Glu Thr His Pro Pro Leu Thr Trp
 1               5                  10                  15

Gln Lys Cys Ser Ser Gly Gly Thr Cys Thr Gln Gln Thr Gly Ser Val
             20                  25                  30

Val Ile Asp Ala Asn Trp Arg Trp Thr His Ala Thr Asn Ser Ser Thr
         35                  40                  45

Asn Cys Tyr Asp Gly Asn Thr Trp Ser Ser Thr Leu Cys Pro Asp Asn
     50                  55                  60

Glu Thr Cys Ala Lys Asn Cys Cys Leu Asp Gly Ala Asp Tyr Ala Ser
 65                  70                  75                  80

Thr Tyr Gly Val Thr Thr Ser Gly Asn Ser Leu Ser Ile Gly Phe Val
                 85                  90                  95

Thr Gln Ser Ala Gln Lys Asn Val Gly Ala Arg Leu Tyr Leu Met Ala
            100                 105                 110

Ser Asp Thr Thr Tyr Gln Glu Phe Thr Leu Leu Gly Asn Glu Phe Ser
        115                 120                 125

Phe Asp Val Asp Val Ser Gln Leu Pro Cys Gly Leu Asn Gly Ala Leu
    130                 135                 140

Tyr Phe Val Ser Met Asp Ala Asp Gly Gly Val Ser Lys Tyr Pro Thr
145                 150                 155                 160

Asn Thr Ala Gly Ala Lys Tyr Gly Thr Gly Tyr Cys Asp Ser Gln Cys
                165                 170                 175

Pro Arg Asp Leu Lys Phe Ile Asn Gly Gln Ala Asn Val Glu Gly Trp
            180                 185                 190

Glu Pro Ser Ser Asn Asn Ala Asn Thr Gly Ile Gly Gly His Gly Ser
        195                 200                 205

Cys Cys Ser Glu Met Asp Ile Trp Glu Ala Asn Ser Ile Ser Glu Ala
    210                 215                 220

Leu Thr Pro His Pro Cys Thr Thr Val Gly Gln Glu Ile Cys Glu Gly
225                 230                 235                 240

Asp Gly Cys Gly Gly Thr Tyr Ser Asp Asn Arg Tyr Gly Gly Thr Cys
                245                 250                 255

Asp Pro Asp Gly Cys Asp Trp Asn Pro Tyr Arg Leu Gly Asn Thr Ser
            260                 265                 270

Phe Tyr Gly Pro Gly Ser Ser Phe Thr Leu Asp Thr Thr Lys Lys Leu
        275                 280                 285

Thr Val Val Thr Gln Phe Glu Thr Ser Gly Ala Ile Asn Arg Tyr Tyr
    290                 295                 300

Val Gln Asn Gly Val Thr Phe Gln Gln Pro Asn Ala Glu Leu Gly Ser
305                 310                 315                 320

Tyr Ser Gly Asn Glu Leu Asn Asp Asp Tyr Cys Thr Ala Glu Glu Ala
                325                 330                 335

Glu Phe Gly Gly Ser Ser Phe Ser Asp Lys Gly Gly Leu Thr Gln Phe
            340                 345                 350

Lys Lys Ala Thr Ser Gly Gly Met Val Leu Val Met Ser Leu Trp Asp
        355                 360                 365

Asp Tyr Tyr Ala Asn Met Leu Trp Leu Asp Ser Thr Tyr Pro Thr Asn
    370                 375                 380

Glu Thr Ser Ser Thr Pro Gly Ala Val Arg Gly Ser Cys Ser Thr Ser
```

```
                385                 390                 395                 400
        Ser Gly Val Pro Ala Gln Val Glu Ser Gln Ser Pro Asn Ala Lys Val
                        405                 410                 415

Thr Phe Ser Asn Ile Lys Phe Gly Pro Ile Gly Ser Thr Gly Asn Pro
                        420                 425                 430

Ser Gly Gly Asn Pro Pro Gly Gly Asn Pro Pro Gly Thr Thr Thr
                        435                 440                 445

Arg Arg Pro Ala Thr Thr Thr Gly Ser Ser Pro Gly Pro Thr Gln Ser
                        450                 455                 460

His Tyr Gly Gln Cys Gly Gly Ile Gly Tyr Ser Gly Pro Thr Val Cys
        465                 470                 475                 480

Ala Ser Gly Thr Thr Cys Gln Val Leu Asn Pro Tyr Tyr Ser Gln Cys
                        485                 490                 495

Leu

<210> SEQ ID NO 13
<211> LENGTH: 1491
<212> TYPE: DNA
<213> ORGANISM: Hypocrea jecorina
<220> FEATURE:
<221> NAME/KEY: CDS
<222> LOCATION: (1)..(1491)

<400> SEQUENCE: 13 cag tcg gcc tgc act ctc caa tcg gag act cac ccg cct ctg aca tgg        48
Gln Ser Ala Cys Thr Leu Gln Ser Glu Thr His Pro Pro Leu Thr Trp
1               5                   10                  15 cag aaa tgc tcg tct ggt ggc act tgc act caa cag aca ggc tcc gtg        96
Gln Lys Cys Ser Ser Gly Gly Thr Cys Thr Gln Gln Thr Gly Ser Val
            20                  25                  30 gtc atc gac gcc aac tgg cgc tgg act cac gct acg aac agc agc acg        144
Val Ile Asp Ala Asn Trp Arg Trp Thr His Ala Thr Asn Ser Ser Thr
        35                  40                  45 aac tgc tac gat ggc aac act tgg agc tcg acc cta tgt cct gac aac        192
Asn Cys Tyr Asp Gly Asn Thr Trp Ser Ser Thr Leu Cys Pro Asp Asn
    50                  55                  60 gag acc tgc gcg aag aac tgc tgt ctg gac ggt gcc gcc tac gcg tcc        240
Glu Thr Cys Ala Lys Asn Cys Cys Leu Asp Gly Ala Ala Tyr Ala Ser
65                  70                  75                  80 acg tac gga gtt acc acg agc ggt aac agc ctc tcc att ggc ttt gtc        288
Thr Tyr Gly Val Thr Thr Ser Gly Asn Ser Leu Ser Ile Gly Phe Val
                85                  90                  95 acc cag tct gcg cag aag aac gtt ggc gct cgc ctt tac ctt atg gcg        336
Thr Gln Ser Ala Gln Lys Asn Val Gly Ala Arg Leu Tyr Leu Met Ala
            100                 105                 110 agc gac acg acc tac cag gaa ttc acc ctg ctt ggc aac gag ttc tct        384
Ser Asp Thr Thr Tyr Gln Glu Phe Thr Leu Leu Gly Asn Glu Phe Ser
        115                 120                 125 ttc gat gtt gat gtt tcg cag ctg ccg tgc ggc ttg aac gga gct ctc        432
Phe Asp Val Asp Val Ser Gln Leu Pro Cys Gly Leu Asn Gly Ala Leu
    130                 135                 140 tac ttc gtg tcc atg gac gcg gat ggt ggc gtg agc aag tat ccc acc        480
Tyr Phe Val Ser Met Asp Ala Asp Gly Gly Val Ser Lys Tyr Pro Thr
145                 150                 155                 160 aac acc gct ggc gcc aag tac ggc acg ggg tac tgt gac agc cag tgt        528
Asn Thr Ala Gly Ala Lys Tyr Gly Thr Gly Tyr Cys Asp Ser Gln Cys
                165                 170                 175 ccc cgc gat ctg aag ttc atc aat ggc cag gcc aac gtt gag ggc tgg        576
Pro Arg Asp Leu Lys Phe Ile Asn Gly Gln Ala Asn Val Glu Gly Trp
            180                 185                 190
```

```
gag ccg tca tcc aac aac gcg aac acg ggc att gga gga cac gga agc    624
Glu Pro Ser Ser Asn Asn Ala Asn Thr Gly Ile Gly Gly His Gly Ser
        195                 200                 205 tgc tgc tct gag atg gat atc tgg gag gcc aac tcc atc tcc gag gct    672
Cys Cys Ser Glu Met Asp Ile Trp Glu Ala Asn Ser Ile Ser Glu Ala
210                 215                 220 ctt acc ccc cac cct tgc acg act gtc ggc cag gag atc tgc gag ggt    720
Leu Thr Pro His Pro Cys Thr Thr Val Gly Gln Glu Ile Cys Glu Gly
225                 230                 235                 240 gat ggg tgc ggc gga act tac tcc gat aac aga tat ggc ggc act tgc    768
Asp Gly Cys Gly Gly Thr Tyr Ser Asp Asn Arg Tyr Gly Gly Thr Cys
                245                 250                 255 gat ccc gat ggc tgc gac tgg aac cca tac cgc ctg ggc aac acc agc    816
Asp Pro Asp Gly Cys Asp Trp Asn Pro Tyr Arg Leu Gly Asn Thr Ser
            260                 265                 270 ttc tac ggc cct ggc tca agc ttt acc ctc gat acc acc aag aaa ttt    864
Phe Tyr Gly Pro Gly Ser Ser Phe Thr Leu Asp Thr Thr Lys Lys Phe
        275                 280                 285 acc gtt gtc acc cag ttc gag acg tcg ggt gcc atc aac cga tac tat    912
Thr Val Val Thr Gln Phe Glu Thr Ser Gly Ala Ile Asn Arg Tyr Tyr
    290                 295                 300 gtc cag aat ggc gtc act ttc cag cag ccc aac gcc gag ctt ggt agt    960
Val Gln Asn Gly Val Thr Phe Gln Gln Pro Asn Ala Glu Leu Gly Ser
305                 310                 315                 320 tac tct ggc aac gag ctc aac gat gat tac tgc aca gct gag gag gca   1008
Tyr Ser Gly Asn Glu Leu Asn Asp Asp Tyr Cys Thr Ala Glu Glu Ala
                325                 330                 335 gaa ttc ggc gga tcc tct ttc tca gac aag ggc ggc ctg act cag ttc   1056
Glu Phe Gly Gly Ser Ser Phe Ser Asp Lys Gly Gly Leu Thr Gln Phe
            340                 345                 350 aag aag gct acc tct ggc ggc atg gtt ctg gtc atg agt ctg tgg gat   1104
Lys Lys Ala Thr Ser Gly Gly Met Val Leu Val Met Ser Leu Trp Asp
        355                 360                 365 gat tac tac gcc aac atg ctg tgg ctg gac tcc acc tac ccg aca aac   1152
Asp Tyr Tyr Ala Asn Met Leu Trp Leu Asp Ser Thr Tyr Pro Thr Asn
    370                 375                 380 gag acc tcc tcc aca ccc ggt gcc gtg cgc gga agc tgc tcc acc agc   1200
Glu Thr Ser Ser Thr Pro Gly Ala Val Arg Gly Ser Cys Ser Thr Ser
385                 390                 395                 400 tcc ggt gtc cct gct cag gtc gaa tct cag tct ccc aac gcc aag gtc   1248
Ser Gly Val Pro Ala Gln Val Glu Ser Gln Ser Pro Asn Ala Lys Val
                405                 410                 415 acc ttc tcc aac atc aag ttc gga ccc att ggc agc acc ggc aac cct   1296
Thr Phe Ser Asn Ile Lys Phe Gly Pro Ile Gly Ser Thr Gly Asn Pro
            420                 425                 430 agc ggc ggc aac cct ccc ggc gga aac ccg cct ggc acc acc acc acc   1344
Ser Gly Gly Asn Pro Pro Gly Gly Asn Pro Pro Gly Thr Thr Thr Thr
        435                 440                 445 cgc cgc cca gcc act acc act gga agc tct ccc gga cct acc cag tct   1392
Arg Arg Pro Ala Thr Thr Thr Gly Ser Ser Pro Gly Pro Thr Gln Ser
    450                 455                 460 cac tac ggc cag tgc ggc ggt att ggc tac agc ggc ccc acg gtc tgc   1440
His Tyr Gly Gln Cys Gly Gly Ile Gly Tyr Ser Gly Pro Thr Val Cys
465                 470                 475                 480 gcc agc ggc aca act tgc cag gtc ctg aac cct tac tac tct cag tgc   1488
Ala Ser Gly Thr Thr Cys Gln Val Leu Asn Pro Tyr Tyr Ser Gln Cys
                485                 490                 495 ctg                                                                1491
Leu
```

-continued

```
<210> SEQ ID NO 14
<211> LENGTH: 497
<212> TYPE: PRT
<213> ORGANISM: Hypocrea jecorina

<400> SEQUENCE: 14
```

| | | | | | | | | | | | | | | | |
|---|---|---|---|---|---|---|---|---|---|---|---|---|---|---|---|
| Gln | Ser | Ala | Cys | Thr | Leu | Gln | Ser | Glu | Thr | His | Pro | Pro | Leu | Thr | Trp |
| 1 | | | | 5 | | | | | 10 | | | | | 15 | |
| Gln | Lys | Cys | Ser | Ser | Gly | Gly | Thr | Cys | Thr | Gln | Gln | Thr | Gly | Ser | Val |
| | | | 20 | | | | | 25 | | | | | 30 | | |
| Val | Ile | Asp | Ala | Asn | Trp | Arg | Trp | Thr | His | Ala | Thr | Asn | Ser | Ser | Thr |
| | | 35 | | | | | 40 | | | | | 45 | | | |
| Asn | Cys | Tyr | Asp | Gly | Asn | Thr | Trp | Ser | Ser | Thr | Leu | Cys | Pro | Asp | Asn |
| | 50 | | | | | 55 | | | | | 60 | | | | |
| Glu | Thr | Cys | Ala | Lys | Asn | Cys | Cys | Leu | Asp | Gly | Ala | Ala | Tyr | Ala | Ser |
| 65 | | | | | 70 | | | | | 75 | | | | | 80 |
| Thr | Tyr | Gly | Val | Thr | Thr | Ser | Gly | Asn | Ser | Leu | Ser | Ile | Gly | Phe | Val |
| | | | | 85 | | | | | 90 | | | | | 95 | |
| Thr | Gln | Ser | Ala | Gln | Lys | Asn | Val | Gly | Ala | Arg | Leu | Tyr | Leu | Met | Ala |
| | | | 100 | | | | | 105 | | | | | 110 | | |
| Ser | Asp | Thr | Thr | Tyr | Gln | Glu | Phe | Thr | Leu | Leu | Gly | Asn | Glu | Phe | Ser |
| | | | 115 | | | | | 120 | | | | | 125 | | |
| Phe | Asp | Val | Asp | Val | Ser | Gln | Leu | Pro | Cys | Gly | Leu | Asn | Gly | Ala | Leu |
| 130 | | | | | 135 | | | | | 140 | | | | | |
| Tyr | Phe | Val | Ser | Met | Asp | Ala | Asp | Gly | Gly | Val | Ser | Lys | Tyr | Pro | Thr |
| 145 | | | | | 150 | | | | | 155 | | | | | 160 |
| Asn | Thr | Ala | Gly | Ala | Lys | Tyr | Gly | Thr | Gly | Tyr | Cys | Asp | Ser | Gln | Cys |
| | | | | 165 | | | | | 170 | | | | | 175 | |
| Pro | Arg | Asp | Leu | Lys | Phe | Ile | Asn | Gly | Gln | Ala | Asn | Val | Glu | Gly | Trp |
| | | | 180 | | | | | 185 | | | | | 190 | | |
| Glu | Pro | Ser | Ser | Asn | Asn | Ala | Asn | Thr | Gly | Ile | Gly | Gly | His | Gly | Ser |
| | | | 195 | | | | | 200 | | | | | 205 | | |
| Cys | Cys | Ser | Glu | Met | Asp | Ile | Trp | Glu | Ala | Asn | Ser | Ile | Ser | Glu | Ala |
| | 210 | | | | | 215 | | | | | 220 | | | | |
| Leu | Thr | Pro | His | Pro | Cys | Thr | Thr | Val | Gly | Gln | Glu | Ile | Cys | Glu | Gly |
| 225 | | | | | 230 | | | | | 235 | | | | | 240 |
| Asp | Gly | Cys | Gly | Gly | Thr | Tyr | Ser | Asp | Asn | Arg | Tyr | Gly | Gly | Thr | Cys |
| | | | | 245 | | | | | 250 | | | | | 255 | |
| Asp | Pro | Asp | Gly | Cys | Asp | Trp | Asn | Pro | Tyr | Arg | Leu | Gly | Asn | Thr | Ser |
| | | | 260 | | | | | 265 | | | | | 270 | | |
| Phe | Tyr | Gly | Pro | Gly | Ser | Ser | Phe | Thr | Leu | Asp | Thr | Thr | Lys | Lys | Phe |
| | | | 275 | | | | | 280 | | | | | 285 | | |
| Thr | Val | Val | Thr | Gln | Phe | Glu | Thr | Ser | Gly | Ala | Ile | Asn | Arg | Tyr | Tyr |
| | 290 | | | | | 295 | | | | | 300 | | | | |
| Val | Gln | Asn | Gly | Val | Thr | Phe | Gln | Gln | Pro | Asn | Ala | Glu | Leu | Gly | Ser |
| 305 | | | | | 310 | | | | | 315 | | | | | 320 |
| Tyr | Ser | Gly | Asn | Glu | Leu | Asn | Asp | Asp | Tyr | Cys | Thr | Ala | Glu | Glu | Ala |
| | | | | 325 | | | | | 330 | | | | | 335 | |
| Glu | Phe | Gly | Gly | Ser | Ser | Phe | Ser | Asp | Lys | Gly | Gly | Leu | Thr | Gln | Phe |
| | | | 340 | | | | | 345 | | | | | 350 | | |
| Lys | Lys | Ala | Thr | Ser | Gly | Gly | Met | Val | Leu | Val | Met | Ser | Leu | Trp | Asp |
| | | | 355 | | | | | 360 | | | | | 365 | | |
| Asp | Tyr | Tyr | Ala | Asn | Met | Leu | Trp | Leu | Asp | Ser | Thr | Tyr | Pro | Thr | Asn |
| | 370 | | | | | 375 | | | | | 380 | | | | |

-continued

```
Glu Thr Ser Ser Thr Pro Gly Ala Val Arg Gly Ser Cys Ser Thr Ser
385                 390                 395                 400

Ser Gly Val Pro Ala Gln Val Glu Ser Gln Ser Pro Asn Ala Lys Val
                405                 410                 415

Thr Phe Ser Asn Ile Lys Phe Gly Pro Ile Gly Ser Thr Gly Asn Pro
            420                 425                 430

Ser Gly Gly Asn Pro Pro Gly Gly Asn Pro Pro Gly Thr Thr Thr Thr
        435                 440                 445

Arg Arg Pro Ala Thr Thr Thr Gly Ser Ser Pro Gly Pro Thr Gln Ser
    450                 455                 460

His Tyr Gly Gln Cys Gly Gly Ile Gly Tyr Ser Gly Pro Thr Val Cys
465                 470                 475                 480

Ala Ser Gly Thr Thr Cys Gln Val Leu Asn Pro Tyr Tyr Ser Gln Cys
                485                 490                 495

Leu
```

```
<210> SEQ ID NO 15
<211> LENGTH: 1491
<212> TYPE: DNA
<213> ORGANISM: Hypocrea jecorina
<220> FEATURE:
<221> NAME/KEY: CDS
<222> LOCATION: (1)..(1491)

<400> SEQUENCE: 15
```

| | | | | | | | | | | | | | | | | |
|---|---|---|---|---|---|---|---|---|---|---|---|---|---|---|---|---|
| cag | tcg | gcc | tgc | act | ctc | caa | tcg | gag | act | cac | ccg | cct | ctg | aca | tgg | 48 |
| Gln | Ser | Ala | Cys | Thr | Leu | Gln | Ser | Glu | Thr | His | Pro | Pro | Leu | Thr | Trp | |
| 1 | | | 5 | | | | | 10 | | | | | 15 | | | |
| cag | aaa | tgc | tcg | tct | ggt | ggc | act | tgc | act | caa | cag | aca | ggc | tcc | gtg | 96 |
| Gln | Lys | Cys | Ser | Ser | Gly | Gly | Thr | Cys | Thr | Gln | Gln | Thr | Gly | Ser | Val | |
| | | | 20 | | | | | 25 | | | | | 30 | | | |
| gtc | atc | gac | gcc | aac | tgg | cgc | tgg | act | cac | gct | acg | aac | agc | agc | acg | 144 |
| Val | Ile | Asp | Ala | Asn | Trp | Arg | Trp | Thr | His | Ala | Thr | Asn | Ser | Ser | Thr | |
| | | | | 35 | | | | | 40 | | | | | 45 | | |
| aac | tgc | tac | gat | ggc | aac | act | tgg | agc | tcg | acc | cta | tgt | cct | gac | aac | 192 |
| Asn | Cys | Tyr | Asp | Gly | Asn | Thr | Trp | Ser | Ser | Thr | Leu | Cys | Pro | Asp | Asn | |
| | 50 | | | | | 55 | | | | | 60 | | | | | |
| gag | acc | tgc | gcg | aag | aac | tgc | tgt | ctg | gac | ggt | gcc | gcc | tac | gcg | tcc | 240 |
| Glu | Thr | Cys | Ala | Lys | Asn | Cys | Cys | Leu | Asp | Gly | Ala | Ala | Tyr | Ala | Ser | |
| 65 | | | | | 70 | | | | | 75 | | | | | 80 | |
| acg | tac | gga | gtt | acc | acg | agc | ggt | aac | agc | ctc | tcc | att | ggc | ttt | gtc | 288 |
| Thr | Tyr | Gly | Val | Thr | Thr | Ser | Gly | Asn | Ser | Leu | Ser | Ile | Gly | Phe | Val | |
| | | | | 85 | | | | | 90 | | | | | 95 | | |
| acc | cag | tct | gcg | cag | aag | aac | gtt | ggc | gct | cgc | ctt | tac | ctt | atg | gcg | 336 |
| Thr | Gln | Ser | Ala | Gln | Lys | Asn | Val | Gly | Ala | Arg | Leu | Tyr | Leu | Met | Ala | |
| | | | 100 | | | | | 105 | | | | | 110 | | | |
| agc | gac | acg | acc | tac | cag | gaa | ttc | acc | ctg | ctt | ggc | aac | gag | ttc | tct | 384 |
| Ser | Asp | Thr | Thr | Tyr | Gln | Glu | Phe | Thr | Leu | Leu | Gly | Asn | Glu | Phe | Ser | |
| | | | 115 | | | | | 120 | | | | | 125 | | | |
| ttc | gat | gtt | gat | gtt | tcg | cag | ctg | ccg | tgc | ggc | ttg | aac | gga | gct | ctc | 432 |
| Phe | Asp | Val | Asp | Val | Ser | Gln | Leu | Pro | Cys | Gly | Leu | Asn | Gly | Ala | Leu | |
| | | | 130 | | | | | 135 | | | | | 140 | | | |
| tac | ttc | gtg | tcc | atg | gac | gcg | gat | ggt | ggc | gtg | agc | aag | tat | ccc | acc | 480 |
| Tyr | Phe | Val | Ser | Met | Asp | Ala | Asp | Gly | Gly | Val | Ser | Lys | Tyr | Pro | Thr | |
| 145 | | | | | 150 | | | | | 155 | | | | | 160 | |
| aac | acc | gct | ggc | gcc | aag | tac | ggc | acg | ggg | tac | tgt | gac | agc | cag | tgt | 528 |
| Asn | Thr | Ala | Gly | Ala | Lys | Tyr | Gly | Thr | Gly | Tyr | Cys | Asp | Ser | Gln | Cys | |
| | | | | 165 | | | | | 170 | | | | | 175 | | |
| ccc | cgc | gat | ctg | aag | ttc | atc | aat | ggc | cag | gcc | aac | gtt | gag | ggc | tgg | 576 |
| Pro | Arg | Asp | Leu | Lys | Phe | Ile | Asn | Gly | Gln | Ala | Asn | Val | Glu | Gly | Trp | |

```
                180               185               190
gag ccg tca tcc aac aac gcg aac acg ggc att gga gga cac gga agc     624
Glu Pro Ser Ser Asn Asn Ala Asn Thr Gly Ile Gly Gly His Gly Ser
        195                 200                 205 tgc tgc tct gag atg gat atc tgg gag gcc aac tcc atc tcc gag gct     672
Cys Cys Ser Glu Met Asp Ile Trp Glu Ala Asn Ser Ile Ser Glu Ala
210                 215                 220 ctt acc ccc cac cct tgc acg act gtc ggc cag gag atc tgc gag ggt     720
Leu Thr Pro His Pro Cys Thr Thr Val Gly Gln Glu Ile Cys Glu Gly
225                 230                 235                 240 gat ggg tgc ggc gga act tac tcc gat aac aga tat ggc ggc act tgc     768
Asp Gly Cys Gly Gly Thr Tyr Ser Asp Asn Arg Tyr Gly Gly Thr Cys
                245                 250                 255 gat ccc gat ggc tgc gac tgg aac cca tac cgc ctg ggc aac acc agc     816
Asp Pro Asp Gly Cys Asp Trp Asn Pro Tyr Arg Leu Gly Asn Thr Ser
            260                 265                 270 ttc tac ggc cct ggc tca agc ttt acc ctc gat acc acc aag aaa ttg     864
Phe Tyr Gly Pro Gly Ser Ser Phe Thr Leu Asp Thr Thr Lys Lys Leu
        275                 280                 285 acc gtt gtc acc cag ttc gag acg tcg ggt gag atc aac cga tac tat     912
Thr Val Val Thr Gln Phe Glu Thr Ser Gly Glu Ile Asn Arg Tyr Tyr
    290                 295                 300 gtc cag aat ggc gtc act ttc cag cag ccc aac gcc gag ctt ggt agt     960
Val Gln Asn Gly Val Thr Phe Gln Gln Pro Asn Ala Glu Leu Gly Ser
305                 310                 315                 320 tac tct ggc aac gag ctc aac gat gat tac tgc aca gct gag gag gca    1008
Tyr Ser Gly Asn Glu Leu Asn Asp Asp Tyr Cys Thr Ala Glu Glu Ala
                325                 330                 335 gaa ttc ggc gga tcc tct ttc tca gac aag ggc ggc ctg act cag ttc    1056
Glu Phe Gly Gly Ser Ser Phe Ser Asp Lys Gly Gly Leu Thr Gln Phe
            340                 345                 350 aag aag gct acc tct ggc ggc atg gtt ctg gtc atg agt ctg tgg gat    1104
Lys Lys Ala Thr Ser Gly Gly Met Val Leu Val Met Ser Leu Trp Asp
        355                 360                 365 gat tac tac gcc aac atg ctg tgg ctg gac tcc acc tac ccg aca aac    1152
Asp Tyr Tyr Ala Asn Met Leu Trp Leu Asp Ser Thr Tyr Pro Thr Asn
    370                 375                 380 gag acc tcc tcc aca ccc ggt gcc gtg cgc gga agc tgc tcc acc agc    1200
Glu Thr Ser Ser Thr Pro Gly Ala Val Arg Gly Ser Cys Ser Thr Ser
385                 390                 395                 400 tcc ggt gtc cct gct cag gtc gaa tct cag tct ccc aac gcc aag gtc    1248
Ser Gly Val Pro Ala Gln Val Glu Ser Gln Ser Pro Asn Ala Lys Val
                405                 410                 415 acc ttc tcc aac atc aag ttc gga ccc att ggc agc acc ggc aac cct    1296
Thr Phe Ser Asn Ile Lys Phe Gly Pro Ile Gly Ser Thr Gly Asn Pro
            420                 425                 430 agc ggc ggc aac cct ccc ggc gga aac ccg cct ggc acc acc acc acc    1344
Ser Gly Gly Asn Pro Pro Gly Gly Asn Pro Pro Gly Thr Thr Thr Thr
        435                 440                 445 cgc cgc cca gcc act acc act gga agc tct ccc gga cct acc cag tct    1392
Arg Arg Pro Ala Thr Thr Thr Gly Ser Ser Pro Gly Pro Thr Gln Ser
    450                 455                 460 cac tac ggc cag tgc ggc ggt att ggc tac agc ggc ccc acg gtc tgc    1440
His Tyr Gly Gln Cys Gly Gly Ile Gly Tyr Ser Gly Pro Thr Val Cys
465                 470                 475                 480 gcc agc ggc aca act tgc cag gtc ctg aac cct tac tac tct cag tgc    1488
Ala Ser Gly Thr Thr Cys Gln Val Leu Asn Pro Tyr Tyr Ser Gln Cys
                485                 490                 495 ctg                                                                1491
Leu
```

<210> SEQ ID NO 16
<211> LENGTH: 497
<212> TYPE: PRT
<213> ORGANISM: Hypocrea jecorina

<400> SEQUENCE: 16

```
Gln Ser Ala Cys Thr Leu Gln Ser Glu Thr His Pro Pro Leu Thr Trp
1               5                   10                  15

Gln Lys Cys Ser Ser Gly Gly Thr Cys Thr Gln Gln Thr Gly Ser Val
            20                  25                  30

Val Ile Asp Ala Asn Trp Arg Trp Thr His Ala Thr Asn Ser Ser Thr
        35                  40                  45

Asn Cys Tyr Asp Gly Asn Thr Trp Ser Ser Thr Leu Cys Pro Asp Asn
    50                  55                  60

Glu Thr Cys Ala Lys Asn Cys Cys Leu Asp Gly Ala Ala Tyr Ala Ser
65                  70                  75                  80

Thr Tyr Gly Val Thr Thr Ser Gly Asn Ser Leu Ser Ile Gly Phe Val
                85                  90                  95

Thr Gln Ser Ala Gln Lys Asn Val Gly Ala Arg Leu Tyr Leu Met Ala
            100                 105                 110

Ser Asp Thr Thr Tyr Gln Glu Phe Thr Leu Leu Gly Asn Glu Phe Ser
        115                 120                 125

Phe Asp Val Asp Val Ser Gln Leu Pro Cys Gly Leu Asn Gly Ala Leu
    130                 135                 140

Tyr Phe Val Ser Met Asp Ala Asp Gly Gly Val Ser Lys Tyr Pro Thr
145                 150                 155                 160

Asn Thr Ala Gly Ala Lys Tyr Gly Thr Gly Tyr Cys Asp Ser Gln Cys
                165                 170                 175

Pro Arg Asp Leu Lys Phe Ile Asn Gly Gln Ala Asn Val Glu Gly Trp
            180                 185                 190

Glu Pro Ser Ser Asn Asn Ala Asn Thr Gly Ile Gly Gly His Gly Ser
        195                 200                 205

Cys Cys Ser Glu Met Asp Ile Trp Glu Ala Asn Ser Ile Ser Glu Ala
    210                 215                 220

Leu Thr Pro His Pro Cys Thr Thr Val Gly Gln Glu Ile Cys Glu Gly
225                 230                 235                 240

Asp Gly Cys Gly Gly Thr Tyr Ser Asp Asn Arg Tyr Gly Gly Thr Cys
                245                 250                 255

Asp Pro Asp Gly Cys Asp Trp Asn Pro Tyr Arg Leu Gly Asn Thr Ser
            260                 265                 270

Phe Tyr Gly Pro Gly Ser Ser Phe Thr Leu Asp Thr Thr Lys Lys Leu
        275                 280                 285

Thr Val Val Thr Gln Phe Glu Thr Ser Gly Glu Ile Asn Arg Tyr Tyr
    290                 295                 300

Val Gln Asn Gly Val Thr Phe Gln Gln Pro Asn Ala Glu Leu Gly Ser
305                 310                 315                 320

Tyr Ser Gly Asn Glu Leu Asn Asp Asp Tyr Cys Thr Ala Glu Glu Ala
                325                 330                 335

Glu Phe Gly Gly Ser Ser Phe Ser Asp Lys Gly Gly Leu Thr Gln Phe
            340                 345                 350

Lys Lys Ala Thr Ser Gly Gly Met Val Leu Val Met Ser Leu Trp Asp
        355                 360                 365

Asp Tyr Tyr Ala Asn Met Leu Trp Leu Asp Ser Thr Tyr Pro Thr Asn
    370                 375                 380
```

| | | | | | | | | | | | | | | | |
|---|---|---|---|---|---|---|---|---|---|---|---|---|---|---|---|
|Glu|Thr|Ser|Ser|Thr|Pro|Gly|Ala|Val|Arg|Gly|Ser|Cys|Ser|Thr|Ser|
|385| | | |390| | | |395| | | |400| | | |

| | | | | | | | | | | | |
|---|---|---|---|---|---|---|---|---|---|---|---|
|Ser|Gly|Val|Pro|Ala|Gln|Val|Glu|Ser|Gln|Ser|Pro|Asn|Ala|Lys|Val|
| | | | |405| | | |410| | | |415| | | |

Thr Phe Ser Asn Ile Lys Phe Gly Ile Gly Ser Thr Gly Asn Pro
              420                 425                 430

Ser Gly Gly Asn Pro Pro Gly Gly Asn Pro Pro Gly Thr Thr Thr
              435                 440                 445

Arg Arg Pro Ala Thr Thr Thr Gly Ser Ser Pro Gly Pro Thr Gln Ser
              450                 455                 460

His Tyr Gly Gln Cys Gly Gly Ile Gly Tyr Ser Gly Pro Thr Val Cys
465                 470                 475                 480

Ala Ser Gly Thr Thr Cys Gln Val Leu Asn Pro Tyr Tyr Ser Gln Cys
              485                 490                 495

Leu

<210> SEQ ID NO 17
<211> LENGTH: 1491
<212> TYPE: DNA
<213> ORGANISM: Hypocrea jecorina
<220> FEATURE:
<221> NAME/KEY: CDS
<222> LOCATION: (1)..(1491)

<400> SEQUENCE: 17

```
cag tcg gcc tgc act ctc caa tcg gag act cac ccg cct ctg aca tgg     48
Gln Ser Ala Cys Thr Leu Gln Ser Glu Thr His Pro Pro Leu Thr Trp
1               5                   10                  15 cag aaa tgc tcg tct ggt ggc act tgc act caa cag aca ggc tcc gtg     96
Gln Lys Cys Ser Ser Gly Gly Thr Cys Thr Gln Gln Thr Gly Ser Val
            20                  25                  30 gtc atc gac gcc aac tgg cgc tgg act cac gct acg aac agc agc acg    144
Val Ile Asp Ala Asn Trp Arg Trp Thr His Ala Thr Asn Ser Ser Thr
        35                  40                  45 aac tgc tac gat ggc aac act tgg agc tcg acc cta tgt cct gac aac    192
Asn Cys Tyr Asp Gly Asn Thr Trp Ser Ser Thr Leu Cys Pro Asp Asn
    50                  55                  60 gag acc tgc gcg aag aac tgc tgt ctg gac ggt gcc gcc tac gcg tcc    240
Glu Thr Cys Ala Lys Asn Cys Cys Leu Asp Gly Ala Ala Tyr Ala Ser
65                  70                  75                  80 acg tac gga gtt acc acg agc ggt aac agc ctc tcc att ggc ttt gtc    288
Thr Tyr Gly Val Thr Thr Ser Gly Asn Ser Leu Ser Ile Gly Phe Val
                85                  90                  95 acc cag tct gcg cag aag aac gtt ggc gct cgc ctt tac ctt atg gcg    336
Thr Gln Ser Ala Gln Lys Asn Val Gly Ala Arg Leu Tyr Leu Met Ala
            100                 105                 110 agc gac acg acc tac cag gaa ttc acc ctg ctt ggc aac gag ttc tct    384
Ser Asp Thr Thr Tyr Gln Glu Phe Thr Leu Leu Gly Asn Glu Phe Ser
        115                 120                 125 ttc gat gtt gat gtt tcg cag ctg ccg tgc ggc ttg aac gga gct ctc    432
Phe Asp Val Asp Val Ser Gln Leu Pro Cys Gly Leu Asn Gly Ala Leu
    130                 135                 140 tac ttc gtg tcc atg gac gcg gat ggt ggc gtg agc aag tat ccc acc    480
Tyr Phe Val Ser Met Asp Ala Asp Gly Gly Val Ser Lys Tyr Pro Thr
145                 150                 155                 160 aac acc gct ggc gcc aag tac ggc acg ggg tac tgt gac agc cag tgt    528
Asn Thr Ala Gly Ala Lys Tyr Gly Thr Gly Tyr Cys Asp Ser Gln Cys
                165                 170                 175 ccc cgc gat ctg aag ttc atc aat ggc cag gcc aac gtt gag ggc tgg    576
```

```
                Pro Arg Asp Leu Lys Phe Ile Asn Gly Gln Ala Asn Val Glu Gly Trp
                            180                 185                 190 gag ccg tca tcc aac aac gcg aac acg ggc att gga gga cac gga agc              624
Glu Pro Ser Ser Asn Asn Ala Asn Thr Gly Ile Gly Gly His Gly Ser
        195                 200                 205 tgc tgc tct gag atg gat atc tgg gag gcc aac tcc atc tcc gag gct              672
Cys Cys Ser Glu Met Asp Ile Trp Glu Ala Asn Ser Ile Ser Glu Ala
    210                 215                 220 ctt acc ccc cac cct tgc acg act gtc ggc cag gag atc tgc gag ggt              720
Leu Thr Pro His Pro Cys Thr Thr Val Gly Gln Glu Ile Cys Glu Gly
225                 230                 235                 240 gat ggg tgc ggc gga act tac tcc gat aac aga tat ggc ggc act tgc              768
Asp Gly Cys Gly Gly Thr Tyr Ser Asp Asn Arg Tyr Gly Gly Thr Cys
                    245                 250                 255 gat ccc gat ggc tgc gac tgg aac cca tac cgc ctg ggc aac acc agc              816
Asp Pro Asp Gly Cys Asp Trp Asn Pro Tyr Arg Leu Gly Asn Thr Ser
            260                 265                 270 ttc tac ggc cct ggc tca agc ttt acc ctc gat acc acc aag aaa ttg              864
Phe Tyr Gly Pro Gly Ser Ser Phe Thr Leu Asp Thr Thr Lys Lys Leu
        275                 280                 285 acc gtt gtc acc cag ttc gag acg tcg ggt gcc atc aag cga tac tat              912
Thr Val Val Thr Gln Phe Glu Thr Ser Gly Ala Ile Lys Arg Tyr Tyr
    290                 295                 300 gtc cag aat ggc gtc act ttc cag cag ccc aac gcc gag ctt ggt agt              960
Val Gln Asn Gly Val Thr Phe Gln Gln Pro Asn Ala Glu Leu Gly Ser
305                 310                 315                 320 tac tct ggc aac gag ctc aac gat gat tac tgc aca gct gag gag gca             1008
Tyr Ser Gly Asn Glu Leu Asn Asp Asp Tyr Cys Thr Ala Glu Glu Ala
                    325                 330                 335 gaa ttc ggc gga tcc tct ttc tca gac aag ggc ggc ctg act cag ttc             1056
Glu Phe Gly Gly Ser Ser Phe Ser Asp Lys Gly Gly Leu Thr Gln Phe
            340                 345                 350 aag aag gct acc tct ggc ggc atg gtt ctg gtc atg agt ctg tgg gat             1104
Lys Lys Ala Thr Ser Gly Gly Met Val Leu Val Met Ser Leu Trp Asp
        355                 360                 365 gat tac tac gcc aac atg ctg tgg ctg gac tcc acc tac ccg aca aac             1152
Asp Tyr Tyr Ala Asn Met Leu Trp Leu Asp Ser Thr Tyr Pro Thr Asn
    370                 375                 380 gag acc tcc tcc aca ccc ggt gcc gtg cgc gga agc tgc tcc acc agc             1200
Glu Thr Ser Ser Thr Pro Gly Ala Val Arg Gly Ser Cys Ser Thr Ser
385                 390                 395                 400 tcc ggt gtc cct gct cag gtc gaa tct cag tct ccc aac gcc aag gtc             1248
Ser Gly Val Pro Ala Gln Val Glu Ser Gln Ser Pro Asn Ala Lys Val
                    405                 410                 415 acc ttc tcc aac atc aag ttc gga ccc att ggc agc acc ggc aac cct             1296
Thr Phe Ser Asn Ile Lys Phe Gly Pro Ile Gly Ser Thr Gly Asn Pro
            420                 425                 430 agc ggc ggc aac cct ccc ggc gga aac ccg cct ggc acc acc acc acc             1344
Ser Gly Gly Asn Pro Pro Gly Gly Asn Pro Pro Gly Thr Thr Thr Thr
        435                 440                 445 cgc cgc cca gcc act acc act gga agc tct ccc gga cct acc cag tct             1392
Arg Arg Pro Ala Thr Thr Thr Gly Ser Ser Pro Gly Pro Thr Gln Ser
    450                 455                 460 cac tac ggc cag tgc ggc ggt att ggc tac agc ggc ccc acg gtc tgc             1440
His Tyr Gly Gln Cys Gly Gly Ile Gly Tyr Ser Gly Pro Thr Val Cys
465                 470                 475                 480 gcc agc ggc aca act tgc cag gtc ctg aac cct tac tac tct cag tgc             1488
Ala Ser Gly Thr Thr Cys Gln Val Leu Asn Pro Tyr Tyr Ser Gln Cys
                    485                 490                 495 ctg                                                                         1491
```

Leu

<210> SEQ ID NO 18
<211> LENGTH: 497
<212> TYPE: PRT
<213> ORGANISM: Hypocrea jecorina

<400> SEQUENCE: 18

```
Gln Ser Ala Cys Thr Leu Gln Ser Glu Thr His Pro Pro Leu Thr Trp
1               5                   10                  15

Gln Lys Cys Ser Ser Gly Gly Thr Cys Thr Gln Gln Thr Gly Ser Val
            20                  25                  30

Val Ile Asp Ala Asn Trp Arg Trp Thr His Ala Thr Asn Ser Ser Thr
        35                  40                  45

Asn Cys Tyr Asp Gly Asn Thr Trp Ser Ser Thr Leu Cys Pro Asp Asn
    50                  55                  60

Glu Thr Cys Ala Lys Asn Cys Cys Leu Asp Gly Ala Ala Tyr Ala Ser
65                  70                  75                  80

Thr Tyr Gly Val Thr Thr Ser Gly Asn Ser Leu Ser Ile Gly Phe Val
                85                  90                  95

Thr Gln Ser Ala Gln Lys Asn Val Gly Ala Arg Leu Tyr Leu Met Ala
            100                 105                 110

Ser Asp Thr Thr Tyr Gln Glu Phe Thr Leu Leu Gly Asn Glu Phe Ser
        115                 120                 125

Phe Asp Val Asp Val Ser Gln Leu Pro Cys Gly Leu Asn Gly Ala Leu
    130                 135                 140

Tyr Phe Val Ser Met Asp Ala Asp Gly Gly Val Ser Lys Tyr Pro Thr
145                 150                 155                 160

Asn Thr Ala Gly Ala Lys Tyr Gly Thr Gly Tyr Cys Asp Ser Gln Cys
                165                 170                 175

Pro Arg Asp Leu Lys Phe Ile Asn Gly Gln Ala Asn Val Glu Gly Trp
            180                 185                 190

Glu Pro Ser Ser Asn Asn Ala Asn Thr Gly Ile Gly Gly His Gly Ser
        195                 200                 205

Cys Cys Ser Glu Met Asp Ile Trp Glu Ala Asn Ser Ile Ser Glu Ala
    210                 215                 220

Leu Thr Pro His Pro Cys Thr Thr Val Gly Gln Glu Ile Cys Glu Gly
225                 230                 235                 240

Asp Gly Cys Gly Gly Thr Tyr Ser Asp Asn Arg Tyr Gly Gly Thr Cys
                245                 250                 255

Asp Pro Asp Gly Cys Asp Trp Asn Pro Tyr Arg Leu Gly Asn Thr Ser
            260                 265                 270

Phe Tyr Gly Pro Gly Ser Ser Phe Thr Leu Asp Thr Thr Lys Lys Leu
        275                 280                 285

Thr Val Val Thr Gln Phe Glu Thr Ser Gly Ala Ile Lys Arg Tyr Tyr
    290                 295                 300

Val Gln Asn Gly Val Thr Phe Gln Gln Pro Asn Ala Glu Leu Gly Ser
305                 310                 315                 320

Tyr Ser Gly Asn Glu Leu Asn Asp Asp Tyr Cys Thr Ala Glu Glu Ala
                325                 330                 335

Glu Phe Gly Gly Ser Ser Phe Ser Asp Lys Gly Gly Leu Thr Gln Phe
            340                 345                 350

Lys Lys Ala Thr Ser Gly Gly Met Val Leu Val Met Ser Leu Trp Asp
        355                 360                 365

Asp Tyr Tyr Ala Asn Met Leu Trp Leu Asp Ser Thr Tyr Pro Thr Asn
```

```
                370             375             380
Glu Thr Ser Ser Thr Pro Gly Ala Val Arg Gly Ser Cys Ser Thr Ser
385                 390                 395                 400

Ser Gly Val Pro Ala Gln Val Glu Ser Gln Ser Pro Asn Ala Lys Val
                405                 410                 415

Thr Phe Ser Asn Ile Lys Phe Gly Pro Ile Gly Ser Thr Gly Asn Pro
            420                 425                 430

Ser Gly Gly Asn Pro Pro Gly Gly Asn Pro Pro Gly Thr Thr Thr Thr
                435                 440                 445

Arg Arg Pro Ala Thr Thr Thr Gly Ser Ser Pro Gly Pro Thr Gln Ser
    450                 455                 460

His Tyr Gly Gln Cys Gly Gly Ile Gly Tyr Ser Gly Pro Thr Val Cys
465                 470                 475                 480

Ala Ser Gly Thr Thr Cys Gln Val Leu Asn Pro Tyr Tyr Ser Gln Cys
                485                 490                 495

Leu

<210> SEQ ID NO 19
<211> LENGTH: 1491
<212> TYPE: DNA
<213> ORGANISM: Hypocrea jecorina
<220> FEATURE:
<221> NAME/KEY: CDS
<222> LOCATION: (1)..(1491)

<400> SEQUENCE: 19 cag tcg gcc tgc act ctc caa tcg gag act cac ccg cct ctg aca tgg      48
Gln Ser Ala Cys Thr Leu Gln Ser Glu Thr His Pro Pro Leu Thr Trp
1               5                   10                  15 cag aaa tgc tcg tct ggt ggc act tgc act caa cag aca ggc tcc gtg      96
Gln Lys Cys Ser Ser Gly Gly Thr Cys Thr Gln Gln Thr Gly Ser Val
            20                  25                  30 gtc atc gac gcc aac tgg cgc tgg act cac gct acg aac agc agc acg     144
Val Ile Asp Ala Asn Trp Arg Trp Thr His Ala Thr Asn Ser Ser Thr
        35                  40                  45 aac tgc tac gat ggc aac act tgg agc tcg acc cta tgt cct gac aac     192
Asn Cys Tyr Asp Gly Asn Thr Trp Ser Ser Thr Leu Cys Pro Asp Asn
    50                  55                  60 gag acc tgc gcg aag aac tgc tgt ctg gac ggt gcc gcc tac gcg tcc     240
Glu Thr Cys Ala Lys Asn Cys Cys Leu Asp Gly Ala Ala Tyr Ala Ser
65                  70                  75                  80 acg tac gga gtt acc acg agc ggt aac agc ctc tcc att ggc ttt gtc     288
Thr Tyr Gly Val Thr Thr Ser Gly Asn Ser Leu Ser Ile Gly Phe Val
                85                  90                  95 acc cag tct gcg cag aag aac gtt ggc gct cgc ctt tac ctt atg gcg     336
Thr Gln Ser Ala Gln Lys Asn Val Gly Ala Arg Leu Tyr Leu Met Ala
            100                 105                 110 agc gac acg acc tac cag gaa ttc acc ctg ctt ggc aac gag ttc tct     384
Ser Asp Thr Thr Tyr Gln Glu Phe Thr Leu Leu Gly Asn Glu Phe Ser
        115                 120                 125 ttc gat gtt gat gtt tcg cag ctg ccg tgc ggc ttg aac gga gct ctc     432
Phe Asp Val Asp Val Ser Gln Leu Pro Cys Gly Leu Asn Gly Ala Leu
    130                 135                 140 tac ttc gtg tcc atg gac gcg gat ggt ggc gtg agc aag tat ccc acc     480
Tyr Phe Val Ser Met Asp Ala Asp Gly Gly Val Ser Lys Tyr Pro Thr
145                 150                 155                 160 aac acc gct ggc gcc aag tac ggc acg ggg tac tgt gac agc cag tgt     528
Asn Thr Ala Gly Ala Lys Tyr Gly Thr Gly Tyr Cys Asp Ser Gln Cys
                165                 170                 175
```

```
ccc cgc gat ctg aag ttc atc aat ggc cag gcc aac gtt gag ggc tgg       576
Pro Arg Asp Leu Lys Phe Ile Asn Gly Gln Ala Asn Val Glu Gly Trp
            180                 185                 190 gag ccg tca tcc aac aac gcg aac acg ggc att gga gga cac gga agc       624
Glu Pro Ser Ser Asn Asn Ala Asn Thr Gly Ile Gly Gly His Gly Ser
        195                 200                 205 tgc tgc tct gag atg gat atc tgg gag gcc aac tcc atc tcc gag gct       672
Cys Cys Ser Glu Met Asp Ile Trp Glu Ala Asn Ser Ile Ser Glu Ala
210                 215                 220 ctt acc ccc cac cct tgc acg act gtc ggc cag gag atc tgc gag ggt       720
Leu Thr Pro His Pro Cys Thr Thr Val Gly Gln Glu Ile Cys Glu Gly
225                 230                 235                 240 gat ggg tgc ggc gga act tac tcc gat aac aga tat ggc ggc act tgc       768
Asp Gly Cys Gly Gly Thr Tyr Ser Asp Asn Arg Tyr Gly Gly Thr Cys
                245                 250                 255 gat ccc gat ggc tgc gac tgg aac cca tac cgc ctg ggc aac acc agc       816
Asp Pro Asp Gly Cys Asp Trp Asn Pro Tyr Arg Leu Gly Asn Thr Ser
        260                 265                 270 ttc tac ggc cct ggc tca agc ttt acc ctc gat acc acc aag aaa ttg       864
Phe Tyr Gly Pro Gly Ser Ser Phe Thr Leu Asp Thr Thr Lys Lys Leu
        275                 280                 285 acc gtt gtc acc cag ttc gag acg tcg ggt gcc atc aac cga tac tat       912
Thr Val Val Thr Gln Phe Glu Thr Ser Gly Ala Ile Asn Arg Tyr Tyr
290                 295                 300 gtc cag aat ggc gtc act ttc cag cag ccc aac gcc gag ctt ggt agt       960
Val Gln Asn Gly Val Thr Phe Gln Gln Pro Asn Ala Glu Leu Gly Ser
305                 310                 315                 320 tac tct ggc aac gag ctc aac gat gat tac tgc aca gct gag gag gca      1008
Tyr Ser Gly Asn Glu Leu Asn Asp Asp Tyr Cys Thr Ala Glu Glu Ala
                325                 330                 335 gaa ttc ggc gga tcc tct ttc tca gac aag ggc ggc ctg act cag ttc      1056
Glu Phe Gly Gly Ser Ser Phe Ser Asp Lys Gly Gly Leu Thr Gln Phe
        340                 345                 350 aag aag gct ctc tct ggc ggc atg gtt ctg gtc atg agt ctg tgg gat      1104
Lys Lys Ala Leu Ser Gly Gly Met Val Leu Val Met Ser Leu Trp Asp
                355                 360                 365 gat tac tac gcc aac atg ctg tgg ctg gac tcc acc tac ccg aca aac      1152
Asp Tyr Tyr Ala Asn Met Leu Trp Leu Asp Ser Thr Tyr Pro Thr Asn
370                 375                 380 gag acc tcc tcc aca ccc ggt gcc gtg cgc gga agc tgc tcc acc agc      1200
Glu Thr Ser Ser Thr Pro Gly Ala Val Arg Gly Ser Cys Ser Thr Ser
385                 390                 395                 400 tcc ggt gtc cct gct cag gtc gaa tct cag tct ccc aac gcc aag gtc      1248
Ser Gly Val Pro Ala Gln Val Glu Ser Gln Ser Pro Asn Ala Lys Val
                405                 410                 415 acc ttc tcc aac atc aag ttc gga ccc att ggc agc acc ggc aac cct      1296
Thr Phe Ser Asn Ile Lys Phe Gly Pro Ile Gly Ser Thr Gly Asn Pro
            420                 425                 430 agc ggc ggc aac cct ccc ggc gga aac ccg cct ggc acc acc acc acc      1344
Ser Gly Gly Asn Pro Pro Gly Gly Asn Pro Pro Gly Thr Thr Thr Thr
                435                 440                 445 cgc cgc cca gcc act acc act gga agc tct ccc gga cct acc cag tct      1392
Arg Arg Pro Ala Thr Thr Thr Gly Ser Ser Pro Gly Pro Thr Gln Ser
450                 455                 460 cac tac ggc cag tgc ggc ggt att ggc tac agc ggc ccc acg gtc tgc      1440
His Tyr Gly Gln Cys Gly Gly Ile Gly Tyr Ser Gly Pro Thr Val Cys
465                 470                 475                 480 gcc agc ggc aca act tgc cag gtc ctg aac cct tac tac tct cag tgc      1488
Ala Ser Gly Thr Thr Cys Gln Val Leu Asn Pro Tyr Tyr Ser Gln Cys
                485                 490                 495
``` ctg        1491
Leu

<210> SEQ ID NO 20
<211> LENGTH: 497
<212> TYPE: PRT
<213> ORGANISM: Hypocrea jecorina

<400> SEQUENCE: 20

Gln Ser Ala Cys Thr Leu Gln Ser Glu Thr His Pro Pro Leu Thr Trp
1               5                   10                  15

Gln Lys Cys Ser Ser Gly Gly Thr Cys Thr Gln Gln Thr Gly Ser Val
            20                  25                  30

Val Ile Asp Ala Asn Trp Arg Trp Thr His Ala Thr Asn Ser Ser Thr
        35                  40                  45

Asn Cys Tyr Asp Gly Asn Thr Trp Ser Ser Thr Leu Cys Pro Asp Asn
    50                  55                  60

Glu Thr Cys Ala Lys Asn Cys Cys Leu Asp Gly Ala Ala Tyr Ala Ser
65                  70                  75                  80

Thr Tyr Gly Val Thr Thr Ser Gly Asn Ser Leu Ser Ile Gly Phe Val
                85                  90                  95

Thr Gln Ser Ala Gln Lys Asn Val Gly Ala Arg Leu Tyr Leu Met Ala
            100                 105                 110

Ser Asp Thr Thr Tyr Gln Glu Phe Thr Leu Leu Gly Asn Glu Phe Ser
        115                 120                 125

Phe Asp Val Asp Val Ser Gln Leu Pro Cys Gly Leu Asn Gly Ala Leu
    130                 135                 140

Tyr Phe Val Ser Met Asp Ala Asp Gly Gly Val Ser Lys Tyr Pro Thr
145                 150                 155                 160

Asn Thr Ala Gly Ala Lys Tyr Gly Thr Gly Tyr Cys Asp Ser Gln Cys
                165                 170                 175

Pro Arg Asp Leu Lys Phe Ile Asn Gly Gln Ala Asn Val Glu Gly Trp
            180                 185                 190

Glu Pro Ser Ser Asn Asn Ala Asn Thr Gly Ile Gly Gly His Gly Ser
        195                 200                 205

Cys Cys Ser Glu Met Asp Ile Trp Glu Ala Asn Ser Ile Ser Glu Ala
    210                 215                 220

Leu Thr Pro His Pro Cys Thr Thr Val Gly Gln Glu Ile Cys Glu Gly
225                 230                 235                 240

Asp Gly Cys Gly Gly Thr Tyr Ser Asp Asn Arg Tyr Gly Gly Thr Cys
                245                 250                 255

Asp Pro Asp Gly Cys Asp Trp Asn Pro Tyr Arg Leu Gly Asn Thr Ser
            260                 265                 270

Phe Tyr Gly Pro Gly Ser Ser Phe Thr Leu Asp Thr Thr Lys Lys Leu
        275                 280                 285

Thr Val Val Thr Gln Phe Glu Thr Ser Gly Ala Ile Asn Arg Tyr Tyr
    290                 295                 300

Val Gln Asn Gly Val Thr Phe Gln Gln Pro Asn Ala Glu Leu Gly Ser
305                 310                 315                 320

Tyr Ser Gly Asn Glu Leu Asn Asp Asp Tyr Cys Thr Ala Glu Glu Ala
                325                 330                 335

Glu Phe Gly Gly Ser Ser Phe Ser Asp Lys Gly Gly Leu Thr Gln Phe
            340                 345                 350

Lys Lys Ala Leu Ser Gly Gly Met Val Leu Val Met Ser Leu Trp Asp
        355                 360                 365

-continued

```
Asp Tyr Tyr Ala Asn Met Leu Trp Leu Asp Ser Thr Tyr Pro Thr Asn
    370                 375                 380

Glu Thr Ser Ser Thr Pro Gly Ala Val Arg Gly Ser Cys Ser Thr Ser
385                 390                 395                 400

Ser Gly Val Pro Ala Gln Val Glu Ser Gln Ser Pro Asn Ala Lys Val
                405                 410                 415

Thr Phe Ser Asn Ile Lys Phe Gly Pro Ile Gly Ser Thr Gly Asn Pro
            420                 425                 430

Ser Gly Gly Asn Pro Pro Gly Gly Asn Pro Pro Gly Thr Thr Thr Thr
        435                 440                 445

Arg Arg Pro Ala Thr Thr Thr Gly Ser Ser Pro Gly Pro Thr Gln Ser
    450                 455                 460

His Tyr Gly Gln Cys Gly Gly Ile Gly Tyr Ser Gly Pro Thr Val Cys
465                 470                 475                 480

Ala Ser Gly Thr Thr Cys Gln Val Leu Asn Pro Tyr Tyr Ser Gln Cys
                485                 490                 495

Leu
```

<210> SEQ ID NO 21
<211> LENGTH: 1491
<212> TYPE: DNA
<213> ORGANISM: Hypocrea jecorina
<220> FEATURE:
<221> NAME/KEY: CDS
<222> LOCATION: (1)..(1491)

<400> SEQUENCE: 21

```
cag tcg gcc tgc act ctc caa tcg gag act cac ccg cct ctg aca tgg      48
Gln Ser Ala Cys Thr Leu Gln Ser Glu Thr His Pro Pro Leu Thr Trp
1               5                   10                  15 cag aaa tgc tcg tct ggt ggc act tgc act caa cag aca ggc tcc gtg      96
Gln Lys Cys Ser Ser Gly Gly Thr Cys Thr Gln Gln Thr Gly Ser Val
            20                  25                  30 gtc atc gac gcc aac tgg cgc tgg act cac gct acg aac agc agc acg     144
Val Ile Asp Ala Asn Trp Arg Trp Thr His Ala Thr Asn Ser Ser Thr
        35                  40                  45 aac tgc tac gat ggc aac act tgg agc tcg acc cta tgt cct gac aac     192
Asn Cys Tyr Asp Gly Asn Thr Trp Ser Ser Thr Leu Cys Pro Asp Asn
    50                  55                  60 gag acc tgc gcg aag aac tgc tgt ctg gac ggt gcc gcc tac gcg tcc     240
Glu Thr Cys Ala Lys Asn Cys Cys Leu Asp Gly Ala Ala Tyr Ala Ser
65                  70                  75                  80 acg tac gga gtt acc acg agc ggt aac agc ctc tcc att ggc ttt gtc     288
Thr Tyr Gly Val Thr Thr Ser Gly Asn Ser Leu Ser Ile Gly Phe Val
                85                  90                  95 acc cag tct gcg cag aag aac gtt ggc gct cgc ctt tac ctt atg gcg     336
Thr Gln Ser Ala Gln Lys Asn Val Gly Ala Arg Leu Tyr Leu Met Ala
            100                 105                 110 agc gac acg acc tac cag gaa ttc acc ctg ctt ggc aac gag ttc tct     384
Ser Asp Thr Thr Tyr Gln Glu Phe Thr Leu Leu Gly Asn Glu Phe Ser
        115                 120                 125 ttc gat gtt gat gtt tcg cag ctg ccg tgc ggc ttg aac gga gct ctc     432
Phe Asp Val Asp Val Ser Gln Leu Pro Cys Gly Leu Asn Gly Ala Leu
    130                 135                 140 tac ttc gtg tcc atg gac gcg gat ggt ggc gtg agc aag tat ccc acc     480
Tyr Phe Val Ser Met Asp Ala Asp Gly Gly Val Ser Lys Tyr Pro Thr
145                 150                 155                 160 aac acc gct ggc gcc aag tac ggc acg ggg tac tgt gac agc cag tgt     528
Asn Thr Ala Gly Ala Lys Tyr Gly Thr Gly Tyr Cys Asp Ser Gln Cys
                165                 170                 175
```

```
ccc cgc gat ctg aag ttc atc aat ggc cag gcc aac gtt gag ggc tgg      576
Pro Arg Asp Leu Lys Phe Ile Asn Gly Gln Ala Asn Val Glu Gly Trp
        180                 185                 190 gag ccg tca tcc aac aac gcg aac acg ggc att gga gga cac gga agc      624
Glu Pro Ser Ser Asn Asn Ala Asn Thr Gly Ile Gly Gly His Gly Ser
            195                 200                 205 tgc tgc tct gag atg gat atc tgg gag gcc aac tcc atc tcc gag gct      672
Cys Cys Ser Glu Met Asp Ile Trp Glu Ala Asn Ser Ile Ser Glu Ala
    210                 215                 220 ctt acc ccc cac cct tgc acg act gtc ggc cag gag atc tgc gag ggt      720
Leu Thr Pro His Pro Cys Thr Thr Val Gly Gln Glu Ile Cys Glu Gly
225                 230                 235                 240 gat ggg tgc ggc gga act tac tcc gat aac aga tat ggc ggc act tgc      768
Asp Gly Cys Gly Gly Thr Tyr Ser Asp Asn Arg Tyr Gly Gly Thr Cys
                245                 250                 255 gat ccc gat ggc tgc gac tgg aac cca tac cgc ctg ggc aac acc agc      816
Asp Pro Asp Gly Cys Asp Trp Asn Pro Tyr Arg Leu Gly Asn Thr Ser
            260                 265                 270 ttc tac ggc cct ggc tca agc ttt acc ctc gat acc acc aag aaa ttg      864
Phe Tyr Gly Pro Gly Ser Ser Phe Thr Leu Asp Thr Thr Lys Lys Leu
        275                 280                 285 acc gtt gtc acc cag ttc gag acg tcg ggt gcc atc aac cga tac tat      912
Thr Val Val Thr Gln Phe Glu Thr Ser Gly Ala Ile Asn Arg Tyr Tyr
    290                 295                 300 gtc cag aat ggc gtc act ttc cag cag ccc aac gcc gag ctt ggt agt      960
Val Gln Asn Gly Val Thr Phe Gln Gln Pro Asn Ala Glu Leu Gly Ser
305                 310                 315                 320 tac tct ggc aac gag ctc aac gat gat tac tgc aca gct gag gag gca     1008
Tyr Ser Gly Asn Glu Leu Asn Asp Asp Tyr Cys Thr Ala Glu Glu Ala
                325                 330                 335 gaa ttc ggc gga tcc tct ttc tca gac aag ggc ggc ctg act cag ttc     1056
Glu Phe Gly Gly Ser Ser Phe Ser Asp Lys Gly Gly Leu Thr Gln Phe
            340                 345                 350 aag aag gct acc tct ggc ggc atg gtt ctg gtc atg agt ctg tgg gat     1104
Lys Lys Ala Thr Ser Gly Gly Met Val Leu Val Met Ser Leu Trp Asp
        355                 360                 365 gat tac tac gcc aac atg ctg tgg ctg gac tcc acc tac ccg aca aac     1152
Asp Tyr Tyr Ala Asn Met Leu Trp Leu Asp Ser Thr Tyr Pro Thr Asn
    370                 375                 380 gag acc tcc tcc aca ccc ggt gcc gtg cgc gga agc tgc tcc acc agc     1200
Glu Thr Ser Ser Thr Pro Gly Ala Val Arg Gly Ser Cys Ser Thr Ser
385                 390                 395                 400 tcc ggt gtc cct gct cag gtc gaa tct cag tct ccc aac gcc aag gtc     1248
Ser Gly Val Pro Ala Gln Val Glu Ser Gln Ser Pro Asn Ala Lys Val
                405                 410                 415 acc ttc tcc aac atc aag ttc gga ccc att ggc agc acc ttc aac cct     1296
Thr Phe Ser Asn Ile Lys Phe Gly Pro Ile Gly Ser Thr Phe Asn Pro
            420                 425                 430 agc ggc ggc aac cct ccc ggc gga aac ccg cct ggc acc acc acc acc     1344
Ser Gly Gly Asn Pro Pro Gly Gly Asn Pro Pro Gly Thr Thr Thr Thr
        435                 440                 445 cgc cgc cca gcc act acc act gga agc tct ccc gga cct acc cag tct     1392
Arg Arg Pro Ala Thr Thr Thr Gly Ser Ser Pro Gly Pro Thr Gln Ser
    450                 455                 460 cac tac ggc cag tgc ggc ggt att ggc tac agc ggc ccc acg gtc tgc     1440
His Tyr Gly Gln Cys Gly Gly Ile Gly Tyr Ser Gly Pro Thr Val Cys
465                 470                 475                 480 gcc agc ggc aca act tgc cag gtc ctg aac cct tac tac tct cag tgc     1488
Ala Ser Gly Thr Thr Cys Gln Val Leu Asn Pro Tyr Tyr Ser Gln Cys
                485                 490                 495
```

```
ctg                                                                        1491
Leu
```

<210> SEQ ID NO 22
<211> LENGTH: 497
<212> TYPE: PRT
<213> ORGANISM: Hypocrea jecorina

<400> SEQUENCE: 22

```
Gln Ser Ala Cys Thr Leu Gln Ser Glu Thr His Pro Pro Leu Thr Trp
 1               5                  10                  15

Gln Lys Cys Ser Ser Gly Gly Thr Cys Thr Gln Thr Gly Ser Val
            20                  25                  30

Val Ile Asp Ala Asn Trp Arg Trp Thr His Ala Thr Asn Ser Ser Thr
        35                  40                  45

Asn Cys Tyr Asp Gly Asn Thr Trp Ser Ser Thr Leu Cys Pro Asp Asn
    50                  55                  60

Glu Thr Cys Ala Lys Asn Cys Cys Leu Asp Gly Ala Ala Tyr Ala Ser
65                  70                  75                  80

Thr Tyr Gly Val Thr Thr Ser Gly Asn Ser Leu Ser Ile Gly Phe Val
                85                  90                  95

Thr Gln Ser Ala Gln Lys Asn Val Gly Ala Arg Leu Tyr Leu Met Ala
            100                 105                 110

Ser Asp Thr Thr Tyr Gln Glu Phe Thr Leu Leu Gly Asn Glu Phe Ser
        115                 120                 125

Phe Asp Val Asp Val Ser Gln Leu Pro Cys Gly Leu Asn Gly Ala Leu
    130                 135                 140

Tyr Phe Val Ser Met Asp Ala Asp Gly Gly Val Ser Lys Tyr Pro Thr
145                 150                 155                 160

Asn Thr Ala Gly Ala Lys Tyr Gly Thr Gly Tyr Cys Asp Ser Gln Cys
                165                 170                 175

Pro Arg Asp Leu Lys Phe Ile Asn Gly Gln Ala Asn Val Glu Gly Trp
            180                 185                 190

Glu Pro Ser Ser Asn Asn Ala Asn Thr Gly Ile Gly Gly His Gly Ser
        195                 200                 205

Cys Cys Ser Glu Met Asp Ile Trp Glu Ala Asn Ser Ile Ser Glu Ala
    210                 215                 220

Leu Thr Pro His Pro Cys Thr Thr Val Gly Gln Glu Ile Cys Glu Gly
225                 230                 235                 240

Asp Gly Cys Gly Gly Thr Tyr Ser Asp Asn Arg Tyr Gly Gly Thr Cys
                245                 250                 255

Asp Pro Asp Gly Cys Asp Trp Asn Pro Tyr Arg Leu Gly Asn Thr Ser
            260                 265                 270

Phe Tyr Gly Pro Gly Ser Ser Phe Thr Leu Asp Thr Thr Lys Lys Leu
        275                 280                 285

Thr Val Val Thr Gln Phe Glu Thr Ser Gly Ala Ile Asn Arg Tyr Tyr
290                 295                 300

Val Gln Asn Gly Val Thr Phe Gln Gln Pro Asn Ala Glu Leu Gly Ser
305                 310                 315                 320

Tyr Ser Gly Asn Glu Leu Asn Asp Asp Tyr Cys Thr Ala Glu Glu Ala
                325                 330                 335

Glu Phe Gly Gly Ser Ser Phe Ser Asp Lys Gly Gly Leu Thr Gln Phe
            340                 345                 350

Lys Lys Ala Thr Ser Gly Gly Met Val Leu Val Met Ser Leu Trp Asp
        355                 360                 365
```

```
Asp Tyr Tyr Ala Asn Met Leu Trp Leu Asp Ser Thr Tyr Pro Thr Asn
    370                 375                 380

Glu Thr Ser Ser Thr Pro Gly Ala Val Arg Gly Ser Cys Ser Thr Ser
385                 390                 395                 400

Ser Gly Val Pro Ala Gln Val Glu Ser Gln Ser Pro Asn Ala Lys Val
                405                 410                 415

Thr Phe Ser Asn Ile Lys Phe Gly Pro Ile Gly Ser Thr Phe Asn Pro
            420                 425                 430

Ser Gly Gly Asn Pro Pro Gly Gly Asn Pro Pro Gly Thr Thr Thr Thr
        435                 440                 445

Arg Arg Pro Ala Thr Thr Thr Gly Ser Ser Pro Gly Pro Thr Gln Ser
    450                 455                 460

His Tyr Gly Gln Cys Gly Gly Ile Gly Tyr Ser Gly Pro Thr Val Cys
465                 470                 475                 480

Ala Ser Gly Thr Thr Cys Gln Val Leu Asn Pro Tyr Tyr Ser Gln Cys
                485                 490                 495

Leu

<210> SEQ ID NO 23
<211> LENGTH: 1491
<212> TYPE: DNA
<213> ORGANISM: Hypocrea jecorina
<220> FEATURE:
<221> NAME/KEY: CDS
<222> LOCATION: (1)..(1491)

<400> SEQUENCE: 23 cag tcg gcc tgc act ctc caa tcg gag act cac ccg cct ctg aca tgg     48
Gln Ser Ala Cys Thr Leu Gln Ser Glu Thr His Pro Pro Leu Thr Trp
1               5                   10                  15 cag aaa tgc tcg tct ggt ggc act tgc act caa cag aca ggc tcc gtg     96
Gln Lys Cys Ser Ser Gly Gly Thr Cys Thr Gln Gln Thr Gly Ser Val
            20                  25                  30 gtc atc gac gcc aac tgg cgc tgg act cac gct acg aac agc agc acg    144
Val Ile Asp Ala Asn Trp Arg Trp Thr His Ala Thr Asn Ser Ser Thr
        35                  40                  45 aac tgc tac gat ggc aac act tgg agc tcg acc cta tgt cct gac aac    192
Asn Cys Tyr Asp Gly Asn Thr Trp Ser Ser Thr Leu Cys Pro Asp Asn
    50                  55                  60 gag acc tgc gcg aag aac tgc tgt ctg gac ggt gcc gcc tac gcg tcc    240
Glu Thr Cys Ala Lys Asn Cys Cys Leu Asp Gly Ala Ala Tyr Ala Ser
65                  70                  75                  80 acg tac gga gtt acc acg agc ggt aac agc ctc tcc att ggc ttt gtc    288
Thr Tyr Gly Val Thr Thr Ser Gly Asn Ser Leu Ser Ile Gly Phe Val
                85                  90                  95 acc cag tct gcg cag aag aac gtt ggc gct cgc ctt tac ctt atg gcg    336
Thr Gln Ser Ala Gln Lys Asn Val Gly Ala Arg Leu Tyr Leu Met Ala
            100                 105                 110 agc gac acg acc tac cag gaa ttc acc ctg ctt ggc aac gag ttc tct    384
Ser Asp Thr Thr Tyr Gln Glu Phe Thr Leu Leu Gly Asn Glu Phe Ser
        115                 120                 125 ttc gat gtt gat gtt tcg cag ctg ccg tgc ggc ttg aac gga gct ctc    432
Phe Asp Val Asp Val Ser Gln Leu Pro Cys Gly Leu Asn Gly Ala Leu
    130                 135                 140 tac ttc gtg tcc atg gac gcg gat ggt ggc gtg agc aag tat ccc acc    480
Tyr Phe Val Ser Met Asp Ala Asp Gly Gly Val Ser Lys Tyr Pro Thr
145                 150                 155                 160 aac acc gct ggc gcc aag tac ggc acg ggg tac tgt gac agc cag tgt    528
Asn Thr Ala Gly Ala Lys Tyr Gly Thr Gly Tyr Cys Asp Ser Gln Cys
```

-continued

|   |   |   |   |   |   |   |   |   |   |   |   |   |   |   |   |     |
|---|---|---|---|---|---|---|---|---|---|---|---|---|---|---|---|-----|
|   |   |   |   | 165 |   |   |   | 170 |   |   |   | 175 |   |   |   |     |
| ccc | cgc | gat | ctg | aag | ttc | atc | aat | ggc | cag | gcc | aac | gtt | gag | ggc | tgg | 576 |
| Pro | Arg | Asp | Leu | Lys | Phe | Ile | Asn | Gly | Gln | Ala | Asn | Val | Glu | Gly | Trp |     |
|   |   |   | 180 |   |   |   |   | 185 |   |   |   |   | 190 |   |   |     |
| gag | ccg | tca | tcc | aac | aac | gcg | aac | acg | ggc | att | gga | gga | cac | gga | agc | 624 |
| Glu | Pro | Ser | Ser | Asn | Asn | Ala | Asn | Thr | Gly | Ile | Gly | Gly | His | Gly | Ser |     |
|   |   | 195 |   |   |   |   | 200 |   |   |   |   | 205 |   |   |   |     |
| tgc | tgc | tct | gag | atg | gat | atc | tgg | gag | gcc | aac | tcc | atc | tcc | gag | gct | 672 |
| Cys | Cys | Ser | Glu | Met | Asp | Ile | Trp | Glu | Ala | Asn | Ser | Ile | Ser | Glu | Ala |     |
|   | 210 |   |   |   |   | 215 |   |   |   |   | 220 |   |   |   |   |     |
| ctt | acc | ccc | cac | cct | tgc | acg | act | gtc | ggc | cag | gag | atc | tgc | gag | ggt | 720 |
| Leu | Thr | Pro | His | Pro | Cys | Thr | Thr | Val | Gly | Gln | Glu | Ile | Cys | Glu | Gly |     |
| 225 |   |   |   |   | 230 |   |   |   |   | 235 |   |   |   |   | 240 |     |
| gat | ggg | tgc | ggc | gga | tgt | tac | tcc | gat | aac | aga | tat | ggc | ggc | act | tgc | 768 |
| Asp | Gly | Cys | Gly | Gly | Cys | Tyr | Ser | Asp | Asn | Arg | Tyr | Gly | Gly | Thr | Cys |     |
|   |   |   |   | 245 |   |   |   |   | 250 |   |   |   |   | 255 |   |     |
| gat | ccc | gat | ggc | tgc | gac | tgg | aac | cca | tac | cgc | ctg | ggc | aac | acc | agc | 816 |
| Asp | Pro | Asp | Gly | Cys | Asp | Trp | Asn | Pro | Tyr | Arg | Leu | Gly | Asn | Thr | Ser |     |
|   |   |   | 260 |   |   |   |   | 265 |   |   |   |   | 270 |   |   |     |
| ttc | tac | ggc | cct | ggc | tca | agc | ttt | acc | ctc | gat | acc | acc | aag | aaa | ttg | 864 |
| Phe | Tyr | Gly | Pro | Gly | Ser | Ser | Phe | Thr | Leu | Asp | Thr | Thr | Lys | Lys | Leu |     |
|   |   | 275 |   |   |   |   | 280 |   |   |   |   | 285 |   |   |   |     |
| acc | gtt | gtc | acc | cag | ttc | gag | acg | tcg | ggt | gcc | atc | aac | cga | tac | tat | 912 |
| Thr | Val | Val | Thr | Gln | Phe | Glu | Thr | Ser | Gly | Ala | Ile | Asn | Arg | Tyr | Tyr |     |
|   | 290 |   |   |   |   | 295 |   |   |   |   | 300 |   |   |   |   |     |
| gtc | cag | aat | ggc | gtc | act | ttc | cag | cag | ccc | aac | gcc | gag | ctt | ggt | agt | 960 |
| Val | Gln | Asn | Gly | Val | Thr | Phe | Gln | Gln | Pro | Asn | Ala | Glu | Leu | Gly | Ser |     |
| 305 |   |   |   |   | 310 |   |   |   |   | 315 |   |   |   |   | 320 |     |
| tac | tct | ggc | aac | gag | ctc | aac | gat | gat | tac | tgc | aca | gct | gag | gag | gca | 1008 |
| Tyr | Ser | Gly | Asn | Glu | Leu | Asn | Asp | Asp | Tyr | Cys | Thr | Ala | Glu | Glu | Ala |     |
|   |   |   |   | 325 |   |   |   |   | 330 |   |   |   |   | 335 |   |     |
| gaa | ttc | ggc | gga | tcc | tct | ttc | tca | gac | aag | ggc | ggc | ctg | act | cag | ttc | 1056 |
| Glu | Phe | Gly | Gly | Ser | Ser | Phe | Ser | Asp | Lys | Gly | Gly | Leu | Thr | Gln | Phe |     |
|   |   |   | 340 |   |   |   |   | 345 |   |   |   |   | 350 |   |   |     |
| aag | aag | gct | acc | tct | ggc | ggc | atg | gtt | ctg | gtc | atg | agt | ctg | tgg | gat | 1104 |
| Lys | Lys | Ala | Thr | Ser | Gly | Gly | Met | Val | Leu | Val | Met | Ser | Leu | Trp | Asp |     |
|   |   | 355 |   |   |   |   | 360 |   |   |   |   | 365 |   |   |   |     |
| gat | tac | tgc | gcc | aac | atg | ctg | tgg | ctg | gac | tcc | acc | tac | ccg | aca | aac | 1152 |
| Asp | Tyr | Cys | Ala | Asn | Met | Leu | Trp | Leu | Asp | Ser | Thr | Tyr | Pro | Thr | Asn |     |
|   | 370 |   |   |   |   | 375 |   |   |   |   | 380 |   |   |   |   |     |
| gag | acc | tcc | tcc | aca | ccc | ggt | gcc | gtg | cgc | gga | agc | tgc | tcc | acc | agc | 1200 |
| Glu | Thr | Ser | Ser | Thr | Pro | Gly | Ala | Val | Arg | Gly | Ser | Cys | Ser | Thr | Ser |     |
| 385 |   |   |   |   | 390 |   |   |   |   | 395 |   |   |   |   | 400 |     |
| tcc | ggt | gtc | cct | gct | cag | gtc | gaa | tct | cag | tct | ccc | aac | gcc | aag | gtc | 1248 |
| Ser | Gly | Val | Pro | Ala | Gln | Val | Glu | Ser | Gln | Ser | Pro | Asn | Ala | Lys | Val |     |
|   |   |   |   | 405 |   |   |   |   | 410 |   |   |   |   | 415 |   |     |
| acc | ttc | tcc | aac | atc | aag | ttc | gga | ccc | att | ggc | agc | acc | ggc | aac | cct | 1296 |
| Thr | Phe | Ser | Asn | Ile | Lys | Phe | Gly | Pro | Ile | Gly | Ser | Thr | Gly | Asn | Pro |     |
|   |   |   | 420 |   |   |   |   | 425 |   |   |   |   | 430 |   |   |     |
| agc | ggc | ggc | aac | cct | ccc | gga | gga | aac | ccg | cct | ggc | acc | acc | acc | acc | 1344 |
| Ser | Gly | Gly | Asn | Pro | Pro | Gly | Gly | Asn | Pro | Pro | Gly | Thr | Thr | Thr | Thr |     |
|   |   | 435 |   |   |   |   | 440 |   |   |   |   | 445 |   |   |   |     |
| cgc | cgc | cca | gcc | act | acc | act | gga | agc | tct | ccc | gga | cct | acc | cag | tct | 1392 |
| Arg | Arg | Pro | Ala | Thr | Thr | Thr | Gly | Ser | Ser | Pro | Gly | Pro | Thr | Gln | Ser |     |
|   | 450 |   |   |   |   | 455 |   |   |   |   | 460 |   |   |   |   |     |
| cac | tac | ggc | cag | tgc | ggc | ggt | att | ggc | tac | agc | ggc | ccc | acg | gtc | tgc | 1440 |
| His | Tyr | Gly | Gln | Cys | Gly | Gly | Ile | Gly | Tyr | Ser | Gly | Pro | Thr | Val | Cys |     |
| 465 |   |   |   |   | 470 |   |   |   |   | 475 |   |   |   |   | 480 |     |
| gcc | agc | ggc | aca | act | tgc | cag | gtc | ctg | aac | cct | tac | tac | tct | cag | tgc | 1488 |
| Ala | Ser | Gly | Thr | Thr | Cys | Gln | Val | Leu | Asn | Pro | Tyr | Tyr | Ser | Gln | Cys |     |

```
                      485         490         495
ctg                                                    1491
Leu <210> SEQ ID NO 24
<211> LENGTH: 497
<212> TYPE: PRT
<213> ORGANISM: Hypocrea jecorina

<400> SEQUENCE: 24

Gln Ser Ala Cys Thr Leu Gln Ser Glu Thr His Pro Pro Leu Thr Trp
1               5                   10                  15

Gln Lys Cys Ser Ser Gly Gly Thr Cys Thr Gln Gln Thr Gly Ser Val
            20                  25                  30

Val Ile Asp Ala Asn Trp Arg Trp Thr His Ala Thr Asn Ser Ser Thr
        35                  40                  45

Asn Cys Tyr Asp Gly Asn Thr Trp Ser Ser Thr Leu Cys Pro Asp Asn
    50                  55                  60

Glu Thr Cys Ala Lys Asn Cys Cys Leu Asp Gly Ala Ala Tyr Ala Ser
65                  70                  75                  80

Thr Tyr Gly Val Thr Thr Ser Gly Asn Ser Leu Ser Ile Gly Phe Val
                85                  90                  95

Thr Gln Ser Ala Gln Lys Asn Val Gly Ala Arg Leu Tyr Leu Met Ala
            100                 105                 110

Ser Asp Thr Thr Tyr Gln Glu Phe Thr Leu Leu Gly Asn Glu Phe Ser
        115                 120                 125

Phe Asp Val Asp Val Ser Gln Leu Pro Cys Gly Leu Asn Gly Ala Leu
    130                 135                 140

Tyr Phe Val Ser Met Asp Ala Asp Gly Gly Val Ser Lys Tyr Pro Thr
145                 150                 155                 160

Asn Thr Ala Gly Ala Lys Tyr Gly Thr Gly Tyr Cys Asp Ser Gln Cys
                165                 170                 175

Pro Arg Asp Leu Lys Phe Ile Asn Gly Gln Ala Asn Val Glu Gly Trp
            180                 185                 190

Glu Pro Ser Ser Asn Asn Ala Asn Thr Gly Ile Gly Gly His Gly Ser
        195                 200                 205

Cys Cys Ser Glu Met Asp Ile Trp Glu Ala Asn Ser Ile Ser Glu Ala
    210                 215                 220

Leu Thr Pro His Pro Cys Thr Thr Val Gly Gln Glu Ile Cys Glu Gly
225                 230                 235                 240

Asp Gly Cys Gly Gly Cys Tyr Ser Asp Asn Arg Tyr Gly Gly Thr Cys
                245                 250                 255

Asp Pro Asp Gly Cys Asp Trp Asn Pro Tyr Arg Leu Gly Asn Thr Ser
            260                 265                 270

Phe Tyr Gly Pro Gly Ser Ser Phe Thr Leu Asp Thr Thr Lys Lys Leu
        275                 280                 285

Thr Val Val Thr Gln Phe Glu Thr Ser Gly Ala Ile Asn Arg Tyr Tyr
    290                 295                 300

Val Gln Asn Gly Val Thr Phe Gln Gln Pro Asn Ala Glu Leu Gly Ser
305                 310                 315                 320

Tyr Ser Gly Asn Glu Leu Asn Asp Asp Tyr Cys Thr Ala Glu Glu Ala
                325                 330                 335

Glu Phe Gly Gly Ser Ser Phe Ser Asp Lys Gly Gly Leu Thr Gln Phe
            340                 345                 350

Lys Lys Ala Thr Ser Gly Gly Met Val Leu Val Met Ser Leu Trp Asp
```

```
                    355                 360                 365
Asp Tyr Cys Ala Asn Met Leu Trp Leu Asp Ser Thr Tyr Pro Thr Asn
    370                 375                 380

Glu Thr Ser Ser Thr Pro Gly Ala Val Arg Gly Ser Cys Ser Thr Ser
385                 390                 395                 400

Ser Gly Val Pro Ala Gln Val Glu Ser Gln Ser Pro Asn Ala Lys Val
                405                 410                 415

Thr Phe Ser Asn Ile Lys Phe Gly Pro Ile Gly Ser Thr Gly Asn Pro
                420                 425                 430

Ser Gly Gly Asn Pro Pro Gly Gly Asn Pro Pro Gly Thr Thr Thr
                435                 440                 445

Arg Arg Pro Ala Thr Thr Thr Gly Ser Ser Pro Gly Pro Thr Gln Ser
    450                 455                 460

His Tyr Gly Gln Cys Gly Gly Ile Gly Tyr Ser Gly Pro Thr Val Cys
465                 470                 475                 480

Ala Ser Gly Thr Thr Cys Gln Val Leu Asn Pro Tyr Tyr Ser Gln Cys
                485                 490                 495

Leu

<210> SEQ ID NO 25
<211> LENGTH: 1491
<212> TYPE: DNA
<213> ORGANISM: Hypocrea jecorina
<220> FEATURE:
<221> NAME/KEY: CDS
<222> LOCATION: (1)..(1491)

<400> SEQUENCE: 25 cag tcg gcc tgc act ctc caa tcg gag act cac ccg cct ctg aca tgg      48
Gln Ser Ala Cys Thr Leu Gln Ser Glu Thr His Pro Pro Leu Thr Trp
1               5                   10                  15 cag aaa tgc tcg tct ggt ggc act tgc act caa cag aca ggc tcc gtg      96
Gln Lys Cys Ser Ser Gly Gly Thr Cys Thr Gln Gln Thr Gly Ser Val
            20                  25                  30 gtc atc gac gcc aac tgg cgc tgg act cac gct acg aac agc agc acg     144
Val Ile Asp Ala Asn Trp Arg Trp Thr His Ala Thr Asn Ser Ser Thr
        35                  40                  45 aac tgc tac gat ggc aac act tgg agc tcg acc cta tgt cct gac aac     192
Asn Cys Tyr Asp Gly Asn Thr Trp Ser Ser Thr Leu Cys Pro Asp Asn
    50                  55                  60 gag acc tgc gcg aag aac tgc tgt ctg gac ggt gcc gcc tac gcg tcc     240
Glu Thr Cys Ala Lys Asn Cys Cys Leu Asp Gly Ala Ala Tyr Ala Ser
65                  70                  75                  80 acg tac gga gtt acc acg agc ggt aac agc ctc tcc att ggc ttt gtc     288
Thr Tyr Gly Val Thr Thr Ser Gly Asn Ser Leu Ser Ile Gly Phe Val
                85                  90                  95 acc cag tct gcg cag aag aac gtt ggc gct cgc ctt tac ctt atg gcg     336
Thr Gln Ser Ala Gln Lys Asn Val Gly Ala Arg Leu Tyr Leu Met Ala
            100                 105                 110 agc gac acg acc tac cag gaa ttc acc ctg ctt ggc aac gag ttc tct     384
Ser Asp Thr Thr Tyr Gln Glu Phe Thr Leu Leu Gly Asn Glu Phe Ser
        115                 120                 125 ttc gat gtt gat gtt tcg cag ctg ccg tgc ggc ttg aac gga gct ctc     432
Phe Asp Val Asp Val Ser Gln Leu Pro Cys Gly Leu Asn Gly Ala Leu
    130                 135                 140 tac ttc gtg tcc atg gac gcg gat ggt ggc gtg agc aag tat ccc acc     480
Tyr Phe Val Ser Met Asp Ala Asp Gly Gly Val Ser Lys Tyr Pro Thr
145                 150                 155                 160 aac acc gct ggc gcc aag tac ggc acg ggg tac tgt gac agc cag tgt     528
```

```
                Asn Thr Ala Gly Ala Lys Tyr Gly Thr Gly Tyr Cys Asp Ser Gln Cys
                                165                 170                 175 ccc cgc gat ctg aag ttc atc aat ggc cag gcc aac gtt gag ggc tgg           576
Pro Arg Asp Leu Lys Phe Ile Asn Gly Gln Ala Asn Val Glu Gly Trp
            180                 185                 190 gag ccg tca tcc aac aac gcg aac acg ggc att gga gga cac gga agc           624
Glu Pro Ser Ser Asn Asn Ala Asn Thr Gly Ile Gly Gly His Gly Ser
        195                 200                 205 tgc tgc tct gag atg gat atc tgg gag gcc aac tcc atc tcc gag gct           672
Cys Cys Ser Glu Met Asp Ile Trp Glu Ala Asn Ser Ile Ser Glu Ala
    210                 215                 220 ctt acc ccc cac cct tgc acg act gtc ggc cag gag atc tgc gag ggt           720
Leu Thr Pro His Pro Cys Thr Thr Val Gly Gln Glu Ile Cys Glu Gly
225                 230                 235                 240 gat ggg tgc ggc gga gct tac tcc gat aac gca gct ggc ggc act tgc           768
Asp Gly Cys Gly Gly Ala Tyr Ser Asp Asn Ala Ala Gly Gly Thr Cys
                245                 250                 255 gat ccc gat ggc tgc gac tgg aac cca tac cgc ctg ggc aac acc agc           816
Asp Pro Asp Gly Cys Asp Trp Asn Pro Tyr Arg Leu Gly Asn Thr Ser
            260                 265                 270 ttc tac ggc cct ggc tca agc ttt acc ctc gat acc acc aag aaa ttg           864
Phe Tyr Gly Pro Gly Ser Ser Phe Thr Leu Asp Thr Thr Lys Lys Leu
        275                 280                 285 acc gtt gtc acc cag ttc gag acg tcg ggt gcc atc aac cga tac tat           912
Thr Val Val Thr Gln Phe Glu Thr Ser Gly Ala Ile Asn Arg Tyr Tyr
    290                 295                 300 gtc cag aat ggc gtc act ttc cag cag ccc aac gcc gag ctt ggt agt           960
Val Gln Asn Gly Val Thr Phe Gln Gln Pro Asn Ala Glu Leu Gly Ser
305                 310                 315                 320 tac tct ggc aac gag ctc aac gat gat tac tgc aca gct gag gag gca          1008
Tyr Ser Gly Asn Glu Leu Asn Asp Asp Tyr Cys Thr Ala Glu Glu Ala
                325                 330                 335 gaa ttc ggc gga tcc tct ttc tca gac aag ggc ggc ctg act cag ttc          1056
Glu Phe Gly Gly Ser Ser Phe Ser Asp Lys Gly Gly Leu Thr Gln Phe
            340                 345                 350 aag aag gct acc tct ggc ggc atg gtt ctg gtc atg agt ctg tgg gat          1104
Lys Lys Ala Thr Ser Gly Gly Met Val Leu Val Met Ser Leu Trp Asp
        355                 360                 365 gat tac tac gcc aac atg ctg tgg ctg gac tcc acc tac ccg aca aac          1152
Asp Tyr Tyr Ala Asn Met Leu Trp Leu Asp Ser Thr Tyr Pro Thr Asn
    370                 375                 380 gag acc tcc tcc aca ccc ggt gcc gtg cgc gga agc tgc tcc acc agc          1200
Glu Thr Ser Ser Thr Pro Gly Ala Val Arg Gly Ser Cys Ser Thr Ser
385                 390                 395                 400 tcc ggt gtc cct gct cag gtc gaa tct cag tct ccc aac gcc aag gtc          1248
Ser Gly Val Pro Ala Gln Val Glu Ser Gln Ser Pro Asn Ala Lys Val
                405                 410                 415 acc ttc tcc aac atc aag ttc gga ccc att ggc agc acc ggc aac cct          1296
Thr Phe Ser Asn Ile Lys Phe Gly Pro Ile Gly Ser Thr Gly Asn Pro
            420                 425                 430 agc ggc ggc aac cct ccc ggc gga aac ccg cct ggc acc acc acc acc          1344
Ser Gly Gly Asn Pro Pro Gly Gly Asn Pro Pro Gly Thr Thr Thr Thr
        435                 440                 445 cgc cgc cca gcc act acc act gga agc tct ccc gga cct acc cag tct          1392
Arg Arg Pro Ala Thr Thr Thr Gly Ser Ser Pro Gly Pro Thr Gln Ser
    450                 455                 460 cac tac ggc cag tgc ggc ggt att ggc tac agc ggc ccc acg gtc tgc          1440
His Tyr Gly Gln Cys Gly Gly Ile Gly Tyr Ser Gly Pro Thr Val Cys
465                 470                 475                 480 gcc agc ggc aca act tgc cag gtc ctg aac cct tac tac tct cag tgc          1488
```

```
Ala Ser Gly Thr Thr Cys Gln Val Leu Asn Pro Tyr Tyr Ser Gln Cys
            485                 490                 495
ctg                                                                      1491
Leu <210> SEQ ID NO 26
<211> LENGTH: 497
<212> TYPE: PRT
<213> ORGANISM: Hypocrea jecorina

<400> SEQUENCE: 26

Gln Ser Ala Cys Thr Leu Gln Ser Glu Thr His Pro Pro Leu Thr Trp
1               5                   10                  15

Gln Lys Cys Ser Ser Gly Gly Thr Cys Thr Gln Gln Thr Gly Ser Val
                20                  25                  30

Val Ile Asp Ala Asn Trp Arg Trp Thr His Ala Thr Asn Ser Ser Thr
            35                  40                  45

Asn Cys Tyr Asp Gly Asn Thr Trp Ser Ser Thr Leu Cys Pro Asp Asn
        50                  55                  60

Glu Thr Cys Ala Lys Asn Cys Cys Leu Asp Gly Ala Ala Tyr Ala Ser
65                  70                  75                  80

Thr Tyr Gly Val Thr Thr Ser Gly Asn Ser Leu Ser Ile Gly Phe Val
                85                  90                  95

Thr Gln Ser Ala Gln Lys Asn Val Gly Ala Arg Leu Tyr Leu Met Ala
            100                 105                 110

Ser Asp Thr Thr Tyr Gln Glu Phe Thr Leu Leu Gly Asn Glu Phe Ser
        115                 120                 125

Phe Asp Val Asp Val Ser Gln Leu Pro Cys Gly Leu Asn Gly Ala Leu
    130                 135                 140

Tyr Phe Val Ser Met Asp Ala Asp Gly Gly Val Ser Lys Tyr Pro Thr
145                 150                 155                 160

Asn Thr Ala Gly Ala Lys Tyr Gly Thr Gly Tyr Cys Asp Ser Gln Cys
                165                 170                 175

Pro Arg Asp Leu Lys Phe Ile Asn Gly Gln Ala Asn Val Glu Gly Trp
            180                 185                 190

Glu Pro Ser Ser Asn Asn Ala Asn Thr Gly Ile Gly Gly His Gly Ser
        195                 200                 205

Cys Cys Ser Glu Met Asp Ile Trp Glu Ala Asn Ser Ile Ser Glu Ala
    210                 215                 220

Leu Thr Pro His Pro Cys Thr Thr Val Gly Gln Glu Ile Cys Glu Gly
225                 230                 235                 240

Asp Gly Cys Gly Gly Ala Tyr Ser Asp Asn Ala Ala Gly Gly Thr Cys
                245                 250                 255

Asp Pro Asp Gly Cys Asp Trp Asn Pro Tyr Arg Leu Gly Asn Thr Ser
            260                 265                 270

Phe Tyr Gly Pro Gly Ser Ser Phe Thr Leu Asp Thr Thr Lys Lys Leu
        275                 280                 285

Thr Val Val Thr Gln Phe Glu Thr Ser Gly Ala Ile Asn Arg Tyr Tyr
    290                 295                 300

Val Gln Asn Gly Val Thr Phe Gln Gln Pro Asn Ala Glu Leu Gly Ser
305                 310                 315                 320

Tyr Ser Gly Asn Glu Leu Asn Asp Asp Tyr Cys Thr Ala Glu Glu Ala
                325                 330                 335

Glu Phe Gly Gly Ser Ser Phe Ser Asp Lys Gly Gly Leu Thr Gln Phe
            340                 345                 350
```

```
Lys Lys Ala Thr Ser Gly Gly Met Val Leu Val Met Ser Leu Trp Asp
        355                 360                 365

Asp Tyr Tyr Ala Asn Met Leu Trp Leu Asp Ser Thr Tyr Pro Thr Asn
370                 375                 380

Glu Thr Ser Ser Thr Pro Gly Ala Val Arg Gly Ser Cys Ser Thr Ser
385                 390                 395                 400

Ser Gly Val Pro Ala Gln Val Glu Ser Gln Ser Pro Asn Ala Lys Val
                405                 410                 415

Thr Phe Ser Asn Ile Lys Phe Gly Pro Ile Gly Ser Thr Gly Asn Pro
                420                 425                 430

Ser Gly Gly Asn Pro Pro Gly Gly Asn Pro Pro Gly Thr Thr Thr
                435                 440                 445

Arg Arg Pro Ala Thr Thr Thr Gly Ser Ser Pro Gly Pro Thr Gln Ser
450                 455                 460

His Tyr Gly Gln Cys Gly Gly Ile Gly Tyr Ser Gly Pro Thr Val Cys
465                 470                 475                 480

Ala Ser Gly Thr Thr Cys Gln Val Leu Asn Pro Tyr Tyr Ser Gln Cys
                485                 490                 495

Leu

<210> SEQ ID NO 27
<211> LENGTH: 1491
<212> TYPE: DNA
<213> ORGANISM: Hypocrea jecorina
<220> FEATURE:
<221> NAME/KEY: CDS
<222> LOCATION: (1)..(1491)

<400> SEQUENCE: 27 cag tcg gcc tgc act ctc caa tcg gag act cac ccg cct ctg aca tgg      48
Gln Ser Ala Cys Thr Leu Gln Ser Glu Thr His Pro Pro Leu Thr Trp
1               5                   10                  15 cag aaa tgc tcg tct ggt ggc act tgc act caa cag aca ggc tcc gtg      96
Gln Lys Cys Ser Ser Gly Gly Thr Cys Thr Gln Gln Thr Gly Ser Val
                20                  25                  30 gtc atc gac gcc aac tgg cgc tgg act cac gct acg aac agc agc acg     144
Val Ile Asp Ala Asn Trp Arg Trp Thr His Ala Thr Asn Ser Ser Thr
            35                  40                  45 aac tgc tac gat ggc aac act tgg agc tcg acc cta tgt cct gac aac     192
Asn Cys Tyr Asp Gly Asn Thr Trp Ser Ser Thr Leu Cys Pro Asp Asn
        50                  55                  60 gag acc tgc gcg aag aac tgc tgt ctg gac ggt gcc gcc tac gcg tcc     240
Glu Thr Cys Ala Lys Asn Cys Cys Leu Asp Gly Ala Ala Tyr Ala Ser
65                  70                  75                  80 acg tac gga gtt acc acg agc ggt aac agc ctc tcc att ggc ttt gtc     288
Thr Tyr Gly Val Thr Thr Ser Gly Asn Ser Leu Ser Ile Gly Phe Val
                85                  90                  95 acc cag tct gcg cag aag aac gtt ggc gct cgc ctt tac ctt atg gcg     336
Thr Gln Ser Ala Gln Lys Asn Val Gly Ala Arg Leu Tyr Leu Met Ala
            100                 105                 110 agc gac acg acc tac cag gaa ttc acc ctg ctt ggc aac gag ttc tct     384
Ser Asp Thr Thr Tyr Gln Glu Phe Thr Leu Leu Gly Asn Glu Phe Ser
        115                 120                 125 ttc gat gtt gat gtt tcg cag ctg ccg tgc ggc ttg aac gga gct ctc     432
Phe Asp Val Asp Val Ser Gln Leu Pro Cys Gly Leu Asn Gly Ala Leu
130                 135                 140 tac ttc gtg tcc atg gac gcg gat ggt ggc gtg agc aag tat ccc acc     480
Tyr Phe Val Ser Met Asp Ala Asp Gly Gly Val Ser Lys Tyr Pro Thr
145                 150                 155                 160
```

```
                                                       -continued aac acc gct ggc gcc aag tac ggc acg ggg tac tgt gac agc cag tgt        528
Asn Thr Ala Gly Ala Lys Tyr Gly Thr Gly Tyr Cys Asp Ser Gln Cys
            165                 170                 175 ccc cgc gat ctg aag ttc atc aat ggc cag gcc aac gtt gag ggc tgg        576
Pro Arg Asp Leu Lys Phe Ile Asn Gly Gln Ala Asn Val Glu Gly Trp
        180                 185                 190 gag ccg tca tcc aac aac gcg aac acg ggc att gga gga cac gga agc        624
Glu Pro Ser Ser Asn Asn Ala Asn Thr Gly Ile Gly Gly His Gly Ser
    195                 200                 205 tgc tgc tct gag atg gat atc tgg gag gcc aac tcc atc tcc gag gct        672
Cys Cys Ser Glu Met Asp Ile Trp Glu Ala Asn Ser Ile Ser Glu Ala
210                 215                 220 ctt acc ccc cac cct tgc acg act gtc ggc cag gag atc tgc gag ggt        720
Leu Thr Pro His Pro Cys Thr Thr Val Gly Gln Glu Ile Cys Glu Gly
225                 230                 235                 240 gat ggg tgc ggc gga act tac tcc gat aac aga tat ggc ggc act tgc        768
Asp Gly Cys Gly Gly Thr Tyr Ser Asp Asn Arg Tyr Gly Gly Thr Cys
            245                 250                 255 gat ccc gat ggc tgc gac tgg aac cca tac cgc ctg ggc aac acc agc        816
Asp Pro Asp Gly Cys Asp Trp Asn Pro Tyr Arg Leu Gly Asn Thr Ser
        260                 265                 270 ttc tac ggc cct ggc tca agc ttt acc ctc gat acc acc aag aaa ttg        864
Phe Tyr Gly Pro Gly Ser Ser Phe Thr Leu Asp Thr Thr Lys Lys Leu
    275                 280                 285 acc gtt gtc acc cag ttc gag acg tcg ggt gcc atc aac cga tac tat        912
Thr Val Val Thr Gln Phe Glu Thr Ser Gly Ala Ile Asn Arg Tyr Tyr
290                 295                 300 gtc cag aat ggc gtc act ttc cag cag ccc aac gcc gag ctt ggt agt        960
Val Gln Asn Gly Val Thr Phe Gln Gln Pro Asn Ala Glu Leu Gly Ser
305                 310                 315                 320 tac tct ggc aac gag ctc aac gat gat tac tgc aca gct gag gag gca       1008
Tyr Ser Gly Asn Glu Leu Asn Asp Asp Tyr Cys Thr Ala Glu Glu Ala
            325                 330                 335 gaa ttc ggc gga tcc tct ttc tca gac aag ggc ggc ctg act cag ttc       1056
Glu Phe Gly Gly Ser Ser Phe Ser Asp Lys Gly Gly Leu Thr Gln Phe
        340                 345                 350 aag aag gct acc tct ggc ggc atg gtt ctg gtc atg agt ctg tgg gat       1104
Lys Lys Ala Thr Ser Gly Gly Met Val Leu Val Met Ser Leu Trp Asp
    355                 360                 365 gat tac tac gcc aac atg ctg tgg ctg gac tcc ggc gac cca aca aac       1152
Asp Tyr Tyr Ala Asn Met Leu Trp Leu Asp Ser Gly Asp Pro Thr Asn
370                 375                 380 gag acc tcc tcc aca ccc ggt gcc gtg gcc gga agc tgc tcc acc agc       1200
Glu Thr Ser Ser Thr Pro Gly Ala Val Ala Gly Ser Cys Ser Thr Ser
385                 390                 395                 400 tcc ggt gtc cct gct cag gtc gaa tct cag tct ccc aac gcc aag gtc       1248
Ser Gly Val Pro Ala Gln Val Glu Ser Gln Ser Pro Asn Ala Lys Val
            405                 410                 415 acc ttc tcc aac atc aag ttc gga ccc att ggc agc acc ggc aac cct       1296
Thr Phe Ser Asn Ile Lys Phe Gly Pro Ile Gly Ser Thr Gly Asn Pro
        420                 425                 430 agc ggc ggc aac cct ccc ggc gga aac ccg cct ggc acc acc acc acc       1344
Ser Gly Gly Asn Pro Pro Gly Gly Asn Pro Pro Gly Thr Thr Thr Thr
    435                 440                 445 cgc cgc cca gcc act acc act gga agc tct ccc gga cct acc cag tct       1392
Arg Arg Pro Ala Thr Thr Thr Gly Ser Ser Pro Gly Pro Thr Gln Ser
450                 455                 460 cac tac ggc cag tgc ggc ggt att ggc tac agc ggc ccc acg gtc tgc       1440
His Tyr Gly Gln Cys Gly Gly Ile Gly Tyr Ser Gly Pro Thr Val Cys
465                 470                 475                 480
```

-continued

```
gcc agc ggc aca act tgc cag gtc ctg aac cct tac tac tct cag tgc      1488
Ala Ser Gly Thr Thr Cys Gln Val Leu Asn Pro Tyr Tyr Ser Gln Cys
            485                 490                 495 ctg                                                                    1491
Leu

<210> SEQ ID NO 28
<211> LENGTH: 497
<212> TYPE: PRT
<213> ORGANISM: Hypocrea jecorina

<400> SEQUENCE: 28

Gln Ser Ala Cys Thr Leu Gln Ser Glu Thr His Pro Pro Leu Thr Trp
1               5                   10                  15

Gln Lys Cys Ser Ser Gly Gly Thr Cys Thr Gln Gln Thr Gly Ser Val
            20                  25                  30

Val Ile Asp Ala Asn Trp Arg Trp Thr His Ala Thr Asn Ser Ser Thr
        35                  40                  45

Asn Cys Tyr Asp Gly Asn Thr Trp Ser Ser Thr Leu Cys Pro Asp Asn
    50                  55                  60

Glu Thr Cys Ala Lys Asn Cys Cys Leu Asp Gly Ala Ala Tyr Ala Ser
65                  70                  75                  80

Thr Tyr Gly Val Thr Thr Ser Gly Asn Ser Leu Ser Ile Gly Phe Val
                85                  90                  95

Thr Gln Ser Ala Gln Lys Asn Val Gly Ala Arg Leu Tyr Leu Met Ala
            100                 105                 110

Ser Asp Thr Thr Tyr Gln Glu Phe Thr Leu Leu Gly Asn Glu Phe Ser
        115                 120                 125

Phe Asp Val Asp Val Ser Gln Leu Pro Cys Gly Leu Asn Gly Ala Leu
    130                 135                 140

Tyr Phe Val Ser Met Asp Ala Asp Gly Gly Val Ser Lys Tyr Pro Thr
145                 150                 155                 160

Asn Thr Ala Gly Ala Lys Tyr Gly Thr Gly Tyr Cys Asp Ser Gln Cys
                165                 170                 175

Pro Arg Asp Leu Lys Phe Ile Asn Gly Gln Ala Asn Val Glu Gly Trp
            180                 185                 190

Glu Pro Ser Ser Asn Asn Ala Asn Thr Gly Ile Gly Gly His Gly Ser
        195                 200                 205

Cys Cys Ser Glu Met Asp Ile Trp Glu Ala Asn Ser Ile Ser Glu Ala
    210                 215                 220

Leu Thr Pro His Pro Cys Thr Thr Val Gly Gln Glu Ile Cys Glu Gly
225                 230                 235                 240

Asp Gly Cys Gly Gly Thr Tyr Ser Asp Asn Arg Tyr Gly Gly Thr Cys
                245                 250                 255

Asp Pro Asp Gly Cys Asp Trp Asn Pro Tyr Arg Leu Gly Asn Thr Ser
            260                 265                 270

Phe Tyr Gly Pro Gly Ser Ser Phe Thr Leu Asp Thr Thr Lys Lys Leu
        275                 280                 285

Thr Val Val Thr Gln Phe Glu Thr Ser Gly Ala Ile Asn Arg Tyr Tyr
    290                 295                 300

Val Gln Asn Gly Val Thr Phe Gln Gln Pro Asn Ala Glu Leu Gly Ser
305                 310                 315                 320

Tyr Ser Gly Asn Glu Leu Asn Asp Asp Tyr Cys Thr Ala Glu Glu Ala
                325                 330                 335

Glu Phe Gly Gly Ser Ser Phe Ser Asp Lys Gly Gly Leu Thr Gln Phe
            340                 345                 350
```

```
Lys Lys Ala Thr Ser Gly Gly Met Val Leu Val Met Ser Leu Trp Asp
        355                 360                 365

Asp Tyr Tyr Ala Asn Met Leu Trp Leu Asp Ser Gly Asp Pro Thr Asn
    370                 375                 380

Glu Thr Ser Ser Thr Pro Gly Ala Val Ala Gly Ser Cys Ser Thr Ser
385                 390                 395                 400

Ser Gly Val Pro Ala Gln Val Glu Ser Gln Ser Pro Asn Ala Lys Val
            405                 410                 415

Thr Phe Ser Asn Ile Lys Phe Gly Pro Ile Gly Ser Thr Gly Asn Pro
        420                 425                 430

Ser Gly Gly Asn Pro Pro Gly Gly Asn Pro Pro Gly Thr Thr Thr Thr
        435                 440                 445

Arg Arg Pro Ala Thr Thr Thr Gly Ser Ser Pro Gly Pro Thr Gln Ser
    450                 455                 460

His Tyr Gly Gln Cys Gly Gly Ile Gly Tyr Ser Gly Pro Thr Val Cys
465                 470                 475                 480

Ala Ser Gly Thr Thr Cys Gln Val Leu Asn Pro Tyr Tyr Ser Gln Cys
            485                 490                 495

Leu

<210> SEQ ID NO 29
<211> LENGTH: 1455
<212> TYPE: DNA
<213> ORGANISM: Hypocrea jecorina
<220> FEATURE:
<221> NAME/KEY: CDS
<222> LOCATION: (1)..(1455)

<400> SEQUENCE: 29 cag tcg gcc tgc act ctc caa tcg gag act cac ccg cct ctg aca tgg      48
Gln Ser Ala Cys Thr Leu Gln Ser Glu Thr His Pro Pro Leu Thr Trp
1               5                   10                  15 cag aaa tgc tcg tct ggt ggc act tgc act caa cag aca ggc tcc gtg      96
Gln Lys Cys Ser Ser Gly Gly Thr Cys Thr Gln Gln Thr Gly Ser Val
            20                  25                  30 gtc atc gac gcc aac tgg cgc tgg act cac gct acg aac agc agc acg     144
Val Ile Asp Ala Asn Trp Arg Trp Thr His Ala Thr Asn Ser Ser Thr
        35                  40                  45 aac tgc tac gat ggc aac act tgg agc tcg acc cta tgt cct gac aac     192
Asn Cys Tyr Asp Gly Asn Thr Trp Ser Ser Thr Leu Cys Pro Asp Asn
    50                  55                  60 gag acc tgc gcg aag aac tgt tgt ctg gac ggt gcc gcc tac gcg tcc     240
Glu Thr Cys Ala Lys Asn Cys Cys Leu Asp Gly Ala Ala Tyr Ala Ser
65                  70                  75                  80 acg tac gga gtt acc acg agc ggt aac agc ctc tcc att ggc ttt gtc     288
Thr Tyr Gly Val Thr Thr Ser Gly Asn Ser Leu Ser Ile Gly Phe Val
                85                  90                  95 acc cag tct gcg cag aag aac gtt ggc gct cgc ctt tac ctt atg gcg     336
Thr Gln Ser Ala Gln Lys Asn Val Gly Ala Arg Leu Tyr Leu Met Ala
            100                 105                 110 agc gac acg acc tac cag gaa ttc acc ctg ctt ggc aac gag ttc tct     384
Ser Asp Thr Thr Tyr Gln Glu Phe Thr Leu Leu Gly Asn Glu Phe Ser
        115                 120                 125 ttc gat gtt gat gtt tcg cag ctg ccg tgc ggc ttg aac gga gct ctc     432
Phe Asp Val Asp Val Ser Gln Leu Pro Cys Gly Leu Asn Gly Ala Leu
    130                 135                 140 tac ttc gtg tcc atg gac gcg gat ggt ggc gtg agc aag tat ccc acc     480
Tyr Phe Val Ser Met Asp Ala Asp Gly Gly Val Ser Lys Tyr Pro Thr
145                 150                 155                 160
```

```
aac acc gct ggc gcc aag tac ggc acg ggg tac tgt gac agc cag tgt        528
Asn Thr Ala Gly Ala Lys Tyr Gly Thr Gly Tyr Cys Asp Ser Gln Cys
                165                 170                 175 ccc cgc gat ctg aag ttc atc aat ggc cag gcc aac gtt gag ggc tgg        576
Pro Arg Asp Leu Lys Phe Ile Asn Gly Gln Ala Asn Val Glu Gly Trp
            180                 185                 190 gag ccg tca tcc aac aac gcg aac acg ggc att gga gga cac gga agc        624
Glu Pro Ser Ser Asn Asn Ala Asn Thr Gly Ile Gly Gly His Gly Ser
        195                 200                 205 tgc tgc tct gag atg gat atc tgg gag gcc aac tcc atc tcc gag gct        672
Cys Cys Ser Glu Met Asp Ile Trp Glu Ala Asn Ser Ile Ser Glu Ala
210                 215                 220 ctt acc ccc cac cct tgc acg act gtc ggc cag gag atc tgc gag ggt        720
Leu Thr Pro His Pro Cys Thr Thr Val Gly Gln Glu Ile Cys Glu Gly
225                 230                 235                 240 gat ggg tgc ggc gga act tac tcc gat aac aga tat ggc ggc act tgc        768
Asp Gly Cys Gly Gly Thr Tyr Ser Asp Asn Arg Tyr Gly Gly Thr Cys
                245                 250                 255 gat ccc gat ggc tgc gac tgg aac cca tac cgc ctg ggc aac acc agc        816
Asp Pro Asp Gly Cys Asp Trp Asn Pro Tyr Arg Leu Gly Asn Thr Ser
            260                 265                 270 ttc tac ggc cct ggc tca agc ttt acc ctc gat acc acc aag aaa ttg        864
Phe Tyr Gly Pro Gly Ser Ser Phe Thr Leu Asp Thr Thr Lys Lys Leu
        275                 280                 285 acc gtt gtc acc cag ttc gag acg tcg ggt gcc atc aac cga tac tat        912
Thr Val Val Thr Gln Phe Glu Thr Ser Gly Ala Ile Asn Arg Tyr Tyr
    290                 295                 300 gtc cag aat ggc gtc act ttc cag cag ccc aac gcc gag ctt ggt agt        960
Val Gln Asn Gly Val Thr Phe Gln Gln Pro Asn Ala Glu Leu Gly Ser
305                 310                 315                 320 tac tct ggc aac gag ctc aac gat gat tac tgc aca gct gag gag gca       1008
Tyr Ser Gly Asn Glu Leu Asn Asp Asp Tyr Cys Thr Ala Glu Glu Ala
                325                 330                 335 gaa ttc ggc gga tcc tct ttc tca gac aag ggc ggc ctg act cag ttc       1056
Glu Phe Gly Gly Ser Ser Phe Ser Asp Lys Gly Gly Leu Thr Gln Phe
            340                 345                 350 aag aag gct acc tct ggc ggc atg gtt ctg gtc atg agt ctg tgg gat       1104
Lys Lys Ala Thr Ser Gly Gly Met Val Leu Val Met Ser Leu Trp Asp
        355                 360                 365 gat tac tac gcc aac atg ctg tgg ctg gac tcc ggc gac gcc gga agc       1152
Asp Tyr Tyr Ala Asn Met Leu Trp Leu Asp Ser Gly Asp Ala Gly Ser
    370                 375                 380 tgc tcc acc agc tcc ggt gtc cct gct cag gtc gaa tct cag tct ccc       1200
Cys Ser Thr Ser Ser Gly Val Pro Ala Gln Val Glu Ser Gln Ser Pro
385                 390                 395                 400 aac gcc aag gtc acc ttc tcc aac atc aag ttc gga ccc att ggc agc       1248
Asn Ala Lys Val Thr Phe Ser Asn Ile Lys Phe Gly Pro Ile Gly Ser
                405                 410                 415 acc ggc aac cct agc ggc ggc aac cct ccc gga aac ccg cct ggc           1296
Thr Gly Asn Pro Ser Gly Gly Asn Pro Pro Gly Asn Pro Pro Gly
            420                 425                 430 acc acc acc acc cgc cgc cca gcc act acc act gga agc tct ccc gga      1344
Thr Thr Thr Thr Arg Arg Pro Ala Thr Thr Thr Gly Ser Ser Pro Gly
        435                 440                 445 cct acc cag tct cac tac ggc cag tgc ggc ggt att ggc tac agc ggc      1392
Pro Thr Gln Ser His Tyr Gly Gln Cys Gly Gly Ile Gly Tyr Ser Gly
    450                 455                 460 ccc acg gtc tgc gcc agc ggc aca act tgc cag gtc ctg aac cct tac      1440
Pro Thr Val Cys Ala Ser Gly Thr Thr Cys Gln Val Leu Asn Pro Tyr
465                 470                 475                 480
```

```
tac tct cag tgc ctg                                          1455
Tyr Ser Gln Cys Leu
            485

<210> SEQ ID NO 30
<211> LENGTH: 485
<212> TYPE: PRT
<213> ORGANISM: Hypocrea jecorina

<400> SEQUENCE: 30

Gln Ser Ala Cys Thr Leu Gln Ser Glu Thr His Pro Pro Leu Thr Trp
1               5                   10                  15

Gln Lys Cys Ser Ser Gly Gly Thr Cys Thr Gln Gln Thr Gly Ser Val
            20                  25                  30

Val Ile Asp Ala Asn Trp Arg Trp Thr His Ala Thr Asn Ser Ser Thr
        35                  40                  45

Asn Cys Tyr Asp Gly Asn Thr Trp Ser Ser Thr Leu Cys Pro Asp Asn
    50                  55                  60

Glu Thr Cys Ala Lys Asn Cys Cys Leu Asp Gly Ala Ala Tyr Ala Ser
65                  70                  75                  80

Thr Tyr Gly Val Thr Thr Ser Gly Asn Ser Leu Ser Ile Gly Phe Val
                85                  90                  95

Thr Gln Ser Ala Gln Lys Asn Val Gly Ala Arg Leu Tyr Leu Met Ala
            100                 105                 110

Ser Asp Thr Thr Tyr Gln Glu Phe Thr Leu Leu Gly Asn Glu Phe Ser
        115                 120                 125

Phe Asp Val Asp Val Ser Gln Leu Pro Cys Gly Leu Asn Gly Ala Leu
    130                 135                 140

Tyr Phe Val Ser Met Asp Ala Asp Gly Gly Val Ser Lys Tyr Pro Thr
145                 150                 155                 160

Asn Thr Ala Gly Ala Lys Tyr Gly Thr Gly Tyr Cys Asp Ser Gln Cys
                165                 170                 175

Pro Arg Asp Leu Lys Phe Ile Asn Gly Gln Ala Asn Val Glu Gly Trp
            180                 185                 190

Glu Pro Ser Ser Asn Asn Ala Asn Thr Gly Ile Gly Gly His Gly Ser
        195                 200                 205

Cys Cys Ser Glu Met Asp Ile Trp Glu Ala Asn Ser Ile Ser Glu Ala
    210                 215                 220

Leu Thr Pro His Pro Cys Thr Thr Val Gly Gln Glu Ile Cys Glu Gly
225                 230                 235                 240

Asp Gly Cys Gly Gly Thr Tyr Ser Asp Asn Arg Tyr Gly Gly Thr Cys
                245                 250                 255

Asp Pro Asp Gly Cys Asp Trp Asn Pro Tyr Arg Leu Gly Asn Thr Ser
            260                 265                 270

Phe Tyr Gly Pro Gly Ser Ser Phe Thr Leu Asp Thr Thr Lys Lys Leu
        275                 280                 285

Thr Val Val Thr Gln Phe Glu Thr Ser Gly Ala Ile Asn Arg Tyr Tyr
    290                 295                 300

Val Gln Asn Gly Val Thr Phe Gln Gln Pro Asn Ala Glu Leu Gly Ser
305                 310                 315                 320

Tyr Ser Gly Asn Glu Leu Asn Asp Asp Tyr Cys Thr Ala Glu Glu Ala
                325                 330                 335

Glu Phe Gly Gly Ser Ser Phe Ser Asp Lys Gly Gly Leu Thr Gln Phe
            340                 345                 350

Lys Lys Ala Thr Ser Gly Gly Met Val Leu Val Met Ser Leu Trp Asp
```

```
                355              360                  365
Asp Tyr Tyr Ala Asn Met Leu Trp Leu Asp Ser Gly Asp Ala Gly Ser
        370                 375                 380

Cys Ser Thr Ser Ser Gly Val Pro Ala Gln Val Glu Ser Gln Ser Pro
385                 390                 395                 400

Asn Ala Lys Val Thr Phe Ser Asn Ile Lys Phe Gly Pro Ile Gly Ser
                405                 410                 415

Thr Gly Asn Pro Ser Gly Gly Asn Pro Gly Gly Asn Pro Gly
                420                 425                 430

Thr Thr Thr Thr Arg Arg Pro Ala Thr Thr Thr Gly Ser Ser Pro Gly
        435                 440                 445

Pro Thr Gln Ser His Tyr Gly Gln Cys Gly Gly Ile Gly Tyr Ser Gly
        450                 455                 460

Pro Thr Val Cys Ala Ser Gly Thr Thr Cys Gln Val Leu Asn Pro Tyr
465                 470                 475                 480

Tyr Ser Gln Cys Leu
                485

<210> SEQ ID NO 31
<211> LENGTH: 1491
<212> TYPE: DNA
<213> ORGANISM: Hypocrea jecorina
<220> FEATURE:
<221> NAME/KEY: CDS
<222> LOCATION: (1)..(1491)

<400> SEQUENCE: 31 cag tcg gcc tgc act ctc caa tcg gag act cac ccg cct ctg aca tgg      48
Gln Ser Ala Cys Thr Leu Gln Ser Glu Thr His Pro Pro Leu Thr Trp
1               5                   10                  15 cag aaa tgc tcg tct ggt ggc act tgc act caa cag aca ggc tcc gtg      96
Gln Lys Cys Ser Ser Gly Gly Thr Cys Thr Gln Gln Thr Gly Ser Val
                20                  25                  30 gtc atc gac gcc aac tgg cgc tgg act cac gct acg aac agc agc acg     144
Val Ile Asp Ala Asn Trp Arg Trp Thr His Ala Thr Asn Ser Ser Thr
            35                  40                  45 aac tgc tac gat ggc aac act tgg agc tcg acc cta tgt cct gac aac     192
Asn Cys Tyr Asp Gly Asn Thr Trp Ser Ser Thr Leu Cys Pro Asp Asn
        50                  55                  60 gag acc tgc gcg aag aac tgc tgt ctg gac ggt gcc gcc tac gcg tcc     240
Glu Thr Cys Ala Lys Asn Cys Cys Leu Asp Gly Ala Ala Tyr Ala Ser
65                  70                  75                  80 acg tac gga gtt acc acg agc ggt aac agc ctc tcc att ggc ttt gtc     288
Thr Tyr Gly Val Thr Thr Ser Gly Asn Ser Leu Ser Ile Gly Phe Val
                85                  90                  95 acc cag tct gcg cag aag aac gtt ggc gct cgc ctt tac ctt atg gcg     336
Thr Gln Ser Ala Gln Lys Asn Val Gly Ala Arg Leu Tyr Leu Met Ala
                100                 105                 110 agc gac acg acc tac cag gaa ttc acc ctg ctt ggc aac gag ttc tct     384
Ser Asp Thr Thr Tyr Gln Glu Phe Thr Leu Leu Gly Asn Glu Phe Ser
            115                 120                 125 ttc gat gtt gat gtt tcg cag ctg ccg tgc ggc ttg aac gga gct ctc     432
Phe Asp Val Asp Val Ser Gln Leu Pro Cys Gly Leu Asn Gly Ala Leu
        130                 135                 140 tac ttc gtg tcc atg gac gcg gat ggt ggc gtg agc aag tat ccc acc     480
Tyr Phe Val Ser Met Asp Ala Asp Gly Gly Val Ser Lys Tyr Pro Thr
145                 150                 155                 160 aac acc gct ggc gcc aag tac ggc acg ggg tac tgt gac agc cag tgt     528
Asn Thr Ala Gly Ala Lys Tyr Gly Thr Gly Tyr Cys Asp Ser Gln Cys
                165                 170                 175
```

```
ccc cgc gat ctg aag ttc atc aat ggc cag gcc aac gtt gag ggc tgg      576
Pro Arg Asp Leu Lys Phe Ile Asn Gly Gln Ala Asn Val Glu Gly Trp
        180                 185                 190 gag ccg tca tcc aac aac gcg aac acg ggc att gga gga cac gga agc      624
Glu Pro Ser Ser Asn Asn Ala Asn Thr Gly Ile Gly Gly His Gly Ser
        195                 200                 205 tgc tgc tct gag atg gat atc tgg gag gcc aac tcc atc tcc gag gct      672
Cys Cys Ser Glu Met Asp Ile Trp Glu Ala Asn Ser Ile Ser Glu Ala
        210                 215                 220 ctt acc ccc cac cct tgc acg act gtc ggc cag gag atc tgc gag ggt      720
Leu Thr Pro His Pro Cys Thr Thr Val Gly Gln Glu Ile Cys Glu Gly
225                 230                 235                 240 gat ggg tgc ggc gga act tac tcc gat aac aga cag ggc gga act tgc      768
Asp Gly Cys Gly Gly Thr Tyr Ser Asp Asn Arg Gln Gly Gly Thr Cys
                    245                 250                 255 gat ccc tgg ggc tgc gac tgg aac cca tac cgc ctg ggc aac acc agc      816
Asp Pro Trp Gly Cys Asp Trp Asn Pro Tyr Arg Leu Gly Asn Thr Ser
            260                 265                 270 ttc tac ggc cct ggc tca agc ttt acc ctc gat acc acc aag aaa ttg      864
Phe Tyr Gly Pro Gly Ser Ser Phe Thr Leu Asp Thr Thr Lys Lys Leu
        275                 280                 285 acc gtt gtc acc cag ttc gag acg tcg ggt gcc atc aac cga tac tat      912
Thr Val Val Thr Gln Phe Glu Thr Ser Gly Ala Ile Asn Arg Tyr Tyr
290                 295                 300 gtc cag aat ggc gtc act ttc cag cag ccc aac gcc gag ctt ggt agt      960
Val Gln Asn Gly Val Thr Phe Gln Gln Pro Asn Ala Glu Leu Gly Ser
305                 310                 315                 320 tac tct ggc aac gag ctc aac gat gat tac tgc aca gct gag gag gca     1008
Tyr Ser Gly Asn Glu Leu Asn Asp Asp Tyr Cys Thr Ala Glu Glu Ala
                    325                 330                 335 gaa ttc ggc gga tcc tat ttc tca gac aag ggc ggc ctg act cag ttc     1056
Glu Phe Gly Gly Ser Tyr Phe Ser Asp Lys Gly Gly Leu Thr Gln Phe
            340                 345                 350 aag aag gct acc tct ggc ggc atg gtt ctg gtc atg agt ctg tgg gat     1104
Lys Lys Ala Thr Ser Gly Gly Met Val Leu Val Met Ser Leu Trp Asp
        355                 360                 365 gat tac tac gcc aac atg ctg tgg ctg gac tcc acc tac ccg aca aac     1152
Asp Tyr Tyr Ala Asn Met Leu Trp Leu Asp Ser Thr Tyr Pro Thr Asn
370                 375                 380 gag acc tcc tcc aca ccc ggt gcc gtg cgc gga agc tgc tcc acc agc     1200
Glu Thr Ser Ser Thr Pro Gly Ala Val Arg Gly Ser Cys Ser Thr Ser
385                 390                 395                 400 tcc ggt gtc cct gct cag gtc gaa tct cag tct ccc aac gcc aag gtc     1248
Ser Gly Val Pro Ala Gln Val Glu Ser Gln Ser Pro Asn Ala Lys Val
                    405                 410                 415 acc ttc tcc aac atc aag ttc gga ccc att ggc agc acc ggc aac cct     1296
Thr Phe Ser Asn Ile Lys Phe Gly Pro Ile Gly Ser Thr Gly Asn Pro
            420                 425                 430 agc ggc ggc aac cct ccc ggc gga aac ccg ctg gcc acc acc acc         1344
Ser Gly Gly Asn Pro Pro Gly Gly Asn Pro Leu Ala Thr Thr Thr
        435                 440                 445 cgc cgc cca gcc act acc act gga agc tct ccc gga cct acc cag tct     1392
Arg Arg Pro Ala Thr Thr Thr Gly Ser Ser Pro Gly Pro Thr Gln Ser
450                 455                 460 cac tac ggc cag tgc ggc ggt att ggc tac agc ggc ccc acg gtc tgc     1440
His Tyr Gly Gln Cys Gly Gly Ile Gly Tyr Ser Gly Pro Thr Val Cys
465                 470                 475                 480 gcc agc ggc aca act tgc cag gtc ctg aac cct tac tac tct cag tgc     1488
Ala Ser Gly Thr Thr Cys Gln Val Leu Asn Pro Tyr Tyr Ser Gln Cys
                    485                 490                 495
```

```
ctg                                                                    1491
Leu <210> SEQ ID NO 32
<211> LENGTH: 497
<212> TYPE: PRT
<213> ORGANISM: Hypocrea jecorina

<400> SEQUENCE: 32

Gln Ser Ala Cys Thr Leu Gln Ser Glu Thr His Pro Pro Leu Thr Trp
1               5                   10                  15

Gln Lys Cys Ser Ser Gly Gly Thr Cys Thr Gln Thr Gly Ser Val
            20                  25                  30

Val Ile Asp Ala Asn Trp Arg Trp Thr His Ala Thr Asn Ser Ser Thr
        35                  40                  45

Asn Cys Tyr Asp Gly Asn Thr Trp Ser Ser Thr Leu Cys Pro Asp Asn
    50                  55                  60

Glu Thr Cys Ala Lys Asn Cys Cys Leu Asp Gly Ala Ala Tyr Ala Ser
65                  70                  75                  80

Thr Tyr Gly Val Thr Thr Ser Gly Asn Ser Leu Ser Ile Gly Phe Val
                85                  90                  95

Thr Gln Ser Ala Gln Lys Asn Val Gly Ala Arg Leu Tyr Leu Met Ala
            100                 105                 110

Ser Asp Thr Thr Tyr Gln Glu Phe Thr Leu Leu Gly Asn Glu Phe Ser
        115                 120                 125

Phe Asp Val Asp Val Ser Gln Leu Pro Cys Gly Leu Asn Gly Ala Leu
    130                 135                 140

Tyr Phe Val Ser Met Asp Ala Asp Gly Gly Val Ser Lys Tyr Pro Thr
145                 150                 155                 160

Asn Thr Ala Gly Ala Lys Tyr Gly Thr Gly Tyr Cys Asp Ser Gln Cys
                165                 170                 175

Pro Arg Asp Leu Lys Phe Ile Asn Gly Gln Ala Asn Val Glu Gly Trp
            180                 185                 190

Glu Pro Ser Ser Asn Asn Ala Asn Thr Gly Ile Gly Gly His Gly Ser
        195                 200                 205

Cys Cys Ser Glu Met Asp Ile Trp Glu Ala Asn Ser Ile Ser Glu Ala
    210                 215                 220

Leu Thr Pro His Pro Cys Thr Thr Val Gly Gln Glu Ile Cys Glu Gly
225                 230                 235                 240

Asp Gly Cys Gly Gly Thr Tyr Ser Asp Asn Arg Gln Gly Gly Thr Cys
                245                 250                 255

Asp Pro Trp Gly Cys Asp Trp Asn Pro Tyr Arg Leu Gly Asn Thr Ser
            260                 265                 270

Phe Tyr Gly Pro Gly Ser Ser Phe Thr Leu Asp Thr Thr Lys Lys Leu
        275                 280                 285

Thr Val Val Thr Gln Phe Glu Thr Ser Gly Ala Ile Asn Arg Tyr Tyr
    290                 295                 300

Val Gln Asn Gly Val Thr Phe Gln Gln Pro Asn Ala Glu Leu Gly Ser
305                 310                 315                 320

Tyr Ser Gly Asn Glu Leu Asn Asp Asp Tyr Cys Thr Ala Glu Glu Ala
                325                 330                 335

Glu Phe Gly Gly Ser Tyr Phe Ser Asp Lys Gly Gly Leu Thr Gln Phe
            340                 345                 350

Lys Lys Ala Thr Ser Gly Gly Met Val Leu Val Met Ser Leu Trp Asp
        355                 360                 365
```

```
Asp Tyr Tyr Ala Asn Met Leu Trp Leu Asp Ser Thr Tyr Pro Thr Asn
    370                 375                 380

Glu Thr Ser Ser Thr Pro Gly Ala Val Arg Gly Ser Cys Ser Thr Ser
385                 390                 395                 400

Ser Gly Val Pro Ala Gln Val Glu Ser Gln Ser Pro Asn Ala Lys Val
            405                 410                 415

Thr Phe Ser Asn Ile Lys Phe Gly Pro Ile Gly Ser Thr Gly Asn Pro
        420                 425                 430

Ser Gly Gly Asn Pro Pro Gly Gly Asn Pro Pro Gly Thr Thr Thr Thr
    435                 440                 445

Arg Arg Pro Ala Thr Thr Thr Gly Ser Ser Pro Gly Pro Thr Gln Ser
    450                 455                 460

His Tyr Gly Gln Cys Gly Gly Ile Gly Tyr Ser Gly Pro Thr Val Cys
465                 470                 475                 480

Ala Ser Gly Thr Thr Cys Gln Val Leu Asn Pro Tyr Tyr Ser Gln Cys
            485                 490                 495

Leu
```

<210> SEQ ID NO 33
<211> LENGTH: 8970
<212> TYPE: DNA
<213> ORGANISM: Artificial Sequence
<220> FEATURE:
<223> OTHER INFORMATION: Plasmid pTrex2

<400> SEQUENCE: 33

```
aagcttaagg tgcacggccc acgtggccac tagtacttct cgagctctgt acatgtccgg      60
tcgcgacgta cgcgtatcga tggcgccagc tgcaggcggc cgcctgcagc cacttgcagt     120
cccgtggaat tctcacggtg aatgtaggcc ttttgtaggg taggaattgt cactcaagca     180
cccccaacct ccattacgcc tcccccatag agttcccaat cagtgagtca tggcactgtt     240
ctcaaataga ttggggagaa gttgacttcc gcccagagct gaaggtcgca caaccgcatg     300
atataggggtc ggcaacggca aaaagcacg tggctcaccg aaaagcaaga tgtttgcgat     360
ctaacatcca ggaacctgga tacatccatc atcacgcacg accactttga tctgctggta     420
aactcgtatt cgccctaaac cgaagtgcgt ggtaaatcta cacgtgggcc cctttcggta     480
tactgcgtgt gtcttctcta ggtgccattc ttttcccttc ctctagtgtt gaattgtttg     540
tgttggagtc cgagctgtaa ctacctctga atctctggag aatggtggac taacgactac     600
cgtgcacctg catcatgtat ataatagtga tcctgagaag ggggggtttgg agcaatgtgg     660
gactttgatg gtcatcaaac aaagaacgaa gacgcctctt ttgcaaagtt ttgtttcggc     720
tacggtgaag aactggatac ttgttgtgtc ttctgtgtat ttttgtggca acaagaggcc     780
agagacaatc tattcaaaca ccaagcttgc tcttttgagc tacaagaacc tgtggggtat     840
atatctagag ttgtgaagtc ggtaatcccg ctgtatagta atacgagtcg catctaaata     900
ctccgaagct gctgcgaacc cggagaatcg agatgtgctg gaaagcttct agcgagcggc     960
taaattagca tgaaaggcta tgagaaattc tggagacggc ttgttgaatc atggcgttcc    1020
attcttcgac aagcaaagcg ttccgtcgca gtagcaggca ctcattccg aaaaaactcg    1080
gagattccta agtagcgatg gaaccggaat aatataatag gcaatacatt gagttgcctc    1140
gacggttgca atgcaggggt actgagcttg gacataactg ttccgtaccc cacctcttct    1200
caacctttgg cgtttccctg attcagcgta cccgtacaag tcgtaatcac tattaaccca    1260
gactgaccgg acgtgttttg cccttcattt ggagaaataa tgtcattgcg atgtgtaatt    1320
```

```
tgcctgcttg accgactggg gctgttcgaa gcccgaatgt aggattgtta tccgaactct    1380
gctcgtagag gcatgttgtg aatctgtgtc gggcaggaca cgcctcgaag gttcacggca    1440
agggaaacca ccgatagcag tgtctagtag caacctgtaa agccgcaatg cagcatcact    1500
ggaaaataca aaccaatggc taaaagtaca taagttaatg cctaaagaag tcatatacca    1560
gcggctaata attgtacaat caagtggcta acgtaccgt aatttgccaa cggcttgtgg     1620
ggttgcagaa gcaacggcaa agccccactt ccccacgttt gtttcttcac tcagtccaat    1680
ctcagctggt gatcccccaa ttgggtcgct tgtttgttcc ggtgaagtga aagaagacag    1740
aggtaagaat gtctgactcg gagcgttttg catacaacca agggcagtga tggaagacag    1800
tgaaatgttg acattcaagg agtatttagc cagggatgct tgagtgtatc gtgtaaggag    1860
gtttgtctgc cgatacgacg aatactgtat agtcacttct gatgaagtgg tccatattga    1920
aatgtaagtc ggcactgaac aggcaaaaga ttgagttgaa actgcctaag atctcgggcc    1980
ctcgggcctt cggcctttgg gtgtacatgt ttgtgctccg gcaaatgca aagtgtggta     2040 ggatcgaaca cactgctgcc tttaccaagc agctgagggt atgtgatagg caaatgttca    2100
ggggccactg catggtttcg aatagaaaga gaagcttagc caagaacaat agccgataaa    2160
gatagcctca ttaaacggaa tgagctagta ggcaaagtca gcgaatgtgt atatataaag    2220
gttcgaggtc cgtgcctccc tcatgctctc cccatctact catcaactca gatcctccag    2280
gagacttgta caccatcttt tgaggcacag aaacccaata gtcaaccgcg gtttaggcgc    2340
gccagctccg tgcgaaagcc tgacgcaccg gtagattctt ggtgagcccg tatcatgacg    2400
gcggcgggag ctacatggcc ccgggtgatt tatttttttt gtatctactt ctgacccttt    2460
tcaaatatac ggtcaactca tcttttcactg gagatgcggc ctgcttggta ttgcgatgtt    2520
gtcagcttgg caaattgtgg ctttcgaaaa cacaaaacga ttccttagta gccatgcatt    2580
ttaagataac ggaatagaag aaagaggaaa ttaaaaaaaa aaaaaaaaca aacatcccgt    2640
tcataacccg tagaatcgcc gctcttcgtg tatcccagta ccagtttaaa cggatctcaa    2700
gcttgcatgc aaagatacac atcaatcgca gctggggtac aatcatccat catcccaact    2760
ggtacgtcat aacaaaaatc gacaagatgg aaaaagaggt cgcctaaata cagctgcatt    2820
ctatgatgcc gggctttgga caagagctct ttctcagctc cgtttgtcct ccctcccttt    2880
tcccccttct tgctaaatgc cttttcttac ttctttcttc ccttccctcc cctatcgcag    2940
cagcctctcg gtgtaggctt tccacgctgc tgatcggtac cgctctgcct cctctacggg    3000
gtctgaggcc ttgaggatgc cccggcccac aatggcaatg tcgctgccgg cgatgccaat    3060
cagcttgtgc ggcgtgttgt actgctggcc ctggccgtct ccaccgaccg atccgttggt    3120
ctgctggtcc tcgtcttcgg ggggcagctg gcagccgggc gtcatgtgga taaaggcatc    3180
gtcgggctcg gtgttgagcg tctcctgcga gatgaagccc atgacaaagt ccttgtgctc    3240
ccgggcggcc tcgacgcagg cctgcgtgta ctccttgttc atgaagttgc cctggctgga    3300
catttgggcg aggatcagga ggcctcggct cagcggcgcc tcctcgatgc ccgggaagag    3360
cgactcgtcg ccctcggcga tggccttgt taaccggggc gaggagacgg actcgtactg     3420
ctgggtgacg gtggtgatgg agacgatgct gcccttgcgg ccgtcgccgg accggttcga    3480
gtagatgggc ttgtccagga cgccaatgga gcccatgccg ttgacggcgc ggcgggctc     3540 ggcgtccctg gagtcggcgt cgtcgtcaaa cgagtccatg gtgggcgtgc cgacggtgac    3600
ggacgtcttg acctcgcagg ggtagcgctc gagccagcgc ttggcgccct gggccagcga    3660
ggccaccgac gccttgccgg gcaccatgtt gacgttgaca atgtgcgccc agtcgatgat    3720
```

| | |
|---|---|
| gcgcgccgac ccgcccgtgt actgcagctc gacggtgtgg ccaatgtcgc caaacttgcg | 3780 |
| gtcctcgaag atgaggaagc cgtgcttgcg cgccagcgac gccagctggg ctcccgtgcc | 3840 |
| cgtctccggg tggaagtccc agcccgagac catgtcgtag tgcgtcttga gcacgacaat | 3900 |
| cgacgggcca atcttgtcgg ccaggtacag cagctcgcgc gctgtcggca cgtcggcgct | 3960 |
| caggcacagg ttggacgcct tgaggtccat gagcttgaac aggtaagccg tcagcgggtg | 4020 |
| cgtcgccgtc tcgctcctgg ccgcgaaggt ggccttgagc gtcgggtgtg gtgccatggc | 4080 |
| tgatgaggct gagagaggct gaggctgcgg ctggttggat agtttaaccc ttagggtgcc | 4140 |
| gttgtggcgg tttagagggg gggaaaaaaa agagagagat ggcacaattc tgctgtgcga | 4200 |
| atgacgttgg aagcgcgaca gccgtgcggg aggaagagga gtaggaactg tcggcgattg | 4260 |
| ggagaatttc gtgcgatccg agtcgtctcg aggcgaggga gttgctttaa tgtcgggctc | 4320 |
| gtccctggt caaaattcta gggagcagcg ctggcaacga gagcagagca gcagtagtcg | 4380 |
| atgctagaaa tcgatagatc cacgatgcca aaaagcttgt tcatttcggc tagcccgtga | 4440 |
| tcctggcgct tctagggctg aaactgtgtt gttaatgtat tattggctgt gtaactgact | 4500 |
| tgaatgggga atgaggagcg cgatggattc gcttgcatgt cccctggcca agacgagccg | 4560 |
| ctttggcggt ttgtgattcg aaggtgtgtc agcggaggcg ccagggcaac acgcactgag | 4620 |
| ccagccaaca tgcattgctg ccgacatgaa tagacacgcg ccgagcagac ataggagacg | 4680 |
| tgttgactgt aaaaattcta ctgaatatta gcacgcatgg tctcaataag agcaatagga | 4740 |
| atgcttgcca atcataagta cgtatgtgct ttttcctgca aatggtacgt acggacagtt | 4800 |
| catgttgtct gtcatccccc actcaggctc tcatgatcat tttatgggac tggggttttg | 4860 |
| ctgactgaat ggattcagcc gcacgaaaca aattgggggc catgcagaag gaagccccc | 4920 |
| ccagccccct gttcataatt tgttaagagt cggagagctg cctagtatga agcagcaatt | 4980 |
| gataacgttg actttgcgca tgagctctga agccgggcat atgtatcacg tttctgccta | 5040 |
| gagccgcacg ggacccaaga agctcttgtc ataaggtatt tatgagtgtt cagctgccaa | 5100 |
| cgctggttct actttggctc aaccgcatcc cataagctga actttgggag ctgccagaat | 5160 |
| gtctcttgat gtacagcgat caacaaccgt gcgccggtcg acaactgttc accgatcagg | 5220 |
| gacgcgaaga ggacccaatc ccggttaacg cacctgctcc gaagaagcaa aagggctatg | 5280 |
| aggtggtgca gcaaggaatc aaagagctct atccacttga caaggccaat gtcgctcccg | 5340 |
| atctggagta agtcaaccct gaagtggaag tttgcttctc tgattagtat gtagcatcgt | 5400 |
| gtttgtccca ggactgggtg caaatcccga agacagctgg aagtccagca agaccgactt | 5460 |
| caattggacc acgcatacag atggcctcca gagagacttc ccaagagctc ggttgcttct | 5520 |
| gtatatgtac gactcagcat ggactggcca gctcaaagta aaacaattca tgggcaatat | 5580 |
| cgcgatgggg ctcttggttg ggctgaggag caagagagag gtaggccaaa cgccagactc | 5640 |
| gaaccgccag ccaagtctca aactgactgc aggcggccgc catatgcatc ctaggcctat | 5700 |
| taatattccg gagtatacgt agccggctaa cgttaacaac cggtacctct agaactatag | 5760 |
| ctagcatgcg caaatttaaa gcgctgatat cgatcgcgcg cagatccata tagggccc | 5820 |
| gggttataat tacctcaggt cgacgtccca tggccattcg aattcgtaat catggtcata | 5880 |
| gctgtttcct gtgtgaaatt gttatccgct cacaattcca cacaacatac gagccggaag | 5940 |
| cataaagtgt aaagcctggg gtgcctaatg agtgagctaa ctcacattaa ttgcgttgcg | 6000 |
| ctcactgccc gctttccagt cgggaaacct gtcgtgccag ctgcattaat gaatcggcca | 6060 |
| acgcgcgggg agaggcggtt tgcgtattgg gcgctcttcc gcttcctcgc tcactgactc | 6120 |

```
gctgcgctcg gtcgttcggc tgcggcgagc ggtatcagct cactcaaagg cggtaatacg   6180
gttatccaca gaatcagggg ataacgcagg aaagaacatg tgagcaaaag gccagcaaaa   6240
ggccaggaac cgtaaaaagg ccgcgttgct ggcgtttttc cataggctcc gcccccctga   6300
cgagcatcac aaaaatcgac gctcaagtca gaggtggcga acccgacag gactataaag    6360 ataccaggcg tttccccctg gaagctccct cgtgcgctct cctgttccga ccctgccgct   6420
taccggatac ctgtccgcct ttctcccttc gggaagcgtg gcgctttctc atagctcacg   6480
ctgtaggtat ctcagttcgg tgtaggtcgt tcgctccaag ctgggctgtg tgcacgaacc   6540
ccccgttcag cccgaccgct gcgccttatc cggtaactat cgtcttgagt ccaacccggt   6600
aagacacgac ttatcgccac tggcagcagc cactggtaac aggattagca gagcgaggta   6660
tgtaggcggt gctacagagt tcttgaagtg gtggcctaac tacggctaca ctagaagaac   6720
agtatttggt atctgcgctc tgctgaagcc agttaccttc ggaaaaagag ttggtagctc   6780
ttgatccggc aaacaaacca ccgctggtag cggtggtttt tttgtttgca agcagcagat   6840
tacgcgcaga aaaaaggat ctcaagaaga tcctttgatc ttttctacgg ggtctgacgc    6900
tcagtggaac gaaaactcac gttaagggat tttggtcatg agattatcaa aaaggatctt   6960
cacctagatc cttttaaatt aaaaatgaag ttttaaatca atctaaagta tatatgagta   7020
aacttggtct gacagttacc aatgcttaat cagtgaggca cctatctcag cgatctgtct   7080
atttcgttca tccatagttg cctgactccc cgtcgtgtag ataactacga tacgggaggg   7140
cttaccatct ggccccagtg ctgcaatgat accgcgagac ccacgctcac cggctccaga   7200
tttatcagca ataaaccagc cagccggaag ggccgagcgc agaagtggtc ctgcaacttt   7260
atccgcctcc atccagtcta ttaattgttg ccgggaagct agagtaagta gttcgccagt   7320
taatagtttg cgcaacgttg ttgccattgc tacaggcatc gtggtgtcac gctcgtcgtt   7380
tggtatggct tcattcagct ccggttccca acgatcaagg cgagttacat gatccccat    7440 gttgtgcaaa aaagcggtta gctccttcgg tcctccgatc gttgtcagaa gtaagttggc   7500
cgcagtgtta tcactcatgg ttatggcagc actgcataat tctcttactg tcatgccatc   7560
cgtaagatgc ttttctgtga ctggtgagta ctcaaccaag tcattctgag aatagtgtat   7620
gcggcgaccg agttgctctt gcccggcgtc aatacgggat aataccgcgc cacatagcag   7680
aactttaaaa gtgctcatca ttggaaaacg ttcttcgggg cgaaaactct caaggatctt   7740
accgctgttg agatccagtt cgatgtaacc cactcgtgca cccaactgat cttcagcatc   7800
ttttactttc accagcgttt ctgggtgagc aaaaacagga aggcaaaatg ccgcaaaaaa   7860
gggaataagg gcgacacgga aatgttgaat actcatactc ttcctttttc aatattattg   7920
aagcatttat cagggttatt gtctcatgag cggatacata tttgaatgta tttagaaaaa   7980
taaacaaata ggggttccgc gcacatttcc ccgaaaagtg ccacctgacg tctaagaaac   8040
cattattatc atgacattaa cctataaaaa taggcgtatc acgaggccct ttcgtctcgc   8100
gcgtttcggt gatgacggtg aaaacctctg acacatgcag ctcccggaga cggtcacagc   8160
ttgtctgtaa gcggatgccg ggagcagaca agcccgtcag ggcgcgtcag cgggtgttgg   8220
cgggtgtcgg ggctggctta actatgcggc atcagagcag attgtactga gagtgcacca   8280
taaaattgta aacgttaata ttttgttaaa attcgcgtta aatttttgtt aaatcagctc   8340
attttttaac caataggccg aaatcggcaa aatcccttat aaatcaaaag aatagcccga   8400
gatagggttg agtgttgttc cagtttggaa caagagtcca ctattaaaga acgtggactc   8460
caacgtcaaa gggcgaaaaa ccgtctatca gggcgatggc ccactacgtg aaccatcacc   8520
```

-continued

```
caaatcaagt tttttggggt cgaggtgccg taaagcacta aatcggaacc ctaaagggag    8580
cccccgattt agagcttgac ggggaaagcc ggcgaacgtg gcgagaaagg aagggaagaa    8640
agcgaaagga gcgggcgcta gggcgctggc aagtgtagcg gtcacgctgc gcgtaaccac    8700 cacaccgcc gcgcttaatg cgccgctaca gggcgcgtac tatggttgct ttgacgtatg     8760
cggtgtgaaa taccgcacag atgcgtaagg agaaaatacc gcatcaggcg ccattcgcca    8820
ttcaggctgc gcaactgttg ggaagggcga tcggtgcggg cctcttcgct attacgccag    8880
ctggcgaaag ggggatgtgc tgcaaggcga ttaagttggg taacgccagg gttttcccag    8940
tcacgacgtt gtaaaacgac ggccagtgcc                                     8970

<210> SEQ ID NO 34
<211> LENGTH: 504
<212> TYPE: PRT
<213> ORGANISM: Phanerochaete chrysosporium

<400> SEQUENCE: 34

Met Arg Thr Ala Leu Ala Leu Ile Leu Ala Leu Ala Ala Phe Ser Ala
1               5                   10                  15

Val Ser Ala Gln Ala Gly Thr Ile Thr Ala Glu Thr His Pro Thr
            20                  25                  30

Leu Thr Ile Gln Gln Cys Thr Gln Ser Gly Gly Cys Ala Pro Leu Thr
        35                  40                  45

Thr Lys Val Val Leu Asp Val Asn Trp Arg Trp Ile His Ser Thr Thr
    50                  55                  60

Gly Tyr Thr Asn Cys Tyr Ser Gly Asn Thr Trp Asp Ala Ile Leu Cys
65                  70                  75                  80

Pro Asp Pro Val Thr Cys Ala Ala Asn Cys Ala Leu Asp Gly Ala Asp
                85                  90                  95

Tyr Thr Gly Thr Phe Gly Ile Leu Pro Ser Gly Thr Ser Val Thr Leu
            100                 105                 110

Arg Pro Val Asp Gly Leu Gly Leu Arg Leu Phe Leu Leu Ala Asp Asp
        115                 120                 125

Ser His Tyr Gln Met Phe Gln Leu Leu Asn Lys Glu Phe Thr Phe Asp
    130                 135                 140

Val Glu Met Pro Asn Met Arg Cys Gly Ser Ser Gly Ala Ile His Leu
145                 150                 155                 160

Thr Ala Met Asp Ala Asp Gly Gly Leu Ala Lys Tyr Pro Gly Asn Gln
                165                 170                 175

Ala Gly Ala Lys Tyr Gly Thr Gly Tyr Cys Ser Ala Gln Cys Pro Lys
            180                 185                 190

Gly Val Lys Phe Ile Asn Gly Gln Ala Asn Val Glu Gly Trp Leu Gly
        195                 200                 205

Thr Thr Ala Thr Thr Gly Thr Gly Phe Phe Gly Ser Cys Cys Thr Asp
    210                 215                 220

Ile Ala Leu Trp Glu Ala Asn Asp Asn Ser Ala Ser Phe Ala Pro His
225                 230                 235                 240

Pro Cys Thr Thr Asn Ser Gln Thr Arg Cys Ser Gly Ser Asp Cys Thr
                245                 250                 255

Ala Asp Ser Gly Leu Cys Asp Ala Asp Gly Cys Asn Phe Asn Ser Phe
            260                 265                 270

Arg Met Gly Asn Thr Thr Phe Phe Gly Ala Gly Met Ser Val Asp Thr
        275                 280                 285

Thr Lys Leu Phe Thr Val Val Thr Gln Phe Ile Thr Ser Asp Asn Thr
```

```
            290                 295                 300
Ser Met Gly Ala Leu Val Glu Ile His Arg Leu Tyr Ile Gln Asn Gly
305                 310                 315                 320

Gln Val Ile Gln Asn Ser Val Val Asn Ile Pro Gly Ile Asn Pro Ala
                325                 330                 335

Thr Ser Ile Thr Asp Asp Leu Cys Ala Gln Glu Asn Ala Ala Phe Gly
                340                 345                 350

Gly Thr Ser Ser Phe Ala Gln His Gly Gly Leu Ala Gln Val Gly Glu
                355                 360                 365

Ala Leu Arg Ser Gly Met Val Leu Ala Leu Ser Ile Val Asn Ser Ala
            370                 375                 380

Ala Asp Thr Leu Trp Leu Asp Ser Asn Tyr Pro Ala Asp Ala Asp Pro
385                 390                 395                 400

Ser Ala Pro Gly Val Ala Arg Gly Thr Cys Pro Gln Asp Ser Ala Ser
                405                 410                 415

Ile Pro Glu Ala Pro Thr Pro Ser Val Val Phe Ser Asn Ile Lys Leu
                420                 425                 430

Gly Asp Ile Gly Thr Thr Phe Gly Ala Gly Ser Ala Leu Phe Ser Gly
                435                 440                 445

Arg Ser Pro Pro Gly Pro Val Pro Gly Ser Ala Pro Ala Ser Ser Ala
            450                 455                 460

Thr Ala Thr Ala Pro Pro Phe Gly Ser Gln Cys Gly Gly Leu Gly Tyr
465                 470                 475                 480

Ala Gly Pro Thr Gly Val Cys Pro Ser Pro Tyr Thr Cys Gln Ala Leu
                485                 490                 495

Asn Ile Tyr Tyr Ser Gln Cys Ile
                500

<210> SEQ ID NO 35
<211> LENGTH: 450
<212> TYPE: PRT
<213> ORGANISM: Phanerochaete chrysosporium

<400> SEQUENCE: 35

Met Arg Thr Ala Leu Ala Leu Ile Leu Ala Leu Ala Ala Phe Ser Ala
1               5                   10                  15

Val Ser Ala Gln Gln Ala Gly Thr Ile Thr Ala Glu Thr His Pro Thr
                20                  25                  30

Leu Thr Ile Gln Gln Cys Thr Gln Ser Gly Gly Cys Ala Pro Leu Thr
            35                  40                  45

Thr Lys Val Val Leu Asp Val Asn Trp Arg Trp Ile His Ser Thr Thr
50                  55                  60

Gly Tyr Thr Asn Cys Tyr Ser Gly Asn Thr Trp Asp Ala Ile Leu Cys
65                  70                  75                  80

Pro Asp Pro Val Thr Cys Ala Ala Asn Cys Ala Leu Asp Gly Ala Asp
                85                  90                  95

Tyr Thr Gly Thr Phe Gly Ile Leu Pro Ser Gly Thr Ser Val Thr Leu
                100                 105                 110

Arg Pro Val Asp Gly Leu Gly Leu Arg Leu Phe Leu Leu Ala Asp Asp
            115                 120                 125

Ser His Tyr Gln Met Phe Gln Leu Leu Asn Lys Glu Phe Thr Phe Asp
            130                 135                 140

Val Glu Met Pro Asn Met Arg Cys Gly Ser Ser Gly Ala Ile His Leu
145                 150                 155                 160

Thr Ala Met Asp Ala Asp Gly Gly Leu Ala Lys Tyr Pro Gly Asn Gln
```

165                 170                 175
Ala Gly Ala Lys Tyr Gly Thr Gly Tyr Cys Ser Ala Gln Cys Pro Lys
            180                 185                 190

Gly Val Lys Phe Ile Asn Gly Gln Ala Asn Val Glu Gly Trp Leu Gly
            195                 200                 205

Thr Thr Ala Thr Thr Gly Thr Gly Phe Phe Gly Ser Cys Cys Thr Asp
            210                 215                 220

Ile Ala Leu Trp Glu Ala Asn Asp Asn Ser Ala Ser Phe Ala Pro His
225                 230                 235                 240

Pro Cys Thr Thr Asn Ser Gln Thr Arg Cys Ser Gly Ser Asp Cys Thr
                245                 250                 255

Ala Asp Ser Gly Leu Cys Asp Ala Asp Gly Cys Asn Phe Asn Ser Phe
            260                 265                 270

Arg Met Gly Asn Thr Thr Phe Phe Gly Ala Gly Met Ser Val Asp Thr
            275                 280                 285

Thr Lys Leu Phe Thr Val Val Thr Gln Phe Ile Thr Ser Asp Asn Thr
            290                 295                 300

Ser Met Gly Ala Leu Val Glu Ile His Arg Leu Tyr Ile Gln Asn Gly
305                 310                 315                 320

Gln Val Ile Gln Asn Ser Val Val Asn Ile Pro Gly Ile Asn Pro Ala
                325                 330                 335

Thr Ser Ile Thr Asp Asp Leu Cys Ala Gln Glu Asn Ala Ala Phe Gly
            340                 345                 350

Gly Thr Ser Ser Phe Ala Gln His Gly Gly Leu Ala Gln Val Gly Glu
            355                 360                 365

Ala Leu Arg Ser Gly Met Val Leu Ala Leu Ser Ile Val Asn Ser Ala
            370                 375                 380

Ala Asp Thr Leu Trp Leu Asp Ser Asn Tyr Pro Ala Asp Ala Asp Pro
385                 390                 395                 400

Ser Ala Pro Gly Val Ala Arg Gly Thr Cys Pro Gln Asp Ser Ala Ser
            405                 410                 415

Ile Pro Glu Ala Pro Thr Pro Ser Val Val Phe Ser Asn Ile Lys Leu
            420                 425                 430

Gly Asp Ile Gly Thr Thr Phe Gly Ala Gly Ser Ala Leu Phe Ser Gly
            435                 440                 445

Arg Ser
    450

<210> SEQ ID NO 36
<211> LENGTH: 449
<212> TYPE: PRT
<213> ORGANISM: Phanerochaete chrysosporium

<400> SEQUENCE: 36

Met Val Asp Ile Gln Ile Ala Thr Phe Leu Leu Leu Gly Val Val Gly
1               5                   10                  15

Val Ala Ala Gln Gln Val Gly Thr Tyr Ile Pro Glu Asn His Pro Leu
            20                  25                  30

Leu Ala Thr Gln Ser Cys Thr Ala Ser Gly Gly Cys Thr Thr Ser Ser
            35                  40                  45

Ser Lys Ile Val Leu Asp Ala Asn Arg Arg Trp Ile His Ser Thr Leu
        50                  55                  60

Gly Thr Thr Ser Cys Leu Thr Ala Asn Gly Trp Asp Pro Thr Leu Cys
65                  70                  75                  80

Pro Asp Gly Ile Thr Cys Ala Asn Tyr Cys Ala Leu Asp Gly Val Ser

```
                     85                  90                  95
Tyr Ser Ser Thr Tyr Gly Ile Thr Thr Ser Gly Ser Ala Leu Arg Leu
                100                 105                 110

Gln Phe Val Thr Gly Thr Asn Ile Gly Ser Arg Val Phe Leu Met Ala
            115                 120                 125

Asp Asp Thr His Tyr Arg Thr Phe Gln Leu Leu Asn Gln Glu Leu Ala
        130                 135                 140

Phe Asp Val Asp Val Ser Lys Leu Pro Cys Gly Leu Asn Gly Ala Leu
145                 150                 155                 160

Tyr Phe Val Ala Met Asp Ala Asp Gly Gly Lys Ser Lys Tyr Pro Gly
                165                 170                 175

Asn Arg Ala Gly Ala Lys Tyr Gly Thr Gly Tyr Cys Asp Ser Gln Cys
            180                 185                 190

Pro Arg Asp Val Gln Phe Ile Asn Gly Gln Ala Asn Val Gln Gly Trp
        195                 200                 205

Asn Ala Thr Ser Ala Thr Thr Gly Thr Gly Ser Tyr Gly Ser Cys Cys
    210                 215                 220

Thr Glu Leu Asp Ile Trp Glu Ala Asn Ser Asn Ala Ala Ala Leu Thr
225                 230                 235                 240

Pro His Thr Cys Thr Asn Asn Ala Gln Thr Arg Cys Ser Gly Ser Asn
                245                 250                 255

Cys Thr Ser Asn Thr Gly Phe Cys Asp Ala Asp Gly Cys Asp Phe Asn
            260                 265                 270

Ser Phe Arg Leu Gly Asn Thr Thr Phe Leu Gly Ala Gly Met Ser Val
        275                 280                 285

Asp Thr Thr Lys Thr Phe Thr Val Val Thr Gln Phe Ile Thr Ser Asp
    290                 295                 300

Asn Thr Ser Thr Gly Asn Leu Thr Glu Ile Arg Arg Phe Tyr Val Gln
305                 310                 315                 320

Asn Gly Asn Val Ile Pro Asn Ser Val Asn Val Thr Gly Ile Gly
                325                 330                 335

Ala Val Asn Ser Ile Thr Asp Pro Phe Cys Ser Gln Gln Lys Lys Ala
            340                 345                 350

Phe Ile Glu Thr Asn Tyr Phe Ala Gln His Gly Gly Leu Ala Gln Leu
        355                 360                 365

Gly Gln Ala Leu Arg Thr Gly Met Val Leu Ala Phe Ser Ile Ser Asp
    370                 375                 380

Asp Pro Ala Asn His Met Leu Trp Leu Asp Ser Asn Phe Pro Pro Ser
385                 390                 395                 400

Ala Asn Pro Ala Val Pro Gly Val Ala Arg Gly Met Cys Ser Ile Thr
                405                 410                 415

Ser Gly Asn Pro Ala Asp Val Gly Ile Leu Asn Pro Ser Pro Tyr Val
            420                 425                 430

Ser Phe Leu Asn Ile Lys Phe Gly Ser Ile Gly Thr Thr Phe Arg Pro
        435                 440                 445

Ala

<210> SEQ ID NO 37
<211> LENGTH: 516
<212> TYPE: PRT
<213> ORGANISM: Phanerochaete chrysosporium

<400> SEQUENCE: 37

Met Phe Arg Thr Ala Thr Leu Leu Ala Phe Thr Met Ala Ala Met Val
1               5                   10                  15
```

```
Phe Gly Gln Gln Val Gly Thr Asn Thr Ala Glu Asn His Arg Thr Leu
                20              25                  30
Thr Ser Gln Lys Cys Thr Lys Ser Gly Gly Cys Ser Asn Leu Asn Thr
            35              40                  45
Lys Ile Val Leu Asp Ala Asn Trp Arg Trp Leu His Ser Thr Ser Gly
 50              55                  60
Tyr Thr Asn Cys Tyr Thr Gly Asn Gln Trp Asp Ala Thr Leu Cys Pro
 65              70                  75                  80
Asp Gly Lys Thr Cys Ala Ala Asn Cys Ala Leu Asp Gly Ala Asp Tyr
                85                  90                  95
Thr Gly Thr Tyr Gly Ile Thr Ala Ser Gly Ser Ser Leu Lys Leu Gln
                100             105                 110
Phe Val Thr Gly Ser Asn Val Gly Ser Arg Val Tyr Leu Met Ala Asp
            115                 120                 125
Asp Thr His Tyr Gln Met Phe Gln Leu Leu Asn Gln Glu Phe Thr Phe
130                 135                 140
Asp Val Asp Met Ser Asn Leu Pro Cys Gly Leu Asn Gly Ala Leu Tyr
145                 150                 155                 160
Leu Ser Ala Met Asp Ala Asp Gly Gly Met Ala Lys Tyr Pro Thr Asn
                165                 170                 175
Lys Ala Gly Ala Lys Tyr Gly Thr Gly Tyr Cys Asp Ser Gln Cys Pro
                180                 185                 190
Arg Asp Ile Lys Phe Ile Asn Gly Glu Ala Asn Val Glu Gly Trp Asn
                195                 200                 205
Ala Thr Ser Ala Asn Ala Gly Thr Gly Asn Tyr Gly Thr Cys Cys Thr
210                 215                 220
Glu Met Asp Ile Trp Glu Ala Asn Asn Asp Ala Ala Ala Tyr Thr Pro
225                 230                 235                 240
His Pro Cys Thr Thr Asn Ala Gln Thr Arg Cys Ser Gly Ser Asp Cys
                245                 250                 255
Thr Arg Asp Thr Gly Leu Cys Asp Ala Asp Gly Cys Asp Phe Asn Ser
                260                 265                 270
Phe Arg Met Gly Asp Gln Thr Phe Leu Gly Lys Gly Leu Thr Val Asp
                275                 280                 285
Thr Ser Lys Pro Phe Thr Val Val Thr Gln Phe Ile Thr Asn Asp Gly
290                 295                 300
Thr Ser Ala Gly Thr Leu Thr Glu Ile Arg Arg Leu Tyr Val Gln Asn
305                 310                 315                 320
Gly Lys Val Ile Gln Asn Ser Ser Val Lys Ile Pro Gly Ile Asp Pro
                325                 330                 335
Val Asn Ser Ile Thr Asp Asn Phe Cys Ser Gln Lys Thr Ala Phe
                340                 345                 350
Gly Asp Thr Asn Tyr Phe Ala Gln His Gly Gly Leu Lys Gln Val Gly
                355                 360                 365
Glu Ala Leu Arg Thr Gly Met Val Leu Ala Leu Ser Ile Trp Asp Asp
370                 375                 380
Tyr Ala Ala Asn Met Leu Trp Leu Asp Ser Asn Tyr Pro Thr Asn Lys
385                 390                 395                 400
Asp Pro Ser Thr Pro Gly Val Ala Arg Gly Thr Cys Ala Thr Thr Ser
                405                 410                 415
Gly Val Pro Ala Gln Ile Glu Ala Gln Ser Pro Asn Ala Tyr Val Val
                420                 425                 430
Phe Ser Asn Ile Lys Phe Gly Asp Leu Asn Thr Thr Tyr Thr Gly Thr
```

```
                  435              440             445
Val Ser Ser Ser Val Ser Ser His Ser Thr Ser Thr Ser
    450             455             460

Ser Ser His Ser Ser Ser Thr Pro Pro Thr Gln Pro Thr Gly Val
465         470             475             480

Thr Val Pro Gln Trp Gly Gln Cys Gly Gly Ile Gly Tyr Thr Gly Ser
            485             490             495

Thr Thr Cys Ala Ser Pro Tyr Thr Cys His Val Leu Asn Pro Tyr Tyr
        500             505             510

Ser Gln Cys Tyr
        515

<210> SEQ ID NO 38
<211> LENGTH: 516
<212> TYPE: PRT
<213> ORGANISM: Phanerochaete chrysosporium

<400> SEQUENCE: 38

Met Phe Arg Thr Ala Thr Leu Leu Ala Phe Thr Met Ala Ala Met Val
1               5                   10                  15

Phe Gly Gln Gln Val Gly Thr Asn Thr Ala Glu Asn His Arg Thr Leu
            20                  25                  30

Thr Ser Gln Lys Cys Thr Lys Ser Gly Gly Cys Ser Asn Leu Asn Thr
        35                  40                  45

Lys Ile Val Leu Asp Ala Asn Trp Arg Trp Leu His Ser Thr Ser Gly
    50                  55                  60

Tyr Thr Asn Cys Tyr Thr Gly Asn Gln Trp Asp Ala Thr Leu Cys Pro
65                  70                  75                  80

Asp Gly Lys Thr Cys Ala Ala Asn Cys Ala Leu Asp Gly Ala Asp Tyr
                85                  90                  95

Thr Gly Thr Tyr Gly Ile Thr Ala Ser Gly Ser Ser Leu Lys Leu Gln
            100                 105                 110

Phe Val Thr Gly Ser Asn Val Gly Ser Arg Val Tyr Leu Met Ala Asp
        115                 120                 125

Asp Thr His Tyr Gln Met Phe Gln Leu Leu Asn Gln Glu Phe Thr Phe
    130                 135                 140

Asp Val Asp Met Ser Asn Leu Pro Cys Gly Leu Asn Gly Ala Leu Tyr
145                 150                 155                 160

Leu Ser Ala Met Asp Ala Asp Gly Gly Met Ala Lys Tyr Pro Thr Asn
                165                 170                 175

Lys Ala Gly Ala Lys Tyr Gly Thr Gly Tyr Cys Asp Ser Gln Cys Pro
            180                 185                 190

Arg Asp Ile Lys Phe Ile Asn Gly Glu Ala Asn Val Glu Gly Trp Asn
        195                 200                 205

Ala Thr Ser Ala Asn Ala Gly Thr Gly Asn Tyr Gly Thr Cys Cys Thr
    210                 215                 220

Glu Met Asp Ile Trp Glu Ala Asn Asn Asp Ala Ala Ala Tyr Thr Pro
225                 230                 235                 240

His Pro Cys Thr Thr Asn Ala Gln Thr Arg Cys Ser Gly Ser Asp Cys
                245                 250                 255

Thr Arg Asp Thr Gly Leu Cys Asp Ala Asp Gly Cys Asp Phe Asn Ser
            260                 265                 270

Phe Arg Met Gly Asp Gln Thr Phe Leu Gly Lys Gly Leu Thr Val Asp
        275                 280                 285

Thr Ser Lys Pro Phe Thr Val Val Thr Gln Phe Ile Thr Asn Asp Gly
```

```
                290               295               300
Thr Ser Ala Gly Thr Leu Thr Glu Ile Arg Arg Leu Tyr Val Gln Asn
305               310               315               320

Gly Lys Val Ile Gln Asn Ser Ser Val Lys Ile Pro Gly Ile Asp Leu
                325               330               335

Val Asn Ser Ile Thr Asp Asn Phe Cys Ser Gln Gln Lys Thr Ala Phe
                340               345               350

Gly Asp Thr Asn Tyr Phe Ala Gln His Gly Gly Leu Lys Gln Val Gly
                355               360               365

Glu Ala Leu Arg Thr Gly Met Val Leu Ala Leu Ser Ile Trp Asp Asp
370               375               380

Tyr Ala Ala Asn Met Leu Trp Leu Asp Ser Asn Tyr Pro Thr Asn Lys
385               390               395               400

Asp Pro Ser Thr Pro Gly Val Ala Arg Gly Thr Cys Ala Thr Thr Ser
                405               410               415

Gly Val Pro Ala Gln Ile Glu Ala Gln Ser Pro Asn Ala Tyr Val Val
                420               425               430

Phe Ser Asn Ile Lys Phe Gly Asp Leu Asn Thr Thr Tyr Thr Gly Thr
                435               440               445

Val Ser Ser Ser Val Ser Ser Ser His Ser Ser Thr Ser Thr Ser Ser
                450               455               460

Ser Ser His Ser Ser Ser Thr Pro Pro Thr Gln Pro Thr Gly Val
465               470               475               480

Thr Val Pro Gln Trp Gly Gln Cys Gly Gly Ile Gly Tyr Thr Gly Ser
                485               490               495

Thr Thr Cys Ala Ser Pro Tyr Thr Cys His Val Leu Asn Pro Tyr Tyr
                500               505               510

Ser Gln Cys Tyr
        515

<210> SEQ ID NO 39
<211> LENGTH: 516
<212> TYPE: PRT
<213> ORGANISM: Phanerochaete chrysosporium

<400> SEQUENCE: 39

Met Phe Arg Thr Ala Thr Leu Leu Ala Phe Thr Met Ala Ala Met Val
1               5                  10                  15

Phe Gly Gln Gln Val Gly Thr Asn Thr Ala Arg Ser His Pro Ala Leu
                20                  25                  30

Thr Ser Gln Lys Cys Thr Lys Ser Gly Gly Cys Ser Asn Leu Asn Thr
            35                  40                  45

Lys Ile Val Leu Asp Ala Asn Trp Arg Trp Leu His Ser Thr Ser Gly
        50                  55                  60

Tyr Thr Asn Cys Tyr Thr Gly Asn Gln Trp Asp Ala Thr Leu Cys Pro
65                  70                  75                  80

Asp Gly Lys Thr Cys Ala Ala Asn Cys Ala Leu Asp Gly Ala Asp Tyr
                85                  90                  95

Thr Gly Thr Tyr Gly Ile Thr Ala Ser Gly Ser Ser Leu Lys Leu Gln
            100                 105                 110

Phe Val Thr Gly Ser Asn Val Gly Ser Arg Val Tyr Leu Met Ala Asp
        115                 120                 125

Asp Thr His Tyr Gln Met Phe Gln Leu Leu Asn Gln Glu Phe Thr Phe
    130                 135                 140

Asp Val Asp Met Ser Asn Leu Pro Cys Gly Leu Asn Gly Ala Leu Tyr
```

```
                145                 150                 155                 160
Leu Ser Ala Met Asp Ala Asp Gly Gly Met Ala Lys Tyr Pro Thr Asn
                165                 170                 175

Lys Ala Gly Ala Lys Tyr Gly Thr Gly Tyr Cys Asp Ser Gln Cys Pro
            180                 185                 190

Arg Asp Ile Lys Phe Ile Asn Gly Glu Ala Asn Val Glu Gly Trp Asn
        195                 200                 205

Ala Thr Ser Ala Asn Ala Gly Thr Gly Asn Tyr Gly Thr Cys Cys Thr
    210                 215                 220

Glu Met Asp Ile Trp Glu Ala Asn Asn Asp Ala Ala Ala Tyr Thr Pro
225                 230                 235                 240

His Pro Cys Thr Thr Asn Ala Gln Thr Arg Cys Ser Gly Ser Asp Cys
                245                 250                 255

Thr Arg Asp Thr Gly Leu Cys Asp Ala Asp Gly Cys Asp Phe Asn Ser
            260                 265                 270

Phe Arg Met Gly Asp Gln Thr Phe Leu Gly Lys Gly Leu Thr Val Asp
        275                 280                 285

Thr Ser Lys Pro Phe Thr Val Val Thr Gln Phe Ile Thr Asn Asp Gly
    290                 295                 300

Thr Ser Ala Gly Thr Leu Thr Glu Ile Arg Arg Leu Tyr Val Gln Asn
305                 310                 315                 320

Gly Lys Val Ile Gln Asn Ser Ser Val Lys Ile Pro Gly Ile Asp Pro
                325                 330                 335

Val Asn Ser Ile Thr Asp Asn Phe Cys Ser Gln Gln Lys Thr Ala Phe
            340                 345                 350

Gly Asp Thr Asn Tyr Phe Ala Gln His Gly Gly Leu Lys Gln Val Gly
        355                 360                 365

Glu Ala Leu Arg Thr Gly Met Val Leu Ala Leu Ser Ile Trp Asp Asp
    370                 375                 380

Tyr Ala Ala Asn Met Leu Trp Leu Asp Ser Asn Tyr Pro Thr Asn Lys
385                 390                 395                 400

Asp Pro Ser Thr Pro Gly Val Ala Arg Gly Thr Cys Ala Thr Thr Ser
                405                 410                 415

Gly Val Pro Ala Gln Ile Glu Ala Gln Ser Pro Asn Ala Tyr Val Val
            420                 425                 430

Phe Ser Asn Ile Lys Phe Gly Asp Leu Asn Thr Thr Tyr Thr Gly Thr
        435                 440                 445

Val Ser Ser Ser Val Ser Ser Ser His Ser Ser Thr Ser Thr Ser Ser
    450                 455                 460

Ser Ser His Ser Ser Ser Thr Pro Pro Thr Gln Pro Thr Gly Val
465                 470                 475                 480

Thr Val Pro Gln Trp Gly Gln Cys Gly Gly Ile Gly Tyr Thr Gly Ser
                485                 490                 495

Thr Thr Cys Ala Ser Pro Tyr Thr Cys His Val Leu Asn Pro Tyr Tyr
            500                 505                 510

Ser Gln Cys Tyr
        515

<210> SEQ ID NO 40
<211> LENGTH: 511
<212> TYPE: PRT
<213> ORGANISM: Phanerochaete chrysosporium

<400> SEQUENCE: 40

Met Phe Arg Ala Ala Ala Leu Leu Ala Phe Thr Cys Leu Ala Met Val
```

-continued

```
1               5                   10                  15
Ser Gly Gln Gln Ala Gly Thr Asn Thr Ala Glu Asn His Pro Gln Leu
                20                  25                  30

Gln Ser Gln Gln Cys Thr Thr Ser Gly Gly Cys Lys Pro Leu Ser Thr
                35                  40                  45

Lys Val Val Leu Asp Ser Asn Trp Arg Trp Val His Ser Thr Ser Gly
                50                  55                  60

Tyr Thr Asn Cys Tyr Thr Gly Asn Glu Trp Asn Thr Ser Leu Cys Pro
65                  70                  75                  80

Asp Gly Lys Thr Cys Ala Ala Asn Cys Ala Leu Asp Gly Ala Asp Tyr
                85                  90                  95

Ser Gly Thr Tyr Gly Ile Thr Ser Thr Gly Thr Ala Leu Thr Leu Lys
                100                 105                 110

Phe Val Thr Gly Ser Asn Val Gly Ser Arg Val Tyr Leu Met Ala Asp
                115                 120                 125

Asp Thr His Tyr Gln Leu Leu Lys Leu Leu Asn Gln Glu Phe Thr Phe
                130                 135                 140

Asp Val Asp Met Ser Asn Leu Pro Cys Gly Leu Asn Gly Ala Leu Tyr
145                 150                 155                 160

Leu Ser Ala Met Asp Ala Asp Gly Gly Met Ser Lys Tyr Pro Gly Asn
                165                 170                 175

Lys Ala Gly Ala Lys Tyr Gly Thr Gly Tyr Cys Asp Ser Gln Cys Pro
                180                 185                 190

Lys Asp Ile Lys Phe Ile Asn Gly Glu Ala Asn Val Gly Asn Trp Thr
                195                 200                 205

Glu Thr Gly Ser Asn Thr Gly Thr Gly Ser Tyr Gly Thr Cys Cys Ser
                210                 215                 220

Glu Met Asp Ile Trp Glu Ala Asn Asn Asp Ala Ala Phe Thr Pro
225                 230                 235                 240

His Pro Cys Thr Thr Gly Gln Thr Arg Cys Ser Gly Asp Asp Cys
                245                 250                 255

Ala Arg Asn Thr Gly Leu Cys Asp His Gly Asp Gly Cys Asp Phe Asn
                260                 265                 270

Ser Phe Arg Met Gly Asp Lys Thr Phe Leu Gly Lys Gly Met Thr Val
                275                 280                 285

Asp Thr Ser Lys Pro Phe Thr Asp Val Thr Gln Phe Leu Thr Asn Asp
                290                 295                 300

Asn Thr Ser Thr Gly Thr Leu Ser Glu Ile Arg Arg Ile Tyr Ile Gln
305                 310                 315                 320

Asn Gly Lys Val Ile Gln Asn Ser Val Ala Asn Ile Pro Gly Val Asp
                325                 330                 335

Pro Val Asn Ser Ile Thr Asp Asn Phe Cys Ala Gln Gln Lys Thr Ala
                340                 345                 350

Phe Gly Asp Thr Asn Trp Phe Ala Gln Lys Gly Gly Leu Lys Gln Met
                355                 360                 365

Gly Glu Ala Leu Gly Asn Gly Met Val Leu Ala Leu Ser Ile Trp Asp
                370                 375                 380

Asp His Ala Ala Asn Met Leu Trp Leu Asp Ser Asp Tyr Pro Thr Asp
385                 390                 395                 400

Lys Asp Pro Ser Ala Pro Gly Val Ala Arg Gly Thr Cys Ala Thr Thr
                405                 410                 415

Ser Gly Val Pro Ser Asp Val Glu Ser Gln Val Pro Asn Ser Gln Val
                420                 425                 430
```

```
Val Phe Ser Asn Ile Lys Phe Gly Asp Ile Gly Ser Thr Phe Ser Gly
            435                 440                 445

Thr Ser Ser Pro Asn Pro Pro Gly Gly Ser Thr Thr Ser Ser Pro Val
        450                 455                 460

Thr Thr Ser Pro Thr Pro Pro Thr Gly Pro Thr Val Pro Gln Trp
465                 470                 475                 480

Gly Gln Cys Gly Gly Ile Gly Tyr Ser Gly Ser Thr Thr Cys Ala Ser
                485                 490                 495

Pro Tyr Thr Cys His Val Leu Asn Pro Tyr Tyr Ser Gln Cys Tyr
                500                 505                 510

<210> SEQ ID NO 41
<211> LENGTH: 510
<212> TYPE: PRT
<213> ORGANISM: Phanerochaete chrysosporium

<400> SEQUENCE: 41

Met Phe Arg Ala Ala Ala Leu Leu Ala Phe Thr Cys Leu Ala Met Val
1               5                   10                  15

Ser Gly Gln Gln Ala Gly Thr Asn Thr Ala Glu Asn His Pro Gln Leu
            20                  25                  30

Gln Ser Gln Gln Cys Thr Thr Ser Gly Gly Cys Lys Pro Leu Ser Thr
        35                  40                  45

Lys Val Val Leu Asp Ser Asn Trp Arg Trp Val His Ser Thr Ser Gly
    50                  55                  60

Tyr Thr Asn Cys Tyr Thr Gly Asn Glu Trp Asp Thr Ser Leu Cys Pro
65                  70                  75                  80

Asp Gly Lys Thr Cys Ala Ala Asn Cys Ala Leu Asp Gly Ala Asp Tyr
                85                  90                  95

Ser Gly Thr Tyr Gly Ile Thr Ser Thr Gly Thr Ala Leu Thr Leu Lys
            100                 105                 110

Phe Val Thr Gly Ser Asn Val Gly Ser Arg Val Tyr Leu Met Ala Asp
        115                 120                 125

Asp Thr His Tyr Gln Leu Leu Lys Leu Leu Asn Gln Glu Phe Thr Phe
    130                 135                 140

Asp Val Asp Met Ser Asn Leu Pro Cys Gly Leu Asn Gly Ala Leu Tyr
145                 150                 155                 160

Leu Ser Ala Met Asp Ala Asp Gly Gly Met Ser Lys Tyr Pro Gly Asn
                165                 170                 175

Lys Ala Gly Ala Lys Tyr Gly Thr Gly Tyr Cys Asp Ser Gln Cys Pro
            180                 185                 190

Lys Asp Ile Lys Phe Ile Asn Gly Glu Ala Asn Val Gly Asn Trp Thr
        195                 200                 205

Glu Thr Gly Ser Asn Thr Gly Thr Gly Ser Tyr Gly Thr Cys Cys Ser
    210                 215                 220

Glu Met Asp Ile Trp Glu Ala Asn Asn Asp Ala Ala Phe Thr Pro
225                 230                 235                 240

His Pro Cys Thr Thr Thr Gly Gln Thr Arg Cys Ser Gly Asp Asp Cys
                245                 250                 255

Ala Arg Asn Thr Gly Leu Cys Asp Gly Asp Gly Cys Asp Phe Asn Ser
            260                 265                 270

Phe Arg Met Gly Asp Lys Thr Phe Leu Gly Lys Gly Met Thr Val Asp
        275                 280                 285

Thr Ser Lys Pro Phe Thr Val Val Thr Gln Phe Leu Thr Asn Asp Asn
    290                 295                 300
```

-continued

Thr Ser Thr Gly Thr Leu Ser Glu Ile Arg Arg Ile Tyr Ile Gln Asn
305                 310                 315                 320

Gly Lys Val Ile Gln Asn Ser Val Ala Asn Ile Pro Gly Val Asp Pro
            325                 330                 335

Val Asn Ser Ile Thr Asp Asn Phe Cys Ala Gln Gln Lys Thr Ala Phe
            340                 345                 350

Gly Asp Thr Asn Trp Phe Ala Gln Lys Gly Gly Leu Lys Gln Met Gly
            355                 360                 365

Glu Ala Leu Gly Asn Gly Met Val Leu Ala Leu Ser Ile Trp Asp Asp
370                 375                 380

His Ala Ala Asn Met Leu Trp Leu Asp Ser Asp Tyr Pro Thr Asp Lys
385                 390                 395                 400

Asp Pro Ser Ala Pro Gly Val Ala Arg Gly Thr Cys Ala Thr Thr Ser
            405                 410                 415

Gly Val Pro Ser Asp Val Glu Ser Gln Val Pro Asn Ser Gln Val Val
            420                 425                 430

Phe Ser Asn Ile Lys Phe Gly Asp Ile Gly Ser Thr Phe Ser Gly Thr
            435                 440                 445

Ser Ser Pro Asn Pro Pro Gly Gly Ser Thr Thr Ser Ser Pro Val Thr
450                 455                 460

Thr Ser Pro Thr Pro Pro Pro Thr Gly Pro Thr Val Pro Gln Trp Gly
465                 470                 475                 480

Gln Cys Gly Gly Ile Gly Tyr Ser Gly Ser Thr Thr Cys Ala Ser Pro
            485                 490                 495

Tyr Thr Cys His Val Leu Asn Pro Tyr Tyr Ser Gln Cys Tyr
            500                 505                 510

<210> SEQ ID NO 42
<211> LENGTH: 540
<212> TYPE: PRT
<213> ORGANISM: Phanerochaete chrysosporium

<400> SEQUENCE: 42

Met Phe Arg Ala Ala Ala Leu Leu Ala Phe Thr Cys Leu Ala Met Val
1               5                   10                  15

Ser Gly Gln Gln Ala Gly Thr Asn Thr Ala Glu Asn His Pro Gln Leu
            20                  25                  30

Gln Ser Gln Gln Cys Thr Thr Ser Gly Gly Cys Lys Pro Leu Ser Thr
        35                  40                  45

Lys Val Val Leu Asp Ser Asn Trp Arg Trp Val His Ser Thr Ser Gly
50                  55                  60

Tyr Thr Asn Cys Tyr Thr Gly Asn Glu Trp Asp Thr Ser Leu Cys Pro
65                  70                  75                  80

Asp Gly Lys Thr Cys Ala Ala Asn Cys Ala Leu Asp Gly Ala Asp Tyr
            85                  90                  95

Ser Gly Thr Tyr Gly Ile Thr Ser Thr Gly Thr Ala Leu Thr Leu Lys
            100                 105                 110

Phe Val Thr Gly Ser Asn Val Gly Ser Arg Val Tyr Leu Met Ala Asp
            115                 120                 125

Asp Thr His Tyr Gln Leu Leu Lys Leu Leu Asn Gln Glu Phe Thr Phe
130                 135                 140

Asp Val Asp Met Ser Asn Leu Pro Cys Gly Leu Asn Gly Ala Leu Tyr
145                 150                 155                 160

Leu Ser Ala Met Asp Ala Asp Gly Gly Met Ser Lys Tyr Pro Gly Asn
            165                 170                 175

-continued

```
Lys Ala Gly Ala Lys Tyr Gly Thr Gly Tyr Cys Asp Ser Gln Cys Pro
                180                 185                 190

Lys Asp Ile Lys Phe Ile Asn Gly Glu Ala Asn Val Gly Asn Trp Thr
            195                 200                 205

Glu Thr Gly Ser Asn Thr Gly Thr Gly Ser Tyr Gly Thr Cys Cys Ser
        210                 215                 220

Glu Met Asp Ile Trp Glu Ala Asn Asn Asp Ala Ala Ala Phe Thr Pro
225                 230                 235                 240

His Pro Cys Thr Thr Thr Gly Gln Thr Arg Cys Ser Gly Asp Asp Cys
                245                 250                 255

Ala Arg Asn Thr Gly Leu Cys Asp Gly Asp Gly Cys Asp Phe Asn Ser
            260                 265                 270

Phe Arg Met Gly Asp Lys Thr Phe Leu Gly Lys Gly Met Thr Val Asp
        275                 280                 285

Thr Ser Lys Pro Phe Thr Val Val Thr Gln Phe Leu Thr Asn Asp Asn
290                 295                 300

Thr Ser Thr Gly Thr Leu Ser Glu Ile Arg Arg Ile Tyr Ile Gln Asn
305                 310                 315                 320

Gly Lys Val Ile Gln Asn Ser Val Ala Asn Ile Pro Gly Val Asp Pro
                325                 330                 335

Val Asn Ser Ile Thr Asp Asn Phe Cys Ala Gln Gln Lys Thr Ala Phe
            340                 345                 350

Gly Asp Thr Asn Trp Phe Ala Gln Lys Gly Gly Leu Lys Gln Met Gly
        355                 360                 365

Glu Ala Leu Gly Asn Gly Met Val Leu Ala Leu Ser Ile Trp Asp Asp
370                 375                 380

His Ala Ala Asn Met Leu Trp Leu Asp Ser Asp Tyr Pro Thr Asp Lys
385                 390                 395                 400

Asp Pro Ser Ala Pro Gly Val Ala Arg Gly Thr Cys Ala Thr Thr Ser
                405                 410                 415

Gly Val Pro Ser Asp Val Glu Ser Gln Val Pro Asn Ser Gln Val Val
            420                 425                 430

Phe Ser Asn Ile Lys Phe Gly Asp Ile Gly Ser Thr Phe Ser Gly Thr
        435                 440                 445

Ser Ser Pro Asn Pro Pro Gly Gly Ser Thr Ser Ser Pro Val Thr
450                 455                 460

Thr Ser Pro Thr Pro Pro Thr Gly Pro Thr Val Pro Gln Trp Gly
465                 470                 475                 480

Gln Cys Gly Gly Ile Gly Tyr Ser Gly Ser Thr Cys Ala Ser Pro
                485                 490                 495

Tyr Thr Cys His Val Leu Asn Pro Cys Glu Ser Ile Leu Ser Leu Gln
            500                 505                 510

Arg Ser Ser Asn Ala Asp Gln Tyr Leu Gln Thr Thr Arg Ser Ala Thr
        515                 520                 525

Lys Arg Arg Leu Asp Thr Ala Leu Gln Pro Arg Lys
            530                 535                 540

<210> SEQ ID NO 43
<211> LENGTH: 523
<212> TYPE: PRT
<213> ORGANISM: Irpex lacteus

<400> SEQUENCE: 43

Met Phe Arg Lys Ala Ala Leu Leu Ala Phe Ser Phe Leu Ala Ile Ala
1               5                   10                  15
```

-continued

```
His Gly Gln Gln Val Gly Thr Asn Gln Ala Glu Asn His Pro Ser Leu
             20                  25                  30

Pro Ser Gln Lys Cys Thr Ala Ser Gly Cys Thr Thr Ser Ser Thr Ser
         35                  40                  45

Val Val Leu Asp Ala Asn Trp Arg Trp Val His Thr Thr Thr Gly Tyr
 50                  55                  60

Thr Asn Cys Tyr Thr Gly Gln Thr Trp Asp Ala Ser Ile Cys Pro Asp
 65                  70                  75                  80

Gly Val Thr Cys Ala Lys Ala Cys Ala Leu Asp Gly Ala Asp Tyr Ser
                 85                  90                  95

Gly Thr Tyr Gly Ile Thr Thr Ser Gly Asn Ala Leu Thr Leu Gln Phe
                100                 105                 110

Val Lys Gly Thr Asn Val Gly Ser Arg Val Tyr Leu Leu Gln Asp Ala
            115                 120                 125

Ser Asn Tyr Gln Met Phe Gln Leu Ile Asn Gln Glu Phe Thr Phe Asp
130                 135                 140

Val Asp Met Ser Asn Leu Pro Cys Gly Leu Asn Gly Ala Val Tyr Leu
145                 150                 155                 160

Ser Gln Met Asp Gln Asp Gly Gly Val Ser Arg Phe Pro Thr Asn Thr
                165                 170                 175

Ala Gly Ala Lys Tyr Gly Thr Gly Tyr Cys Asp Ser Gln Cys Pro Arg
                180                 185                 190

Asp Ile Lys Phe Ile Asn Gly Glu Ala Asn Val Glu Gly Trp Thr Gly
            195                 200                 205

Ser Ser Thr Asp Ser Asn Ser Gly Thr Gly Asn Tyr Gly Thr Cys Cys
210                 215                 220

Ser Glu Met Asp Ile Trp Glu Ala Asn Ser Val Ala Ala Ala Tyr Thr
225                 230                 235                 240

Pro His Pro Cys Ser Val Asn Gln Gln Thr Arg Cys Thr Gly Ala Asp
                245                 250                 255

Cys Gly Gln Gly Asp Asp Arg Tyr Asp Gly Val Cys Asp Pro Asp Gly
                260                 265                 270

Cys Asp Phe Asn Ser Phe Arg Met Gly Asp Gln Thr Phe Leu Gly Lys
            275                 280                 285

Gly Leu Thr Val Asp Thr Ser Arg Lys Phe Thr Ile Val Thr Gln Phe
290                 295                 300

Ile Ser Asp Asp Gly Thr Thr Ser Gly Asn Leu Ala Glu Ile Arg Arg
305                 310                 315                 320

Phe Tyr Val Gln Asp Gly Asn Val Ile Pro Asn Ser Lys Val Ser Ile
                325                 330                 335

Ala Gly Ile Asp Ala Val Asn Ser Ile Thr Asp Asp Phe Cys Thr Gln
                340                 345                 350

Gln Lys Thr Ala Phe Gly Asp Thr Asn Arg Phe Ala Ala Gln Gly Gly
            355                 360                 365

Leu Lys Gln Met Gly Ala Ala Leu Lys Ser Gly Met Val Leu Ala Leu
370                 375                 380

Ser Leu Trp Asp Asp His Ala Ala Asn Met Leu Trp Leu Asp Ser Asp
385                 390                 395                 400

Tyr Pro Thr Thr Ala Asp Ala Ser Asn Pro Gly Val Ala Arg Gly Thr
                405                 410                 415

Cys Pro Thr Thr Ser Gly Phe Pro Arg Asp Val Glu Ser Gln Ser Gly
                420                 425                 430

Ser Ala Thr Val Thr Tyr Ser Asn Ile Lys Trp Gly Asp Leu Asn Ser
            435                 440                 445
```

-continued

```
Thr Phe Thr Gly Thr Leu Thr Thr Pro Ser Gly Ser Ser Pro Ser
    450                 455                 460

Ser Pro Ala Ser Thr Ser Gly Ser Ser Thr Ser Ala Ser Ser Ala
465                 470                 475                 480

Ser Val Pro Thr Gln Ser Gly Thr Val Ala Gln Trp Ala Gln Cys Gly
                485                 490                 495

Gly Ile Gly Tyr Ser Gly Ala Thr Thr Cys Val Ser Pro Tyr Thr Cys
            500                 505                 510

His Val Val Asn Ala Tyr Tyr Ser Gln Cys Tyr
        515                 520

<210> SEQ ID NO 44
<211> LENGTH: 526
<212> TYPE: PRT
<213> ORGANISM: Irpex lacteus

<400> SEQUENCE: 44

Met Phe His Lys Ala Val Leu Val Ala Phe Ser Leu Val Thr Ile Val
1               5                   10                  15

His Gly Gln Gln Ala Gly Thr Gln Thr Ala Glu Asn His Pro Gln Leu
            20                  25                  30

Ser Ser Gln Lys Cys Thr Ala Gly Gly Ser Cys Thr Ser Ala Ser Thr
        35                  40                  45

Ser Val Val Leu Asp Ser Asn Trp Arg Trp Val His Thr Thr Ser Gly
50                  55                  60

Tyr Thr Asn Cys Tyr Thr Gly Asn Thr Trp Asp Ala Ser Ile Cys Ser
65                  70                  75                  80

Asp Pro Val Ser Cys Ala Gln Asn Cys Ala Leu Asp Gly Ala Asp Tyr
                85                  90                  95

Ala Gly Thr Tyr Gly Ile Thr Thr Ser Gly Asp Ala Leu Thr Leu Lys
            100                 105                 110

Phe Val Thr Gly Ser Asn Val Gly Ser Arg Val Tyr Leu Met Glu Asp
        115                 120                 125

Glu Thr Asn Tyr Gln Met Phe Lys Leu Met Asn Gln Glu Phe Thr Phe
    130                 135                 140

Asp Val Asp Val Ser Asn Leu Pro Cys Gly Leu Asn Gly Ala Val Tyr
145                 150                 155                 160

Phe Val Gln Met Asp Gln Asp Gly Gly Thr Ser Lys Phe Pro Asn Asn
                165                 170                 175

Lys Ala Gly Ala Lys Phe Gly Thr Gly Tyr Cys Asp Ser Gln Cys Pro
            180                 185                 190

Gln Asp Ile Lys Phe Ile Asn Gly Glu Ala Asn Ile Val Asp Trp Thr
        195                 200                 205

Ala Ser Ala Gly Asp Ala Asn Ser Gly Thr Gly Ser Phe Gly Thr Cys
    210                 215                 220

Cys Gln Glu Met Asp Ile Trp Glu Ala Asn Ser Ile Ser Ala Ala Tyr
225                 230                 235                 240

Thr Pro His Pro Cys Thr Val Thr Glu Gln Thr Arg Cys Ser Gly Ser
                245                 250                 255

Asp Cys Gly Gln Gly Ser Asp Arg Phe Asn Gly Ile Cys Asp Pro Asp
            260                 265                 270

Gly Cys Asp Phe Asn Ser Phe Arg Met Gly Asn Thr Glu Phe Tyr Gly
        275                 280                 285

Lys Gly Leu Thr Val Asp Thr Ser Gln Lys Phe Thr Ile Val Thr Gln
    290                 295                 300
```

```
Phe Ile Ser Asp Asp Gly Thr Ala Asp Gly Asn Leu Ala Glu Ile Arg
305                 310                 315                 320

Arg Phe Tyr Val Gln Asn Gly Lys Val Ile Pro Asn Ser Val Val Gln
            325                 330                 335

Ile Thr Gly Ile Asp Pro Val Asn Ser Ile Thr Glu Asp Phe Cys Thr
        340                 345                 350

Gln Gln Lys Thr Val Phe Gly Asp Thr Asn Asn Phe Ala Ala Lys Gly
            355                 360                 365

Gly Leu Lys Gln Met Gly Glu Ala Val Lys Asn Gly Met Val Leu Ala
        370                 375                 380

Leu Ser Leu Trp Asp Asp Tyr Ala Ala Gln Met Leu Trp Leu Asp Ser
385                 390                 395                 400

Asp Tyr Pro Thr Thr Ala Asp Pro Ser Gln Pro Gly Val Ala Arg Gly
            405                 410                 415

Thr Cys Pro Thr Thr Ser Gly Val Pro Ser Gln Val Glu Gly Gln Glu
        420                 425                 430

Gly Ser Ser Ser Val Ile Tyr Ser Asn Ile Lys Phe Gly Asp Leu Asn
            435                 440                 445

Ser Thr Phe Thr Gly Thr Leu Thr Asn Pro Ser Ser Pro Ala Gly Pro
450                 455                 460

Pro Val Thr Ser Ser Pro Ser Glu Pro Ser Gln Ser Thr Gln Pro Ser
465                 470                 475                 480

Gln Pro Ala Gln Pro Thr Gln Pro Ala Gly Thr Ala Ala Gln Trp Ala
            485                 490                 495

Gln Cys Gly Gly Met Gly Phe Thr Gly Pro Thr Val Cys Ala Ser Pro
        500                 505                 510

Phe Thr Cys His Val Leu Asn Pro Tyr Tyr Ser Gln Cys Tyr
            515                 520                 525

<210> SEQ ID NO 45
<211> LENGTH: 517
<212> TYPE: PRT
<213> ORGANISM: Irpex lacteus

<400> SEQUENCE: 45

Met Phe Pro Lys Ala Ser Leu Ile Ala Leu Ser Phe Ile Ala Ala Val
1               5                   10                  15

Tyr Gly Gln Gln Val Gly Thr Gln Met Ala Glu Val His Pro Lys Leu
            20                  25                  30

Pro Ser Gln Leu Cys Thr Lys Ser Gly Cys Thr Asn Gln Asn Thr Ala
        35                  40                  45

Val Val Leu Asp Ala Asn Trp Arg Trp Leu His Thr Thr Ser Gly Tyr
    50                  55                  60

Thr Asn Cys Tyr Thr Gly Asn Ser Trp Asp Ala Thr Leu Cys Pro Asp
65                  70                  75                  80

Ala Thr Thr Cys Ala Gln Asn Cys Ala Val Asp Gly Ala Asp Tyr Ser
                85                  90                  95

Gly Thr Tyr Gly Ile Thr Thr Ser Gly Asn Ala Leu Thr Leu Lys Phe
            100                 105                 110

Lys Thr Gly Thr Asn Val Gly Ser Arg Val Tyr Leu Met Gln Thr Asp
        115                 120                 125

Thr Ala Tyr Gln Met Phe Gln Leu Leu Asn Gln Glu Phe Thr Phe Asp
    130                 135                 140

Val Asp Met Ser Asn Leu Pro Cys Gly Leu Asn Gly Ala Leu Tyr Leu
145                 150                 155                 160
```

Ser Gln Met Asp Gln Asp Gly Gly Leu Ser Lys Phe Pro Thr Asn Lys
                165                 170                 175

Ala Gly Ala Lys Tyr Gly Thr Gly Tyr Cys Asp Ser Gln Cys Pro His
            180                 185                 190

Asp Ile Lys Phe Ile Asn Gly Met Ala Asn Val Ala Gly Trp Ala Gly
        195                 200                 205

Ser Ala Ser Asp Pro Asn Ala Gly Ser Gly Thr Leu Gly Thr Cys Cys
    210                 215                 220

Ser Glu Met Asp Ile Trp Glu Ala Asn Asn Asp Ala Ala Ala Phe Thr
225                 230                 235                 240

Pro His Pro Cys Ser Val Asp Gly Gln Thr Gln Cys Ser Gly Thr Gln
                245                 250                 255

Cys Gly Asp Asp Glu Arg Tyr Ser Gly Leu Cys Asp Lys Asp Gly
            260                 265                 270

Cys Asp Phe Asn Ser Phe Arg Met Gly Asp Lys Ser Phe Leu Gly Lys
        275                 280                 285

Gly Met Thr Val Asp Thr Ser Arg Lys Phe Thr Val Thr Gln Phe
    290                 295                 300

Val Thr Thr Asp Gly Thr Asn Gly Asp Leu His Glu Ile Arg Arg
305                 310                 315                 320

Leu Tyr Val Gln Asp Gly Lys Val Ile Gln Asn Ser Val Ser Ile
                325                 330                 335

Pro Gly Ile Asp Ala Val Asp Ser Ile Thr Asp Asn Phe Cys Ala Gln
            340                 345                 350

Gln Lys Ser Val Phe Gly Asp Thr Asn Tyr Phe Ala Thr Leu Gly Gly
        355                 360                 365

Leu Lys Lys Met Gly Ala Ala Leu Lys Ser Gly Met Val Leu Ala Met
    370                 375                 380

Ser Val Trp Asp Asp His Ala Ala Ser Met Gln Trp Leu Asp Ser Asn
385                 390                 395                 400

Tyr Pro Ala Asp Gly Asp Ala Thr Lys Pro Gly Val Ala Arg Gly Thr
                405                 410                 415

Cys Ser Ala Asp Ser Gly Leu Pro Thr Asn Val Glu Ser Gln Ser Ala
            420                 425                 430

Ser Ala Ser Val Thr Phe Ser Asn Ile Lys Trp Gly Asp Ile Asn Thr
        435                 440                 445

Thr Phe Thr Gly Thr Gly Ser Thr Ser Pro Ser Ser Pro Ala Gly Pro
    450                 455                 460

Val Ser Ser Ser Thr Ser Val Ala Ser Gln Pro Thr Gln Pro Ala Gln
465                 470                 475                 480

Gly Thr Val Ala Gln Trp Gly Gln Cys Gly Gly Thr Gly Phe Thr Gly
                485                 490                 495

Pro Thr Val Cys Ala Ser Pro Phe Thr Cys His Val Val Asn Pro Tyr
            500                 505                 510

Tyr Ser Gln Cys Tyr
        515

<210> SEQ ID NO 46
<211> LENGTH: 423
<212> TYPE: PRT
<213> ORGANISM: Alternaria alternata

<400> SEQUENCE: 46

Met Thr Trp Gln Ser Cys Thr Ala Lys Gly Ser Cys Thr Asn Lys Asn
1               5                   10                  15

-continued

```
Gly Lys Ile Val Ile Asp Ala Asn Trp Arg Trp Leu His Lys Glu
             20                  25                  30
Gly Tyr Asp Asn Cys Tyr Thr Gly Asn Glu Trp Asp Ala Thr Ala Cys
         35                  40                  45
Pro Asp Asn Lys Ala Cys Ala Asn Cys Ala Val Asp Gly Ala Asp
 50                  55                  60
Tyr Ser Gly Thr Tyr Gly Ile Thr Ala Gly Ser Asn Ser Leu Lys Leu
 65                  70                  75                  80
Lys Phe Ile Thr Lys Gly Ser Tyr Ser Thr Asn Ile Gly Ser Arg Thr
                 85                  90                  95
Tyr Leu Met Lys Asp Asp Thr Thr Tyr Glu Met Phe Lys Phe Thr Gly
             100                 105                 110
Asn Gln Glu Phe Thr Phe Asp Val Asp Val Ser Asn Leu Pro Cys Gly
         115                 120                 125
Phe Asn Gly Ala Leu Tyr Phe Val Ser Met Asp Ala Asp Gly Gly Leu
 130                 135                 140
Lys Lys Tyr Ser Thr Asn Lys Ala Gly Ala Lys Tyr Gly Thr Gly Tyr
 145                 150                 155                 160
Cys Asp Ala Gln Cys Pro Arg Asp Leu Lys Phe Ile Asn Gly Glu Gly
                 165                 170                 175
Asn Val Glu Gly Trp Lys Pro Ser Ser Asn Asp Ala Asn Ala Gly Val
             180                 185                 190
Gly Gly His Gly Ser Cys Cys Ala Glu Met Asp Ile Trp Glu Ala Asn
         195                 200                 205
Ser Val Ser Thr Ala Val Thr Pro His Ser Cys Ser Thr Ile Glu Gln
 210                 215                 220
Ser Arg Cys Asp Gly Asp Gly Cys Gly Gly Thr Tyr Ser Ala Asp Arg
225                 230                 235                 240
Tyr Ala Gly Val Cys Asp Pro Asp Gly Cys Asp Phe Asn Ser Tyr Arg
                 245                 250                 255
Met Gly Val Lys Asp Phe Tyr Gly Lys Gly Lys Thr Val Asp Thr Ser
             260                 265                 270
Lys Lys Phe Thr Val Val Thr Gln Phe Ile Gly Thr Gly Asp Ala Met
         275                 280                 285
Glu Ile Lys Arg Phe Tyr Val Gln Asn Gly Lys Thr Ile Ala Gln Pro
 290                 295                 300
Ala Ser Ala Val Pro Gly Val Glu Gly Asn Ser Ile Thr Thr Lys Phe
305                 310                 315                 320
Cys Asp Gln Gln Lys Ala Val Phe Gly Asp Thr Tyr Thr Phe Lys Asp
                 325                 330                 335
Lys Gly Gly Met Ala Asn Met Ala Lys Ala Leu Ala Asn Gly Met Val
             340                 345                 350
Leu Val Met Ser Leu Trp Asp Asp His Tyr Ser Asn Met Leu Trp Leu
         355                 360                 365
Asp Ser Thr Tyr Pro Thr Asp Lys Asn Pro Thr Asp Leu Gly Thr
 370                 375                 380
Gly Arg Gly Glu Cys Glu Thr Ser Ser Gly Val Pro Ala Asp Val Glu
385                 390                 395                 400
Ser Gln His Ala Asp Ala Thr Val Val Tyr Ser Asn Ile Lys Phe Gly
                 405                 410                 415
Pro Leu Asn Ser Thr Phe Gly
             420
```

<210> SEQ ID NO 47
<211> LENGTH: 438
<212> TYPE: PRT
<213> ORGANISM: Leptocphaeria maculans

<400> SEQUENCE: 47

| Met | Tyr | Arg | Ser | Leu | Ile | Phe | Ala | Thr | Ser | Leu | Leu | Ser | Leu | Ala | Lys |
|---|---|---|---|---|---|---|---|---|---|---|---|---|---|---|---|
| 1 | | | | 5 | | | | | 10 | | | | | 15 | |

| Gly | Gln | Leu | Val | Gly | Asn | Leu | Tyr | Cys | Lys | Gly | Ser | Cys | Thr | Ala | Lys |
|---|---|---|---|---|---|---|---|---|---|---|---|---|---|---|---|
| | | | 20 | | | | | 25 | | | | | 30 | | |

| Asn | Gly | Lys | Val | Val | Ile | Asp | Ala | Asn | Trp | Arg | Trp | Leu | His | Val | Lys |
|---|---|---|---|---|---|---|---|---|---|---|---|---|---|---|---|
| | | 35 | | | | | 40 | | | | | 45 | | | |

| Gly | Gly | Tyr | Thr | Asn | Cys | Tyr | Thr | Gly | Asn | Glu | Trp | Asn | Ala | Thr | Ala |
|---|---|---|---|---|---|---|---|---|---|---|---|---|---|---|---|
| | 50 | | | | | 55 | | | | | 60 | | | | |

| Cys | Pro | Asp | Asn | Lys | Ser | Cys | Ala | Thr | Asn | Cys | Ala | Ile | Asp | Gly | Ala |
|---|---|---|---|---|---|---|---|---|---|---|---|---|---|---|---|
| 65 | | | | | 70 | | | | | 75 | | | | | 80 |

| Asp | Tyr | Arg | Arg | Leu | Arg | His | Tyr | Cys | Glu | Arg | Gln | Leu | Leu | Gly | Thr |
|---|---|---|---|---|---|---|---|---|---|---|---|---|---|---|---|
| | | | | 85 | | | | | 90 | | | | | 95 | |

| Glu | Val | His | His | Gln | Gly | Leu | Tyr | Ser | Thr | Asn | Ile | Gly | Ser | Arg | Thr |
|---|---|---|---|---|---|---|---|---|---|---|---|---|---|---|---|
| | | | 100 | | | | | 105 | | | | | 110 | | |

| Tyr | Leu | Met | Gln | Asp | Asp | Ser | Thr | Tyr | Gln | Leu | Phe | Lys | Phe | Thr | Gly |
|---|---|---|---|---|---|---|---|---|---|---|---|---|---|---|---|
| | | | 115 | | | | | 120 | | | | | 125 | | |

| Ser | Gln | Glu | Phe | Thr | Phe | Asp | Val | Asp | Leu | Ser | Asn | Leu | Pro | Cys | Gly |
|---|---|---|---|---|---|---|---|---|---|---|---|---|---|---|---|
| | 130 | | | | | 135 | | | | | 140 | | | | |

| Leu | Asn | Gly | Ala | Leu | Tyr | Phe | Val | Ser | Met | Asp | Ala | Asp | Gly | Gly | Leu |
|---|---|---|---|---|---|---|---|---|---|---|---|---|---|---|---|
| 145 | | | | | 150 | | | | | 155 | | | | | 160 |

| Lys | Lys | Tyr | Pro | Thr | Asn | Lys | Ala | Gly | Ala | Lys | Tyr | Gly | Thr | Gly | Tyr |
|---|---|---|---|---|---|---|---|---|---|---|---|---|---|---|---|
| | | | | 165 | | | | | 170 | | | | | 175 | |

| Cys | Asp | Ala | Gln | Cys | Pro | Arg | Asp | Leu | Lys | Phe | Ile | Asn | Gly | Glu | Gly |
|---|---|---|---|---|---|---|---|---|---|---|---|---|---|---|---|
| | | | 180 | | | | | 185 | | | | | 190 | | |

| Asn | Val | Glu | Gly | Trp | Gln | Pro | Ser | Lys | Asn | Asp | Gln | Asn | Ala | Gly | Val |
|---|---|---|---|---|---|---|---|---|---|---|---|---|---|---|---|
| | | 195 | | | | | 200 | | | | | 205 | | | |

| Gly | Gly | His | Gly | Ser | Cys | Cys | Ala | Glu | Met | Asp | Ile | Trp | Glu | Ala | Asn |
|---|---|---|---|---|---|---|---|---|---|---|---|---|---|---|---|
| | 210 | | | | | 215 | | | | | 220 | | | | |

| Ser | Val | Ser | Thr | Ala | Val | Thr | Pro | His | Ser | Cys | Ser | Thr | Ile | Glu | Gln |
|---|---|---|---|---|---|---|---|---|---|---|---|---|---|---|---|
| 225 | | | | | 230 | | | | | 235 | | | | | 240 |

| Ser | Arg | Cys | Asp | Gly | Asp | Gly | Cys | Gly | Gly | Thr | Tyr | Ser | Ala | Asp | Arg |
|---|---|---|---|---|---|---|---|---|---|---|---|---|---|---|---|
| | | | | 245 | | | | | 250 | | | | | 255 | |

| Tyr | Ala | Gly | Val | Cys | Asp | Pro | Asp | Gly | Cys | Asp | Phe | Asn | Ser | Tyr | Arg |
|---|---|---|---|---|---|---|---|---|---|---|---|---|---|---|---|
| | | | 260 | | | | | 265 | | | | | 270 | | |

| Met | Gly | Val | Lys | Asp | Phe | Tyr | Gly | Lys | Gly | Lys | Thr | Val | Asp | Thr | Ser |
|---|---|---|---|---|---|---|---|---|---|---|---|---|---|---|---|
| | | 275 | | | | | 280 | | | | | 285 | | | |

| Lys | Lys | Phe | Thr | Val | Val | Thr | Gln | Phe | Ile | Gly | Ser | Gly | Asp | Ala | Met |
|---|---|---|---|---|---|---|---|---|---|---|---|---|---|---|---|
| | 290 | | | | | 295 | | | | | 300 | | | | |

| Glu | Ile | Lys | Arg | Phe | Tyr | Val | Gln | Asn | Gly | Lys | Thr | Ile | Pro | Gln | Pro |
|---|---|---|---|---|---|---|---|---|---|---|---|---|---|---|---|
| 305 | | | | | 310 | | | | | 315 | | | | | 320 |

| Asp | Ser | Thr | Ile | Pro | Gly | Val | Thr | Gly | Asn | Ser | Ile | Thr | Thr | Phe | Phe |
|---|---|---|---|---|---|---|---|---|---|---|---|---|---|---|---|
| | | | | 325 | | | | | 330 | | | | | 335 | |

| Cys | Asp | Ala | Gln | Lys | Lys | Ala | Phe | Gly | Asp | Lys | Tyr | Thr | Phe | Lys | Asp |
|---|---|---|---|---|---|---|---|---|---|---|---|---|---|---|---|
| | | | 340 | | | | | 345 | | | | | 350 | | |

| Lys | Gly | Gly | Met | Ala | Asn | Met | Pro | Ser | Thr | Cys | Asn | Gly | Met | Val | Leu |
|---|---|---|---|---|---|---|---|---|---|---|---|---|---|---|---|
| | | 355 | | | | | 360 | | | | | 365 | | | |

| Val | Met | Ser | Leu | Trp | Asp | Asp | His | Tyr | Ser | Asn | Met | Leu | Trp | Leu | Asp |
|---|---|---|---|---|---|---|---|---|---|---|---|---|---|---|---|
| | 370 | | | | | 375 | | | | | 380 | | | | |

| Ser | Thr | Tyr | Pro | Thr | Asp | Lys | Asn | Pro | Asp | Thr | Asp | Ala | Gly | Ser | Gly |

```
385                 390                 395                 400

Arg Gly Glu Cys Ala Ile Thr Ser Gly Val Pro Ala Asp Val Glu Ser
                405                 410                 415

Gln His Pro Asp Ala Ser Val Ile Tyr Ser Asn Ile Lys Phe Gly Pro
            420                 425                 430

Ile Asn Thr Thr Phe Gly
        435

<210> SEQ ID NO 48
<211> LENGTH: 452
<212> TYPE: PRT
<213> ORGANISM: Cryphonectria parasitica
<400> SEQUENCE: 48

Met Phe Ser Lys Phe Ala Leu Thr Gly Ser Leu Leu Ala Gly Ala Val
1               5                   10                  15
Asn Ala Gln Gly Val Gly Thr Gln Gln Thr Glu Thr His Pro Gln Met
            20                  25                  30

Thr Trp Gln Ser Cys Thr Ser Pro Ser Ser Cys Thr Thr Asn Gln Gly
        35                  40                  45

Glu Val Val Ile Asp Ser Asn Trp Arg Trp Val His Asp Lys Asp Gly
    50                  55                  60

Tyr Val Asn Cys Tyr Thr Gly Asn Thr Trp Asn Thr Thr Leu Cys Pro
65                  70                  75                  80

Asp Asp Lys Thr Cys Ala Ala Asn Cys Val Leu Asp Gly Ala Asp Tyr
                85                  90                  95

Ser Ser Thr Tyr Gly Ile Thr Thr Ser Gly Asn Ala Leu Ser Leu Gln
            100                 105                 110

Phe Val Thr Gln Ser Ser Gly Lys Asn Ile Gly Ser Arg Thr Tyr Leu
        115                 120                 125

Met Glu Ser Ser Thr Lys Tyr His Leu Phe Asp Leu Ile Gly Asn Glu
    130                 135                 140

Phe Ala Phe Asp Val Asp Leu Ser Lys Leu Pro Cys Gly Leu Asn Gly
145                 150                 155                 160

Ala Leu Tyr Phe Val Thr Met Asp Ala Asp Gly Gly Met Ala Lys Tyr
                165                 170                 175

Ser Thr Asn Thr Ala Gly Ala Glu Tyr Gly Thr Gly Tyr Cys Asp Ser
            180                 185                 190

Gln Cys Pro Arg Asp Leu Lys Phe Ile Asn Gly Gln Gly Asn Val Glu
        195                 200                 205

Gly Trp Thr Pro Ser Thr Asn Asp Ala Asn Ala Gly Val Gly Gly Leu
    210                 215                 220

Gly Ser Cys Cys Ser Glu Met Asp Val Trp Glu Ala Asn Ser Met Asp
225                 230                 235                 240

Met Ala Tyr Thr Pro His Pro Cys Glu Thr Ala Ala Gln His Ser Cys
                245                 250                 255

Asn Ala Asp Glu Cys Gly Gly Thr Tyr Ser Ser Ser Arg Tyr Ala Gly
            260                 265                 270

Asp Cys Asp Pro Asp Gly Cys Asp Trp Asn Pro Phe Arg Met Gly Asn
        275                 280                 285

Lys Asp Phe Tyr Gly Ser Gly Asp Thr Val Asp Thr Ser Gln Lys Phe
    290                 295                 300

Thr Val Val Thr Gln Phe His Gly Ser Gly Ser Ser Leu Thr Glu Ile
305                 310                 315                 320

Ser Gln Tyr Tyr Ile Gln Gly Gly Thr Lys Ile Gln Gln Pro Asn Ser
```

```
                325                 330                 335
Thr Trp Pro Thr Leu Thr Gly Tyr Asn Ser Ile Thr Asp Asp Phe Cys
            340                 345                 350
Lys Ala Gln Lys Val Glu Phe Asn Asp Thr Asp Val Phe Ser Glu Lys
            355                 360                 365
Gly Gly Leu Ala Gln Met Gly Ala Gly Met Ala Asp Gly Met Val Leu
            370                 375                 380
Val Met Ser Leu Trp Asp Asp His Tyr Ala Asn Met Leu Trp Leu Asp
385                 390                 395                 400
Ser Thr Tyr Pro Val Asp Ala Asp Ala Ser Ser Pro Gly Lys Gln Arg
                405                 410                 415
Gly Thr Cys Ala Thr Thr Ser Gly Val Pro Ala Asp Val Glu Ser Ser
                420                 425                 430
Asp Ala Ser Ala Thr Val Ile Tyr Ser Asn Ile Lys Phe Gly Pro Ile
                435                 440                 445
Gly Ala Thr Tyr
            450

<210> SEQ ID NO 49
<211> LENGTH: 456
<212> TYPE: PRT
<213> ORGANISM: Cochliobolus carbonum

<400> SEQUENCE: 49

Met Tyr Arg Thr Leu Ala Phe Ala Ser Leu Ser Leu Tyr Gly Ala Ala
1               5                   10                  15
Arg Ala Gln Gln Val Gly Thr Ser Thr Ala Glu Asn His Pro Lys Leu
            20                  25                  30
Thr Trp Gln Thr Cys Thr Gly Thr Gly Gly Thr Asn Cys Ser Asn Lys
        35                  40                  45
Ser Gly Ser Val Val Leu Asp Ser Asn Trp Arg Trp Ala His Asn Val
    50                  55                  60
Gly Gly Tyr Thr Asn Cys Tyr Thr Gly Asn Ser Trp Ser Thr Gln Tyr
65                  70                  75                  80
Cys Pro Asp Gly Asp Ser Cys Thr Lys Asn Cys Ala Ile Asp Gly Ala
                85                  90                  95
Asp Tyr Ser Gly Thr Tyr Gly Ile Thr Thr Ser Asn Asn Ala Leu Ser
            100                 105                 110
Leu Lys Phe Val Thr Lys Gly Ser Phe Ser Ser Asn Ile Gly Ser Arg
        115                 120                 125
Thr Tyr Leu Met Glu Thr Asp Thr Lys Tyr Gln Met Phe Asn Leu Ile
    130                 135                 140
Asn Lys Glu Phe Thr Phe Asp Val Asp Val Ser Lys Leu Pro Cys Gly
145                 150                 155                 160
Leu Asn Gly Ala Leu Tyr Phe Val Glu Met Ala Ala Asp Gly Gly Ile
                165                 170                 175
Gly Lys Gly Asn Asn Lys Ala Gly Ala Lys Tyr Gly Thr Gly Tyr Cys
            180                 185                 190
Asp Ser Gln Cys Pro His Asp Ile Lys Phe Ile Asn Gly Lys Ala Asn
        195                 200                 205
Val Glu Gly Trp Asn Pro Ser Asp Ala Asp Pro Asn Gly Gly Ala Gly
    210                 215                 220
Lys Ile Gly Ala Cys Cys Pro Glu Met Asp Ile Trp Glu Ala Asn Ser
225                 230                 235                 240
Ile Ser Thr Ala Tyr Thr Pro His Pro Cys Arg Gly Val Gly Leu Gln
```

-continued

```
                    245                 250                 255
Glu Cys Ser Asp Ala Ala Ser Cys Gly Asp Gly Ser Asn Arg Tyr Asp
                260                 265                 270

Gly Gln Cys Asp Lys Asp Gly Cys Asp Phe Asn Ser Tyr Arg Met Gly
            275                 280                 285

Val Lys Asp Phe Tyr Gly Pro Gly Ala Thr Leu Asp Thr Thr Lys Lys
        290                 295                 300

Met Thr Val Ile Thr Gln Phe Leu Gly Ser Gly Ser Ser Leu Ser Glu
305                 310                 315                 320

Ile Lys Arg Phe Tyr Val Gln Asn Gly Lys Val Tyr Lys Asn Ser Gln
                325                 330                 335

Ser Ala Val Ala Gly Val Thr Gly Asn Ser Ile Thr Glu Ser Phe Cys
            340                 345                 350

Thr Ala Gln Lys Lys Ala Phe Gly Asp Thr Ser Ser Phe Ala Ala Leu
        355                 360                 365

Gly Gly Leu Asn Glu Met Gly Ala Ser Leu Ala Arg Gly His Val Leu
    370                 375                 380

Ile Met Ser Leu Trp Gly Asp His Ala Val Asn Met Leu Trp Leu Asp
385                 390                 395                 400

Ser Thr Tyr Pro Thr Asp Ala Asp Pro Ser Lys Pro Gly Ala Ala Arg
                405                 410                 415

Gly Thr Cys Pro Thr Thr Ser Gly Lys Pro Glu Asp Val Glu Lys Asn
            420                 425                 430

Ser Pro Asp Ala Thr Val Val Phe Ser Asn Ile Lys Phe Gly Pro Ile
        435                 440                 445

Gly Ser Thr Phe Ala Gln Pro Ala
    450                 455

<210> SEQ ID NO 50
<211> LENGTH: 525
<212> TYPE: PRT
<213> ORGANISM: Humicola grisea

<400> SEQUENCE: 50

Met Arg Thr Ala Lys Phe Ala Thr Leu Ala Ala Leu Val Ala Ser Ala
1               5                   10                  15

Ala Ala Gln Gln Ala Cys Ser Leu Thr Thr Glu Arg His Pro Ser Leu
            20                  25                  30

Ser Trp Asn Lys Cys Thr Ala Gly Gly Gln Cys Gln Thr Val Gln Ala
        35                  40                  45

Ser Ile Thr Leu Asp Ser Asn Trp Arg Trp Thr His Gln Val Ser Gly
    50                  55                  60

Ser Thr Asn Cys Tyr Thr Gly Asn Lys Trp Asp Thr Ser Ile Cys Thr
65                  70                  75                  80

Asp Ala Lys Ser Cys Ala Gln Asn Cys Cys Val Asp Gly Ala Asp Tyr
                85                  90                  95

Thr Ser Thr Tyr Gly Ile Thr Thr Asn Gly Asp Ser Leu Ser Leu Lys
            100                 105                 110

Phe Val Thr Lys Gly Gln His Ser Thr Asn Val Gly Ser Arg Thr Tyr
        115                 120                 125

Leu Met Asp Gly Glu Asp Lys Tyr Gln Thr Phe Glu Leu Leu Gly Asn
    130                 135                 140

Glu Phe Thr Phe Asp Val Asp Val Ser Asn Ile Gly Cys Gly Leu Asn
145                 150                 155                 160

Gly Ala Leu Tyr Phe Val Ser Met Asp Ala Asp Gly Gly Leu Ser Arg
```

```
                    165                 170                 175
Tyr Pro Gly Asn Lys Ala Gly Ala Lys Tyr Gly Thr Gly Tyr Cys Asp
                180                 185                 190
Ala Gln Cys Pro Arg Asp Ile Lys Phe Ile Asn Gly Glu Ala Asn Ile
                195                 200                 205
Glu Gly Trp Thr Gly Ser Thr Asn Asp Pro Asn Ala Gly Ala Gly Arg
            210                 215                 220
Tyr Gly Thr Cys Cys Ser Glu Met Asp Ile Trp Glu Ala Asn Asn Met
225                 230                 235                 240
Ala Thr Ala Phe Thr Pro His Pro Cys Thr Ile Ile Gly Gln Ser Arg
                245                 250                 255
Cys Glu Gly Asp Ser Cys Gly Gly Thr Tyr Ser Asn Glu Arg Tyr Ala
                260                 265                 270
Gly Val Cys Asp Pro Asp Gly Cys Asp Phe Asn Ser Tyr Arg Gln Gly
            275                 280                 285
Asn Lys Thr Phe Tyr Gly Lys Gly Met Thr Val Asp Thr Thr Lys Lys
            290                 295                 300
Ile Thr Val Val Thr Gln Phe Leu Lys Asp Ala Asn Gly Asp Leu Gly
305                 310                 315                 320
Glu Ile Lys Arg Phe Tyr Val Gln Asp Gly Lys Ile Ile Pro Asn Ser
                325                 330                 335
Glu Ser Thr Ile Pro Gly Val Glu Gly Asn Ser Ile Thr Gln Asp Trp
            340                 345                 350
Cys Asp Arg Gln Lys Val Ala Phe Gly Asp Ile Asp Asp Phe Asn Arg
                355                 360                 365
Lys Gly Gly Met Lys Gln Met Gly Lys Ala Leu Ala Gly Pro Met Val
            370                 375                 380
Leu Val Met Ser Ile Trp Asp Asp His Ala Ser Asn Met Leu Trp Leu
385                 390                 395                 400
Asp Ser Thr Phe Pro Val Asp Ala Ala Gly Lys Pro Gly Ala Glu Arg
                405                 410                 415
Gly Ala Cys Pro Thr Thr Ser Gly Val Pro Ala Glu Val Glu Ala Glu
                420                 425                 430
Ala Pro Asn Ser Asn Val Val Phe Ser Asn Ile Arg Phe Gly Pro Ile
                435                 440                 445
Gly Ser Thr Val Ala Gly Leu Pro Gly Ala Gly Asn Gly Gly Asn Asn
            450                 455                 460
Gly Gly Asn Pro Pro Pro Thr Thr Thr Ser Ser Ala Pro Ala
465                 470                 475                 480
Thr Thr Thr Thr Ala Ser Ala Gly Pro Lys Ala Gly Arg Trp Gln Gln
                485                 490                 495
Cys Gly Gly Ile Gly Phe Thr Gly Pro Thr Gln Cys Glu Glu Pro Tyr
            500                 505                 510
Ile Cys Thr Lys Leu Asn Asp Trp Tyr Ser Gln Cys Leu
            515                 520                 525

<210> SEQ ID NO 51
<211> LENGTH: 525
<212> TYPE: PRT
<213> ORGANISM: Humicola grisea

<400> SEQUENCE: 51

Met Arg Thr Ala Lys Phe Ala Thr Leu Ala Ala Leu Val Ala Ser Ala
1               5                   10                  15

Ala Ala Gln Gln Ala Cys Ser Leu Thr Thr Glu Arg His Pro Ser Leu
```

-continued

```
                    20                  25                  30
Ser Trp Lys Lys Cys Thr Ala Gly Gln Cys Gln Thr Val Gln Ala
         35                  40                  45
Ser Ile Thr Leu Asp Ser Asn Trp Arg Trp Thr His Gln Val Ser Gly
     50                  55                  60
Ser Thr Asn Cys Tyr Thr Gly Asn Lys Trp Asp Thr Ser Ile Cys Thr
 65                  70                  75                  80
Asp Ala Lys Ser Cys Ala Gln Asn Cys Cys Val Asp Gly Ala Asp Tyr
                 85                  90                  95
Thr Ser Thr Tyr Gly Ile Thr Thr Asn Gly Asp Ser Leu Ser Leu Lys
                100                 105                 110
Phe Val Thr Lys Gly Gln Tyr Ser Thr Asn Val Gly Ser Arg Thr Tyr
            115                 120                 125
Leu Met Asp Gly Glu Asp Lys Tyr Gln Thr Phe Glu Leu Leu Gly Asn
        130                 135                 140
Glu Phe Thr Phe Asp Val Asp Val Ser Asn Ile Gly Cys Gly Leu Asn
145                 150                 155                 160
Gly Ala Leu Tyr Phe Val Ser Met Asp Ala Asp Gly Gly Leu Ser Arg
                165                 170                 175
Tyr Pro Gly Asn Lys Ala Gly Ala Lys Tyr Gly Thr Gly Tyr Cys Asp
                180                 185                 190
Ala Gln Cys Pro Arg Asp Ile Lys Phe Ile Asn Gly Glu Ala Asn Ile
            195                 200                 205
Glu Gly Trp Thr Gly Ser Thr Asn Asp Pro Asn Ala Gly Ala Gly Arg
        210                 215                 220
Tyr Gly Thr Cys Cys Ser Glu Met Asp Ile Trp Glu Ala Asn Asn Met
225                 230                 235                 240
Ala Thr Ala Phe Thr Pro His Pro Cys Thr Ile Ile Gly Gln Ser Arg
                245                 250                 255
Cys Glu Gly Asp Ser Cys Gly Gly Thr Tyr Ser Asn Glu Arg Tyr Ala
                260                 265                 270
Gly Val Cys Asp Pro Asp Gly Cys Asp Phe Asn Ser Tyr Arg Gln Gly
            275                 280                 285
Asn Lys Thr Phe Tyr Gly Lys Gly Met Thr Val Asp Thr Thr Lys Lys
        290                 295                 300
Ile Thr Val Val Thr Gln Phe Leu Lys Asp Ala Asn Gly Asp Leu Gly
305                 310                 315                 320
Glu Ile Lys Arg Phe Tyr Val Gln Asp Gly Lys Ile Ile Pro Asn Ser
                325                 330                 335
Glu Ser Thr Ile Pro Gly Val Glu Gly Asn Ser Ile Thr Gln Asp Trp
            340                 345                 350
Cys Asp Arg Gln Lys Val Ala Phe Gly Asp Ile Asp Phe Asn Arg
        355                 360                 365
Lys Gly Gly Met Lys Gln Met Gly Lys Ala Leu Ala Gly Pro Met Val
        370                 375                 380
Leu Val Met Ser Ile Trp Asp Asp His Ala Ser Asn Met Leu Trp Leu
385                 390                 395                 400
Asp Ser Thr Phe Pro Val Asp Ala Ala Gly Lys Pro Gly Ala Glu Arg
                405                 410                 415
Gly Ala Cys Pro Thr Thr Ser Gly Val Pro Ala Glu Val Glu Ala Glu
            420                 425                 430
Ala Pro Asn Ser Asn Val Val Phe Ser Asn Ile Arg Phe Gly Pro Ile
        435                 440                 445
```

-continued

Gly Ser Thr Val Ala Gly Leu Pro Gly Ala Gly Asn Gly Gly Asn Asn
    450                 455                 460

Gly Gly Asn Pro Pro Pro Thr Thr Thr Thr Ser Ser Ala Pro Ala
465             470                 475                 480

Thr Thr Thr Thr Ala Ser Ala Gly Pro Lys Ala Gly Arg Trp Gln Gln
            485                 490                 495

Cys Gly Gly Ile Gly Phe Thr Gly Pro Thr Gln Cys Glu Glu Pro Tyr
            500                 505                 510

Ile Cys Thr Lys Leu Asn Asp Trp Tyr Ser Gln Cys Leu
            515                 520                 525

<210> SEQ ID NO 52
<211> LENGTH: 514
<212> TYPE: PRT
<213> ORGANISM: Fusarium oxysporum

<400> SEQUENCE: 52

Met Tyr Arg Ile Val Ala Thr Ala Ser Ala Leu Ile Ala Ala Ala Arg
1               5                   10                  15

Ala Gln Gln Val Cys Ser Leu Asn Thr Glu Thr Lys Pro Ala Leu Thr
            20                  25                  30

Trp Ser Lys Cys Thr Ser Ser Gly Cys Ser Asp Val Lys Gly Ser Val
        35                  40                  45

Val Ile Asp Ala Asn Trp Arg Trp Thr His Gln Thr Ser Gly Ser Thr
    50                  55                  60

Asn Cys Tyr Thr Gly Asn Lys Trp Asp Thr Ser Ile Cys Thr Asp Gly
65                  70                  75                  80

Lys Thr Cys Ala Glu Lys Cys Cys Leu Asp Gly Ala Asp Tyr Ser Gly
                85                  90                  95

Thr Tyr Gly Ile Thr Ser Ser Gly Asn Gln Leu Ser Leu Gly Phe Val
            100                 105                 110

Thr Asn Gly Pro Tyr Ser Lys Asn Ile Gly Ser Arg Thr Tyr Leu Met
        115                 120                 125

Glu Asn Glu Asn Thr Tyr Gln Met Phe Gln Leu Leu Gly Asn Glu Phe
130                 135                 140

Thr Phe Asp Val Asp Val Ser Gly Ile Gly Cys Gly Leu Asn Gly Ala
145                 150                 155                 160

Pro His Phe Val Ser Met Asp Glu Asp Gly Gly Lys Ala Lys Tyr Ser
                165                 170                 175

Gly Asn Lys Ala Gly Ala Lys Tyr Gly Thr Gly Tyr Cys Asp Ala Gln
            180                 185                 190

Cys Pro Arg Asp Val Lys Phe Ile Asn Gly Val Ala Asn Ser Glu Gly
        195                 200                 205

Trp Lys Pro Ser Asp Ser Asp Val Asn Ala Gly Val Gly Asn Leu Gly
    210                 215                 220

Thr Cys Cys Pro Glu Met Asp Ile Trp Glu Ala Asn Ser Ile Ser Thr
225                 230                 235                 240

Ala Phe Thr Pro His Pro Cys Thr Lys Leu Thr Gln His Ser Cys Thr
                245                 250                 255

Gly Asp Ser Cys Gly Gly Thr Tyr Ser Ser Asp Arg Tyr Gly Gly Thr
            260                 265                 270

Cys Asp Ala Asp Gly Cys Asp Phe Asn Ala Tyr Arg Gln Gly Asn Lys
        275                 280                 285

Thr Phe Tyr Gly Pro Gly Ser Asn Phe Asn Ile Asp Thr Thr Lys Lys
    290                 295                 300

Met Thr Val Val Thr Gln Phe His Lys Gly Ser Asn Gly Arg Leu Ser
305 310 315 320

Glu Ile Thr Arg Leu Tyr Val Gln Asn Gly Lys Val Ile Ala Asn Ser
325 330 335

Glu Ser Lys Ile Ala Gly Asn Pro Gly Ser Ser Leu Thr Ser Asp Phe
340 345 350

Cys Ser Lys Gln Lys Ser Val Phe Gly Asp Ile Asp Asp Phe Ser Lys
355 360 365

Lys Gly Gly Trp Asn Gly Met Ser Asp Ala Leu Ser Ala Pro Met Val
370 375 380

Leu Val Met Ser Leu Trp His Asp His His Ser Asn Met Leu Trp Leu
385 390 395 400

Asp Ser Thr Tyr Pro Thr Asp Ser Thr Lys Val Gly Ser Gln Arg Gly
405 410 415

Ser Cys Ala Thr Thr Ser Gly Lys Pro Ser Asp Leu Glu Arg Asp Val
420 425 430

Pro Asn Ser Lys Val Ser Phe Ser Asn Ile Lys Phe Gly Pro Ile Gly
435 440 445

Ser Thr Tyr Lys Ser Asp Gly Thr Thr Pro Asn Pro Pro Ala Ser Ser
450 455 460

Ser Thr Thr Gly Ser Ser Thr Pro Thr Asn Pro Pro Ala Gly Ser Val
465 470 475 480

Asp Gln Trp Gly Gln Cys Gly Gly Gln Asn Tyr Ser Gly Pro Thr Thr
485 490 495

Cys Lys Ser Pro Phe Thr Cys Lys Lys Ile Asn Asp Phe Tyr Ser Gln
500 505 510

Cys Gln

<210> SEQ ID NO 53
<211> LENGTH: 456
<212> TYPE: PRT
<213> ORGANISM: Clavceps purpurea

<400> SEQUENCE: 53

Met His Pro Ser Leu Gln Thr Ile Leu Leu Ser Ala Leu Phe Thr Thr
1 5 10 15

Ala His Ala Gln Gln Ala Cys Ser Ser Lys Pro Glu Thr His Pro Pro
20 25 30

Leu Ser Trp Ser Arg Cys Ser Arg Ser Gly Cys Arg Ser Val Gln Gly
35 40 45

Ala Val Thr Val Asp Ala Asn Trp Leu Trp Thr Thr Val Asp Gly Ser
50 55 60

Gln Asn Cys Tyr Thr Gly Asn Arg Trp Asp Thr Ser Ile Cys Ser Ser
65 70 75 80

Glu Lys Thr Cys Ser Glu Ser Cys Cys Ile Asp Gly Ala Asp Tyr Ala
85 90 95

Gly Thr Tyr Gly Val Thr Thr Thr Gly Asp Ala Leu Ser Leu Lys Phe
100 105 110

Val Gln Gln Gly Pro Tyr Ser Lys Asn Val Gly Ser Arg Leu Tyr Leu
115 120 125

Met Lys Asp Glu Ser Arg Tyr Glu Met Phe Thr Leu Leu Gly Asn Glu
130 135 140

Phe Thr Phe Asp Val Asp Val Ser Lys Leu Gly Cys Gly Leu Asn Gly
145 150 155 160

Ala Leu Tyr Phe Val Ser Met Asp Glu Asp Gly Gly Met Lys Arg Phe

```
                165                 170                 175
Pro Met Asn Lys Ala Gly Ala Lys Phe Gly Thr Gly Tyr Cys Asp Ser
        180                 185                 190

Gln Cys Pro Arg Asp Val Lys Phe Ile Asn Gly Met Ala Asn Ser Lys
        195                 200                 205

Asp Trp Ile Pro Ser Lys Ser Asp Ala Asn Ala Gly Ile Gly Ser Leu
        210                 215                 220

Gly Ala Cys Cys Arg Glu Met Asp Ile Trp Glu Ala Asn Asn Ile Ala
225                 230                 235                 240

Ser Ala Phe Thr Pro His Pro Cys Lys Asn Ser Ala Tyr His Ser Cys
                245                 250                 255

Thr Gly Asp Gly Cys Gly Gly Thr Tyr Ser Lys Asn Arg Tyr Ser Gly
        260                 265                 270

Asp Cys Asp Pro Asp Gly Cys Asp Phe Asn Ser Tyr Arg Leu Gly Asn
        275                 280                 285

Thr Thr Phe Tyr Gly Pro Gly Pro Lys Phe Thr Ile Asp Thr Thr Arg
        290                 295                 300

Lys Ile Ser Val Val Thr Gln Phe Leu Lys Gly Arg Asp Gly Ser Leu
305                 310                 315                 320

Arg Glu Ile Lys Arg Phe Tyr Val Gln Asn Gly Lys Val Ile Pro Asn
                325                 330                 335

Ser Val Ser Arg Val Arg Gly Val Pro Gly Asn Ser Ile Thr Gln Gly
        340                 345                 350

Phe Cys Asn Ala Gln Lys Lys Met Phe Gly Ala His Glu Ser Phe Asn
        355                 360                 365

Ala Lys Gly Gly Met Lys Gly Met Ser Ala Ala Val Ser Lys Pro Met
        370                 375                 380

Val Leu Val Met Ser Leu Trp Asp Asp His Asn Ser Asn Met Leu Trp
385                 390                 395                 400

Leu Asp Ser Thr Tyr Pro Thr Asn Ser Arg Gly Arg Gly Ser Lys Arg
                405                 410                 415

Gly Ser Cys Pro Ala Ser Ser Gly Arg Pro Thr Asp Val Glu Ser Ser
        420                 425                 430

Ala Pro Asp Ser Thr Val Val Phe Ser Asn Ile Lys Phe Gly Pro Ile
        435                 440                 445

Gly Ser Thr Phe Ser Arg Gly Lys
        450                 455

<210> SEQ ID NO 54
<211> LENGTH: 451
<212> TYPE: PRT
<213> ORGANISM: Humicol grsea var. thermoidea

<400> SEQUENCE: 54

Met Gln Ile Lys Ser Tyr Ile Gln Tyr Leu Ala Ala Ala Leu Pro Leu
1               5                   10                  15

Leu Ser Ser Val Ala Ala Gln Gln Ala Gly Thr Ile Thr Ala Glu Asn
                20                  25                  30

His Pro Arg Met Thr Trp Lys Arg Cys Ser Gly Pro Gly Asn Cys Gln
        35                  40                  45

Thr Val Gln Gly Glu Val Val Ile Asp Ala Asn Trp Arg Trp Leu His
        50                  55                  60

Asn Asn Gly Gln Asn Cys Tyr Glu Gly Asn Lys Trp Thr Ser Gln Cys
65              70                  75                  80

Ser Ser Ala Thr Asp Cys Ala Gln Arg Cys Ala Leu Asp Gly Ala Asn
```

```
                        85                  90                  95
Tyr Gln Ser Thr Tyr Gly Ala Ser Thr Ser Gly Asp Ser Leu Thr Leu
                100                 105                 110

Lys Phe Val Thr Lys His Glu Tyr Gly Thr Asn Ile Gly Ser Arg Phe
            115                 120                 125

Tyr Leu Met Ala Asn Gln Asn Lys Tyr Gln Met Phe Thr Leu Met Asn
        130                 135                 140

Asn Glu Phe Ala Phe Asp Val Asp Leu Ser Lys Val Glu Cys Gly Ile
145                 150                 155                 160

Asn Ser Ala Leu Tyr Phe Val Ala Met Glu Glu Asp Gly Gly Met Ala
                165                 170                 175

Ser Tyr Pro Ser Asn Arg Ala Gly Ala Lys Tyr Gly Thr Gly Tyr Cys
                180                 185                 190

Asp Ala Gln Cys Ala Arg Asp Leu Lys Phe Ile Gly Gly Lys Ala Asn
            195                 200                 205

Ile Glu Gly Trp Arg Pro Ser Thr Asn Asp Pro Asn Ala Gly Val Gly
        210                 215                 220

Pro Met Gly Ala Cys Cys Ala Glu Ile Asp Val Trp Glu Ser Asn Ala
225                 230                 235                 240

Tyr Ala Tyr Ala Phe Thr Pro His Ala Cys Gly Ser Lys Asn Arg Tyr
                245                 250                 255

His Ile Cys Glu Thr Asn Asn Cys Gly Gly Thr Tyr Ser Asp Asp Arg
            260                 265                 270

Phe Ala Gly Tyr Cys Asp Ala Asn Gly Cys Asp Tyr Asn Pro Tyr Arg
        275                 280                 285

Met Gly Asn Lys Asp Phe Tyr Gly Lys Gly Lys Thr Val Asp Thr Asn
    290                 295                 300

Arg Lys Phe Thr Val Val Ser Arg Phe Glu Arg Asn Arg Leu Ser Gln
305                 310                 315                 320

Phe Phe Val Gln Asp Gly Arg Lys Ile Glu Val Pro Pro Thr Trp
                325                 330                 335

Pro Gly Leu Pro Asn Ser Ala Asp Ile Thr Pro Glu Leu Cys Asp Ala
            340                 345                 350

Gln Phe Arg Val Phe Asp Asp Arg Asn Arg Phe Ala Glu Thr Gly Gly
        355                 360                 365

Phe Asp Ala Leu Asn Glu Ala Leu Thr Ile Pro Met Val Leu Val Met
    370                 375                 380

Ser Ile Trp Asp Asp His His Ser Asn Met Leu Trp Leu Asp Ser Ser
385                 390                 395                 400

Tyr Pro Pro Glu Lys Ala Gly Leu Pro Gly Gly Asp Arg Gly Pro Cys
                405                 410                 415

Pro Thr Thr Ser Gly Val Pro Ala Glu Val Glu Ala Gln Tyr Pro Asn
            420                 425                 430

Ala Gln Val Val Trp Ser Asn Ile Arg Phe Gly Pro Ile Gly Ser Thr
        435                 440                 445

Val Asn Val
    450

<210> SEQ ID NO 55
<211> LENGTH: 451
<212> TYPE: PRT
<213> ORGANISM: Humicol grsea var. thermoidea

<400> SEQUENCE: 55

Met Gln Ile Lys Ser Tyr Ile Gln Tyr Leu Ala Ala Ala Leu Pro Leu
```

-continued

```
1               5                   10                  15
Leu Ser Ser Val Ala Gln Gln Ala Gly Thr Ile Thr Ala Glu Asn
                20                  25                  30
His Pro Arg Met Thr Trp Lys Arg Cys Ser Gly Pro Asn Cys Gln
                35                  40                  45
Thr Val Gln Gly Glu Val Val Ile Asp Ala Asn Trp Arg Trp Leu His
    50                  55                  60
Asn Asn Gly Gln Asn Cys Tyr Glu Gly Asn Lys Trp Ser Gln Cys
65                  70                  75                  80
Ser Ser Ala Thr Asp Cys Ala Gln Arg Cys Ala Leu Asp Gly Ala Asn
                85                  90                  95
Tyr Gln Ser Thr Tyr Gly Ala Ser Thr Ser Gly Asp Ser Leu Thr Leu
                100                 105                 110
Lys Phe Val Thr Lys His Glu Tyr Gly Thr Asn Ile Gly Ser Arg Phe
                115                 120                 125
Tyr Leu Met Ala Asn Gln Asn Lys Tyr Gln Met Phe Thr Leu Met Asn
        130                 135                 140
Asn Glu Phe Ala Phe Asp Val Asp Leu Ser Lys Val Glu Cys Gly Ile
145                 150                 155                 160
Asn Ser Ala Leu Tyr Phe Val Ala Met Glu Glu Asp Gly Gly Met Ala
                165                 170                 175
Ser Tyr Pro Ser Asn Arg Ala Gly Ala Lys Tyr Gly Thr Gly Tyr Cys
                180                 185                 190
Asp Ala Gln Cys Ala Arg Asp Leu Lys Phe Ile Gly Gly Lys Ala Asn
                195                 200                 205
Ile Glu Gly Trp Arg Pro Ser Thr Asn Asp Pro Asn Ala Gly Val Gly
        210                 215                 220
Pro Met Gly Ala Cys Cys Ala Glu Ile Asp Val Trp Glu Ser Asn Ala
225                 230                 235                 240
Tyr Ala Tyr Ala Phe Thr Pro His Ala Cys Gly Ser Lys Asn Arg Tyr
                245                 250                 255
His Ile Cys Glu Thr Asn Asn Cys Gly Gly Thr Tyr Ser Asp Asp Arg
                260                 265                 270
Phe Ala Gly Tyr Cys Asp Ala Asn Gly Cys Asp Tyr Asn Pro Tyr Arg
                275                 280                 285
Met Gly Asn Lys Asp Phe Tyr Gly Lys Gly Lys Thr Val Asp Thr Asn
        290                 295                 300
Arg Lys Phe Thr Val Ser Arg Phe Glu Arg Asn Arg Leu Ser Gln
305                 310                 315                 320
Phe Phe Val Gln Asp Gly Arg Lys Ile Glu Val Pro Pro Thr Trp
                325                 330                 335
Pro Gly Leu Pro Asn Ser Ala Asp Ile Thr Pro Glu Leu Cys Asp Ala
                340                 345                 350
Gln Phe Arg Val Phe Asp Asp Arg Asn Arg Phe Ala Glu Thr Gly Gly
                355                 360                 365
Phe Asp Ala Leu Asn Glu Ala Leu Thr Ile Pro Met Val Leu Val Met
        370                 375                 380
Ser Ile Trp Asp Asp His His Ser Asn Met Leu Trp Leu Asp Ser Ser
385                 390                 395                 400
Tyr Pro Pro Glu Lys Ala Gly Leu Pro Gly Asp Arg Gly Pro Cys
                405                 410                 415
Pro Thr Thr Ser Gly Val Pro Ala Glu Val Glu Ala Gln Tyr Pro Asp
                420                 425                 430
```

```
Ala Gln Val Val Trp Ser Asn Ile Arg Phe Gly Pro Ile Gly Ser Thr
        435                 440                 445

Val Asn Val
    450

<210> SEQ ID NO 56
<211> LENGTH: 447
<212> TYPE: PRT
<213> ORGANISM: Leptocphaeria maculans

<400> SEQUENCE: 56

Met Leu Ser Ala Ser Lys Ala Ala Ile Leu Ala Phe Cys Ala His
1               5                   10                  15

Thr Ala Ser Ala Trp Val Val Gly Asp Gln Gln Thr Glu Thr His Pro
            20                  25                  30

Lys Leu Asn Trp Gln Arg Cys Thr Gly Lys Gly Arg Ser Ser Cys Thr
            35                  40                  45

Asn Val Asn Gly Glu Val Val Ile Asp Ala Asn Trp Arg Trp Leu Ala
    50                  55                  60

His Arg Ser Gly Tyr Thr Asn Cys Tyr Thr Gly Ser Glu Trp Asn Gln
65              70                  75                  80

Ser Ala Cys Pro Asn Asn Glu Ala Cys Thr Lys Asn Cys Ala Ile Glu
            85                  90                  95

Gly Ser Asp Tyr Ala Gly Thr Tyr Gly Ile Thr Thr Ser Gly Asn Gln
            100                 105                 110

Met Asn Ile Lys Phe Ile Thr Lys Arg Pro Tyr Ser Thr Asn Ile Gly
            115                 120                 125

Ala Arg Thr Tyr Leu Met Lys Asp Glu Gln Asn Tyr Glu Met Phe Gln
        130                 135                 140

Leu Ile Gly Asn Glu Phe Thr Phe Asp Val Asp Leu Ser Gln Arg Cys
145             150                 155                 160

Gly Met Asn Gly Ala Leu Tyr Phe Val Ser Met Pro Gln Lys Gly Gln
            165                 170                 175

Gly Ala Pro Gly Ala Lys Tyr Gly Thr Gly Tyr Cys Asp Ala Gln Cys
            180                 185                 190

Ala Arg Asp Leu Lys Phe Val Arg Gly Ser Ala Asn Ala Glu Gly Trp
        195                 200                 205

Thr Lys Ser Ala Ser Asp Pro Asn Ser Gly Val Gly Lys Lys Gly Ala
        210                 215                 220

Cys Cys Ala Gln Met Asp Val Trp Glu Ala Asn Ser Ala Ala Thr Ala
225             230                 235                 240

Leu Thr Pro His Ser Cys Gln Pro Ala Gly Tyr Ser Val Cys Glu Asp
            245                 250                 255

Thr Asn Cys Gly Gly Thr Tyr Ser Glu Asp Arg Tyr Ala Gly Thr Cys
            260                 265                 270

Asp Ala Asn Gly Cys Asp Phe Asn Pro Phe Arg Val Gly Val Lys Asp
        275                 280                 285

Phe Tyr Gly Lys Gly Lys Thr Val Asp Thr Thr Lys Lys Met Thr Val
    290                 295                 300

Val Thr Gln Phe Val Gly Ser Gly Asn Gln Leu Ser Glu Ile Lys Arg
305             310                 315                 320

Phe Tyr Val Gln Asp Gly Lys Val Ile Ala Asn Pro Glu Pro Thr Ile
                325                 330                 335

Pro Gly Met Glu Trp Cys Asn Thr Gln Lys Lys Val Phe Gln Glu Glu
            340                 345                 350
```

-continued

```
Ala Tyr Pro Phe Asn Glu Phe Gly Gly Met Ala Ser Met Ser Glu Gly
        355                 360                 365

Met Ser Gln Gly Met Val Leu Val Met Ser Leu Trp Asp Asp His Tyr
    370                 375                 380

Ala Asn Met Leu Trp Leu Asp Ser Asn Trp Pro Arg Glu Ala Asp Pro
385                 390                 395                 400

Ala Lys Pro Gly Val Ala Arg Arg Asp Cys Pro Thr Ser Gly Gly Lys
            405                 410                 415

Pro Ser Glu Val Glu Ala Ala Asn Pro Asn Ala Gln Val Met Phe Ser
                420                 425                 430

Asn Ile Lys Phe Gly Pro Ile Gly Ser Thr Phe Ala His Ala Ala
            435                 440                 445

<210> SEQ ID NO 57
<211> LENGTH: 516
<212> TYPE: PRT
<213> ORGANISM: Neurospora crassa

<400> SEQUENCE: 57

Met Arg Ala Ser Leu Leu Ala Phe Ser Leu Ala Ala Val Ala Gly
1               5                   10                  15

Gly Gln Gln Ala Gly Thr Leu Thr Ala Lys Arg His Pro Ser Leu Thr
                20                  25                  30

Trp Gln Lys Cys Thr Arg Gly Gly Cys Pro Thr Leu Asn Thr Thr Met
            35                  40                  45

Val Leu Asp Ala Asn Trp Arg Trp Thr His Ala Thr Ser Gly Ser Thr
    50                  55                  60

Lys Cys Tyr Thr Gly Asn Lys Trp Gln Ala Thr Leu Cys Pro Asp Gly
65                  70                  75                  80

Lys Ser Cys Ala Ala Asn Cys Ala Leu Asp Gly Ala Asp Tyr Thr Gly
                85                  90                  95

Thr Tyr Gly Ile Thr Gly Ser Gly Trp Ser Leu Thr Leu Gln Phe Val
            100                 105                 110

Thr Asp Asn Val Gly Ala Arg Ala Tyr Leu Met Ala Asp Asp Thr Gln
        115                 120                 125

Tyr Gln Met Leu Glu Leu Leu Asn Gln Glu Leu Trp Phe Asp Val Asp
    130                 135                 140

Met Ser Asn Ile Pro Cys Gly Leu Asn Gly Ala Leu Tyr Leu Ser Ala
145                 150                 155                 160

Met Asp Ala Asp Gly Gly Met Arg Lys Tyr Pro Thr Asn Lys Ala Gly
                165                 170                 175

Ala Lys Tyr Ala Thr Gly Tyr Cys Asp Ala Gln Cys Pro Arg Asp Leu
            180                 185                 190

Lys Tyr Ile Asn Gly Ile Ala Asn Val Glu Gly Trp Thr Pro Ser Thr
        195                 200                 205

Asn Asp Ala Asn Gly Ile Gly Asp His Gly Ser Cys Cys Ser Glu Met
    210                 215                 220

Asp Ile Trp Glu Ala Asn Lys Val Ser Thr Ala Phe Thr Pro His Pro
225                 230                 235                 240

Cys Thr Thr Ile Glu Gln His Met Cys Glu Gly Asp Ser Cys Gly Gly
                245                 250                 255

Thr Tyr Ser Asp Asp Arg Tyr Gly Val Leu Cys Asp Ala Asp Gly Cys
            260                 265                 270

Asp Phe Asn Ser Tyr Arg Met Gly Asn Thr Thr Phe Tyr Gly Glu Gly
        275                 280                 285
```

```
Lys Thr Val Asp Thr Ser Ser Lys Phe Thr Val Thr Gln Phe Ile
        290                 295                 300

Lys Asp Ser Ala Gly Asp Leu Ala Glu Ile Lys Ala Phe Tyr Val Gln
305                 310                 315                 320

Asn Gly Lys Val Ile Glu Asn Ser Gln Ser Asn Val Asp Gly Val Ser
                325                 330                 335

Gly Asn Ser Ile Thr Gln Ser Phe Cys Lys Ser Gln Lys Thr Ala Phe
            340                 345                 350

Gly Asp Ile Asp Asp Phe Asn Lys Lys Gly Leu Lys Gln Met Gly
        355                 360                 365

Lys Ala Leu Ala Gln Ala Met Val Leu Val Met Ser Ile Trp Asp Asp
370                 375                 380

His Ala Ala Asn Met Leu Trp Leu Asp Ser Thr Tyr Pro Val Pro Lys
385                 390                 395                 400

Val Pro Gly Ala Tyr Arg Gly Ser Gly Pro Thr Thr Ser Gly Val Pro
                405                 410                 415

Ala Glu Val Asp Ala Asn Ala Pro Asn Ser Lys Val Ala Phe Ser Asn
            420                 425                 430

Ile Lys Phe Gly His Leu Gly Ile Ser Pro Phe Ser Gly Gly Ser Ser
        435                 440                 445

Gly Thr Pro Pro Ser Asn Pro Ser Ser Ser Ala Ser Pro Thr Ser Ser
450                 455                 460

Thr Ala Lys Pro Ser Ser Thr Ser Thr Ala Ser Asn Pro Ser Gly Thr
465                 470                 475                 480

Gly Ala Ala His Trp Ala Gln Cys Gly Gly Ile Gly Phe Ser Gly Pro
                485                 490                 495

Thr Thr Cys Pro Glu Pro Tyr Thr Cys Ala Lys Asp His Asp Ile Tyr
            500                 505                 510

Ser Gln Cys Val
        515

<210> SEQ ID NO 58
<211> LENGTH: 540
<212> TYPE: PRT
<213> ORGANISM: Aspergillus aculeatus

<400> SEQUENCE: 58

Met Val Asp Ser Phe Ser Ile Tyr Lys Thr Ala Leu Leu Leu Ser Met
1               5                   10                  15

Leu Ala Thr Ser Asn Ala Gln Gln Val Gly Thr Tyr Thr Ala Glu Thr
            20                  25                  30

His Pro Ser Leu Thr Trp Gln Thr Cys Ser Gly Ser Gly Ser Cys Thr
        35                  40                  45

Thr Thr Ser Gly Ser Val Val Ile Asp Ala Asn Trp Arg Trp Val His
    50                  55                  60

Glu Val Gly Gly Tyr Thr Asn Cys Tyr Ser Gly Asn Thr Trp Asp Ser
65                  70                  75                  80

Ser Ile Cys Ser Thr Asp Thr Thr Cys Ala Ser Glu Cys Ala Leu Glu
                85                  90                  95

Gly Ala Thr Tyr Glu Ser Thr Tyr Gly Val Thr Thr Ser Gly Ser Ser
            100                 105                 110

Leu Arg Leu Asn Phe Val Thr Thr Ala Ser Gln Lys Asn Ile Gly Ser
        115                 120                 125

Arg Leu Tyr Leu Leu Ala Asp Asp Ser Thr Tyr Glu Thr Phe Lys Leu
    130                 135                 140
```

```
Phe Asn Arg Glu Phe Thr Phe Asp Val Asp Val Ser Asn Leu Pro Cys
145                 150                 155                 160

Gly Leu Asn Gly Ala Leu Tyr Phe Val Ser Met Asp Ala Asp Gly Gly
            165                 170                 175

Val Ser Arg Phe Pro Thr Asn Lys Ala Gly Ala Lys Tyr Gly Thr Gly
            180                 185                 190

Tyr Cys Asp Ser Gln Cys Pro Arg Asp Leu Lys Phe Ile Asp Gly Gln
        195                 200                 205

Ala Asn Ile Glu Gly Trp Glu Pro Ser Ser Thr Asp Val Asn Ala Gly
210                 215                 220

Thr Gly Asn His Gly Ser Cys Cys Pro Glu Met Asp Ile Trp Glu Ala
225                 230                 235                 240

Asn Ser Ile Ser Ser Ala Phe Thr Ala His Pro Cys Asp Ser Val Gln
            245                 250                 255

Gln Thr Met Cys Thr Gly Asp Thr Cys Gly Gly Thr Tyr Ser Asp Thr
                260                 265                 270

Thr Asp Arg Tyr Ser Gly Thr Cys Asp Pro Asp Gly Cys Asp Phe Asn
        275                 280                 285

Pro Tyr Arg Phe Gly Asn Thr Asn Phe Tyr Gly Pro Gly Lys Thr Val
290                 295                 300

Asp Asn Ser Lys Pro Phe Thr Val Val Thr Gln Phe Ile Thr His Asp
305                 310                 315                 320

Gly Thr Asp Thr Gly Thr Leu Thr Glu Ile Arg Arg Leu Tyr Val Gln
                325                 330                 335

Asn Gly Val Val Ile Gly Asn Gly Pro Ser Thr Tyr Thr Ala Ala Ser
            340                 345                 350

Gly Asn Ser Ile Thr Glu Ser Phe Cys Lys Ala Glu Lys Thr Leu Phe
        355                 360                 365

Gly Asp Thr Asn Val Phe Glu Thr His Gly Gly Leu Ser Ala Met Gly
370                 375                 380

Asp Ala Leu Gly Asp Gly Met Val Leu Val Leu Ser Leu Trp Asp Asp
385                 390                 395                 400

His Ala Ala Asp Met Leu Trp Leu Asp Ser Asp Tyr Pro Thr Thr Ser
                405                 410                 415

Cys Ala Ser Ser Pro Gly Val Ala Arg Gly Thr Cys Pro Thr Thr Thr
            420                 425                 430

Gly Asn Ala Thr Tyr Val Glu Ala Asn Tyr Pro Asn Ser Tyr Val Thr
        435                 440                 445

Tyr Ser Asn Ile Lys Phe Gly Thr Leu Asn Ser Thr Tyr Ser Gly Thr
450                 455                 460

Ser Ser Gly Gly Ser Ser Ser Ser Thr Thr Leu Thr Thr Lys Ala
465                 470                 475                 480

Ser Thr Ser Thr Thr Ser Ser Lys Thr Thr Thr Thr Ser Lys Thr
                485                 490                 495

Ser Thr Thr Ser Ser Ser Ser Thr Asn Val Ala Gln Leu Tyr Gly Gln
            500                 505                 510

Cys Gly Gly Gln Gly Trp Thr Gly Pro Thr Thr Cys Ala Ser Gly Thr
        515                 520                 525

Cys Thr Lys Gln Asn Asp Tyr Tyr Ser Gln Cys Leu
530                 535                 540

<210> SEQ ID NO 59
<211> LENGTH: 537
<212> TYPE: PRT
<213> ORGANISM: Penicillium janthinellum
```

```
<220> FEATURE:
<221> NAME/KEY: misc_feature
<222> LOCATION: (48)..(48)
<223> OTHER INFORMATION: Xaa can be any naturally occurring amino acid
<220> FEATURE:
<221> NAME/KEY: misc_feature
<222> LOCATION: (64)..(64)
<223> OTHER INFORMATION: Xaa can be any naturally occurring amino acid

<400> SEQUENCE: 59

Met Lys Gly Ser Ile Ser Tyr Gln Ile Tyr Lys Gly Ala Leu Leu Leu
1               5                   10                  15

Ser Ala Leu Leu Asn Ser Val Ser Ala Gln Gln Val Gly Thr Leu Thr
            20                  25                  30

Ala Glu Thr His Pro Ala Leu Thr Trp Ser Lys Cys Thr Ala Gly Xaa
        35                  40                  45

Cys Ser Gln Val Ser Gly Ser Val Val Ile Asp Ala Asn Trp Pro Xaa
    50                  55                  60

Val His Ser Thr Ser Gly Ser Thr Asn Cys Tyr Thr Gly Asn Thr Trp
65                  70                  75                  80

Asp Ala Thr Leu Cys Pro Asp Asp Val Thr Cys Ala Ala Asn Cys Ala
                85                  90                  95

Val Asp Gly Ala Arg Arg Gln His Leu Arg Val Thr Thr Ser Gly Asn
            100                 105                 110

Ser Leu Arg Ile Asn Phe Val Thr Thr Ala Ser Gln Lys Asn Ile Gly
        115                 120                 125

Ser Arg Leu Tyr Leu Leu Glu Asn Asp Thr Thr Tyr Gln Lys Phe Asn
    130                 135                 140

Leu Leu Asn Gln Glu Phe Thr Phe Asp Val Asp Val Ser Asn Leu Pro
145                 150                 155                 160

Cys Gly Leu Asn Gly Ala Leu Tyr Phe Val Asp Met Asp Ala Asp Gly
                165                 170                 175

Gly Met Ala Lys Tyr Pro Thr Asn Lys Ala Gly Ala Lys Tyr Gly Thr
            180                 185                 190

Gly Tyr Cys Asp Ser Gln Cys Pro Arg Asp Leu Lys Phe Ile Asn Gly
        195                 200                 205

Gln Ala Asn Val Asp Gly Trp Thr Pro Ser Lys Asn Asp Val Asn Ser
    210                 215                 220

Gly Ile Gly Asn His Gly Ser Cys Cys Ala Glu Met Asp Ile Trp Glu
225                 230                 235                 240

Ala Asn Ser Ile Ser Asn Ala Val Thr Pro His Pro Cys Asp Thr Pro
                245                 250                 255

Ser Gln Thr Met Cys Thr Gly Gln Arg Cys Gly Gly Thr Tyr Ser Thr
            260                 265                 270

Asp Arg Tyr Gly Gly Thr Cys Asp Pro Asp Gly Cys Asp Phe Asn Pro
        275                 280                 285

Tyr Arg Met Gly Val Thr Asn Phe Tyr Gly Pro Gly Glu Thr Ile Asp
    290                 295                 300

Thr Lys Ser Pro Phe Thr Val Val Thr Gln Phe Leu Thr Asn Asp Gly
305                 310                 315                 320

Thr Ser Thr Gly Thr Leu Ser Glu Ile Lys Arg Phe Tyr Val Gln Gly
                325                 330                 335

Gly Lys Val Ile Gly Asn Pro Gln Ser Thr Ile Val Gly Val Ser Gly
            340                 345                 350

Asn Ser Ile Thr Asp Ser Trp Cys Asn Ala Gln Lys Ser Ala Phe Gly
        355                 360                 365
```

-continued

Asp Thr Asn Glu Phe Ser Lys His Gly Gly Met Ala Gly Met Gly Ala
    370                 375                 380

Gly Leu Ala Asp Gly Met Val Leu Val Met Ser Leu Trp Asp Asp His
385                 390                 395                 400

Ala Ser Asp Met Leu Trp Leu Asp Ser Thr Tyr Pro Thr Asn Ala Thr
                405                 410                 415

Ser Thr Thr Pro Gly Ala Lys Arg Gly Thr Cys Asp Ile Ser Arg Arg
            420                 425                 430

Pro Asn Thr Val Glu Ser Thr Tyr Pro Asn Ala Tyr Val Ile Tyr Ser
                435                 440                 445

Asn Ile Lys Thr Gly Pro Leu Asn Ser Thr Phe Thr Gly Gly Thr Thr
        450                 455                 460

Ser Ser Ser Ser Thr Thr Thr Thr Thr Ser Lys Ser Thr Ser Thr Ser
465                 470                 475                 480

Ser Ser Ser Lys Thr Thr Thr Val Thr Thr Thr Thr Ser Ser
                485                 490                 495

Gly Ser Ser Gly Thr Gly Ala Arg Asp Trp Ala Gln Cys Gly Gly Asn
            500                 505                 510

Gly Trp Thr Gly Pro Thr Thr Cys Val Ser Pro Tyr Thr Cys Thr Lys
            515                 520                 525

Gln Asn Asp Trp Tyr Ser Gln Cys Leu
    530                 535

<210> SEQ ID NO 60
<211> LENGTH: 452
<212> TYPE: PRT
<213> ORGANISM: Aspergillus niger

<400> SEQUENCE: 60

Met His Gln Arg Ala Leu Leu Phe Ser Ala Leu Leu Thr Ala Val Arg
1               5                   10                  15

Ala Gln Gln Ala Gly Thr Leu Thr Glu Glu Val His Pro Ser Leu Thr
                20                  25                  30

Trp Gln Lys Cys Thr Ser Glu Gly Ser Cys Thr Glu Gln Ser Gly Ser
            35                  40                  45

Val Val Ile Asp Ser Asn Trp Arg Trp Thr His Ser Val Asn Asp Ser
    50                  55                  60

Thr Asn Cys Tyr Thr Gly Asn Thr Trp Asp Ala Thr Leu Cys Pro Asp
65              70                  75                  80

Asp Glu Thr Cys Ala Ala Asn Cys Ala Leu Asp Gly Ala Asp Tyr Glu
                85                  90                  95

Ser Thr Tyr Gly Val Thr Thr Asp Gly Asp Ser Leu Thr Leu Lys Phe
            100                 105                 110

Val Thr Gly Ser Asn Val Gly Ser Arg Leu Tyr Leu Met Asp Thr Ser
        115                 120                 125

Asp Glu Gly Tyr Gln Thr Phe Asn Leu Leu Asp Ala Glu Phe Thr Phe
    130                 135                 140

Asp Val Asp Val Ser Asn Leu Pro Cys Gly Leu Asn Gly Ala Leu Tyr
145                 150                 155                 160

Phe Thr Ala Met Asp Ala Asp Gly Gly Val Ser Lys Tyr Pro Ala Asn
                165                 170                 175

Lys Ala Gly Ala Lys Tyr Gly Thr Gly Tyr Cys Asp Ser Gln Cys Pro
            180                 185                 190

Arg Asp Leu Lys Phe Ile Asp Gly Gln Ala Asn Val Asp Gly Trp Glu
        195                 200                 205

-continued

Pro Ser Ser Asn Asn Asp Asn Thr Gly Ile Gly Asn His Gly Ser Cys
    210                 215                 220

Cys Pro Glu Met Asp Ile Trp Glu Ala Asn Lys Ile Ser Thr Ala Leu
225                 230                 235                 240

Thr Pro His Pro Cys Asp Ser Ser Glu Gln Thr Met Cys Glu Gly Asn
                245                 250                 255

Asp Cys Gly Gly Thr Tyr Ser Asp Asp Arg Tyr Gly Gly Thr Cys Asp
            260                 265                 270

Pro Asp Gly Cys Asp Phe Asn Pro Tyr Arg Met Gly Asn Asp Ser Phe
        275                 280                 285

Tyr Gly Pro Gly Lys Thr Ile Asp Thr Gly Ser Lys Met Thr Val Val
    290                 295                 300

Thr Gln Phe Ile Thr Asp Gly Ser Gly Ser Leu Ser Glu Ile Lys Arg
305                 310                 315                 320

Tyr Tyr Val Gln Asn Gly Asn Val Ile Ala Asn Ala Asp Ser Asn Ile
                325                 330                 335

Ser Gly Val Thr Gly Asn Ser Ile Thr Thr Asp Phe Cys Thr Ala Gln
            340                 345                 350

Lys Lys Ala Phe Gly Asp Glu Asp Ile Phe Ala Glu His Asn Gly Leu
        355                 360                 365

Ala Gly Ile Ser Asp Ala Met Ser Ser Met Val Leu Ile Leu Ser Leu
    370                 375                 380

Trp Asp Asp Tyr Tyr Ala Ser Met Glu Trp Leu Asp Ser Asp Tyr Pro
385                 390                 395                 400

Glu Asn Ala Thr Ala Thr Asp Pro Gly Val Ala Arg Gly Thr Cys Asp
                405                 410                 415

Ser Glu Ser Gly Val Pro Ala Thr Val Glu Gly Ala His Pro Asp Ser
            420                 425                 430

Ser Val Thr Phe Ser Asn Ile Lys Phe Gly Pro Ile Asn Ser Thr Phe
        435                 440                 445

Ser Ala Ser Ala
    450

<210> SEQ ID NO 61
<211> LENGTH: 536
<212> TYPE: PRT
<213> ORGANISM: Aspergillus niger

<400> SEQUENCE: 61

Met Ser Ser Phe Gln Ile Tyr Arg Ala Ala Leu Leu Leu Ser Ile Leu
1               5                   10                  15

Ala Thr Ala Asn Ala Gln Gln Val Gly Thr Tyr Thr Thr Glu Thr His
            20                  25                  30

Pro Ser Leu Thr Trp Gln Thr Cys Thr Ser Asp Gly Ser Cys Thr Thr
        35                  40                  45

Asn Asp Gly Glu Val Val Ile Asp Ala Asn Trp Arg Trp Val His Ser
    50                  55                  60

Thr Ser Ser Ala Thr Asn Cys Tyr Thr Gly Asn Glu Trp Asp Thr Ser
65                  70                  75                  80

Ile Cys Thr Asp Asp Val Thr Cys Ala Ala Asn Cys Ala Leu Asp Gly
                85                  90                  95

Ala Thr Tyr Glu Ala Thr Tyr Gly Val Thr Thr Ser Gly Ser Glu Leu
            100                 105                 110

Arg Leu Asn Phe Val Thr Gln Gly Ser Ser Lys Asn Ile Gly Ser Arg
        115                 120                 125

```
Leu Tyr Leu Met Ser Asp Asp Ser Asn Tyr Glu Leu Phe Lys Leu Leu
            130                 135                 140

Gly Gln Glu Phe Thr Phe Asp Val Asp Val Ser Asn Leu Pro Cys Gly
145                 150                 155                 160

Leu Asn Gly Ala Leu Tyr Phe Val Ala Met Asp Ala Asp Gly Gly Thr
                165                 170                 175

Ser Glu Tyr Ser Gly Asn Lys Ala Gly Ala Lys Tyr Gly Thr Gly Tyr
            180                 185                 190

Cys Asp Ser Gln Cys Pro Arg Asp Leu Lys Phe Ile Asn Gly Glu Ala
            195                 200                 205

Asn Cys Asp Gly Trp Glu Pro Ser Ser Asn Val Asn Thr Gly Val
210                 215                 220

Gly Asp His Gly Ser Cys Cys Ala Glu Met Asp Val Trp Glu Ala Asn
225                 230                 235                 240

Ser Ile Ser Asn Ala Phe Thr Ala His Pro Cys Asp Ser Val Ser Gln
                245                 250                 255

Thr Met Cys Asp Gly Asp Ser Cys Gly Gly Thr Tyr Ser Ala Ser Gly
            260                 265                 270

Asp Arg Tyr Ser Gly Thr Cys Asp Pro Asp Gly Cys Asp Tyr Asn Pro
            275                 280                 285

Tyr Arg Leu Gly Asn Thr Asp Phe Tyr Gly Pro Gly Leu Thr Val Asp
            290                 295                 300

Thr Asn Ser Pro Phe Thr Val Val Thr Gln Phe Ile Thr Asp Asp Gly
305                 310                 315                 320

Thr Ser Ser Gly Thr Leu Thr Glu Ile Lys Arg Leu Tyr Val Gln Asn
                325                 330                 335

Gly Glu Val Ile Ala Asn Gly Ala Ser Thr Tyr Ser Ser Val Asn Gly
            340                 345                 350

Ser Ser Ile Thr Ser Ala Phe Cys Glu Ser Glu Lys Thr Leu Phe Gly
            355                 360                 365

Asp Glu Asn Val Phe Asp Lys His Gly Gly Leu Glu Gly Met Gly Glu
            370                 375                 380

Ala Met Ala Lys Gly Met Val Leu Val Leu Ser Leu Trp Asp Asp Tyr
385                 390                 395                 400

Ala Ala Asp Met Leu Trp Leu Asp Ser Asp Tyr Pro Val Asn Ser Ser
                405                 410                 415

Ala Ser Thr Pro Gly Val Ala Arg Gly Thr Cys Ser Thr Asp Ser Gly
            420                 425                 430

Val Pro Ala Thr Val Glu Ala Glu Ser Pro Asn Ala Tyr Val Thr Tyr
            435                 440                 445

Ser Asn Ile Lys Phe Gly Pro Ile Gly Ser Thr Tyr Ser Ser Gly Ser
            450                 455                 460

Ser Ser Gly Ser Gly Ser Ser Ser Ser Ser Ser Thr Thr Thr Lys
465                 470                 475                 480

Ala Thr Ser Thr Thr Leu Lys Thr Thr Ser Thr Thr Ser Ser Gly Ser
                485                 490                 495

Ser Ser Thr Ser Ala Ala Gln Ala Tyr Gly Gln Cys Gly Gly Gln Gly
            500                 505                 510

Trp Thr Gly Pro Thr Thr Cys Val Ser Gly Tyr Thr Cys Thr Tyr Glu
            515                 520                 525

Asn Ala Tyr Tyr Ser Gln Cys Leu
530                 535

<210> SEQ ID NO 62
```

<211> LENGTH: 513
<212> TYPE: PRT
<213> ORGANISM: Hypocrea ceramica

<400> SEQUENCE: 62

```
Met Tyr Arg Lys Leu Ala Val Ile Ser Ala Phe Leu Ala Thr Ala Arg
1               5                   10                  15

Ala Gln Ser Ala Cys Thr Leu Gln Ser Glu Thr His Pro Pro Leu Thr
            20                  25                  30

Trp Gln Lys Cys Ser Ser Gly Gly Thr Cys Thr Gln Thr Gly Ser
        35                  40                  45

Val Val Ile Asp Ala Asn Trp Arg Trp Thr His Ala Thr Asn Ser Ser
50                  55                  60

Thr Asn Cys Tyr Asp Gly Asn Thr Trp Ser Ser Thr Leu Cys Pro Asp
65                  70                  75                  80

Asn Glu Thr Cys Ala Lys Asn Cys Cys Leu Asp Gly Ala Ala Tyr Ala
                85                  90                  95

Ser Ala Tyr Gly Val Thr Thr Ser Gly Asn Ser Leu Ser Ile Gly Phe
            100                 105                 110

Val Thr Gln Ser Ala Gln Lys Asn Val Gly Ala Arg Leu Tyr Leu Met
        115                 120                 125

Ala Ser Asp Thr Thr Tyr Gln Glu Phe Thr Leu Leu Gly Asn Glu Phe
130                 135                 140

Ser Phe Asp Val Asp Val Ser Gln Leu Pro Cys Gly Leu Asn Gly Ala
145                 150                 155                 160

Leu Tyr Phe Val Ser Met Asp Ala Asp Gly Gly Val Ser Lys Tyr Pro
                165                 170                 175

Thr Asn Thr Ala Gly Ala Lys Tyr Gly Thr Gly Tyr Cys Asp Ser Gln
            180                 185                 190

Cys Pro Arg Asp Leu Lys Phe Ile Asn Gly Gln Ala Asn Val Glu Gly
        195                 200                 205

Trp Glu Pro Ser Ser Asn Asn Ala Asn Thr Gly Ile Gly Gly His Gly
210                 215                 220

Ser Cys Cys Ser Glu Met Asp Ile Trp Glu Ala Asn Ser Ile Ser Glu
225                 230                 235                 240

Ala Leu Thr Pro His Pro Cys Thr Thr Val Gly Gln Glu Ile Cys Glu
                245                 250                 255

Gly Asp Gly Cys Gly Gly Thr Tyr Ser Asp Asn Arg Tyr Gly Gly Thr
            260                 265                 270

Cys Asp Pro Asp Gly Cys Asp Trp Asn Pro Tyr Arg Leu Gly Asn Thr
        275                 280                 285

Ser Phe Tyr Gly Pro Gly Ser Ser Phe Thr Leu Asp Thr Thr Lys Lys
290                 295                 300

Leu Thr Val Val Thr Gln Phe Glu Thr Ser Gly Ala Ile Asn Arg Tyr
305                 310                 315                 320

Tyr Val Gln Asn Gly Val Thr Phe Gln Gln Pro Asn Ala Glu Leu Gly
                325                 330                 335

Ser Tyr Ser Gly Asn Glu Leu Asn Asp Asp Tyr Cys Thr Ala Glu Glu
            340                 345                 350

Ala Glu Phe Gly Gly Ser Ser Phe Ser Asp Lys Gly Gly Leu Thr Gln
        355                 360                 365

Phe Lys Lys Ala Thr Ser Gly Gly Met Val Leu Val Met Ser Leu Trp
370                 375                 380

Asp Asp Tyr Tyr Ala Asn Met Leu Trp Leu Asp Ser Thr Tyr Pro Thr
385                 390                 395                 400
```

```
Asn Glu Thr Ser Ser Thr Pro Gly Ala Val Arg Gly Ser Cys Ser Thr
            405                 410                 415

Ser Ser Gly Val Pro Ala Gln Val Glu Ser Gln Ser Pro Asn Ala Lys
            420                 425                 430

Val Thr Phe Ser Asn Ile Lys Phe Gly Pro Ile Gly Ser Thr Gly Asn
            435                 440                 445

Pro Ser Gly Gly Asn Pro Pro Gly Gly Asn Arg Gly Thr Thr Thr Thr
            450                 455                 460

Arg Arg Pro Ala Thr Thr Thr Gly Ser Ser Pro Gly Pro Thr Gln Ser
465                 470                 475                 480

His Tyr Gly Gln Cys Gly Gly Ile Gly Tyr Ser Gly Pro Thr Val Cys
                485                 490                 495

Ala Ser Gly Thr Thr Cys Gln Val Leu Asn Pro Tyr Tyr Ser Gln Cys
            500                 505                 510

Leu

<210> SEQ ID NO 63
<211> LENGTH: 490
<212> TYPE: PRT
<213> ORGANISM: Hypocrea jecorina
<220> FEATURE:
<221> NAME/KEY: misc_feature
<222> LOCATION: (348)..(349)
<223> OTHER INFORMATION: Xaa can be any naturally occurring amino acid

<400> SEQUENCE: 63

Glu Ser Ala Cys Thr Leu Gln Ser Glu Thr His Pro Pro Leu Thr Trp
1               5                   10                  15

Gln Lys Cys Ser Ser Gly Gly Thr Cys Thr Gln Gln Thr Gly Ser Val
                20                  25                  30

Val Ile Asp Ala Asn Trp Arg Trp Thr His Ala Thr Asn Ser Ser Thr
            35                  40                  45

Asn Cys Tyr Asp Gly Asn Thr Trp Ser Ser Thr Leu Cys Pro Asp Asn
    50                  55                  60

Glu Thr Cys Ala Lys Asn Cys Cys Leu Asp Gly Ala Ala Tyr Thr Ser
65                  70                  75                  80

Ala Tyr Ser Ser Glx Pro Gly Gly Gly Gly Val Val Ile Phe Phe
                85                  90                  95

Lys Asn Val Gly Ala Arg Leu Tyr Leu Met Ala Ser Asp Thr Thr Tyr
                100                 105                 110

Gln Glu Phe Thr Leu Leu Gly Asn Glu Phe Ser Phe Asp Val Asp Val
            115                 120                 125

Ser Gln Leu Pro Cys Gly Leu Asn Gly Ala Leu Tyr Phe Val Ser Met
130                 135                 140

Asp Ala Asp Gly Gly Val Ser Lys Tyr Pro Thr Asn Thr Ala Gly Ala
145                 150                 155                 160

Lys Tyr Gly Thr Gly Tyr Cys Asp Ser Gln Cys Pro Arg Asp Leu Lys
                165                 170                 175

Phe Ile Asn Gly Gln Ala Asn Val Glu Gly Trp Glu Pro Ser Ser Asn
            180                 185                 190

Asn Ala Asn Thr Gly Ile Gly Gly His Gly Ser Cys Cys Ser Glu Met
        195                 200                 205

Asp Ile Trp Glu Ala Asn Ser Ile Ser Glu Ala Leu Thr Pro His Pro
210                 215                 220

Cys Thr Thr Val Gly Gln Glu Ile Cys Glu Gly Asp Gly Cys Gly Gly
225                 230                 235                 240
```

```
Thr Tyr Ser Asp Asn Arg Tyr Gly Gly Thr Cys Asp Pro Asp Gly Cys
                245                 250                 255

Asp Trp Asn Pro Tyr Arg Leu Gly Asn Thr Ser Phe Tyr Gly Pro Gly
            260                 265                 270

Ser Ser Phe Thr Leu Asp Thr Lys Lys Leu Thr Val Val Thr Gln
        275                 280                 285

Phe Glu Thr Ser Gly Ala Ile Asn Arg Tyr Tyr Val Gln Asp Gly Val
    290                 295                 300

Thr Phe Gln Gln Pro Asn Ala Glu Leu Gly Ser Tyr Ser Gly Asn Glu
305                 310                 315                 320

Leu Asn Asp Asp Tyr Cys Thr Ala Glu Glu Ala Phe Gly Gly Ser
                325                 330                 335

Ser Phe Ser Asp Lys Gly Gly Leu Thr Gln Phe Xaa Xaa Ala Thr Ser
            340                 345                 350

Gly Gly Met Val Leu Val Met Ser Leu Trp Asp Asp Tyr Tyr Ala Asn
            355                 360                 365

Met Leu Trp Leu Asp Ser Thr Tyr Pro Thr Asn Glu Thr Ser Ser Thr
        370                 375                 380

Pro Gly Ala Val Arg Gly Ser Cys Ser Thr Ser Ser Gly Val Pro Ala
385                 390                 395                 400

Gln Val Glu Ser Gln Ser Pro Asn Ala Lys Val Thr Phe Ser Asn Ile
            405                 410                 415

Lys Phe Gly Pro Ile Gly Ser Thr Gly Asn Pro Ser Gly Gly Asn Pro
            420                 425                 430

Pro Gly Gly Asn Pro Pro Gly Thr Thr Thr Thr Thr Thr Ser Ser
        435                 440                 445

Ser Glx Pro Pro Gly Ala His Arg Arg Tyr Gly Gln Cys Gly Gly
        450                 455                 460

Ile Gly Tyr Ser Gly Pro Thr Val Cys Ala Ser Gly Thr Thr Cys Gln
465                 470                 475                 480

Val Leu Asn Pro Tyr Tyr Ser Gln Cys Leu
                485                 490

<210> SEQ ID NO 64
<211> LENGTH: 513
<212> TYPE: PRT
<213> ORGANISM: Trichoderma viride

<400> SEQUENCE: 64

Met Tyr Gln Lys Leu Ala Leu Ile Ser Ala Phe Leu Ala Thr Ala Arg
1               5                   10                  15

Ala Gln Ser Ala Cys Thr Leu Gln Ala Glu Thr His Pro Pro Leu Thr
            20                  25                  30

Trp Gln Lys Cys Ser Ser Gly Gly Thr Cys Thr Gln Thr Gly Ser
        35                  40                  45

Val Val Ile Asp Ala Asn Trp Arg Trp Thr His Ala Thr Asn Ser Ser
    50                  55                  60

Thr Asn Cys Tyr Asp Gly Asn Thr Trp Ser Ser Thr Leu Cys Pro Asp
65                  70                  75                  80

Asn Glu Thr Cys Ala Lys Asn Cys Cys Leu Asp Gly Ala Ala Tyr Ala
                85                  90                  95

Ser Thr Tyr Gly Val Thr Thr Ser Ala Asp Ser Leu Ser Ile Gly Phe
            100                 105                 110

Val Thr Gln Ser Ala Gln Lys Asn Val Gly Ala Arg Leu Tyr Leu Met
        115                 120                 125
```

```
Ala Ser Asp Thr Thr Tyr Gln Glu Phe Thr Leu Leu Gly Asn Glu Phe
    130                 135                 140

Ser Phe Asp Val Asp Val Ser Gln Leu Pro Cys Gly Leu Asn Gly Ala
145                 150                 155                 160

Leu Tyr Phe Val Ser Met Asp Ala Asp Gly Gly Val Thr Lys Tyr Pro
                165                 170                 175

Thr Asn Thr Ala Gly Ala Lys Tyr Gly Thr Gly Tyr Cys Asp Ser Gln
            180                 185                 190

Cys Pro Arg Asp Leu Lys Phe Ile Asn Gly Gln Ala Asn Val Glu Gly
        195                 200                 205

Trp Glu Pro Ser Ser Asn Asn Ala Asn Thr Gly Ile Gly Gly His Gly
    210                 215                 220

Ser Cys Cys Ser Glu Met Asp Ile Trp Glu Ala Asn Ser Ile Ser Glu
225                 230                 235                 240

Ala Leu Thr Pro His Pro Cys Thr Thr Val Gly Gln Glu Ile Cys Glu
                245                 250                 255

Gly Asp Ser Cys Gly Gly Thr Tyr Ser Gly Asp Arg Tyr Gly Gly Thr
            260                 265                 270

Cys Asp Pro Asp Gly Cys Asp Trp Asn Pro Tyr Arg Leu Gly Asn Thr
        275                 280                 285

Ser Phe Tyr Gly Pro Gly Ser Ser Phe Thr Leu Asp Thr Thr Lys Lys
    290                 295                 300

Leu Thr Val Val Thr Gln Phe Glu Thr Ser Gly Ala Ile Asn Arg Tyr
305                 310                 315                 320

Tyr Val Gln Asn Gly Val Thr Phe Gln Gln Pro Asn Ala Glu Leu Gly
                325                 330                 335

Asp Tyr Ser Gly Asn Ser Leu Asp Asp Tyr Cys Ala Ala Glu Glu
            340                 345                 350

Ala Glu Phe Gly Gly Ser Ser Phe Ser Asp Lys Gly Gly Leu Thr Gln
        355                 360                 365

Phe Lys Lys Ala Thr Ser Gly Gly Met Val Leu Val Met Ser Leu Trp
    370                 375                 380

Asp Asp Tyr Tyr Ala Asn Met Leu Trp Leu Asp Ser Thr Tyr Pro Thr
385                 390                 395                 400

Asp Glu Thr Ser Ser Thr Pro Gly Ala Val Arg Gly Ser Ser Ser Thr
                405                 410                 415

Ser Ser Gly Val Pro Ala Gln Leu Glu Ser Asn Ser Pro Asn Ala Lys
            420                 425                 430

Val Val Tyr Ser Asn Ile Lys Phe Gly Pro Ile Gly Ser Thr Gly Asn
        435                 440                 445

Pro Ser Gly Gly Asn Pro Gly Gly Asn Pro Gly Thr Thr Thr
    450                 455                 460

Pro Arg Pro Ala Thr Ser Thr Gly Ser Ser Pro Gly Pro Thr Gln Thr
465                 470                 475                 480

His Tyr Gly Gln Cys Gly Gly Ile Gly Tyr Ile Gly Pro Thr Val Cys
                485                 490                 495

Ala Ser Gly Ser Thr Cys Gln Val Leu Asn Pro Tyr Tyr Ser Gln Cys
            500                 505                 510

Leu

<210> SEQ ID NO 65
<211> LENGTH: 514
<212> TYPE: PRT
<213> ORGANISM: Trichoderma viride
```

<400> SEQUENCE: 65

```
Met Tyr Gln Lys Leu Ala Leu Ile Ser Ala Phe Leu Ala Thr Ala Arg
1               5                   10                  15

Ala Gln Ser Ala Cys Thr Leu Gln Ala Glu Thr His Pro Pro Leu Thr
            20                  25                  30

Trp Gln Lys Cys Ser Ser Gly Gly Thr Cys Thr Gln Thr Gly Ser
        35                  40                  45

Val Val Ile Asp Ala Asn Trp Arg Trp Thr His Ala Thr Asn Ser Ser
50                  55                  60

Thr Asn Cys Tyr Asp Gly Asn Thr Trp Ser Ser Thr Leu Cys Pro Asp
65                  70                  75                  80

Asn Glu Thr Cys Ala Lys Asn Cys Cys Leu Asp Gly Ala Ala Tyr Ala
                85                  90                  95

Ser Thr Tyr Gly Val Thr Thr Ser Ala Asp Ser Leu Ser Ile Gly Phe
            100                 105                 110

Val Thr Gln Ser Ala Gln Lys Asn Val Gly Ala Arg Leu Tyr Leu Met
        115                 120                 125

Ala Ser Asp Thr Thr Tyr Gln Glu Phe Thr Leu Leu Gly Asn Glu Phe
130                 135                 140

Ser Phe Asp Val Asp Val Ser Gln Leu Pro Cys Gly Leu Asn Gly Ala
145                 150                 155                 160

Leu Tyr Phe Val Ser Met Asp Ala Asp Gly Gly Val Ser Lys Tyr Pro
                165                 170                 175

Thr Asn Thr Ala Gly Ala Lys Tyr Gly Thr Gly Tyr Cys Asp Ser Gln
            180                 185                 190

Cys Pro Arg Asp Leu Lys Phe Ile Asn Gly Gln Ala Asn Val Glu Gly
        195                 200                 205

Trp Glu Pro Ser Ser Asn Asn Ala Asn Thr Gly Ile Gly Gly His Gly
210                 215                 220

Ser Cys Cys Ser Glu Met Asp Ile Trp Glu Ala Asn Ser Ile Ser Glu
225                 230                 235                 240

Ala Leu Thr Pro His Pro Cys Thr Thr Val Gly Gln Glu Ile Cys Asp
                245                 250                 255

Gly Asp Ser Cys Gly Gly Thr Tyr Ser Gly Asp Arg Tyr Gly Gly Thr
            260                 265                 270

Cys Asp Pro Asp Gly Cys Asp Trp Asn Pro Tyr Arg Leu Gly Asn Thr
        275                 280                 285

Ser Phe Tyr Gly Pro Gly Ser Ser Phe Thr Leu Asp Thr Thr Lys Lys
290                 295                 300

Leu Thr Val Val Thr Gln Phe Glu Thr Ser Gly Ala Ile Asn Arg Tyr
305                 310                 315                 320

Tyr Val Gln Asn Gly Val Thr Phe Gln Gln Pro Asn Ala Glu Leu Gly
                325                 330                 335

Asp Tyr Ser Gly Asn Ser Leu Asp Asp Tyr Cys Ala Ala Glu Glu
            340                 345                 350

Ala Glu Phe Gly Gly Ser Ser Phe Ser Asp Lys Gly Gly Leu Thr Gln
        355                 360                 365

Phe Lys Lys Ala Thr Ser Gly Gly Met Val Leu Val Met Ser Leu Trp
370                 375                 380

Asp Asp Tyr Tyr Ala Asn Met Leu Trp Leu Asp Ser Thr Tyr Pro Thr
385                 390                 395                 400

Asn Glu Thr Ser Ser Thr Pro Gly Ala Val Arg Gly Ser Cys Ser Thr
                405                 410                 415
```

```
Ser Ser Gly Val Pro Ala Gln Leu Glu Ser Asn Ser Pro Asn Ala Lys
        420                 425                 430

Val Val Tyr Ser Asn Ile Lys Phe Gly Pro Ile Gly Ser Thr Gly Asn
        435                 440                 445

Ser Ser Gly Gly Asn Pro Gly Gly Asn Pro Pro Gly Thr Thr Thr
        450                 455                 460

Thr Arg Arg Pro Ala Thr Ser Thr Gly Ser Ser Pro Gly Pro Thr Gln
465                 470                 475                 480

Thr His Tyr Gly Gln Cys Gly Gly Ile Gly Tyr Ser Gly Pro Thr Val
                485                 490                 495

Cys Ala Ser Gly Ser Thr Cys Gln Val Leu Asn Pro Tyr Tyr Ser Gln
                500                 505                 510

Cys Leu

<210> SEQ ID NO 66
<211> LENGTH: 505
<212> TYPE: PRT
<213> ORGANISM: Trichoderma harzianum

<400> SEQUENCE: 66

Met Tyr Arg Lys Leu Ala Val Ile Ser Ala Phe Leu Ala Ala Ala Arg
1               5                   10                  15

Ala Gln Gln Val Cys Thr Gln Ala Glu Thr His Pro Pro Leu Thr
                20                  25                  30

Trp Gln Lys Cys Thr Ala Ser Gly Cys Thr Pro Gln Gln Gly Ser Val
            35                  40                  45

Val Leu Asp Ala Asn Trp Arg Trp Thr His Asp Thr Lys Ser Thr Thr
50                  55                  60

Asn Cys Tyr Asp Gly Asn Thr Trp Ser Ser Thr Leu Cys Pro Asp Asp
65                  70                  75                  80

Ala Thr Cys Ala Lys Asn Cys Cys Leu Asp Gly Ala Asn Tyr Ser Gly
                85                  90                  95

Thr Tyr Gly Val Thr Thr Ser Gly Asp Ala Leu Thr Leu Gln Phe Val
                100                 105                 110

Thr Ala Ser Asn Val Gly Ser Arg Leu Tyr Leu Met Ala Asn Asp Ser
            115                 120                 125

Thr Tyr Gln Glu Phe Thr Leu Ser Gly Asn Glu Phe Ser Phe Asp Val
            130                 135                 140

Asp Val Ser Gln Leu Pro Cys Gly Leu Asn Gly Ala Leu Tyr Phe Val
145                 150                 155                 160

Ser Met Asp Ala Asp Gly Gly Gln Ser Lys Tyr Pro Gly Asn Ala Ala
                165                 170                 175

Gly Ala Lys Tyr Gly Thr Gly Tyr Cys Asp Ser Gln Cys Pro Arg Asp
            180                 185                 190

Leu Lys Phe Ile Asn Gly Gln Ala Asn Val Glu Gly Trp Glu Pro Ser
            195                 200                 205

Ser Asn Asn Ala Asn Thr Gly Val Gly Gly His Gly Ser Cys Cys Ser
        210                 215                 220

Glu Met Asp Ile Trp Glu Ala Asn Ser Ile Ser Glu Ala Leu Thr Pro
225                 230                 235                 240

His Pro Cys Glu Thr Val Gly Gln Thr Met Cys Ser Gly Asp Ser Cys
                245                 250                 255

Gly Gly Thr Tyr Ser Asn Asp Arg Tyr Gly Gly Thr Cys Asp Pro Asp
            260                 265                 270
```

-continued

Gly Cys Asp Trp Asn Pro Tyr Arg Leu Gly Asn Thr Ser Phe Tyr Gly
                275                 280                 285

Pro Gly Ser Ser Phe Ala Leu Asp Thr Thr Lys Lys Leu Thr Val Val
            290                 295                 300

Thr Gln Phe Ala Thr Asp Gly Ser Ile Ser Arg Tyr Tyr Val Gln Asn
305                 310                 315                 320

Gly Val Lys Phe Gln Gln Pro Asn Ala Gln Val Gly Ser Tyr Ser Gly
                325                 330                 335

Asn Thr Ile Asn Thr Asp Tyr Cys Ala Ala Glu Gln Thr Ala Phe Gly
                340                 345                 350

Gly Thr Ser Phe Thr Asp Lys Gly Gly Leu Ala Gln Ile Asn Lys Ala
                355                 360                 365

Phe Gln Gly Gly Met Val Leu Val Met Ser Leu Trp Asp Asp Tyr Ala
            370                 375                 380

Val Asn Met Leu Trp Leu Asp Ser Thr Tyr Pro Thr Asn Ala Thr Ala
385                 390                 395                 400

Ser Thr Pro Gly Ala Lys Arg Gly Ser Cys Ser Thr Ser Ser Gly Val
                405                 410                 415

Pro Ala Gln Val Glu Ala Gln Ser Pro Asn Ser Lys Val Ile Tyr Ser
            420                 425                 430

Asn Ile Arg Phe Gly Pro Ile Gly Ser Thr Gly Gly Asn Thr Gly Ser
            435                 440                 445

Asn Pro Pro Gly Thr Ser Thr Thr Arg Ala Pro Pro Ser Ser Thr Gly
450                 455                 460

Ser Ser Pro Thr Ala Thr Gln Thr His Tyr Gly Gln Cys Gly Gly Thr
465                 470                 475                 480

Gly Trp Thr Gly Pro Thr Arg Cys Ala Ser Gly Tyr Thr Cys Gln Val
                485                 490                 495

Leu Asn Pro Phe Tyr Ser Gln Cys Leu
                500                 505

<210> SEQ ID NO 67
<211> LENGTH: 506
<212> TYPE: PRT
<213> ORGANISM: Agaricus bisporus

<400> SEQUENCE: 67

Met Phe Pro Arg Ser Ile Leu Leu Ala Leu Ser Leu Thr Ala Val Ala
1               5                   10                  15

Leu Gly Gln Gln Val Gly Thr Asn Met Ala Glu Asn His Pro Ser Leu
                20                  25                  30

Thr Trp Gln Arg Cys Thr Ser Ser Gly Cys Gln Asn Val Asn Gly Lys
            35                  40                  45

Val Thr Leu Asp Ala Asn Trp Arg Trp Thr His Arg Ile Asn Asp Phe
50                  55                  60

Thr Asn Cys Tyr Thr Gly Asn Glu Trp Asp Thr Ser Ile Cys Pro Asp
65                  70                  75                  80

Gly Val Thr Cys Ala Glu Asn Cys Ala Leu Asp Gly Ala Asp Tyr Ala
                85                  90                  95

Gly Thr Tyr Gly Val Thr Ser Ser Gly Thr Ala Leu Thr Leu Lys Phe
            100                 105                 110

Val Thr Glu Ser Gln Gln Lys Asn Ile Gly Ser Arg Leu Tyr Leu Met
            115                 120                 125

Ala Asp Asp Ser Asn Tyr Glu Ile Phe Asn Leu Leu Asn Lys Glu Phe
        130                 135                 140

-continued

```
Thr Phe Asp Val Asp Val Ser Lys Leu Pro Cys Gly Leu Asn Gly Ala
145                 150                 155                 160

Leu Tyr Phe Ser Glu Met Ala Ala Asp Gly Met Ser Ser Thr Asn
            165                 170                 175

Thr Ala Gly Ala Lys Tyr Gly Thr Gly Tyr Cys Asp Ser Gln Cys Pro
        180                 185                 190

Arg Asp Ile Lys Phe Ile Asp Gly Glu Ala Asn Ser Glu Gly Trp Glu
    195                 200                 205

Gly Ser Pro Asn Asp Val Asn Ala Gly Thr Gly Asn Phe Gly Ala Cys
        210                 215                 220

Cys Gly Glu Met Asp Ile Trp Glu Ala Asn Ser Ile Ser Ser Ala Tyr
225                 230                 235                 240

Thr Pro His Pro Cys Arg Glu Pro Gly Leu Gln Arg Cys Glu Gly Asn
            245                 250                 255

Thr Cys Ser Val Asn Asp Arg Tyr Ala Thr Glu Cys Asp Pro Asp Gly
        260                 265                 270

Cys Asp Phe Asn Ser Phe Arg Met Gly Asp Lys Ser Phe Tyr Gly Pro
    275                 280                 285

Gly Met Thr Val Asp Thr Asn Gln Pro Ile Thr Val Val Thr Gln Phe
        290                 295                 300

Ile Thr Asp Asn Gly Ser Asp Asn Gly Asn Leu Gln Glu Ile Arg Arg
305                 310                 315                 320

Ile Tyr Val Gln Asn Gly Gln Val Ile Gln Asn Ser Asn Val Asn Ile
            325                 330                 335

Pro Gly Ile Asp Ser Gly Asn Ser Ile Ser Ala Glu Phe Cys Asp Gln
        340                 345                 350

Ala Lys Glu Ala Phe Gly Asp Glu Arg Ser Phe Gln Asp Arg Gly Gly
    355                 360                 365

Leu Ser Gly Met Gly Ser Ala Leu Asp Arg Gly Met Val Leu Val Leu
        370                 375                 380

Ser Ile Trp Asp Asp His Ala Val Asn Met Leu Trp Leu Asp Ser Asp
385                 390                 395                 400

Tyr Pro Leu Asp Ala Ser Pro Ser Gln Pro Gly Ile Ser Arg Gly Thr
            405                 410                 415

Cys Ser Arg Asp Ser Gly Lys Pro Glu Asp Val Glu Ala Asn Ala Gly
        420                 425                 430

Gly Val Gln Val Val Tyr Ser Asn Ile Lys Phe Gly Asp Ile Asn Ser
    435                 440                 445

Thr Phe Asn Asn Asn Gly Gly Gly Gly Asn Pro Ser Pro Thr Thr
        450                 455                 460

Thr Arg Pro Asn Ser Pro Ala Gln Thr Met Trp Gly Gln Cys Gly Gly
465                 470                 475                 480

Gln Gly Trp Thr Gly Pro Thr Ala Cys Gln Ser Pro Ser Thr Cys His
            485                 490                 495

Val Ile Asn Asp Phe Tyr Ser Gln Cys Phe
        500                 505

<210> SEQ ID NO 68
<211> LENGTH: 536
<212> TYPE: PRT
<213> ORGANISM: Volvariella volvacea

<400> SEQUENCE: 68

Met Arg Ala Ser Leu Leu Ala Phe Ser Leu Asn Ser Ala Ala Gly Gln
1               5                   10                  15
```

```
Gln Ala Gly Thr Leu Gln Thr Lys Asn His Pro Ser Leu Thr Ser Gln
            20                  25                  30

Lys Cys Arg Gln Gly Gly Cys Pro Gln Val Asn Thr Thr Ile Val Leu
            35                  40                  45

Asp Ala Asn Trp Arg Trp Thr His Ser Thr Ser Gly Ser Thr Asn Cys
 50                  55                  60

Tyr Thr Gly Asn Thr Trp Gln Ala Thr Leu Cys Pro Asp Gly Lys Thr
 65                  70                  75                  80

Cys Ala Ala Asn Cys Ala Leu Asp Gly Ala Asp Tyr Thr Gly Thr Tyr
                85                  90                  95

Gly Val Thr Thr Ser Gly Asn Ser Leu Thr Leu Gln Phe Val Thr Gln
            100                 105                 110

Ser Asn Val Gly Ala Arg Leu Gly Tyr Leu Met Ala Asp Asp Thr Thr
            115                 120                 125

Tyr Gln Met Phe Asn Leu Leu Asn Gln Glu Phe Trp Phe Asp Val Asp
            130                 135                 140

Met Ser Asn Leu Pro Cys Gly Leu Asn Gly Ala Leu Tyr Phe Ser Ala
145                 150                 155                 160

Met Ala Arg Thr Ala Ala Trp Met Pro Met Val Val Cys Ala Ser Thr
                165                 170                 175

Pro Leu Ile Ser Thr Arg Arg Ser Thr Ala Arg Leu Leu Arg Leu Pro
            180                 185                 190

Val Pro Pro Arg Ser Arg Tyr Gly Arg Gly Ile Cys Asp Ser Gln Cys
            195                 200                 205

Pro Arg Asp Ile Lys Phe Ile Asn Gly Glu Ala Asn Val Gln Gly Trp
            210                 215                 220

Gln Pro Ser Pro Asn Asp Thr Asn Ala Gly Thr Gly Asn Tyr Gly Ala
225                 230                 235                 240

Cys Cys Asn Lys Met Asp Val Trp Glu Ala Asn Ser Ile Ser Thr Ala
                245                 250                 255

Tyr Thr Pro His Pro Cys Thr Gln Arg Gly Leu Val Arg Cys Ser Gly
            260                 265                 270

Thr Ala Cys Gly Gly Gly Ser Asn Arg Tyr Gly Ser Ile Cys Asp His
            275                 280                 285

Asp Gly Leu Gly Phe Gln Asn Leu Phe Gly Met Gly Arg Thr Arg Val
            290                 295                 300

Arg Ala Arg Val Gly Arg Val Lys Gln Phe Asn Arg Ser Ser Arg Val
305                 310                 315                 320

Val Glu Pro Ile Ser Trp Thr Lys Gln Thr Thr Leu His Leu Gly Asn
                325                 330                 335

Leu Pro Trp Lys Ser Ala Asp Cys Asn Val Gln Asn Gly Arg Val Ile
            340                 345                 350

Gln Asn Ser Lys Val Asn Ile Pro Gly Met Pro Ser Thr Met Asp Ser
            355                 360                 365

Val Thr Thr Glu Phe Cys Asn Ala Gln Lys Thr Ala Phe Asn Asp Thr
            370                 375                 380

Phe Ser Phe Gln Gln Lys Gly Gly Met Ala Asn Met Ser Glu Ala Leu
385                 390                 395                 400

Arg Arg Gly Met Val Leu Val Leu Ser Ile Trp Asp Asp His Ala Ala
                405                 410                 415

Asn Met Leu Trp Leu Asp Ser Ile Thr Ser Ala Ala Ala Cys Arg Ser
            420                 425                 430

Thr Pro Ser Glu Val His Ala Thr Pro Leu Arg Glu Ser Gln Ile Arg
            435                 440                 445
```

Ser Ser His Ser Arg Gln Thr Arg Tyr Val Thr Phe Thr Asn Ile Lys
        450                 455                 460

Phe Gly Pro Phe Asn Ser Thr Gly Thr Thr Tyr Thr Thr Gly Ser Val
465                 470                 475                 480

Pro Thr Thr Ser Thr Ser Thr Gly Thr Thr Gly Ser Ser Thr Pro Pro
                485                 490                 495

Gln Pro Thr Gly Val Thr Val Pro Gln Gly Gln Cys Gly Gly Ile Gly
            500                 505                 510

Tyr Thr Gly Pro Thr Thr Cys Ala Ser Pro Thr Thr Cys His Val Leu
        515                 520                 525

Asn Pro Tyr Tyr Ser Gln Cys Tyr
    530                 535

<210> SEQ ID NO 69
<211> LENGTH: 463
<212> TYPE: PRT
<213> ORGANISM: Trichoderma longibrachiatum

<400> SEQUENCE: 69

Met Ala Pro Ser Ala Thr Leu Pro Leu Thr Thr Ala Ile Leu Ala Ile
1               5                   10                  15

Gly Arg Leu Val Ala Ala Gln Gln Pro Gly Thr Ser Thr Pro Glu Val
            20                  25                  30

His Pro Lys Leu Thr Thr Tyr Lys Cys Thr Thr Ser Gly Gly Cys Val
        35                  40                  45

Ala Gln Asp Thr Ser Val Val Leu Asp Trp Asn Tyr Arg Trp Met His
    50                  55                  60

Asp Ala Asn Tyr Asn Ser Cys Thr Val Asn Gly Gly Val Asn Thr Thr
65                  70                  75                  80

Leu Cys Pro Asp Glu Ala Thr Cys Gly Lys Asn Cys Tyr Ile Glu Gly
                85                  90                  95

Val Asp Tyr Ala Ala Ser Gly Val Thr Ala Ser Gly Ser Thr Leu Thr
            100                 105                 110

Leu Asn Gln Tyr Met Pro Ser Ser Gly Gly Tyr Ser Ser Val Ser
        115                 120                 125

Pro Arg Leu Tyr Leu Leu Gly Pro Asp Gly Glu Tyr Val Met Leu Lys
    130                 135                 140

Leu Asn Gly Gln Glu Leu Ser Phe Asp Val Asp Leu Ser Ala Leu Pro
145                 150                 155                 160

Cys Gly Glu Asn Gly Ser Leu Tyr Leu Ser Gln Met Asp Glu Asn Gly
                165                 170                 175

Gly Ala Asn Gln Tyr Asn Thr Ala Gly Ala Asn Tyr Gly Ser Gly Tyr
            180                 185                 190

Cys Asp Ala Gln Cys Pro Val Gln Thr Trp Arg Asn Gly Thr Leu Asn
        195                 200                 205

Thr Ser Gly Gln Gly Phe Cys Cys Asn Glu Met Asp Ile Leu Glu Gly
    210                 215                 220

Asn Ser Arg Ala Asn Ala Leu Thr Pro His Ser Cys Thr Ala Thr Ala
225                 230                 235                 240

Cys Asp Ser Ala Gly Cys Gly Phe Asn Pro Tyr Gly Ser Gly Tyr Pro
                245                 250                 255

Asn Tyr Phe Gly Pro Gly Asp Thr Val Asp Thr Ser Lys Thr Phe Thr
            260                 265                 270

Ile Ile Thr Gln Phe Asn Thr Asp Asn Gly Ser Pro Ser Gly Asn Leu
        275                 280                 285

Val Ser Ile Thr Arg Lys Tyr Arg Gln Asn Gly Val Asp Ile Pro Ser
    290                 295                 300

Ala Lys Pro Gly Gly Asp Thr Ile Ser Ser Cys Pro Ser Ala Ser Ala
305                 310                 315                 320

Tyr Gly Gly Leu Ala Thr Met Gly Lys Ala Leu Ser Ser Gly Met Val
                325                 330                 335

Leu Val Phe Ser Ile Trp Asn Asp Asn Ser Gln Tyr Met Asn Trp Leu
                340                 345                 350

Asp Ser Gly Arg Ala Gly Pro Cys Ser Ser Thr Glu Gly Asn Pro Ser
                355                 360                 365

Asn Ile Leu Ala Asn Asn Pro Gly Thr His Val Val Tyr Ser Asn Ile
        370                 375                 380

Arg Trp Gly Asp Ile Gly Ser Thr Thr Asn Ser Thr Gly Gly Asn Pro
385                 390                 395                 400

Pro Pro Pro Pro Pro Ala Ser Ser Thr Thr Phe Ser Thr Thr Arg
                405                 410                 415

Arg Ser Ser Thr Thr Ser Ser Ser Pro Ser Cys Thr Gln Thr His Trp
                420                 425                 430

Gly Gln Cys Gly Gly Ile Gly Tyr Thr Gly Cys Lys Thr Cys Thr Ser
            435                 440                 445

Gly Thr Thr Cys Gln Tyr Gly Asn Asp Tyr Tyr Ser Gln Cys Leu
    450                 455                 460

<210> SEQ ID NO 70
<211> LENGTH: 459
<212> TYPE: PRT
<213> ORGANISM: Hypocrea jecorina

<400> SEQUENCE: 70

Met Ala Pro Ser Val Thr Leu Pro Leu Thr Thr Ala Ile Leu Ala Ile
1               5                   10                  15

Ala Arg Leu Val Ala Ala Gln Gln Pro Gly Thr Ser Thr Pro Glu Val
                20                  25                  30

His Pro Lys Leu Thr Thr Tyr Lys Cys Thr Thr Ser Gly Gly Cys Val
            35                  40                  45

Ala Gln Asp Thr Ser Val Val Leu Asp Trp Asn Tyr Arg Trp Met His
        50                  55                  60

Asp Ala Asn Tyr Asn Ser Cys Thr Val Asn Gly Gly Val Asn Thr Thr
65                  70                  75                  80

Leu Cys Pro Asp Glu Ala Thr Cys Gly Lys Asn Cys Tyr Ile Glu Gly
                85                  90                  95

Val Asp Tyr Ala Ala Ser Gly Val Thr Ala Ser Gly Ser Ser Leu Thr
                100                 105                 110

Leu Met Gln Tyr Met Pro Ser Ser Gly Gly Tyr Ser Ser Val Ser
            115                 120                 125

Pro Arg Leu Tyr Leu Leu Asp Ser Asp Gly Glu Tyr Val Met Leu Lys
        130                 135                 140

Leu Asn Gly Gln Glu Leu Ser Phe Asp Val Asp Leu Ser Ala Leu Pro
145                 150                 155                 160

Cys Gly Glu Asn Gly Ser Leu Tyr Leu Ser Gln Met Asp Glu Asn Gly
                165                 170                 175

Gly Ala Asn Gln Tyr Asn Thr Ala Gly Ala Asn Tyr Gly Ser Gly Tyr
            180                 185                 190

Cys Asp Ala Gln Cys Pro Val Gln Thr Trp Arg Asn Gly Thr Leu Asn
        195                 200                 205

```
Thr Ser His Gln Gly Phe Cys Cys Asn Glu Met Asp Ile Leu Glu Gly
    210                 215                 220

Asn Ser Arg Ala Asn Ala Leu Thr Pro His Ser Cys Thr Ala Thr Ala
225                 230                 235                 240

Cys Asp Ser Ala Gly Cys Gly Phe Asn Pro Tyr Gly Ser Gly Tyr Lys
                245                 250                 255

Ser Tyr Tyr Gly Pro Gly Asp Thr Val Asp Thr Ser Lys Thr Phe Thr
            260                 265                 270

Ile Ile Thr Gln Phe Asn Thr Asp Asn Gly Ser Pro Ser Gly Asn Leu
        275                 280                 285

Val Ser Ile Thr Arg Lys Tyr Gln Gln Asn Gly Val Asp Ile Pro Ser
    290                 295                 300

Ala Gln Pro Gly Gly Asp Thr Ile Ser Ser Cys Pro Ser Ala Ser Ala
305                 310                 315                 320

Tyr Gly Gly Leu Ala Thr Met Gly Lys Ala Leu Ser Ser Gly Met Val
                325                 330                 335

Leu Val Phe Ser Ile Trp Asn Asp Asn Ser Gln Tyr Met Asn Trp Leu
            340                 345                 350

Asp Ser Gly Asn Ala Gly Pro Cys Ser Ser Thr Glu Gly Asn Pro Ser
        355                 360                 365

Asn Ile Leu Ala Asn Asn Pro Asn Thr His Val Val Phe Ser Asn Ile
    370                 375                 380

Arg Trp Gly Asp Ile Gly Ser Thr Thr Asn Ser Thr Ala Pro Pro Pro
385                 390                 395                 400

Pro Pro Ala Ser Ser Thr Thr Phe Ser Thr Thr Arg Arg Ser Ser Thr
                405                 410                 415

Thr Ser Ser Ser Pro Ser Cys Thr Gln Thr His Trp Gly Gln Cys Gly
            420                 425                 430

Gly Ile Gly Tyr Ser Gly Cys Lys Thr Cys Thr Ser Gly Thr Thr Cys
        435                 440                 445

Gln Tyr Gly Asn Asp Tyr Tyr Ser Gln Cys Leu
    450                 455

<210> SEQ ID NO 71
<211> LENGTH: 416
<212> TYPE: PRT
<213> ORGANISM: Aspergillus oryzae

<400> SEQUENCE: 71

Met Ile Trp Thr Leu Ala Pro Phe Val Ala Leu Leu Pro Leu Val Thr
1               5                   10                  15

Ala Gln Gln Val Gly Thr Thr Ala Asp Ala His Pro Arg Leu Thr Thr
            20                  25                  30

Tyr Lys Cys Thr Ser Gln Asn Gly Cys Thr Arg Gln Asn Thr Ser Leu
        35                  40                  45

Val Leu Asp Ala Ala Thr His Phe Ile His Lys Lys Gly Thr Gln Thr
    50                  55                  60

Ser Cys Thr Asn Ser Asn Gly Leu Asp Thr Ala Ile Cys Pro Asp Lys
65                  70                  75                  80

Gln Thr Cys Ala Asp Asn Cys Val Val Asp Gly Ile Thr Asp Tyr Ala
                85                  90                  95

Ser Tyr Gly Val Gln Thr Lys Asn Asp Thr Leu Thr Leu Gln Gln Tyr
            100                 105                 110

Leu Gln Thr Gly Asn Ala Thr Lys Ser Leu Ser Pro Arg Val Tyr Leu
        115                 120                 125
```

Leu Ala Glu Asp Gly Glu Asn Tyr Ser Met Leu Lys Leu Leu Asn Gln
130                 135                 140

Glu Phe Thr Phe Asp Val Asp Ala Ser Thr Leu Val Cys Gly Met Asn
145                 150                 155                 160

Gly Ala Leu Tyr Leu Ser Glu Met Glu Ala Ser Gly Gly Lys Ser Ser
                165                 170                 175

Leu Asn Gln Ala Gly Ala Lys Tyr Gly Thr Gly Tyr Cys Asp Ala Gln
            180                 185                 190

Cys Tyr Thr Thr Pro Trp Ile Asn Gly Glu Gly Asn Thr Glu Ser Val
        195                 200                 205

Gly Ser Cys Cys Gln Glu Met Asp Ile Trp Glu Ala Asn Ala Arg Ala
    210                 215                 220

Thr Gly Leu Thr Pro His Pro Cys Asn Thr Thr Gly Leu Tyr Glu Cys
225                 230                 235                 240

Ser Gly Ser Gly Cys Gly Asp Ser Gly Val Cys Asp Lys Ala Gly Cys
                245                 250                 255

Gly Phe Asn Pro Tyr Gly Leu Gly Ala Lys Asp Tyr Tyr Gly Tyr Gly
            260                 265                 270

Leu Lys Val Asn Thr Asn Glu Thr Phe Thr Val Thr Gln Phe Leu
        275                 280                 285

Thr Asn Asp Asn Thr Thr Ser Gly Gln Leu Ser Glu Ile Arg Arg Leu
290                 295                 300

Tyr Ile Gln Asn Gly Gln Val Ile Gln Asn Ala Ala Val Thr Ser Gly
305                 310                 315                 320

Gly Lys Thr Val Asp Ser Ile Thr Lys Asp Phe Cys Ser Gly Glu Gly
                325                 330                 335

Ser Ala Phe Asn Arg Leu Gly Gly Leu Glu Glu Met Gly His Ala Leu
            340                 345                 350

Gly Arg Gly Met Val Leu Ala Leu Ser Ile Trp Asn Asp Ala Gly Ser
        355                 360                 365

Phe Met Gln Trp Leu Asp Gly Gly Ser Ala Gly Pro Cys Asn Ala Thr
    370                 375                 380

Glu Gly Asn Pro Ala Leu Ile Glu Lys Leu Tyr Pro Asp Thr His Val
385                 390                 395                 400

Lys Phe Ser Lys Ile Arg Trp Gly Asp Ile Gly Ser Thr Tyr Arg His
                405                 410                 415

<210> SEQ ID NO 72
<211> LENGTH: 381
<212> TYPE: PRT
<213> ORGANISM: Artificial
<220> FEATURE:
<223> OTHER INFORMATION: consensus sequence

<400> SEQUENCE: 72

Met Phe Ile Leu Met Val Ala Ala Gln Gln Gly Thr Thr Ala Glu His
1               5                   10                  15

Pro Leu Thr Trp Gln Lys Cys Thr Gly Cys Thr Gly Ser Val Val Leu
                20                  25                  30

Asp Ala Asn Trp Arg Trp Ile His Thr Gly Tyr Thr Asn Cys Tyr Thr
            35                  40                  45

Gly Asn Trp Asp Ser Thr Leu Cys Pro Asp Thr Cys Ala Asn Cys Ala
        50                  55                  60

Leu Asp Gly Ala Asp Tyr Ser Gly Thr Tyr Gly Ile Thr Thr Ser Gly
65                  70                  75                  80

```
Ser Leu Ser Leu Phe Val Thr Gly Ser Asn Val Gly Ser Arg Val Tyr
                85                  90                  95
Leu Met Ala Asp Asp Thr Tyr Gln Met Phe Leu Leu Asn Asn Glu Phe
            100                 105                 110
Thr Phe Asp Val Asp Met Ser Asn Leu Pro Cys Gly Leu Asn Gly Ala
        115                 120                 125
Leu Tyr Phe Val Met Ala Asp Gly Gly Val Ser Lys Tyr Pro Asn
    130                 135                 140
Lys Ala Gly Ala Lys Tyr Gly Thr Gly Tyr Cys Asp Ser Gln Cys Pro
145                 150                 155                 160
Arg Asp Leu Lys Phe Ile Asn Gly Ala Asn Val Glu Gly Trp Ser Ser
                165                 170                 175
Asn Gly Gly Gly Ser Cys Cys Ser Glu Met Asp Ile Trp Glu Ala Asn
            180                 185                 190
Ser Ile Ala Ala Phe Thr Pro His Pro Cys Thr Thr Gly Gln Thr Cys
        195                 200                 205
Gly Asp Cys Gly Gly Thr Tyr Ser Asp Arg Tyr Gly Cys Asp Asp Gly
    210                 215                 220
Cys Asp Phe Asn Tyr Arg Met Gly Asn Ser Phe Tyr Gly Gly Thr Val
225                 230                 235                 240
Asp Thr Thr Lys Lys Phe Thr Val Val Thr Gln Phe Val Thr Ser Gly
                245                 250                 255
Leu Glu Ile Arg Arg Phe Tyr Val Gln Asn Gly Lys Val Ile Asn Ile
            260                 265                 270
Pro Gly Val Gly Asn Ser Ile Thr Asp Glu Phe Cys Gln Lys Phe Gly
        275                 280                 285
Asp Ser Phe Gly Gly Leu Gln Met Gly Ala Leu Gly Met Val Leu Val
    290                 295                 300
Met Ser Ile Trp Asp Asp His Ala Ala Asn Met Leu Trp Leu Asp Ser
305                 310                 315                 320
Tyr Pro Thr Ser Pro Gln Arg Gly Ser Cys Thr Thr Ser Gly Val Pro
                325                 330                 335
Ala Val Glu Gln Pro Asn Val Val Phe Ser Asn Ile Lys Phe Gly Pro
            340                 345                 350
Ile Gly Ser Thr Tyr Gly Ser Ser Phe Gly Gln Cys Gly Gly Tyr
        355                 360                 365
Thr Gly Thr Cys Ser Thr Cys Asn Thr Thr Ser Gln Cys
    370                 375                 380

<210> SEQ ID NO 73
<211> LENGTH: 21
<212> TYPE: DNA
<213> ORGANISM: Artificial Sequence
<220> FEATURE:
<223> OTHER INFORMATION: complementary synthetic linker

<400> SEQUENCE: 73
ggtttggatc cggtcaccag g                                           21

<210> SEQ ID NO 74
<211> LENGTH: 27
<212> TYPE: DNA
<213> ORGANISM: Artificial Sequence
<220> FEATURE:
<223> OTHER INFORMATION: Complementary synthetic linkers

<400> SEQUENCE: 74
cgcgcctggt gaccggatcc aaaccgc                                     27
```

<210> SEQ ID NO 75
<211> LENGTH: 19
<212> TYPE: DNA
<213> ORGANISM: Artificial sequence
<220> FEATURE:
<223> OTHER INFORMATION: Primer

<400> SEQUENCE: 75
atgtatcgga agttggccg                                              19

<210> SEQ ID NO 76
<211> LENGTH: 19
<212> TYPE: DNA
<213> ORGANISM: Artificial sequence
<220> FEATURE:
<223> OTHER INFORMATION: Primer

<400> SEQUENCE: 76
ttacaggcac tgagagtag                                              19

<210> SEQ ID NO 77
<211> LENGTH: 18
<212> TYPE: DNA
<213> ORGANISM: Artificial sequence
<220> FEATURE:
<223> OTHER INFORMATION: Cloning polylinker

<400> SEQUENCE: 77
ggggtttaaa cccgcggg                                               18

<210> SEQ ID NO 78
<211> LENGTH: 22
<212> TYPE: DNA
<213> ORGANISM: Artificial sequence
<220> FEATURE:
<223> OTHER INFORMATION: Cloning polylinker

<400> SEQUENCE: 78
aattcccgcg ggtttaaacc cc                                          22

<210> SEQ ID NO 79
<211> LENGTH: 15
<212> TYPE: DNA
<213> ORGANISM: Artificial sequence
<220> FEATURE:
<223> OTHER INFORMATION: synthetic cloning polylinker

<400> SEQUENCE: 79
tgagccgagg cctcc                                                  15

<210> SEQ ID NO 80
<211> LENGTH: 14
<212> TYPE: DNA
<213> ORGANISM: Artificial sequence
<220> FEATURE:
<223> OTHER INFORMATION: Cloning polylinker

<400> SEQUENCE: 80
agcttgagat ctga                                                   14

```
<210> SEQ ID NO 81
<211> LENGTH: 14
<212> TYPE: DNA
<213> ORGANISM: Artificial sequence
<220> FEATURE:
<223> OTHER INFORMATION: Cloning polylinker

<400> SEQUENCE: 81
agcttcagat ctca                                                     14
```